US009006237B2

(12) United States Patent
Andrews et al.

(10) Patent No.: US 9,006,237 B2
(45) Date of Patent: Apr. 14, 2015

(54) FUSED PYRAZINE COMPOUNDS USEFUL FOR THE TREATMENT OF DEGENERATIVE AND INFLAMMATORY DISEASES

(75) Inventors: Martin James Inglis Andrews, Mechelen (BE); Mark Stuart Chambers, Saffron Walden (GB); Wolfgang Schmidt, Saffron Walden (GB); Giovanni Alessandro Tricarico, Mechelen (BE); Grégory Louis Joseph Bar, Mechelen (BE); Kim Louise Hirst, Saffron Walden (GB); Olga Raquel Pinto Santos Oliveira Roussel, Saffron Walden (GB); Juha Andrew Clase, Chapel-en-le-Frith (GB)

(73) Assignee: Janssen Pharmaceutica NV, Beerse (BE)

( * ) Notice: Subject to any disclaimer, the term of this patent is extended or adjusted under 35 U.S.C. 154(b) by 218 days.

(21) Appl. No.: 13/411,450

(22) Filed: Mar. 2, 2012

(65) Prior Publication Data

US 2012/0232075 A1 Sep. 13, 2012

Related U.S. Application Data

(62) Division of application No. 12/151,585, filed on May 7, 2008, now Pat. No. 8,148,369.

(60) Provisional application No. 60/928,600, filed on May 10, 2007, provisional application No. 60/931,764, filed on May 25, 2007.

(51) Int. Cl.
*A61K 31/503* (2006.01)
*A61K 31/4985* (2006.01)
*C07D 403/12* (2006.01)
*C07D 407/04* (2006.01)
*C07D 487/04* (2006.01)

(52) U.S. Cl.
CPC ................................. *C07D 487/04* (2013.01)

(58) Field of Classification Search
CPC ............ A61K 31/506; A61K 31/4985; C07D 403/12; C07D 407/04
USPC ......................... 514/233.2, 249; 544/117, 350
See application file for complete search history.

(56) References Cited

U.S. PATENT DOCUMENTS

| | | | |
|---|---|---|---|
| 6,316,444 B1 | 11/2001 | Hunt et al. | |
| 6,919,340 B2 | 7/2005 | Currie et al. | |
| 6,919,341 B2 | 7/2005 | Paruch et al. | |
| 7,157,460 B2 | 1/2007 | Sun et al. | |
| 7,186,832 B2 | 3/2007 | Sun et al. | |
| 7,576,085 B2 | 8/2009 | Guzi et al. | |
| 2005/0009832 A1* | 1/2005 | Sun et al. ....................... | 514/249 |

FOREIGN PATENT DOCUMENTS

| | | |
|---|---|---|
| WO | WO02/056888 A2 | 7/2002 |
| WO | WO02/060492 A1 | 8/2002 |
| WO | WO02/060495 A1 | 8/2002 |
| WO | WO2004/072081 A1 | 8/2004 |
| WO | WO2005/005429 A1 | 1/2005 |
| WO | WO2005/037836 A2 | 4/2005 |
| WO | WO2005/120513 A1 | 12/2005 |
| WO | WO2006/053121 A2 | 5/2006 |
| WO | WO2006/086545 A2 | 8/2006 |
| WO | WO2007/056468 A1 | 5/2007 |
| WO | WO2007/058942 A1 | 5/2007 |
| WO | WO2007/131991 A1 | 11/2007 |
| WO | WO2007/138072 A2 | 12/2007 |
| WO | WO2008/138842 A1 | 11/2008 |

OTHER PUBLICATIONS

Andreakos et al, "Heterogeneious Requirement of IkB Kinase 2 for Inflammatory Cytokine and Matrix metalloproteinase Production . . . "*Arthritis Rheum*. (2003) 48:1901-12.
Choy et al, "Cytokine Pathways and Joint Inflammation in Rheumatoid Arthritis" *N. Engl.J. Med.* (2001) 344:907-16.
Coussens et al, "Matrix Metalloproteinase Inhibitors and Cancer: Trials and Tribulations" *Science*(2002) 295:2387-92.
Creemers et al, "Matrix Metalloproteinase Inhibition After Mycocardial Infarction" *Circ. Res.* (2001) 89:201-10.
Cunnane et al, "Early Joint Erosions and Serum Levels of Matrix Metalloproteinase 1, Matrix Metalloproteinase 3, and Tissue . . . "*Arthritis Rheum*. (2002) 44:2263-74.
Edwards, J.C.W. et al., Efficacy of B-Cell-Targeted Therapy with Rituximab in Patients with Rheumatoid Arthritis (2004). N. Engl. J. Med. 350:2572-2581.
Firestein, "Evolving Concepts of Rheumatoid Arthritis", *Nature* (2003) 423:356-61.
Gapski et al, "Effecto f Systemic Matrix Metalloproteinase Inhibition on Periodontal Wound Repair: A Proof of Concept Trial" *J. Periodontal.* (2004) 75:441-52.
Gomez-Reino et al, "Treatment of Rheumatoid Arthritis with Tumor Necrosis Factor Inhibitors May Predispose to Significant Increase . . . "*Arthritis Rheum* (2003) 48:2122.
Kremer et al, "Treatment of Rheumatoid Arthritis by Selective Inhibition of T-Cell Activation with Fusion Protein CTLA4Ig" *N. Eg.l. J. Med.* (2003) 349:1907-1915.
Lee, "Rheumatoid Arthritis", *Lancet* (2001) 358:903-11.

(Continued)

*Primary Examiner* — James O Wilson
*Assistant Examiner* — Ebenezer O Sackey

(57) ABSTRACT

Novel fused pyrazine compounds are disclosed that have a formula represented by the following:

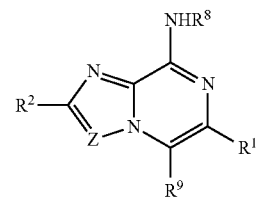

The compounds may be prepared as pharmaceutical compositions, and may be used for the prevention and treatment of a variety of conditions in mammals including humans, including by way of non-limiting example, inflammation, rheumatoid arthritis and others.

62 Claims, 5 Drawing Sheets

(56) References Cited

OTHER PUBLICATIONS

New et al, "Regulation of PRAK Subcellular Location by p38 MAP Kinases", *Mol. Biol. Cell.* (2003) 14(6):2603-16.

O'Dell U.R. et .al. "Therapeutic Strategies for Rhematoid Arthritis." (2004)N. Engl. J. Med., 350(25):2591-602.

O'Dell et al, "Therapeutic Strategies for Rhematoid Arthritis. Treatment of Rheumatoid Arthritis with Methotrexate and Hydroxychloroquine . . . "*Arthritis Rheum.* (2002) 46:116.

Rein et al, "Matrix Metalloproteinases 2 and 9 are Markers of Inflammation but Not of the Degree of Fibrosis in Chronic Hepatitis C", *Digestion* (2005) 71:124-130.

Rosenberg, "Matrix Metalloproteinases in Neuroinflmaation" *Gila* (2002) 39;279-91.

Schanstra et al, In vivo Bradykinin B2 Receptor Activation Reduces Renal Fibrosis, *J. Clin. Invest.* (2002) 110:371-9.

Seternes, "Activation of MK5/PRAK by the atypical MPA Kinase ERK3 Defines a Novel Signal Transduction Pathway", *EMBO J.* (2004) 23:4780-91.

Shi et al, "Elimination of Protein Kinases MK5/PRAK Activity by Targeted Homologous Recombination" *Mol. Cell Biol.* (2003) 23:7732-41.

Smolen, "Therapeutic Strategies for Rheumatoid Arthritis" *Nat. ev. Drug Discov.* (2003) 2:473-88.

St. Clair et al, "Combination of infliximab and Methotrexate Therapy for Early Rheumatoid Arthritis: A randomized, controlled trail" *Arthritis Rheum.* (2004) 50:3432-43.

Suzuki et al., "Matrix Metalloproteinases in the Pathogenesis of Asthma and COPD: Implications for Therapy" *Treat Respir Med.* (2004) 3:17-27.

\* cited by examiner

Schematic view of a normal joint and its changes in rheumatoid arthritis
(From Smolen and Steiner, 2003)

Increased expression of MMP1 by SFs triggered with cytokines involved in rheumatoid arthritis pathology.

Dose-dependent inhibition of the "TNF-α -based trigger"-induced expression of MMP1 by SFs by a known anti-inflammatory compound.

Reduction, at the protein level, of the expression of MAPKAPK5 in SFs by infection of the cells with Ad-siRNA virus targeting MAPKAPK5.

Reduction of 'complex trigger' induced levels of MMP1 expression by SFs by an Ad-siRNA virus targeting MAPKAPK5.

SEQUENCE LISTING

<160> NUMBER OF SEQ ID NOS: 6

<210> SEQ ID NO 1
<211> LENGTH: 19
<212> TYPE: DNA
<213> ORGANISM: artificial
<220> FEATURE:
<223> OTHER INFORMATION: Knock-down sequence

<400> SEQUENCE: 1
gctgaccctg aagttcatc                                              19

<210> SEQ ID NO 2
<211> LENGTH: 19
<212> TYPE: DNA
<213> ORGANISM: artificial
<220> FEATURE:
<223> OTHER INFORMATION: Knock-down sequence

<400> SEQUENCE: 2
ggttacctaa gggtgtggc                                              19

<210> SEQ ID NO 3
<211> LENGTH: 19
<212> TYPE: DNA
<213> ORGANISM: Artificial
<220> FEATURE:
<223> OTHER INFORMATION: Knock-down sequence

<400> SEQUENCE: 3
ctctgagtgc agtgaaatc                                              19

<210> SEQ ID NO 4
<211> LENGTH: 19
<212> TYPE: DNA
<213> ORGANISM: Artificial
<220> FEATURE:
<223> OTHER INFORMATION: Knock-down sequence

<400> SEQUENCE: 4
acaagagcaa gatgtggac                                              19

<210> SEQ ID NO 5
<211> LENGTH: 19
<212> TYPE: DNA
<213> ORGANISM: artificial
<220> FEATURE:
<223> OTHER INFORMATION: Knock-down sequence

<400> SEQUENCE: 5
cggcacttta cagagaagc                                              19

<210> SEQ ID NO 6
<211> LENGTH: 19
<212> TYPE: DNA
<213> ORGANISM: Artificial
<220> FEATURE:
<223> OTHER INFORMATION: Knock-down sequence

<400> SEQUENCE: 6
atgatgtgtg ccacacacc                                              19

FUSED PYRAZINE COMPOUNDS USEFUL FOR THE TREATMENT OF DEGENERATIVE AND INFLAMMATORY DISEASES

RELATED APPLICATIONS

The present application is a divisional application of U.S. application Ser. No. 12/151,585, filed May 7, 2008 now U.S. Pat. No. 8,148,369, which claims the benefit under 35 U.S.C. §119 of U.S. Provisional Application Ser. No. 60/928,600 filed May 10, 2007, and Ser. No. 60/931,764, filed May 25, 2007, the contents of all of which applications are hereby incorporated by reference in their entireties.

FIELD OF THE INVENTION

The present invention relates to a class of fused pyrazine compounds capable of binding to the active site of a serine/threonine kinase, the expression of which is involved in the pathway resulting in the degradation of extra-cellular matrix (ECM), joint degeneration and diseases involving such degradation and/or inflammation.

Diseases involving the degradation of extra-cellular matrix include, but are not limited to, psoriatic arthritis, juvenile arthritis, early arthritis, reactive arthritis, osteoarthritis, ankylosing spondylitis, osteoporosis, muskulo skeletal diseases like tendonitis and periodontal disease, cancer metastasis, airway diseases (COPD, asthma), renal and liver fibrosis, cardio-vascular diseases like atherosclerosis and heart failure, and neurological diseases like neuroinflammation and multiple sclerosis. Diseases involving primarily joint degeneration include, but are not limited to, psoriatic arthritis, juvenile arthritis, early arthritis, reactive arthritis, osteoarthritis, and ankylosing spondylitis.

Rheumatoid arthritis (RA) is a chronic joint degenerative disease, characterized by inflammation and destruction of the joint structures. When the disease is unchecked, it leads to substantial disability and pain due to loss of joint functionality and even premature death. The aim of an RA therapy, therefore, is not to slow down the disease but to attain remission in order to stop the joint destruction. Besides the severity of the disease outcome, the high prevalence of RA (~0.8% of the adults are affected worldwide) means a high socio-economic impact. (For reviews on RA, we refer to Smolen and Steiner (2003); Lee and Weinblatt (2001); Choy and Panayi (2001); O'Dell (2004) and Firestein (2003)).

Although it is widely accepted that RA is an auto-immune disease, there is no consensus concerning the precise mechanisms driving the 'initiation stage' of the disease. What is known is that the initial trigger(s) does mediate, in a predisposed host, a cascade of events that leads to the activation of various cell types (B-cells, T-cells, macrophages, fibroblasts, endothelial cells, dendritic cells and others). Concomitantly, an increased production of various cytokines is observed in the joints and tissues surrounding the joint (e.g. TNF-α, IL-6, IL-1, IL-15, IL-18 and others). When the disease progresses, the cellular activation and cytokine production cascade becomes self-perpetuating. At this early stage, the destruction of joint structures is already very clear at this early stage. Thirty percent of the patients have radiographic evidence of bony erosions at the time of diagnosis and this proportion increases to 60 percent after two years.

Histological analysis of the joints of RA patients clearly evidences the mechanisms involved in the RA-associated degradative processes. This analysis shows that the main effector responsible for RA-associated joint degradation is the pannus, where the synovial fibroblast, by producing diverse proteolytic enzymes, is the prime driver of cartilage and bone erosion. A joint classically contains two adjacent bones that articulate on a cartilage layer and are surrounded by the synovial membrane and joint capsule. In the advanced RA patient, the synovium of joint increases in size to form the pannus, due to the proliferation of the synovial fibroblasts and the infiltration of mononuclear cells such as T-cells, B-cells, monocytes, macrophages and neutrophils. The pannus mediates the degradation of the adjacent cartilage, leading to the narrowing of the joint space, and has the potential to invade adjacent bone and cartilage. As bone and cartilage tissues are composed mainly of collagen type I or II, respectively, the pannus destructive and invasive properties are mediated by the secretion of collagenolytic proteases, principally the matrix metallo proteinases (MMPs). The erosion of the bone under and adjacent to the cartilage is also part of the RA process, and results principally from the presence of osteoclasts at the interface of bone and pannus. Osteoclasts are multinucleated cells that, upon adhesion to the bone tissue, form a closed compartment, within which the osteoclasts secrete proteases (Cathepsin K, MMP9) that degrade the bone tissue. The osteoclast population in the joint is abnormally increased by osteoblast formation from precursor cells induced by the secretion of the receptor activator of NFκB ligand (RANKL) by activated SFs and T-cells.

Various collagen types have a key role in defining the stability of the extracellular matrix (ECM). Collagen type I and collagen type II, for example, are the main components of bone and cartilage, respectively. Collagen proteins typically organise into multimeric structures referred to as collagen fibrils. Native collagen fibrils are very resistant to proteolytic cleavage. Only a few types of ECM-degrading proteins have been reported to have the capacity to degrade native collagen: MMPs and Cathepsins. Among the Cathepsins, cathepsin K, which is active mainly in osteoclasts, is the best characterised. Among the MMPs, MMP1, MMP2, MMP8 MMP13 and MMP14 are known to have collagenolytic properties. The correlation between an increased expression of MMP1 by synovial fibroblasts (SFs) and the progression of the arthritic disease is well-established and is predictive for joint erosive processes (Cunnane et al., 2001). In the context of RA, therefore, MMP1 represents a highly relevant collagen degrading protein. In vitro, the treatment of cultured SFs with cytokines relevant in the RA pathology (e.g. TNF-α and IL1β) will increase the expression of MMP1 by these cells (Andreakos et al., 2003). Monitoring the levels of MMP1 expressed by SFs therefore is a relevant readout in the field of RA as it is indicative for the activation of SFs towards an erosive phenotype that, in vivo, is responsible for cartilage degradation. Inhibition of the MMP1 expression by SFs represents a valuable therapeutic approach towards the treatment of RA.

The activity of the ECM-degrading proteins can also be causative or correlate with the progression of various diseases different from RA, as e.g. other diseases that involve the degradation of the joints. These diseases include, but are not limited to, psoriatic arthritis, juvenile arthritis, early arthritis, reactive arthritis, osteoarthritis, and ankylosing spondylitis. Other diseases that may be treatable with compounds identified according to the present invention and using the targets involved in the expression of MMPs as described herein are osteoporosis, muscular skeletal diseases like tendonitis and periodontal disease (Gapski et al., 2004), cancer metastasis (Coussens et al., 2002), airway diseases (COPD, asthma) (Suzuki et al., 2004), lung, renal fibrosis (Schanstra et al., 2002), liver fibrosis associated with chronic hepatitis C (Reiff et al., 2005), cardio-vascular diseases like atherosclerosis and heart failure (Creemers et al., 2001), and neurological diseases like neuroinflammation and multiple sclerosis (Rosenberg, 2002). Patients suffering from such diseases may benefit from stabilizing the ECM (by protecting it from degradation).

The 471-amino acid serine/threonine kinase identified as Mitogen-Activated Protein Kinase-Activated Protein Kinase 5 (MAPKAPK5 or PRAK) is expressed in a wide panel of tissues. The protein contains its catalytic domain at the N-terminal end and both a nuclear localization signal (NLS) and nuclear export signal (NES) at its C-terminal end. Endogenous MAPKAPK5 is predominantly present in the cytoplasm, but stress or cytokine activation of the cells mediates its translocation into the nucleus (New et al., 2003). This event is dependent on phosphorylation of MAPKAPK5. Thr182 is the regulatory phosphorylation site of MAPKAPK5. Although the p38α kinase is able to phosphorylate MAPKAPK5 in an overexpression setting, experiments with endogenous MAPKAPK5 do not support this hypothesis (Shi et al., 2003). MAPKAPK5 knock-out mice have been generated that are viable and fertile. The phenotype of these mice is quite different from that of mice deficient for MAPKAPK2, a MAPKAPK5 related kinase that is regulated by p38α (Shi et al., 2003). This indicates that the function of each protein is distinct and that neither kinase can compensate for the other's activity. Taken together, MAPKAPK5 and MAPKAPK2 represent distinct targets with a non-redundant role. MAPK6 (also referred to as ERK3) has recently been identified as a physiologically relevant substrate for MAPKAPK5, defining a novel signal transduction pathway (Seternes et al., 2004).

BACKGROUND OF THE INVENTION

NSAIDS (Non-steroidal anti-inflammatory drugs) are used to reduce the pain associated with RA and improve life quality of the patients. These drugs will not, however, put a brake on the RA-associated joint destruction.

Corticosteroids were found to decrease the progression of RA as detected radiographically and are used at low doses to treat part of the RA patients (30 to 60%). Serious side effects, however, are associated with long corticosteroid use (Skin thinning, osteoporosis, cataracts, hypertension and hyperlipidemia).

Synthetic DMARDs (Disease-Modifying Anti-Rheumatic Drugs) (e.g. methotrexate, leflunomide, sulfasalazine) mainly tackle the immuno-inflammatory component of RA. As a main disadvantage, these drugs only have a limited efficacy (joint destruction is only slowed down but not blocked by DMARDs such that disease progression in the long term continues). The lack of efficacy is indicated by the fact that, on average, only 30% of the patients achieve an ACR40 score after 24 months treatment with methotrexate. This means that, according to the American College of Rheumatology, only 30% of the patients do achieve a 50% improvement of their symptoms (O'Dell et al., 1996). In addition, the precise mechanism of action of DMARDs is often unclear.

Biological DMARDs (Infliximab, Etanercept, Adalimumab, Rituximab; CTLA4-Ig) are therapeutic proteins that do inactivate cytokines (e.g. TNF-α) or cells (e.g. T-cells or B-cells) that have an important role in the RA pathophysiology (Kremer et al., 2003; Edwards et al., 2004). Although the TNF-α-blockers (Infliximab, Etanercept, Adalimumab) and methotrexate combination therapy is the most effective RA treatment currently available, it is striking that even this therapy only achieves a 50% improvement (ACR40) in disease symptoms in 50-60% of patients after 12 months therapy (St Clair et al., 2004). Some adverse events warnings for anti-TNF-α drugs exist, shedding a light on the side effects associated to this type of drugs. Increased risk for infections (tuberculosis), hematologic events and demyelinating disorders have been described for the TNF-α blockers (see also Gomez-Reino et al., 2003). Besides the serious side effects, the TNF-α blockers also share the general disadvantages of the biological class of therapeutics, which are the unpleasant way of administration (frequent injections accompanied by infusion site reactions) and the high production cost. Newer agents in late development phase target T-cell co-stimulatory molecules and B-cells. The efficacy of these agents is expected to be similar to that of the TNF-α blockers. The fact that a variety of targeted therapies have similar but limited efficacies, suggests that there is a multiplicity of pathogenic factors for RA. This is also indicative for the deficiencies in our understanding of pathogenic events relevant to RA.

The current therapies for RA are not satisfactory due to a limited efficacy (No adequate therapy exists for 30% of the patients). This calls for additional strategies to achieve remission. Remission is required since residual disease bears the risk of progressive joint damage and thus progressive disability. Inhibiting the immuno-inflammatory component of the RA disease, which represents the main target of drugs currently used for RA treatment, does not result in a blockade of joint degradation, the major hallmark of the disease.

US 2005/0009832 describes substituted imidazo[1,2-a]pyrazine-8-yl-amines as modulators of protein kinases, including MAPKAPK5. WO02/056888 describes inhibitors of MAPKAPK5 as TNF modulators able to regulate the expression of certain cytokines. Neither of these prior art references discloses any compound within the scope of the class of compounds described herein below.

SUMMARY OF THE INVENTION

The present invention is based on the discovery that MAPKAPK5 functions in the pathway that results in the expression of MMP1, and that inhibitors of MAPKAPK5 activity, such as the compounds of the present invention, are useful for the treatment of diseases involving the abnormally high expression of MMP activity.

The compounds of the present invention may be described generally as fused pyrazines, in particular imidazo[1,2-a]pyrazine-8-yl-amines and [1.2.4]triazolo[1,5-a]pyrazine-8-yl-amines substituted in the 5-position by an aromatic group capable of donating electrons to, and an 8-amino substituent capable of accepting electrons from, the fused pyrazine, i.e. the imidazo[1,2.a]pyrazine or the [1.2.4]triazolo[1,5-a]pyrazine ring. In particular, the 5-substituent group is characterized as having a hydrogen bond donor-acceptor functionality, whereas the substituent on the 8-amino group must be sufficiently electron-withdrawing to polarise the N—H bond of the 8-substituent, or alternatively, the 8-NH group is capable of participating in pi-conjugation with the substituent group on the 8-NH group.

The compounds of the present invention may show less toxicity, good absorption, good half-life, good solubility, low protein binding affinity, less drug-drug interaction, and good metabolic stability.

More particularly, the present invention relates to compounds according to formula (I):

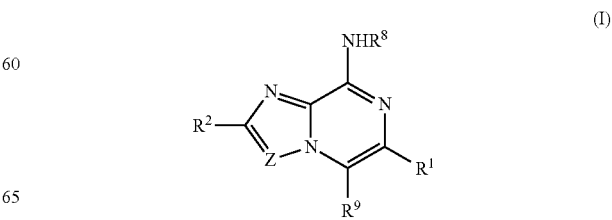

wherein

Z is CH or N; $R^1$ is H, or substituted or unsubstituted $C_1$-$C_6$ alkyl; $R^2$ is H, $C_1$-$C_6$ alkyl, $C_3$-$C_7$ cycloalkyl or $C_3$-$C_7$ cycloalkyl-$C_1$-$C_6$ alkyl, optionally substituted with one or more of F and Cl; $R^8$ is substituted or unsubstituted heteroaryl; $R^9$ is selected from substituted or unsubstituted aryl and substituted or unsubstituted heteroaryl; or a pharmaceutically acceptable salt, solvate or prodrug thereof; and stereoisomers, isotopic variants and tautomers thereof.

In one embodiment, with respect to compounds of formula I, $R^1$ is H.

In one embodiment, with respect to compounds of formula I, $R^2$ is H.

In one embodiment, with respect to compounds of formula I, $R^8$ is substituted or unsubstituted 5-membered heteroaryl.

In another embodiment, with respect to compounds of formula I, $R^8$ is selected from substituted or unsubstituted pyrrolyl, furanyl, thienyl, pyrazolyl, oxazolyl, imidazolyl, thiazolyl, 1,3,4-thiadiazolyl, and 1,2,4-thiadiazolyl.

In another embodiment, with respect to compounds of formula I, $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is selected from alkyl, substituted alkyl, carbamoyl, hydroxyalkyl, haloalkyl, alkoxy, cyano, amino, sulfo, aryl, heterocycloalkyl, aralkyl, heterocycloalkyl and heteroaryl.

In another embodiment, with respect to compounds of formula I, $R^9$ is selected from substituted or unsubstituted phenyl.

In another embodiment, with respect to compounds of formula I, $R^9$ is selected from substituted or unsubstituted pyridyl.

In another embodiment, with respect to compounds of formula I, $R^9$ is selected from substituted or unsubstituted phenyl, indolyl, isoinolyl, pyrrolyl, furanyl, thienyl, pyrazolyl, oxazolyl, and thiazolyl.

In a further aspect, the present invention provides pharmaceutical compositions comprising a fused pyrazine compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

Another aspect of this invention relates to the use of a compound of the invention in a therapeutic method, a pharmaceutical composition, and the manufacture of such composition, useful for the treatment of diseases involving inflammation, collagen degradation, and in particular, diseases characteristic of abnormal matrix metallo protease (MMP1) and/or Mitogen-Activated Protein-Kinase Activated Protein Kinase 5 (MAPKAPK5) activity, of which rheumatoid arthritis (RA) is a particular such disease. This invention also relates to processes for the preparation of the present compounds.

Another aspect of this invention relates to a compound of the invention for use in the treatment of diseases involving inflammation, collagen degradation, and in particular, diseases characteristic of abnormal matrix metallo protease (MMP1) and/or Mitogen-Activated Protein-Kinase Activated Protein Kinase 5 (MAPKAPK5) activity, of which rheumatoid arthritis (RA) is a particular such disease.

Other objects and advantages will become apparent to those skilled in the art from a consideration of the ensuing detailed description, considered in conjunction with the following illustrative drawings.

DETAILED DESCRIPTION OF THE INVENTION

Figure 1:
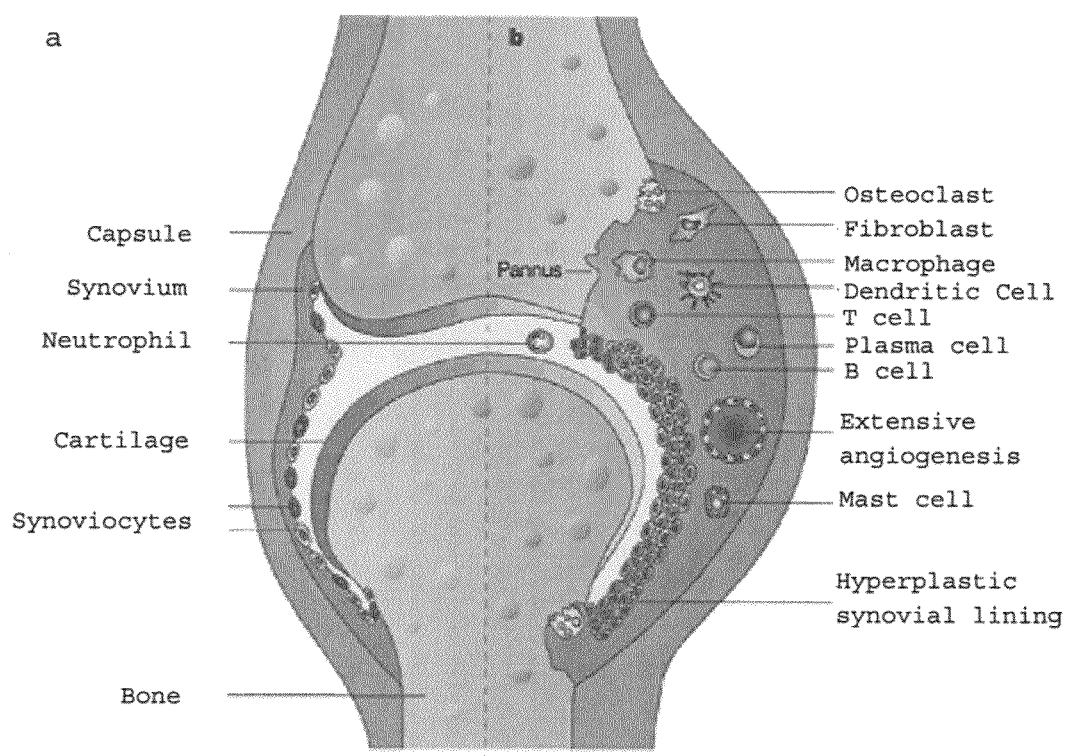
FIG. 1. This diagram shows the striking histological differences between a healthy joint and that of a RA patient.

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein.

The articles "a" and "an" may be used herein to refer to one or to more than one (i.e. at least one) of the grammatical objects of the article. By way of example "an analogue" means one analogue or more than one analogue.

'Acyl' refers to a radical —C(O)$R^{20}$, where $R^{20}$ is hydrogen, alkyl, cycloalkyl, cycloheteroalkyl, aryl, arylalkyl, heteroalkyl, heteroaryl or heteroarylalkyl as defined herein. Representative examples include, but are not limited to, formyl, acetyl, cylcohexylcarbonyl, cylcohexylmethylcarbonyl, benzoyl and benzylcarbonyl. Exemplary 'acyl' groups are —C(O)H, —C(O)—$C_1$-$C_8$ alkyl, —C(O)—$(CH_2)_t(C_6$-$C_{10}$ aryl), —C(O)—$(CH_2)_t(C_5$-$C_{10}$ heteroaryl), —C(O)—$(CH_2)_t$ ($C_3$-$C_{10}$ cycloalkyl), and —C(O)—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Acylamino' refers to a radical —$NR^{21}C(O)R^{22}$, where $R^{21}$ is hydrogen, alkyl, cycloalkyl, cycloheteroalkyl, aryl, arylalkyl, heteroalkyl, heteroaryl or heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino and benzylcarbonylamino. Exemplary 'acylamino' groups are —$NR^{21}C(O)$—$C_1$-$C_8$ alkyl, —$NR^{21}C(O)$—$(CH_2)_t(C_6$-$C_{10}$ aryl), —$NR^{21}C(O)$—$(CH_2)_t(C_5$-$C_{10}$ heteroaryl), —$NR^{21}C(O)$—$(CH_2)_t(C_3$-$C_{10}$ cycloalkyl), and —$NR^{21}C(O)$ $(CH_2)_t(C_5$-$C_{10}$ heterocycloalkyl), wherein t is an integer from 0 to 4, each $R^{21}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_1$-$C_4$ haloalkyl, $C_1$-$C_4$ hydroxyalkyl, or $C_1$-$C_4$ haloalkoxy or hydroxy.

'Acyloxy' refers to the group —OC(O)$R^{23}$ where $R^{23}$ is hydrogen, alkyl, aryl or cycloalkyl. Exemplary 'acyloxy' groups are OC(O)—$C_1$-$C_8$ alkyl, —OC(O)—(CH$_2$)$_t$($C_6$-$C_{10}$ aryl), —OC(O)—(CH$_2$)$_t$($C_5$-$C_{10}$ heteroaryl), —OC(O)—(CH$_2$)$_t$($C_3$-$C_{10}$ cycloalkyl), and —OC(O)—(CH$_2$)$_t$($C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Alkoxy' refers to the group —OR$^{24}$ where $R^{24}$ is alkyl. Particular alkoxy groups are, methoxy, ethoxy, n-propoxy, isopropoxy, n-butoxy, tert-butoxy, sec-butoxy, n-pentoxy, n-hexoxy and 1,2-dimethylbutoxy. Particular alkoxy groups are lower alkoxy, i.e. with between 1 and 6 carbon atoms.

'Substituted alkoxy' refers to an alkoxy group substituted with one or more of those groups recited in the definition of "substituted" herein, and particularly refers to an alkoxy group having 1 or more substituents, for instance from 1 to 5 substituents, and particularly from 1 to 3 substituents, in particular 1 substituent, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Exemplary 'substituted alkoxy' groups are —O—(CH$_2$)$_t$($C_6$-$C_{10}$ aryl), —O—(CH$_2$)$_t$($C_5$-$C_{10}$ heteroaryl), —O—(CH$_2$)$_t$($C_3$-$C_{10}$ cycloalkyl), and —O—(CH$_2$)$_t$($C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Alkoxycarbonylamino' refers to the group —NR$^{25}$C(O)OR$^{26}$, where $R^{25}$ is hydrogen, alkyl, aryl or cycloalkyl, and $R^{26}$ is alkyl or cycloalkyl.

'Alkyl' means straight or branched aliphatic hydrocarbon having 1 to about 20 carbon atoms. Particular alkyl has 1 to about 12 carbon atoms. More particular is lower alkyl which has 1 to 6 carbon atoms. Most particular are groups such as methyl, ethyl and propyl. Branched means that one or more lower alkyl groups such as methyl, ethyl or propyl is attached to a linear alkyl chain. The term $C_1$-$C_6$ alkyl includes both branched and straight chain groups, exemplary straight chain groups include ethyl, propyl, butyl, exemplary branched chain groups include isopropyl, isoamyl, and the like.

'Substituted alkyl' refers to an alkyl group substituted with one or more of those groups recited in the definition of "substituted" herein, and particularly refers to an alkyl group having 1 or more substituents, for instance from 1 to 5 substituents, and particularly from 1 to 3 substituents, in particular 1 substituent, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—. In a particular embodiment 'substituted alkyl' refers to a $C_1$-$C_6$ alkyl group substituted with halo, cyano, nitro, trifluoromethyl, trifluoromethoxy, azido, —NR'''SO$_2$R'', —SO$_2$NR''R''', —C(O)R'', —C(O)OR'', —OC(O)R'', —NR''C(O)R'', —C(O)NR''R''', —NR''R''', or —(CR'''R'''')$_m$OR'''; wherein each R'' is independently selected from H, $C_1$-$C_8$ alkyl, —(CH$_2$)$_t$($C_6$-$C_{10}$ aryl), —(CH$_2$)$_t$($C_5$-$C_{10}$ heteroaryl), —(CH$_2$)$_t$($C_3$-$C_{10}$ cycloalkyl), and —(CH$_2$)$_t$($C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. Each of R''' and R'''' independently represents H or $C_1$-$C_6$ alkyl.

'Alkylene' refers to divalent alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—) and the propylene isomers (e.g., —CH$_2$CH$_2$CH$_2$— and —CH(CH$_3$)CH$_2$—).

'Substituted alkylene' refers to an alkylene group substituted with one or more of those groups recited in the definition of 'substituted' herein, and particularly refers to an alkylene group having 1 or more substituents, for instance from 1 to 5 substituents, and particularly from 1 to 3 substituents, in particular 1 substituent.

'Alkenyl' refers to monovalent olefinically (unsaturated) hydrocarbon groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl.

'Substituted alkenyl' refers to an alkenyl group substituted with one or more of those groups recited in the definition of 'substituted' herein, and particularly refers to an alkenyl group having 1 or more substituents, for instance from 1 to 5 substituents, and particularly from 1 to 3 substituents, in particular 1 substituent.

'Alkenylene' refers to divalent olefinically (unsaturated) hydrocarbon groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—) and the propenylene isomers (e.g., —CH=CHCH$_2$— and —C(CH$_3$)=CH— and —CH=C(CH$_3$)—).

'Alkynyl' refers to acetylenically or alkynically (unsaturated) hydrocarbon groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), and propargyl (—CH$_2$C≡CH).

'Substituted alkynyl' refers to an alkynyl group substituted with one or more of those groups recited in the definition of "substituted" herein, and particularly refers to an alkynyl group having 1 or more substituents, for instance from 1 to 5 substituents, and particularly from 1 to 3 substituents, in particular 1 substituent.

'Alkanoyl' or 'acyl' as used herein refers to the group $R^{27}$—C(O)—, where $R^{27}$ is hydrogen or alkyl as defined above.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene; pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl. The term 'aryl' includes 'bicycloaryl' as defined below.

'Bicycloaryl' refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene and tetrahydronaphthalene. Particularly, an aryl group comprises from 8 to 11 carbon atoms.

'Substituted Aryl' refers to an aryl group substituted with one or more of those groups recited in the definition of 'substituted' herein, and particularly refers to an aryl group that may optionally be substituted with 1 or more substituents, for instance from 1 to 5 substituents, particularly 1 to 3 substituents, in particular 1 substituent.

'Fused Aryl' refers to an aryl having two of its ring carbon in common with a second aryl ring or with an aliphatic ring.

'Alkaryl' or 'arylalkyl' refers to an aryl group, as defined above, substituted with one or more alkyl groups, as defined above.

'Substituted Aralkyl' or 'substituted arylalkyl' refers to an alkyl group, as defined above, substituted with one or more aryl groups, as defined above.

'Aryloxy' refers to —O-aryl groups wherein 'aryl' is as defined above.

'Alkylamino' refers to the group alkyl-$NR^{28}R^{29}$, wherein each of $R^{28}$ and $R^{29}$ are independently selected from hydrogen and alkyl.

'Arylamino' refers to the group aryl-$NR^{30}R^{31}$, wherein each of $R^{30}$ and $R^{31}$ are independently selected from hydrogen, aryl and heteroaryl.

'Alkoxyamino' refers to a radical —$N(H)OR^{32}$ where $R^{32}$ represents an alkyl or cycloalkyl group as defined herein.

'Alkoxycarbonyl' refers to a radical —C(O)-alkoxy where alkoxy is as defined herein. Exemplary "alkoxycarbonyl" groups are C(O)O—$C_1$-$C_8$ alkyl, —C(O)O—$(CH_2)_t(C_6$-$C_{10}$ aryl), —C(O)O—$(CH_2)_t(C_5$-$C_{13}$ heteroaryl), —C(O)O—$(CH_2)_t(C_3$-$C_{10}$ cycloalkyl), and —C(O)O—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Alkylarylamino' refers to a radical —$NR^{33}R^{34}$ where $R^{33}$ represents an alkyl or cycloalkyl group and $R^{34}$ is an aryl as defined herein.

'Alkylsulfonyl' refers to a radical —$S(O)_2R^{35}$ where $R^{35}$ is an alkyl or cycloalkyl group as defined herein. Representative examples include, but are not limited to, methylsulfonyl, ethylsulfonyl, propylsulfonyl and butylsulfonyl.

'Alkylsulfinyl' refers to a radical —$S(O)R^{35}$ where $R^{35}$ is an alkyl or cycloalkyl group as defined herein. Representative examples include, but are not limited to, methylsulfinyl, ethylsulfinyl, propylsulfinyl and butylsulfinyl.

'Alkylthio' refers to a radical —$SR^{35}$ where $R^{35}$ is an alkyl or cycloalkyl group as defined herein that may be optionally substituted as defined herein. Representative examples include, but are not limited to, methylthio, ethylthio, propylthio and butylthio. Exemplary 'alkylthio' groups are S—$C_1$-$C_8$ alkyl, —S—$(CH_2)_t(C_6$-$C_{10}$ aryl), —S—$(CH_2)_t(C_5$-$C_{10}$ heteroaryl), —S—$(CH_2)_t(C_3$-$C_{10}$ cycloalkyl), and —S—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Amino' refers to the radical —$NH_2$.

'Substituted amino' refers to an amino group substituted with one or more of those groups recited in the definition of 'substituted' herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group. Exemplary 'substituted amino' groups are —$NR^{36}$—$C_1$-$C_8$ alkyl, —$NR^{36}$—$(CH_2)_t(C_6$-$C_{10}$, aryl), —$NR^{36}$—$(CH_2)_t(C_5$-$C_{10}$ heteroaryl), —$NR^{36}$—$(CH_2)_t(C_3$-$C_{10}$, cycloalkyl), and —$NR^{36}$—$(CH_2)_t(C_5$-$C_{10}$ heterocycloalkyl), wherein t is an integer from 0 to 4, each $R^{36}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Aminocarbonyl' refers to the group —$C(O)NR^{37}R^{37}$ where each $R^{37}$ is independently hydrogen, alkyl, aryl and cycloalkyl, or where the $R^{37}$ groups are joined to form an alkylene group.

'Aminocarbonylamino' refers to the group —$NR^{38}C(O)NR^{38}R^{38}$ where each $R^{38}$ is independently hydrogen, alkyl, aryl or cycloalkyl, or where two R groups are joined to form an alkylene group.

'Aminocarbonyloxy' refers to the group —$OC(O)NR^{39}R^{39}$ where each $R^{39}$ is independently hydrogen, alkyl, aryl or cycloalkyl, or where the R groups are joined to form an alkylene group.

'Arylalkyloxy' refers to an —O-arylalkyl radical where arylalkyl is as defined herein.

'Arylamino' means a radical —$NHR^{40}$ where $R^{40}$ represents an aryl group as defined herein.

'Aryloxycarbonyl' refers to a radical —C(O)—O-aryl where aryl is as defined herein.

'Arylsulfonyl' refers to a radical —$S(O)_2R^{41}$ where $R^{41}$ is an aryl or heteroaryl group as defined herein.

'Azido' refers to the radical —$N_3$.

'Carbamoyl' refers to the radical —$C(O)N(R^{42})_2$ where each $R^{42}$ group is independently hydrogen, alkyl, cycloalkyl or aryl, as defined herein, which may be optionally substituted as defined herein. A particular carbamoyl group is —$C(O)NH_2$. Exemplary 'carbamoyl' groups are —C(O)$NR^{42}$—$C_1$-$C_8$ alkyl, —$C(O)NR^{42}$—$(CH_2)_t(C_6$-$C_{10}$ aryl), —$C(O)NR^{42}$—$(CH_2)_t(C_5$-$C_{10}$, heteroaryl), —$C(O)NR^{42}$—$(CH_2)_t(C_3$-$C_{10}$ cycloalkyl), and —$C(O)NR^{42}$—$(CH_2)_t(C_5$-$C_{10}$ heterocycloalkyl), wherein t is an integer from 0 to 4, each $R^{42}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Carboxy' refers to the radical —C(O)OH.

'Carboxyamino' refers to the radical —N(H)C(O)OH.

'Cycloalkyl' refers to cyclic non-aromatic hydrocarbyl groups having from 4 to about 7 carbon atoms and having a single cyclic ring, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl and 2-methylcyclooctyl.

'Substituted cycloalkyl' refers to a cycloalkyl group substituted with one or more of those groups recited in the definition of 'substituted' herein, and particularly refers to a cycloalkyl group having 1 or more substituents, for instance from 1 to 5 substituents, and particularly from 1 to 3 substituents, in particular 1 substituent 'Cycloalkoxy' refers to the group —$OR^{43}$ where $R^{43}$ is cycloalkyl. Such cycloalkoxy groups include, by way of example, cyclopentoxy and cyclohexoxy.

'Cycloalkenyl' refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl and cyclopropenyl.

'Substituted cycloalkenyl' refers to a cycloalkenyl group substituted with one or more of those groups recited in the definition of "substituted" herein, and particularly refers to a cycloalkenyl group having 1 or more substituents, for instance from 1 to 5 substituents, and particularly from 1 to 3 substituents, in particular 1 substituent 'Fused Cycloalkenyl' refers to a cycloalkenyl having two of its ring carbon atoms in common with a second aliphatic or aromatic ring and having its olefinic unsaturation located to impart aromaticity to the cycloalkenyl ring.

'Cyanato' refers to the radical —OCN.

'Cyano' refers to the radical —CN.

'Dialkylamino' means a radical —$NR^{44}R^{45}$ where $R^{44}$ and $R^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

'Ethenyl' refers to substituted or unsubstituted —(C=C)—.

'Ethylene' refers to substituted or unsubstituted —(C—C)—.

'Ethynyl' refers to —(C≡C)—.

'Halo' or 'halogen' refers to fluoro (F), chloro (Cl), bromo (Br) and iodo (I). Preferred halo groups are either fluoro or chloro.

'Hydrogen' means in the context of a substituent that —H is present at the compound position and also includes its isotope, deuterium.

'Hydroxy' refers to the radical —OH.

'Nitro' refers to the radical —$NO_2$.

'Substituted' refers to a group in which one or more hydrogen atoms are each independently replaced with the same or different substituent(s). Typical substituents are selected from the group consisting of: —X, —$R^{46}$, —$O^+$, =O, —$OR^{46}$, —$SR^{46}$, —$S^-$, =S, —$NR^{46}R^{47}$, =$NR^{46}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{46}$, —$OS(O_2)O^-$, —OS$(O)_2R^{46}$, —$P(O)(O^-)_2$, —$P(O)(OR^{46})(O^-)$, —$OP(O)(OR^{46})(OR^{47})$, —$C(O)R^{46}$, —$C(S)R^{46}$, —$C(O)OR^{46}$, —$C(O)NR^{46}R^{47}$, —$C(O)O^-$, —$C(S)OR^{46}$, —$NR^{48}C(O)NR^{46}R^{47}$, $NR^{48}C(S)NR^{46}R^{47}$, —$NR^{49}C(NR^{48})NR^{46}R^{47}$ and —$C(NR^{48})NR^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{50}R^{51}$, —$C(O)R^{50}$ or —$S(O)_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl. In a particular embodiment, substituted groups are substituted with one or more substituents, particularly with 1 to 3 substituents, in particular with one substituent group. In a further particular embodiment the substituent group or groups are selected from halo, cyano, nitro, trifluoromethyl, trifluoromethoxy, azido, —NR'''$SO_2$R'', —$SO_2$NR''R''', —C(O)R'', —C(O)OR'', —OC(O)R'', —NR'''C(O)R'', —C(O)NR''R''', —NR''R''', —(CR'''R''')$_m$OR''', wherein, each R'' is independently selected from H, $C_1$-$C_8$ alkyl, —$(CH_2)_t$($C_6$-$C_{10}$ aryl), —$(CH_2)_t$($C_5$-$C_{10}$ heteroaryl), —$(CH_2)_t$($C_3$-$C_{10}$ cycloalkyl), and —$(CH_2)_t$($C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. Each R''' independently represents H or $C_1$-$C_6$alkyl.

Examples of representative substituted aryls include the following

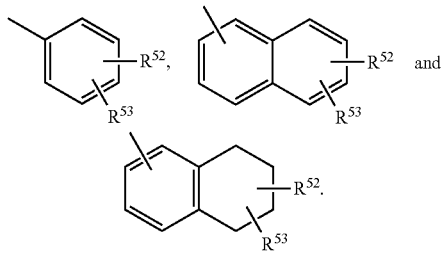

In these formulae one of $R^{52}$ and $R^{53}$ may be hydrogen and at least one of $R^{52}$ and $R^{53}$ is each independently selected from alkyl, alkenyl, alkynyl, cycloheteroalkyl, alkanoyl, alkoxy, aryloxy, heteroaryloxy, alkylamino, arylamino, heteroarylamino, $NR^{54}COR^{55}$, $NR^{54}SOR^{55}$, $NR^{54}SO_2R^{57}$, COOalkyl, COOaryl, $CONR^{54}R^{55}$, $CONR^{54}OR^{55}$, $NR^{54}R^{55}$, $SO_2NR^{54}R^{55}$, S-alkyl, S-alkyl, SOalkyl, $SO_2$alkyl, Saryl, SOaryl, $SO_2$aryl; or $R^{52}$ and $R^{53}$ may be joined to form a cyclic ring (saturated or unsaturated) from 5 to 8 atoms, optionally containing one or more heteroatoms selected from the group N, O or S. $R^{54}$, $R^{55}$, and $R^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

'Heteroaryl' means an aromatic ring structure, mono-cyclic or polycyclic, that includes one or more heteroatoms and 5 to 12 ring members, more usually 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to about four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, pyrazole, triazole and tetrazole groups. Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzfuran, benzthiophene, benzimidazole, benzoxazole, isobenzoxazole, benzisoxazole, benzthiazole, benzisothiazole, isobenzofuran, indole, isoindole, isoindolone, indolizine, indoline, isoindoline, purine (e.g., adenine, guanine), indazole, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, oxazole and pyrazine.

Examples of representative heteroaryls include the following:

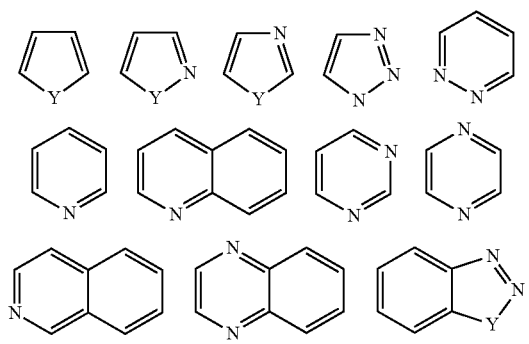

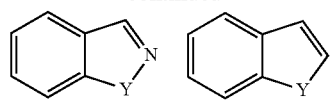

wherein each Y is selected from carbonyl, N, NR$^{58}$, O and S; and R$^{58}$ is independently hydrogen, alkyl, cycloalkyl, cycloheteroalkyl, aryl, heteroaryl and heteroalkyl. The term 'heteroaryl' includes 'bicycloheteroaryl' as defined below.

'Bicycloheteroaryl' refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoindolone, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline and tetrahydroquinoline. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

As used herein, the term 'heterocycloalkyl' refers to a 4-7 membered, stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

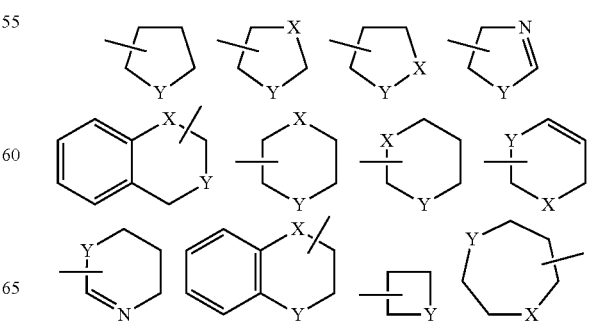

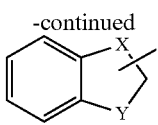

wherein each X is selected from $CR^{58}$, $CR^{58}_2$, $NR^{58}$, O and S; and each Y is selected from $NR^{58}$, O and S; and $R^{58}$ is independently hydrogen, alkyl, cycloalkyl, heterocycloalkyl, aryl, heteroaryl, heteroalkyl or the like. These heterocycloalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives. The term 'heterocycloalkyl' includes 'heterocycloalkenyl' as defined below.

Examples of representative heterocycloalkenyls include the following:

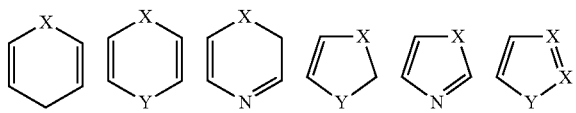

wherein each X is selected from $CR^{58}$, $CR^{58}_2$, $NR^{58}$, O and S; and each Y is selected from carbonyl, N, $NR^{58}$, O and S; and $R^{58}$ is independently hydrogen, alkyl, cycloalkyl, cycloheteroalkyl, aryl, heteroaryl, heteroalkyl or the like.

Examples of representative aryl having hetero atoms containing substitution include the following:

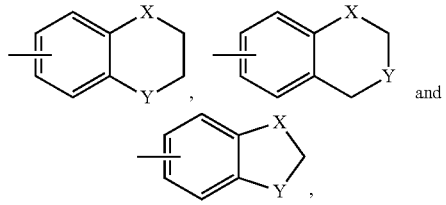

wherein each X is selected from $CR^{58}_2$, $NR^{58}$, O and S; and each Y is selected from carbonyl, $NR^{58}$, O and S; and $R^{58}$ is independently hydrogen, alkyl, cycloalkyl, cycloheteroalkyl, aryl, heteroaryl, heteroalkyl or the like.

'Hetero substituent' refers to a halo, O, S or N atom-containing functionality that may be present as an 'R' in a 'R'C group present as substituents directly on a variable ring atom of the compounds of this invention or may be present as a substituent in the "substituted" aryl and aliphatic groups present in the compounds. Examples of hetero substituents include:

- -halo,
- —NO$_2$, —NH$_2$, —NHR$^{59}$, —N(R$^{59}$)$_2$,
- —NRCOR, —NR$^{59}$SOR$^{59}$, —NR$^{59}$SO$_2$R$^{59}$, OH, CN,
- —CO$_2$H,
- —R$^{59}$—OH, —COOR$^{59}$,
- —CON(R$^{59}$)$_2$, —CONROR$^{59}$,
- —SO$_3$H, —SO$_2$N(R$^{59}$)$_2$,
- —S(O)R$^{59}$, —S(O)$_2$R$^{59}$ wherein each $R^{59}$ is independently an aryl or aliphatic, optionally with substitution. Among hetero substituents containing $R^{59}$ groups, preference is given to those materials having aryl and alkyl $R^{59}$ groups as defined herein. Preferred hetero substituents are those listed above.

'Hydrogen bond donor' group refers to a group containing O—H, N—H functionality. Examples of "hydrogen bond donor" groups include —OH, —NH$_2$, and —NH—R$^{59a}$, wherein $R^{59a}$ is alkyl, cycloalkyl, aryl or heteroaryl.

'Dihydroxyphosphoryl' refers to the radical —PO(OH)$_2$.

'Substituted dihydroxyphosphoryl' refers to a dihydroxyphosphoryl group substituted with one or more of those groups recited in the definition of 'substituted' herein, and particularly refers to a dihydroxyphosphoryl radical wherein one or both of the hydroxyl groups are substituted.

'Aminohydroxyphosphoryl' refers to the radical —PO(OH)NH$_2$.

'Substituted aminohydroxyphosphoryl' refers to an aminohydroxyphosphoryl group substituted with one or more of those groups recited in the definition of 'substituted' herein, and particularly refers to an aminohydroxyphosphoryl wherein the amino group is substituted with one or two substituents. In certain embodiments, the hydroxyl group can also be substituted.

'Thioalkoxy' refers to the group —SR$^{60}$ where $R^{60}$ is alkyl.

'Substituted thioalkoxy' refers to a thioalkoxy group substituted with one or more of those groups recited in the definition of 'substituted' herein, and particularly refers to a thioalkoxy group having 1 or more substituents, for instance from 1 to 5 substituents, and particularly from 1 to 3 substituents.

'Sulfanyl' refers to the radical HS—. 'Substituted sulfanyl' refers to a sulfanyl group substituted with one or more of those groups recited in the definition of 'substituted' herein. Exemplary 'substituted sulfanyl' groups are —S—C$_1$-C$_8$ alkyl, —S—(CH$_2$)$_t$(C$_6$-C$_{10}$ aryl), —S—(CH$_2$)$_t$(C$_5$-C$_{10}$ heteroaryl), —S—(CH$_2$)$_t$(C$_3$-C$_{10}$ cycloalkyl), and —S—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_{1-4}$ haloalkyl, C$_1$-C$_4$ hydroxyalkyl, or C$_1$-C$_4$ haloalkoxy or hydroxy.

'Sulfonyl' refers to the divalent radical —S(O$_2$)—. 'Substituted sulfonyl' refers to a radical such as —S(O$_2$)—R$^{61}$, wherein $R^{61}$ is any substituent described herein. Exemplary 'substituted sulfonyl' groups are —SO$_2$—C$_1$-C$_8$ alkyl, —SO$_2$—(CH$_2$)$_t$(C$_6$-C$_{10}$ aryl), —SO$_2$—(CH$_2$)$_t$(C$_5$-C$_{10}$ heteroaryl), —SO$_2$—(CH$_2$)$_t$(C$_3$-C$_{10}$ cycloalkyl), and —SO$_2$—(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by C$_1$-C$_4$ alkyl, halo, C$_1$-C$_4$ alkoxy, C$_{1-4}$ haloalkyl, C$_1$-C$_4$ hydroxyalkyl, or C$_1$-C$_4$ haloalkoxy or hydroxy.

"Aminosulfonyl" or "Sulfonamide" refers to the radical —S(O$_2$)NH$_2$, and "substituted aminosulfonyl" or "substituted sulfonamide" refers to a radical such as —S(O$_2$)NR$^{62}_2$ wherein each $R^{62}$ is independently any substituent described herein.

Exemplary "substituted aminosulfonyl" or "substituted sulfonamide" groups are —S(O$_2$)N(R$^{62}$)—C$_1$-C$_8$ alkyl, —S(O$_2$)N(R$^{62}$)—(CH$_2$)$_t$(C$_6$-C$_{10}$ aryl), —S(O$_2$)N(R$^{62}$)—(CH$_2$)$_t$(C$_5$-C$_{10}$ heteroaryl), —S(O$_2$)N(R$^{62}$)—(CH$_2$)$_t$(C$_3$-C$_{10}$ cycloalkyl), and —S(O$_2$)N(R$^{62}$)—(CH$_2$)$_t$(C$_5$-C$_{10}$ heterocycloalkyl), wherein t is an integer from 0 to 4; each $R^{62}$ independently represents H or C$_1$-C$_6$ alkyl; and any aryl, heteroaryl, cycloalkyl or heterocycloalkyl groups present, may themselves be substituted by C$_1$-C$_4$ alkyl, halo, C$_1$-C$_4$ alkoxy, $C_{1-4}$ haloalkyl, $C_1$-$C_4$ hydroxyalkyl, or $C_1$-$C_4$ haloalkoxy or hydroxy. Each $R^{B'}$ independently represents H or $C_1$-$C_6$ alkyl.

'Sulfone' refers to the group —$SO_2R^{63}$. In particular embodiments, $R^{63}$ is selected from H, lower alkyl, alkyl, aryl and heteroaryl.

"Sulfo" or "sulfonic acid" refers to a radical such as —$SO_3H$.

"Substituted sulfo" or "sulfonic acid ester" refers to a radical such as —$SO_3R^{61b}$ wherein $R^{61b}$ is substituted or unsubstituted alkyl or substituted or unsubstituted aryl. Exemplary "Substituted Sulfo" or "sulfonic acid ester" groups are $SO_3$—$C_1$-$C_8$ alkyl, $SO_3$—$(CH_2)_t(C_6$-$C_{10}$ aryl), $SO_3$—$(CH_2)_t(C_5$-$C_{10}$ heteroaryl), $SO_3$—$(CH_2)_t(C_3$-$C_{10}$ cycloalkyl), and $SO_3$—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. "Sulfinyl" refers to the divalent radical —$S(O)$—. "Substituted sulfinyl" refers to a radical such as —$SOR^{61a}$, wherein $R^{61a}$ is any substituent described herein. Exemplary "substituted sulfinyl" groups are $SO$—$C_1$-$C_8$ alkyl, $SO$—$(CH_2)_t(C_6$-$C_{10}$ aryl), $SO$—$(CH_2)_t(C_5$-$C_{10}$ heteroaryl). $SO$—$(CH_2)_t(C_5$-$C_{10}$ cycloalkyl), and $SO$—$(CH_2)_t(C_5$-$C_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Thioaryloxy' refers to the group —$SR^{64}$ where $R^{64}$ is aryl.

'Thioketo' refers to the group =S.

'Thiol' refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Preventing' or 'prevention' refers to a reduction in risk of acquiring a disease or disorder (i.e., causing at least one of the clinical symptoms of the disease not to develop in a subject that may be exposed to or predisposed to the disease but does not yet experience or display symptoms of the disease). This term encompasses the term 'prophylaxis', which means a measure taken for the prevention of a disease.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Therapeutically effective amount' means the amount of a compound that, when administered to a subject for treating a disease, is sufficient to effect such treatment for the disease. The "therapeutically effective amount" can vary depending on the compound, the disease and its severity, and the age, weight, etc., of the subject to be treated. In particular, with regard to treating an disease involving cartilage or joint degradation and/or inflammation, the terms "therapeutically effective amount" or "effective MAPKAPK5-inhibiting amount" is intended to mean that effective amount of an compound of the present invention that will bring about a biologically meaningful decrease in MAPKAPK5 expression or activity in the subject's disease affected tissues, such that cartilage or joint degradation and/or inflammation is meaningfully reduced. A compound having MAPKAPK5-inhibiting properties or a "MAPKAPK5-inhibiting compound" means a compound of the present invention that provided to a cell in effective amounts is able to cause a biologically meaningful decrease in MAPKAPK5 expression or activity in such cells.

'Treating' or 'treatment' of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, 'treating' or 'treatment' refers to delaying the onset of the disease or disorder.

'Compounds of the present invention', and equivalent expressions, are meant to embrace compounds of the Formula (e) as hereinbefore described, which expression includes the prodrugs, the pharmaceutically acceptable salts, and the solvates, e.g., hydrates, where the context so permits. Similarly, reference to intermediates, whether or not they themselves are claimed, is meant to embrace their salts, and solvates, where the context so permits.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H/D$, any carbon may be $^{13}C$, or any nitrogen may be $^{15}N$, and that the presence and placement of such atoms may be determined within skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

THE COMPOUNDS

The present invention is based on the discovery of that MAPKAPK5 functions in the pathway that results in the expression of MMP1, and that inhibitors of MAPKAPK5 activity, such as the compounds of the present invention, are useful for the treatment of diseases involving the abnormally high expression of MMP activity.

The compounds of the present invention may be described generally as fused pyrazines, in particular imidazo[1,2-a] pyrazines and [1.2.4]triazolo[1,5-a]pyrazine substituted in the 5-position by an aryl and heteroaryl group, and an in the 8-position by a heteroarylamino group.

More particularly, the present invention relates to compounds according to formula (I):

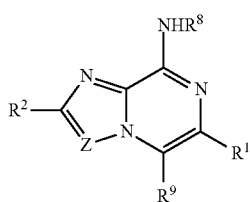

(I)

wherein

Z is CH or N; $R^1$ is H, or substituted or unsubstituted $C_1$-$C_6$ alkyl; $R^2$ is H, $C_1$-$C_6$ alkyl, $C_3$-$C_7$ cycloalkyl or $C_3$-$C_7$ cycloalkyl-$C_1$-$C_6$ alkyl, optionally substituted with one or more of F and Cl; $R^8$ is substituted or unsubstituted heteroaryl; $R^9$ is selected from substituted or unsubstituted aryl and substituted or unsubstituted heteroaryl; or a pharmaceutically acceptable salt, solvate or prodrug thereof; and stereoisomers, isotopic variants and tautomers thereof.

In one embodiment, with respect to compounds of formula I, $R^1$ is H.

In one embodiment, with respect to compounds of formula I, $R^2$ is H.

In one embodiment, with respect to compounds of formula I, $R^8$ is substituted or unsubstituted 5-membered heteroaryl.

In another embodiment, with respect to compounds of formula I, $R^8$ is selected from substituted or unsubstituted pyrrolyl, furanyl, thienyl, pyrazolyl, oxazolyl, imidazolyl, thiazolyl, 1,3,4-thiadiazolyl, and 1,2,4-thiadiazolyl.

In another embodiment, with respect to compounds of formula I, $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is selected from $C_1$-$C_6$ alkyl, substituted $C_1$-$C_6$ alkyl, carbamoyl, $C_1$-$C_6$ hydroxyalkyl, $C_1$-$C_6$ haloalkyl, $C_1$-$C_6$ alkoxy, cyano, amino, sulfo, aryl, $C_3$-$C_7$ cycloalkyl, aralkyl, heterocycloalkyl and heteroaryl.

In one embodiment, with respect to compounds of formula I, $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is selected from is Me, i-Pr, cyclopropyl, $CH_2OH$, $CONH_2$, $CONMe_2$, $NMe_2$, $NEt_2$, $SO_2Me$, or $SO_2Et$.

In one embodiment, with respect to compounds of formula I, $R^8$ is

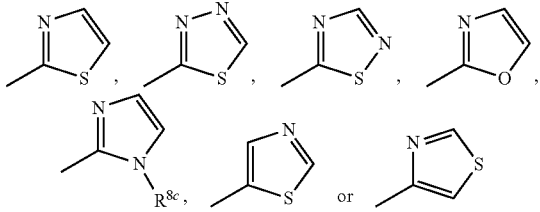

wherein $R^8$ is unsubstituted or substituted with $C_1$-$C_6$ alkyl, substituted $C_1$-$C_6$ alkyl, carbamoyl, $C_1$-$C_6$ hydroxyalkyl, $C_1$-$C_6$ haloalkyl, $C_1$-$C_6$ alkoxy, cyano, amino, sulfo, aryl, 3-7-membered heterocycloalkyl, aralkyl, heterocycloalkyl and heteroaryl; and wherein $R^{8c}$ is independently selected from hydrogen, and unsubstituted or substituted $C_1$-$C_6$ alkyl.

In one embodiment, with respect to compounds of formula I, $R^8$ is

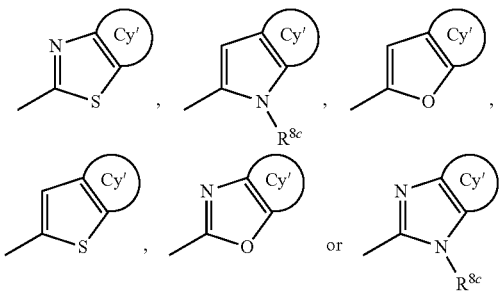

wherein Cy' is $C_3$-$C_7$ cycloalkyl, heterocycloalkyl, aryl or heteroaryl ring; and $R^{8c}$ is independently selected from hydrogen, and unsubstituted or substituted $C_1$-$C_6$ alkyl.

In one embodiment, with respect to compounds of formula I, $R^8$ is

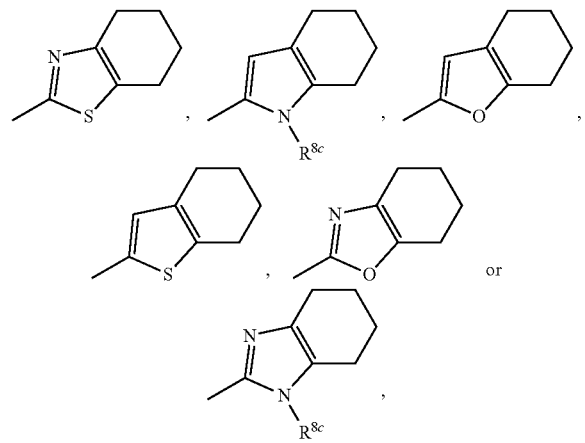

wherein $R^{8c}$ is independently selected from hydrogen, and unsubstituted or substituted $C_1$-$C_6$ alkyl.

In one embodiment, with respect to compounds of formula I, $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is -L-$R^{8d}$;

wherein

L is selected from bond, alkylene, heteroalkylene, —O—, —N($R^{8e}$)—, —CO—, —$CO_2$—, —SO—, —$SO_2$—, —CON($R^{8e}$)—, —$SO_2$N($R^{8e}$)—, —N($R^{8e}$)CO—, —N(e)$SO_2$—, —N($R^{8e}$)CO N($R^{8e}$)—, —N($R^{8e}$)$SO_2$N($R^{8e}$)—; and $R^{8d}$ is selected from substituted or unsubstituted $C_1$-$C_6$ alkyl, substituted or unsubstituted $C_3$-$C_7$ cycloalkyl, substituted or unsubstituted aryl, substituted or unsubstituted 3-7-membered heterocycloalkyl, substituted or unsubstituted heteroaryl, substituted or unsubstituted amino, substituted or unsubstituted aralkyl, substituted or unsubstituted heteroarylalkyl and substituted or unsubstituted aminoalkyl; and $R^{8e}$ is selected from H, substituted or unsubstituted $C_1$-$C_6$ alkyl and substituted or unsubstituted $C_3$-$C_7$ cycloalkyl.

In one embodiment, with respect to compounds of formula I, $R^{8c}$ is -L-$R^{8d}$ In one embodiment, with respect to compounds of formula I, $R^8$ is

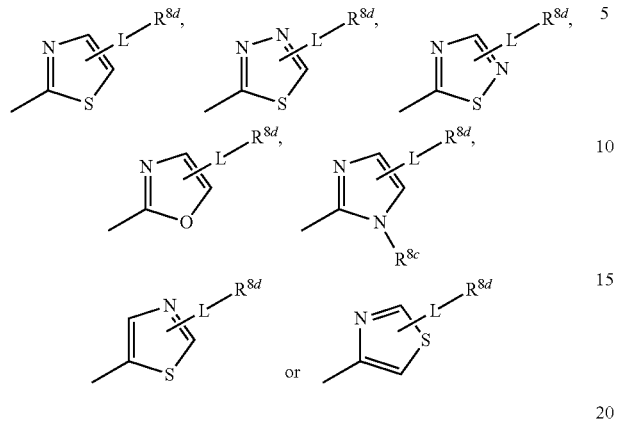

wherein L, and $R^{8d}$ are as described in the preceding paragraph; and $R^{8c}$ is independently selected from hydrogen, and substituted or unsubstituted $C_1$-$C_6$ alkyl.

In one embodiment, with respect to compounds of formula I, $R^8$ is as described above; L is —CON($R^{8e}$)— or SO$_2$N($R^{8e}$)—;

$R^{8d}$ is selected from substituted or unsubstituted $C_1$-$C_6$ alkyl, substituted or unsubstituted $C_3$-$C_7$ cycloalkyl, substituted or unsubstituted aryl, substituted or unsubstituted 3-7-membered heterocycloalkyl, substituted or unsubstituted heteroaryl, substituted or unsubstituted aralkyl, substituted or unsubstituted $C_1$-$C_6$ heteroarylalkyl and substituted or unsubstituted $C_1$-$C_6$ aminoalkyl; and $R^{8e}$ is selected from H, substituted or unsubstituted $C_1$-$C_6$ alkyl.

In one embodiment, with respect to compounds of formula I, $R^8$ is L is —CONH— or SO$_2$NH—; and $R^{8d}$ is selected from H, $C_1$-$C_6$ alkylaminoethyl, di$C_1$-$C_6$ alkylaminoethyl, $C_3$-$C_7$ cycloalkyl, 3-7-membered heterocycloalkyl, arylalkyl, and heteroarylalkyl.

In one embodiment, with respect to compounds of formula I, $R^8$ is L is —CONH— or SO$_2$NH—; and $R^{8d}$ is selected from H, methylaminoethyl, ethylaminoethyl, dimethylaminoethyl, diethylaminoethyl, substituted or unsubstituted pyrrolidinyl, benzyl and pyridylmethyl.

In one embodiment, with respect to compounds of formula I, $R^8$ is L is bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; and $R^{8d}$ is

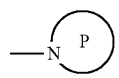

wherein the ring P is substituted or unsubstituted 3-7-membered heterocycloalkyl.

In one embodiment, with respect to compounds of formula I, the compound is according to formula IIa, IIb, IIc, IId, IIe or IIf:

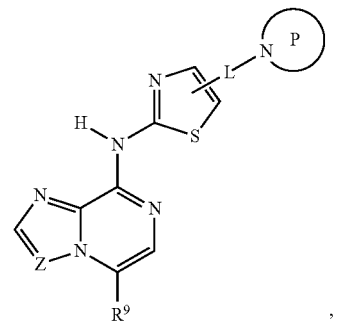
IIa

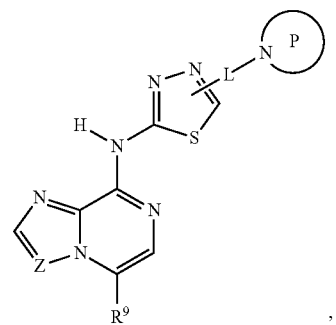
IIb

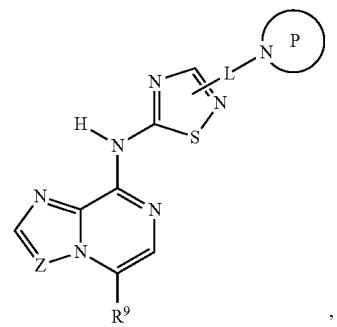
IIc

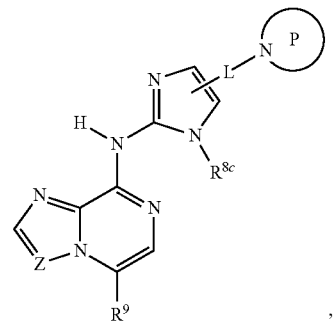
IId

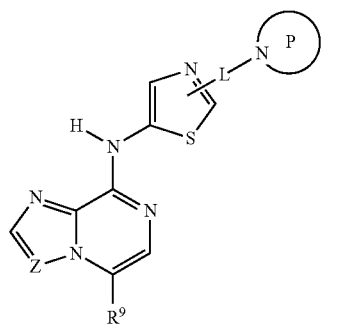
IIe or

IIf

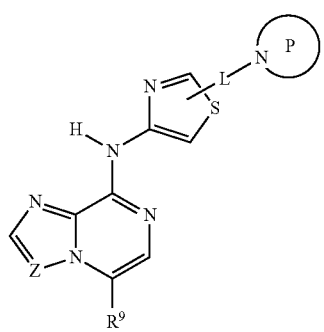

and wherein L, $R^{8c}$, and the ring P are as described above; and $R^9$ is independently selected from substituted or unsubstituted aryl and heteroaryl; or a pharmaceutically acceptable salt, solvate or prodrug thereof; and stereoisomers, isotopic variants and tautomers thereof.

In one embodiment, with respect to compounds of formulae IIa-IIf, L is a bond.

In one embodiment, with respect to compounds of formulae L is —CO—.

In one embodiment, with respect to compounds of formulae IIa-IIf, L is —SO$_2$—.

In one embodiment, with respect to compounds of formulae IIa-IIf, L is —CON(H)—CH$_2$—CH$_2$—, or —SO$_2$NH—CH$_2$—CH$_2$—.

In one embodiment, with respect to compounds of formulae IIa-IIf, L is —OCH$_2$—CH$_2$— or —NHCH$_2$—CH$_2$—.

In one embodiment, with respect to compounds of formulae IIa-IIf the ring P is substituted or unsubstituted piperidine, morpholine or piperazine.

In one embodiment, with respect to compounds of formulae IIa-IIf, the ring P is substituted or unsubstituted:

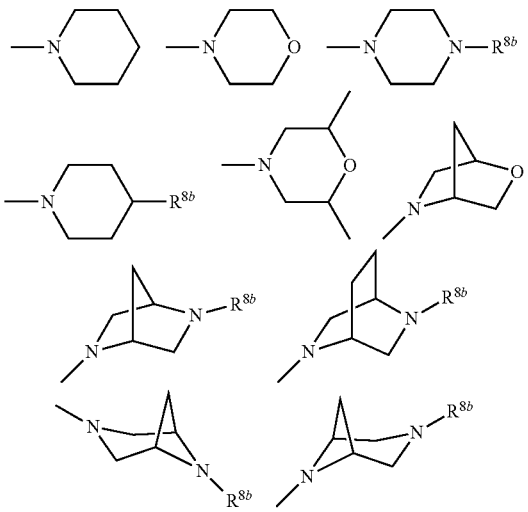

and $R^{8b}$ is hydrogen, substituted or unsubstituted $C_1$-$C_6$ alkyl or substituted or unsubstituted $C_3$-$C_7$ cycloalkyl.

In one embodiment, with respect to compounds of formulae IIa-IIf, the ring P is as described above and $R^{8b}$ is H, Me, Et, Pr, i-Pr, t-Bu, i-Bu, CH$_2$CONH$_2$, or cyclopropylmethyl.

In one embodiment, with respect to compounds of formulae IIa-IIf, the ring P is as described above and $R^{8b}$ is substituted or unsubstituted $C_3$-$C_7$ cycloalkyl. In yet another embodiment, $R^{8b}$ is cyclohexyl, cyclopentyl. In further embodiments, $R^{8b}$ is cyclopropyl.

In further embodiments, with respect to compounds of formula I, the compound is according to formula IIIa, IIIb, IIIc, IIId, IIIe, IIIf, IIIg, IIIh, IIIi, IIIj, IIIk, IIIl, or IIIm:

IIIa

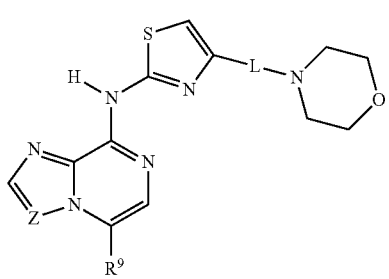

IIIb

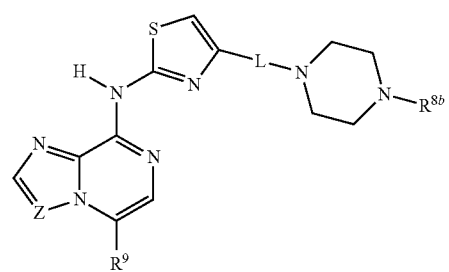

IIIc

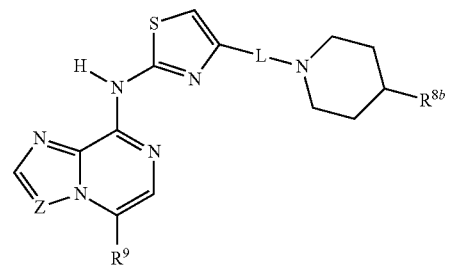

IIId

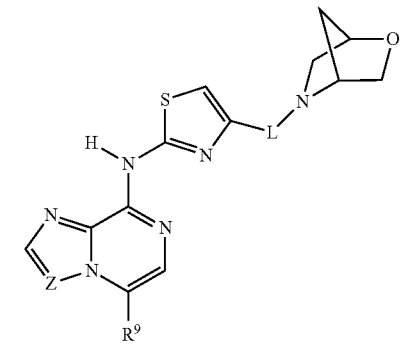

IIIe

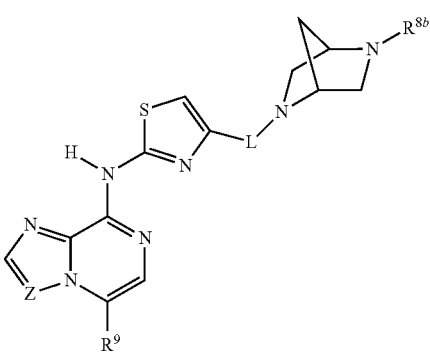

IIIf
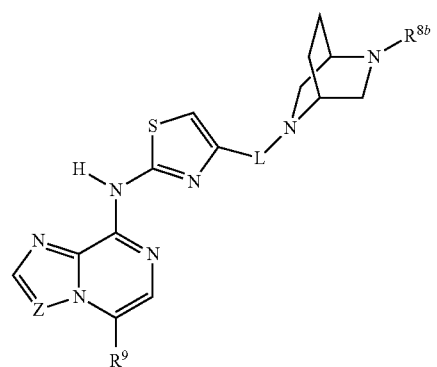

IIIg
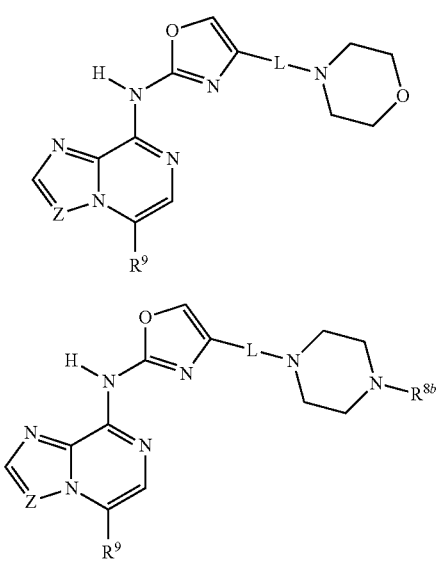

IIIh

IIIi
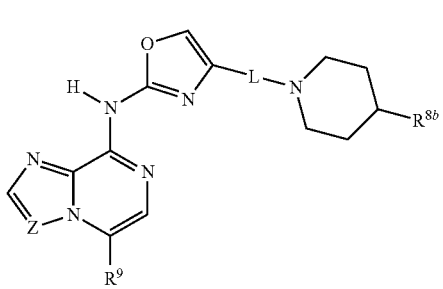

IIIk
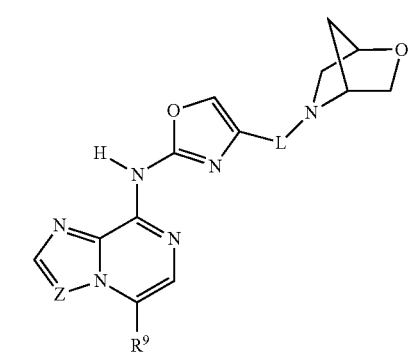

IIIl
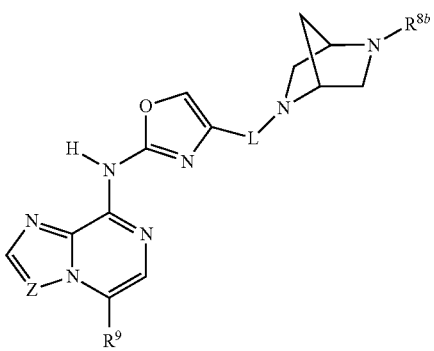

IIIm
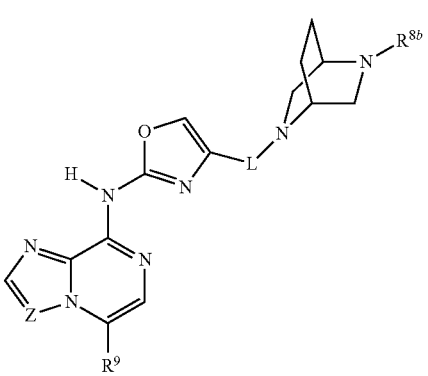

and wherein L is a bond, CO, or substituted or unsubstituted $C_1$-$C_4$ alkylene; $R^{8b}$ is hydrogen, substituted or unsubstituted $C_1$-$C_6$ alkyl or substituted or unsubstituted $C_3$-$C_7$ cycloalkyl; and $R^9$ is independently selected from substituted or unsubstituted aryl and heteroaryl; or a pharmaceutically acceptable salt, solvate or prodrug thereof; and stereoisomers, isotopic variants and tautomers thereof.

In further embodiments, with respect to compounds of formula I, the compound is according to formulae IIIn, IIIo, IIIp, IIIq, IIIs, IIIt, IIIu, IIIv, IIIw, IIIx, or IIIy:

IIIn
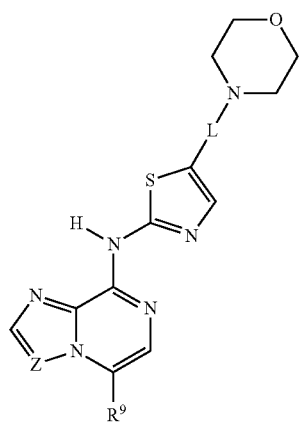

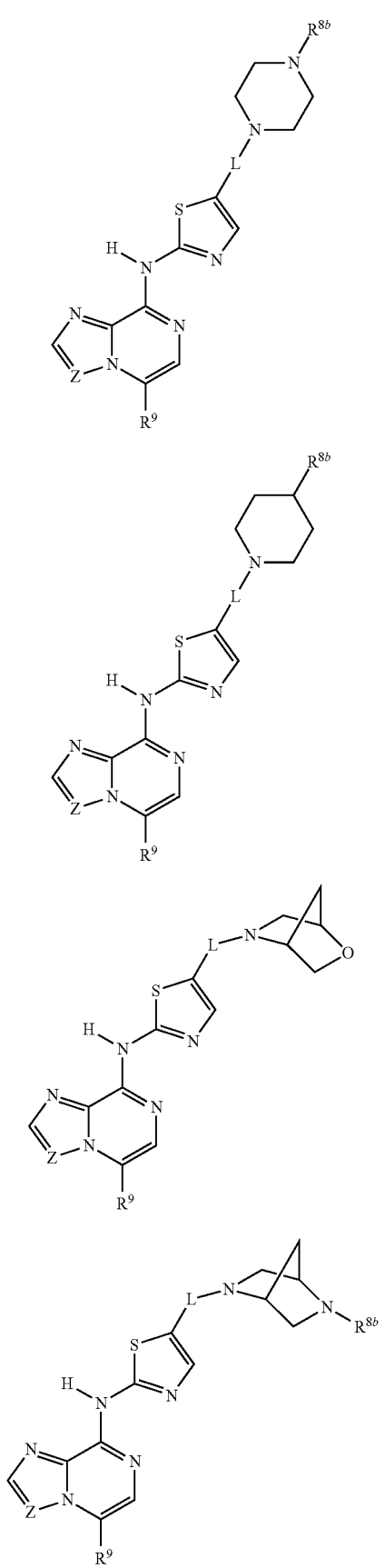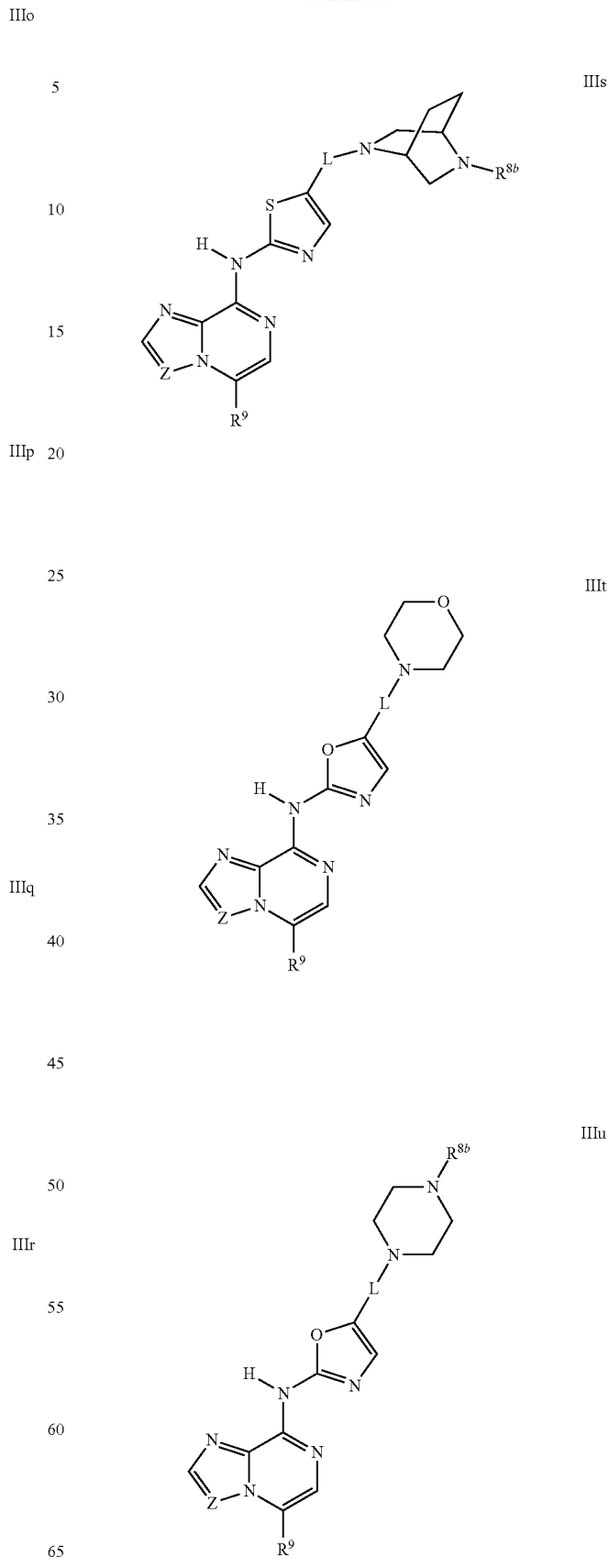

-continued

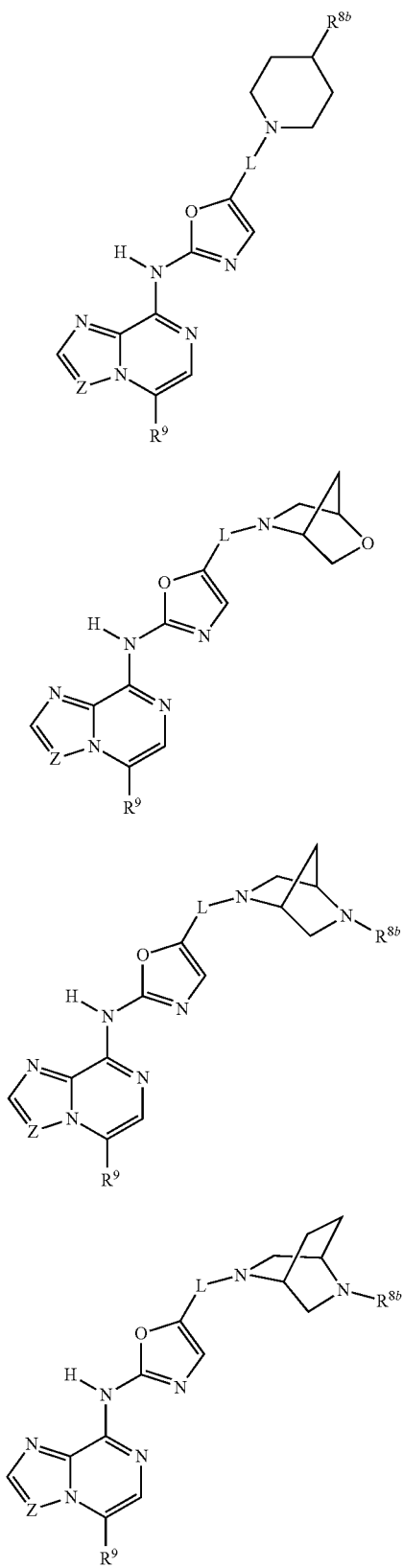

IIIv

IIIw

IIIx

IIIy and wherein L is a bond, CO, or substituted or unsubstituted C₁-C₄ alkylene; R$^{8b}$ is hydrogen, substituted or unsubstituted C₁-C₆ alkyl or substituted or unsubstituted C₃-C₇ cycloalkyl; and R$^9$ is independently selected from substituted or unsubstituted aryl and heteroaryl; or a pharmaceutically acceptable salt, solvate or prodrug thereof; and stereoisomers, isotopic variants and tautomers thereof.

In further embodiments, with respect to compounds of formula I, the compound is according to formula IIIz, IIIaa, IIIab, IIIac, IIIad, or IIIae:

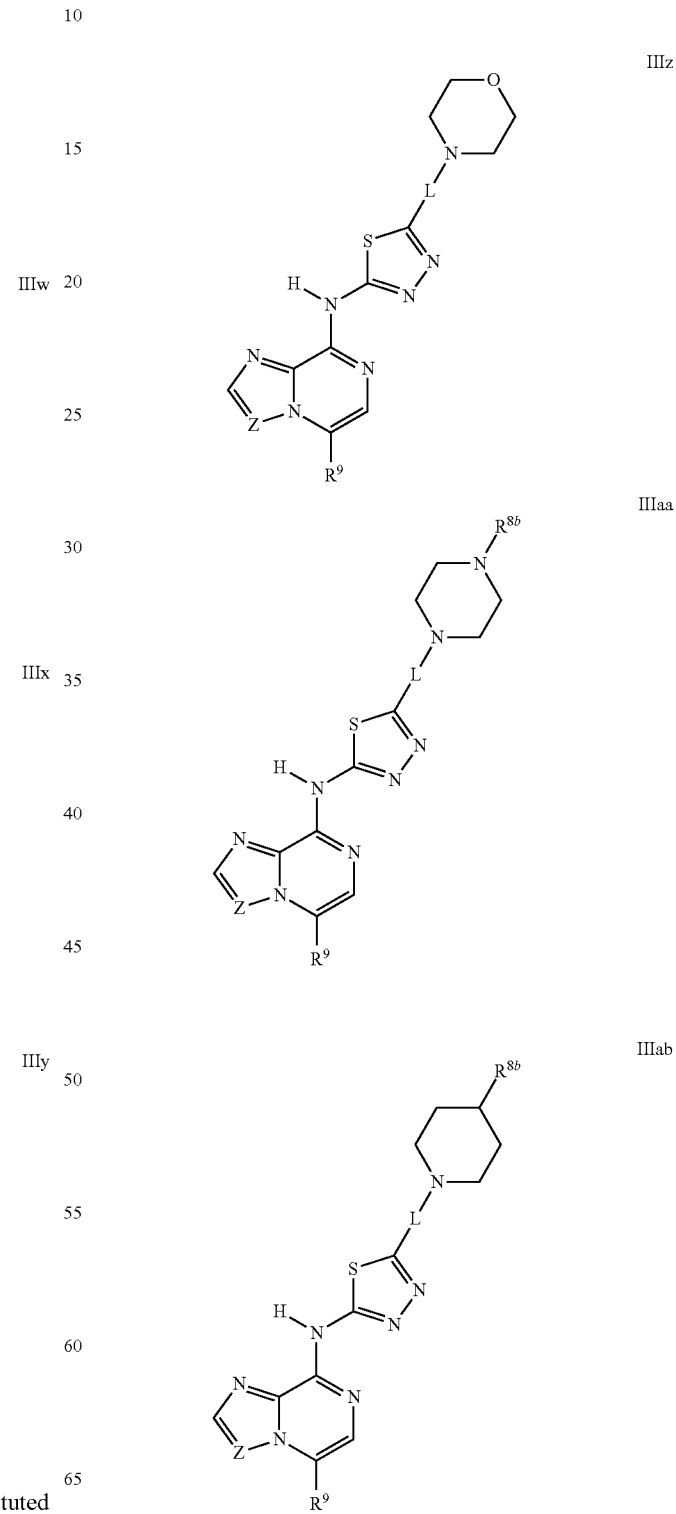

IIIz

IIIaa

IIIab

-continued

IIIac
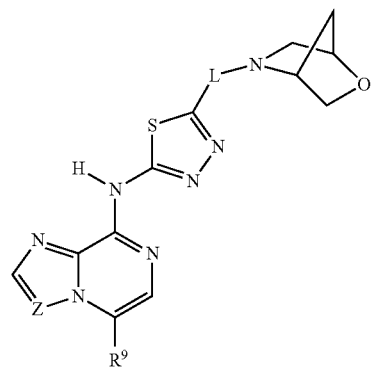

IIIad
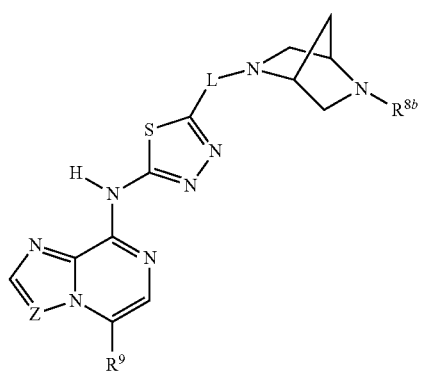

IIIae
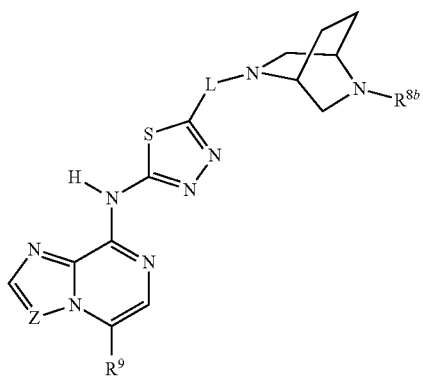

and wherein L is a bond, CO, or substituted or unsubstituted $C_1$-$C_4$ alkylene; $R^{8b}$ is hydrogen, substituted or unsubstituted $C_1$-$C_6$ alkyl or substituted or unsubstituted $C_3$-$C_7$ cycloalkyl; and $R^9$ is independently selected from substituted or unsubstituted aryl and heteroaryl; or a pharmaceutically acceptable salt, solvate or prodrug thereof; and stereoisomers, isotopic variants and tautomers thereof.

In one embodiment, with respect to compounds of formulae IIIa-ae, L is a bond.

In one embodiment, with respect to compounds of formulae IIIa-ae, L is —CH$_2$—.

In one embodiment, with respect to compounds of formulae IIIa-ae, L is —CO—.

In one embodiment, with respect to compounds of formulae IIIa-ae, L is —SO$_2$—.

In one embodiment, with respect to compounds of formulae IIIa-ae, L is —CON(H)—CH$_2$—CH$_2$—, or —SO$_2$NH—CH$_2$—CH$_2$—.

In one embodiment, with respect to compounds of formulae IIIa-ae, L is —OCH$_2$—CH$_2$— or —NHCH$_2$—CH$_2$—.

In one embodiment, with respect to compounds of formulae IIIa-ae, $R^{8b}$ is H. In another embodiment, $R^{8b}$ is substituted or unsubstituted alkyl. In yet another embodiment, $R^{8b}$ is Me, Et, Pr, i-Pr, t-Bu, i-Bu, CH$_2$CONH$_2$, or cyclopropylmethyl.

In one embodiment, $R^{8b}$ is substituted or unsubstituted cycloalkyl. In yet another embodiment, $R^{8b}$ is cyclohexyl, cyclopentyl. In further embodiments, $R^{8b}$ is cyclopropyl.

In one embodiment, with respect to compounds of formula I, $R^8$ is fused heteroaryl according to compounds of formulae IIIaf, IIIag, or IIIah IIIaf
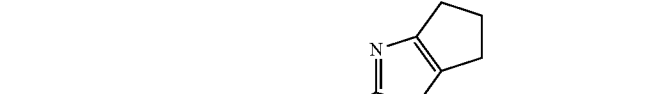

IIIag
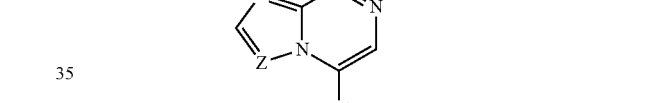

IIIah
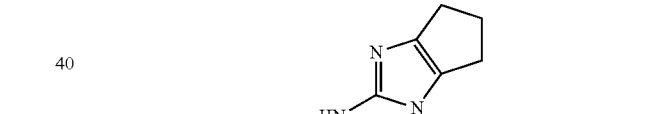

and wherein $R^{8c}$ is hydrogen, or substituted or unsubstituted $C_1$-$C_6$alkyl.

In one embodiment, with respect to compounds of formulae I-IIIr, $R^9$ is selected from substituted or unsubstituted phenyl, pyridyl, indolyl, isoindolyl, pyrrolyl, furanyl, thienyl, pyrazolyl, oxazolyl, and thiazolyl.

In one embodiment, with respect to compounds of formulae I-IIIah, $R^9$ is

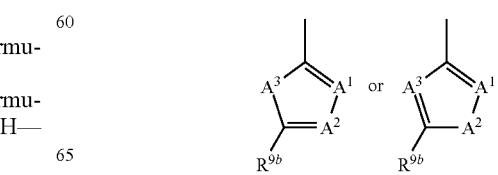

and each of $A^1$, $A^2$ and $A^3$ is independently selected from S, O, N, $NR^{9a}$, and $CR^{9a}$; each of $R^{9a}$ is independently H or substituted or unsubstituted $C_1$-$C_6$ alkyl; and $R^{9b}$ is $CONH_2$, CONHMe, or CN.

In further embodiment, with respect to compounds of formulae I-IIIr, $R^9$ is

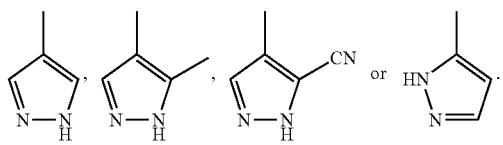

In further embodiment, with respect to compounds of formulae I-IIIr, $R^9$ is

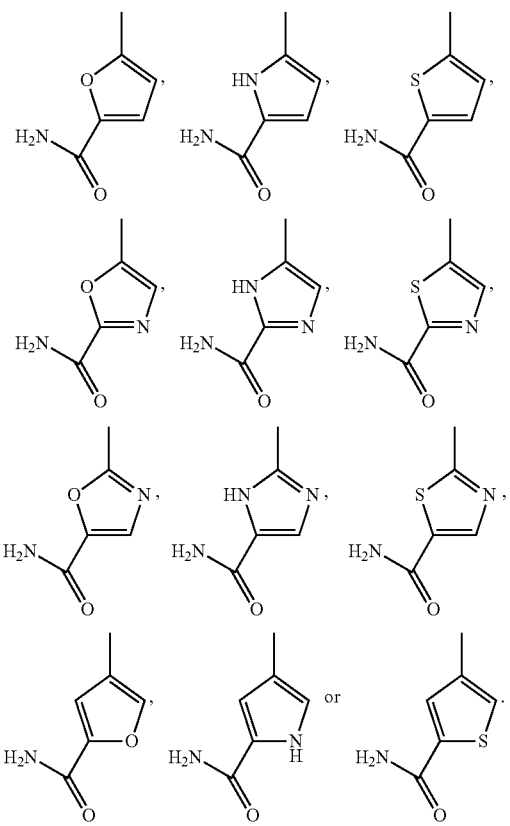

In further embodiment, with respect to compounds of formulae I-IIIr, $R^9$ is

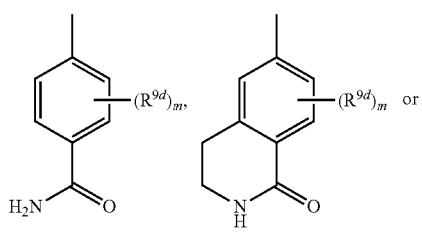

-continued

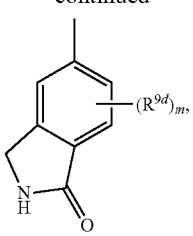

wherein the subscript m is selected from 0-4 and each $R^{9d}$ is independently substituted or unsubstituted $C_1$-$C_6$ alkyl or halo.

In a further embodiment, with respect to compounds of formulae I-IIIr, $R^9$ is

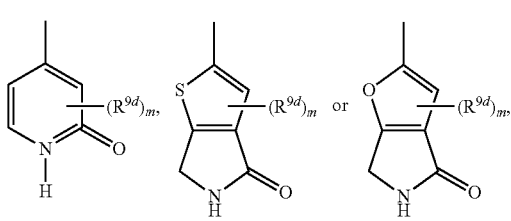

wherein the subscript m is selected from 0-3 and each $R^{9d}$ is independently substituted or unsubstituted alkyl or halo.

In a further embodiment, with respect to compounds of formulae I-IIIr, $R^9$ is as described above; m is 1 or 2 and each $R^{9d}$ is independently Me, Cl or F.

In one embodiment, with respect to compounds of formula I, the compound is according to formula IVa, IVb, IVc, IVd, IVe, IVf, IVg, IVh, IVi, IVj, IVk or IVl:

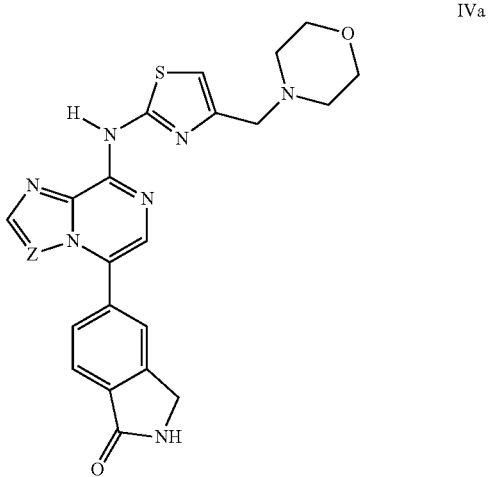

IVa

37
-continued
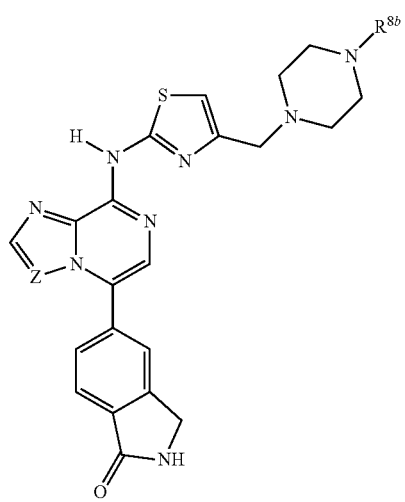
IVb
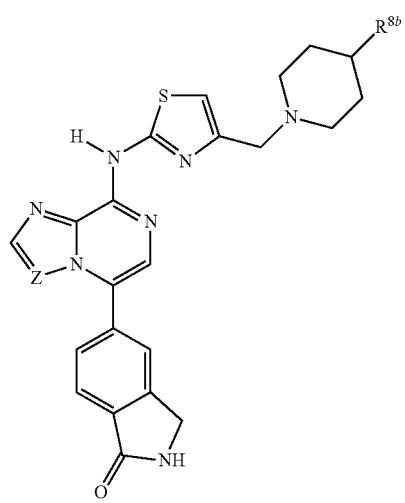
IVc
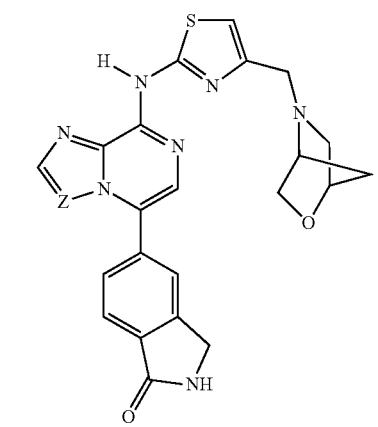
IVd
38
-continued
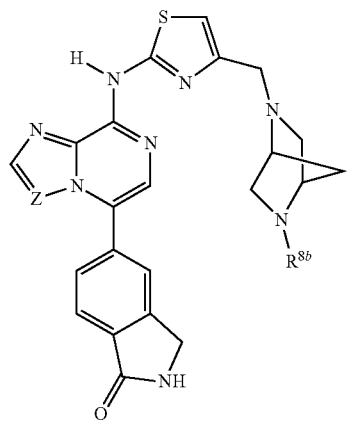
IVe
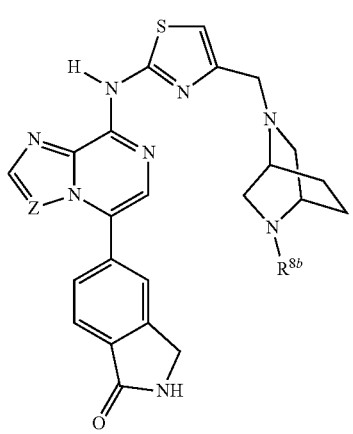
IVf
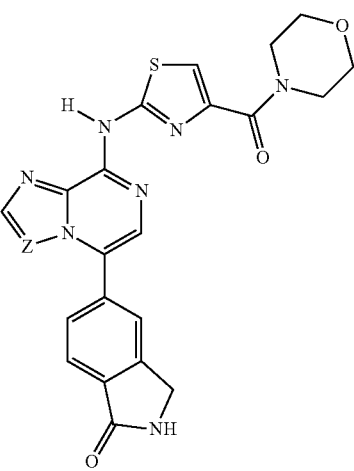
IVg

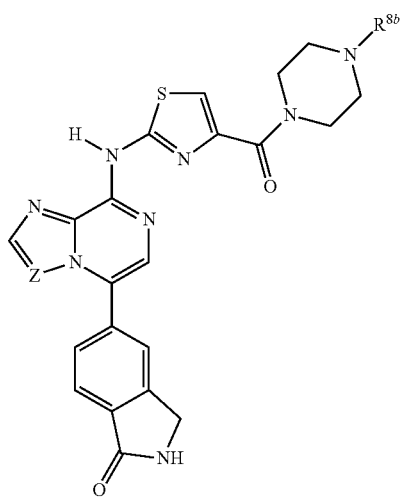

IVh

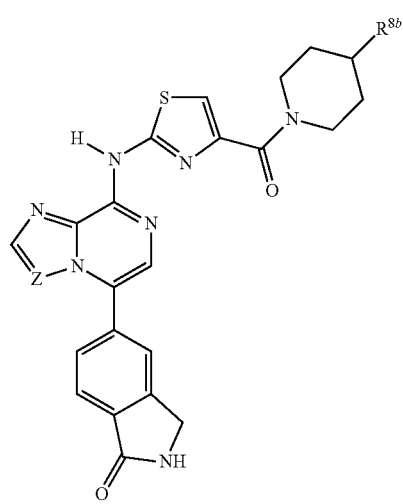

IVi

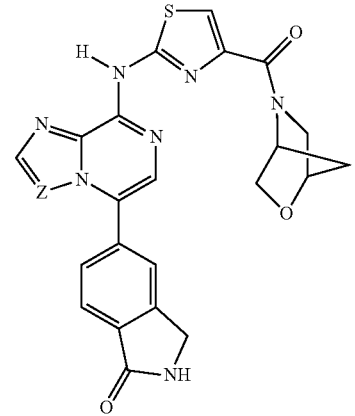

IVj

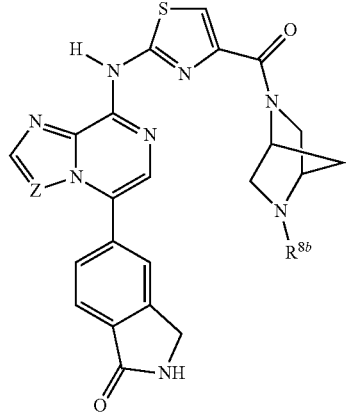

IVk

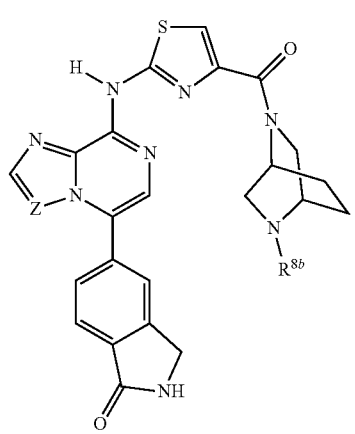

IVl and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula IVm, IVn, IVo, IVp, IVq, IVr, IVs, IVt, IVu, IVv, IVw or IVx:

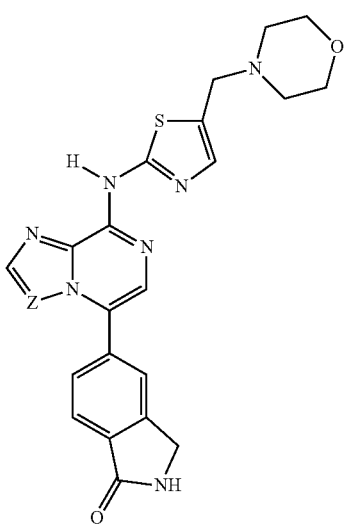

IVm

IVn
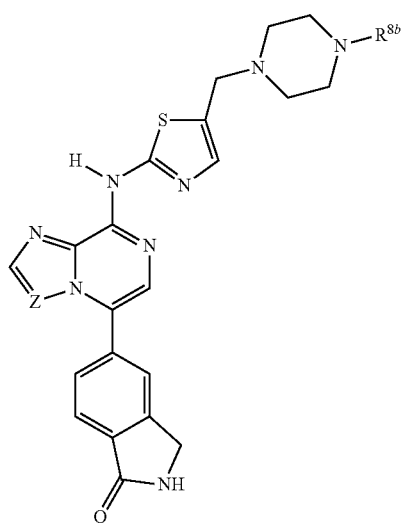
IVo
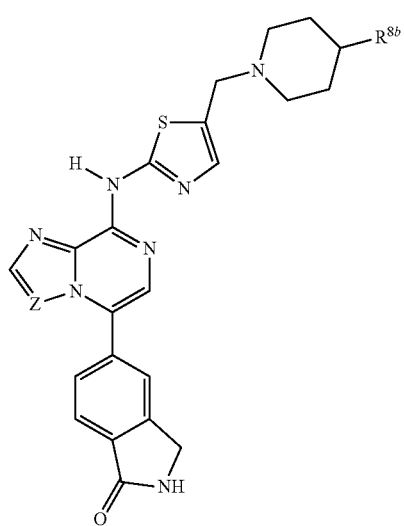
IVp
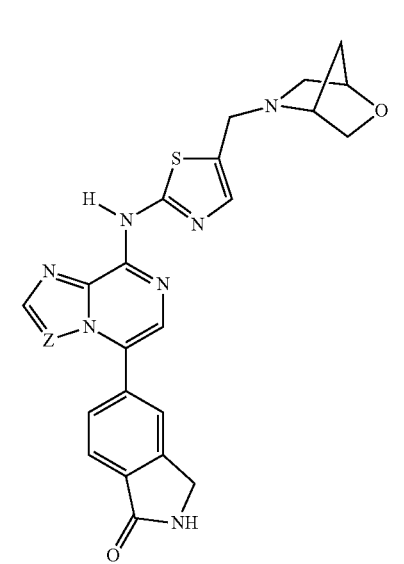
IVq
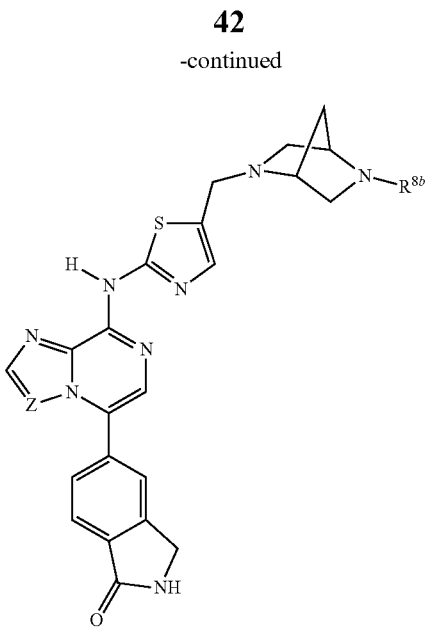
IVr
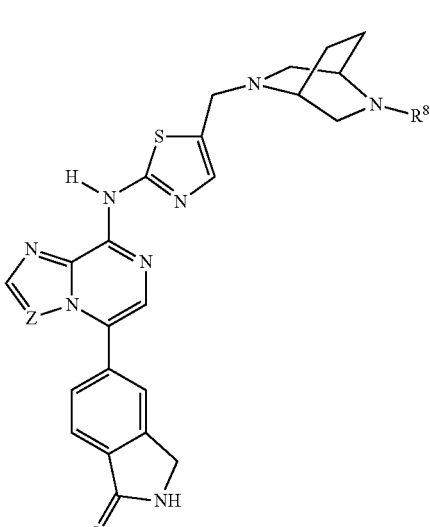
IVs
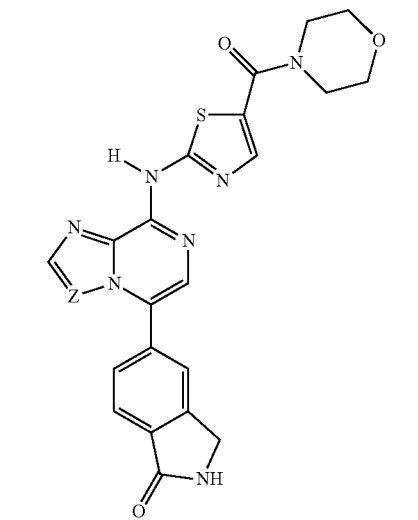

-continued

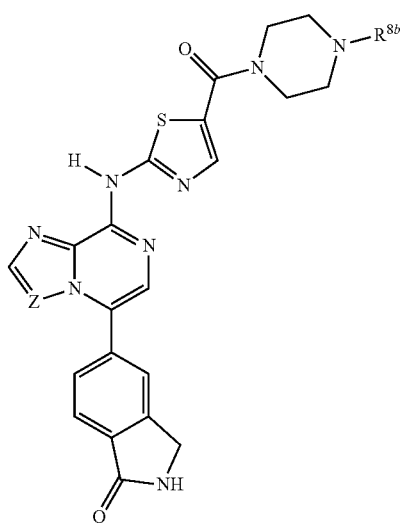
IVt

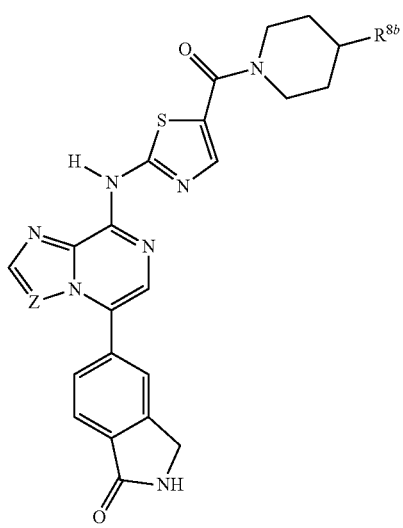
IVu

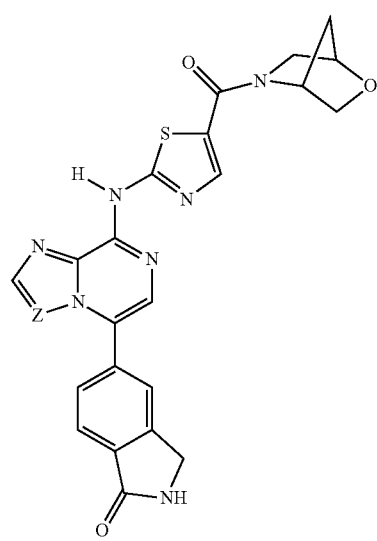
IVv

-continued

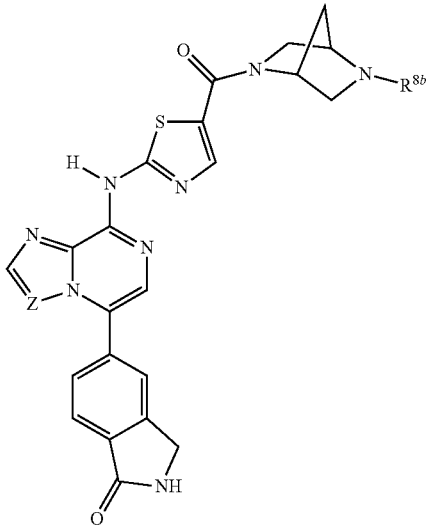
IVw

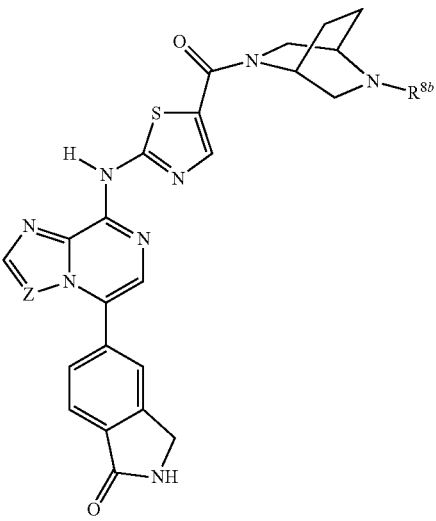
IVx and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula Va, Vb, Vc, Vd, Ve, Vf, Vg, Vh, Vi, Vj, Vk or Vl:

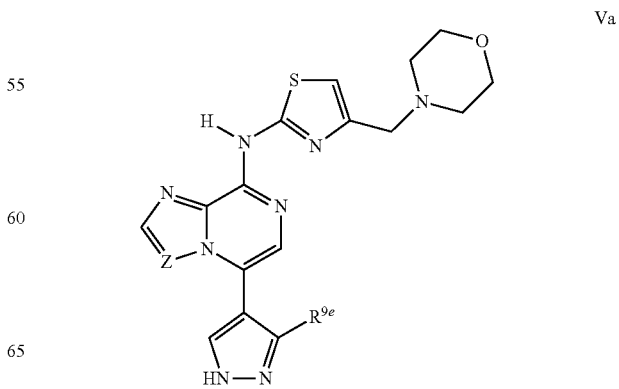
Va

Vb
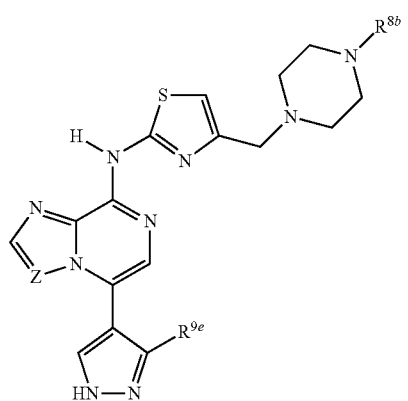
Vc
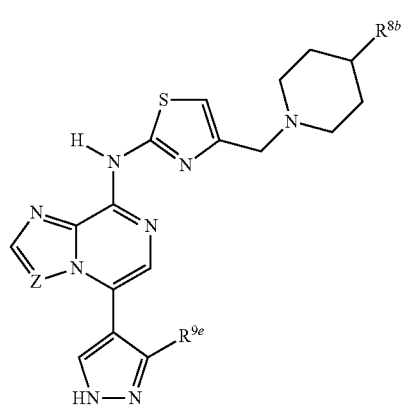
Vd
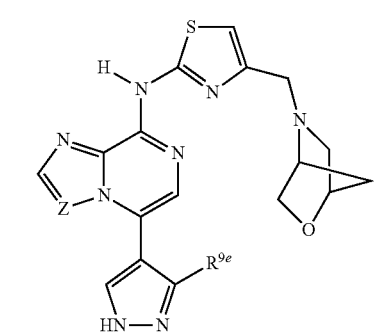
Ve
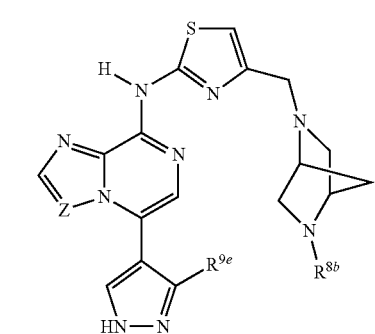
Vf
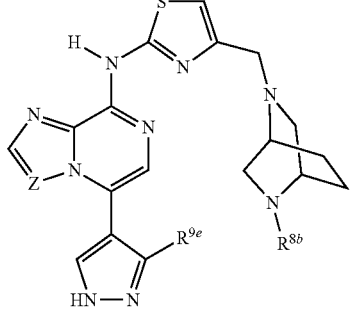
Vg
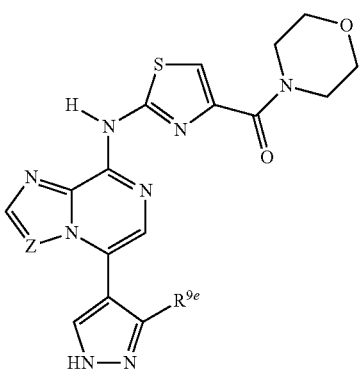
Vh
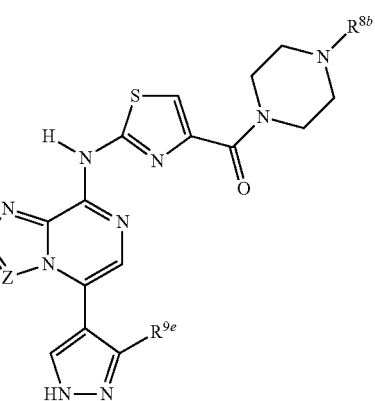
Vi
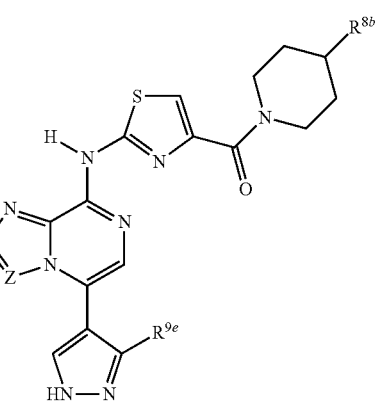

Vj
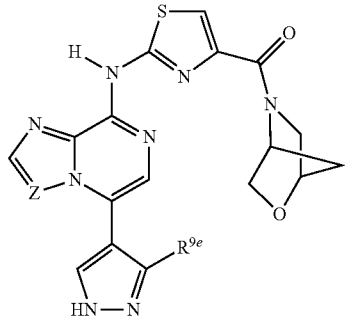

Vk
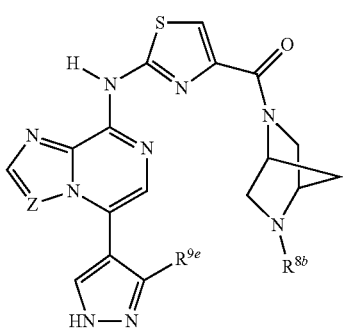

Vl
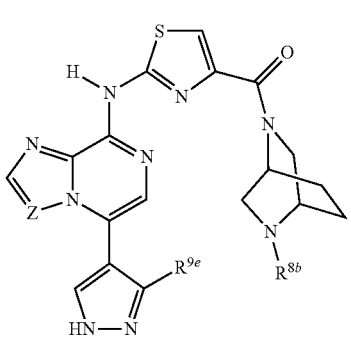

and wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formula I, the compound is according to formula Vm, Vn, Vo, Vp, Vq, Vr, Vs, Vt, Vu, Vv, Vw or Vx:

Vm
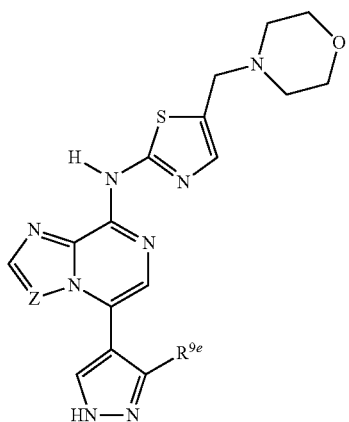

Vn
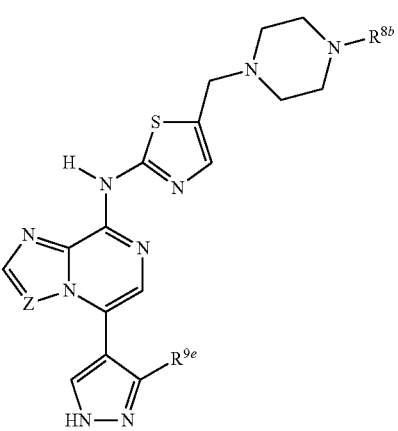

Vo
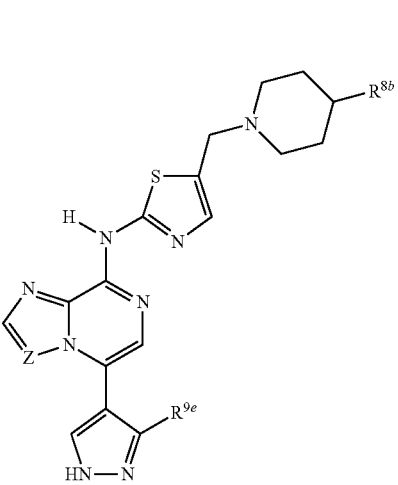

Vp
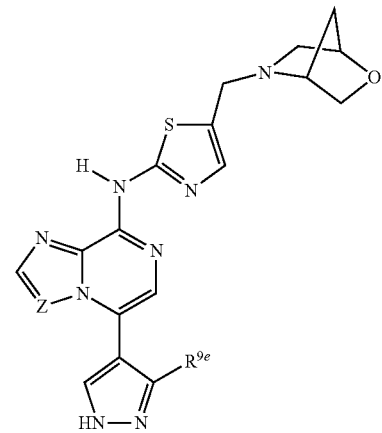

Vq
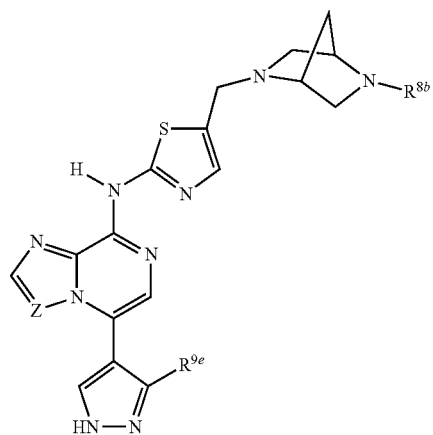
Vt
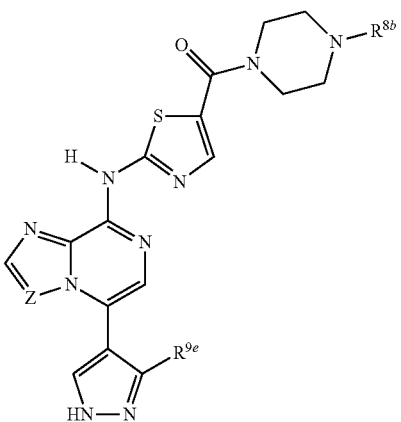
Vr
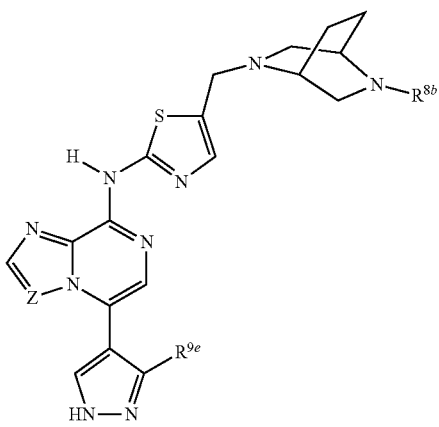
Vu
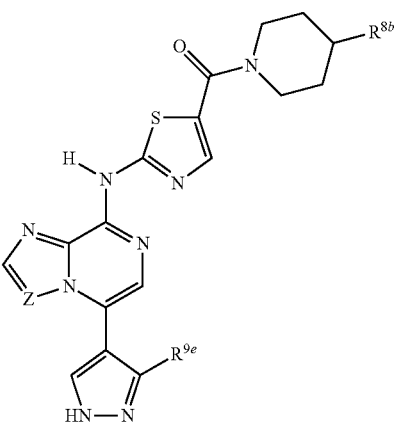
Vs
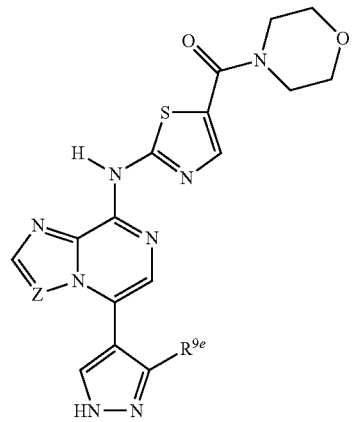
Vv
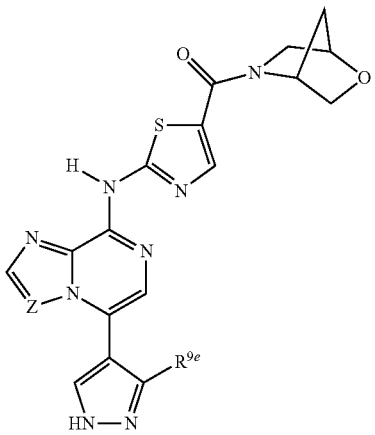

Vw

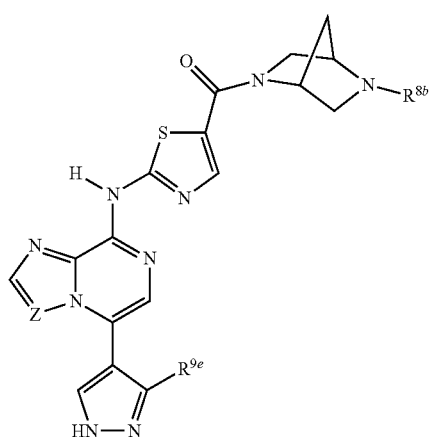

Vx

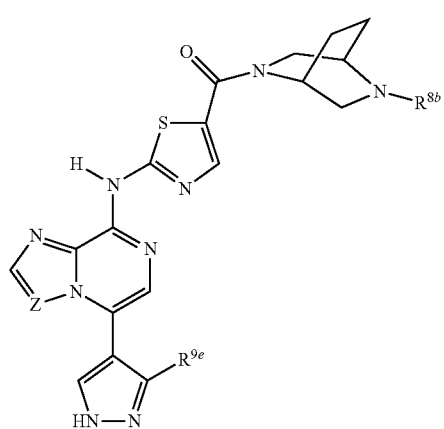

wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formula I, the compound is according to formula VIa, VIb, VIc, VId, VIe, VIf, VIg, VIh, VIi, VIj, VIk or VIl:

VIa

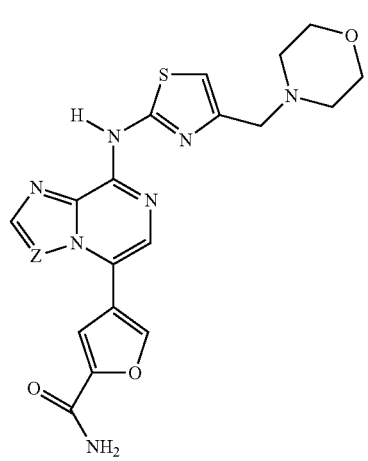

VIb

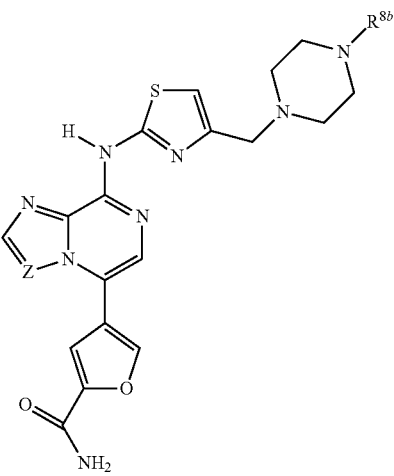

VIc

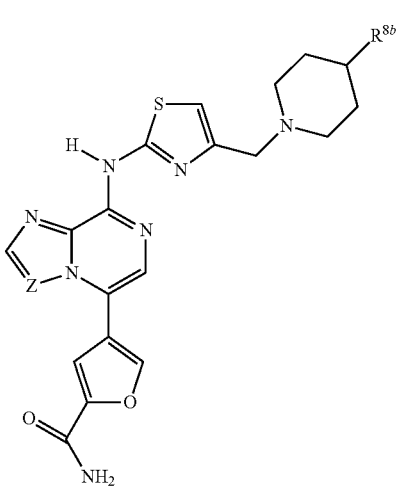

VId

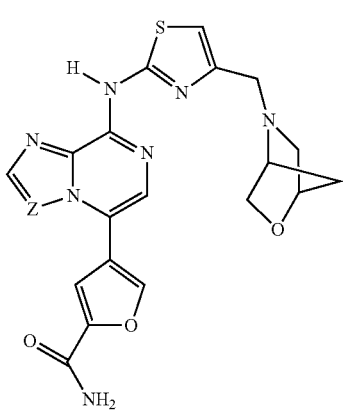

VIe
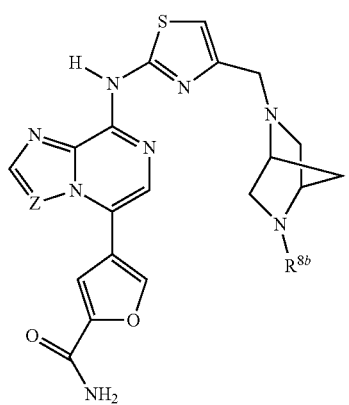
VIf
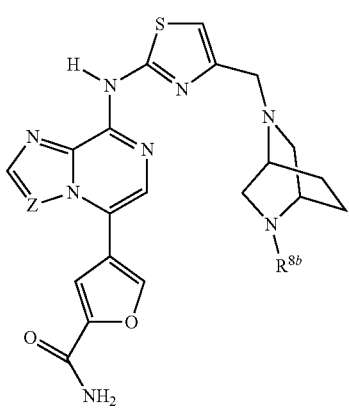
VIg
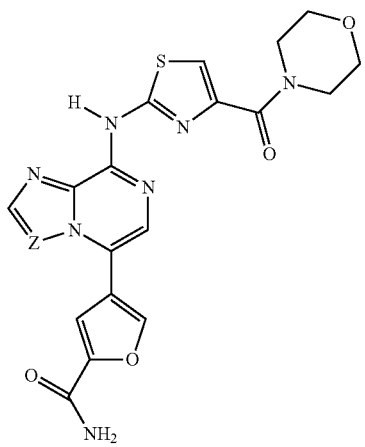
VIh
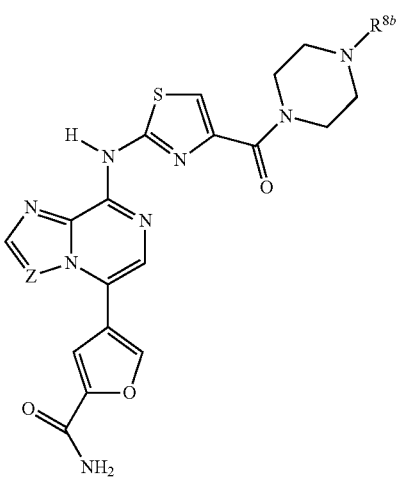
VIi
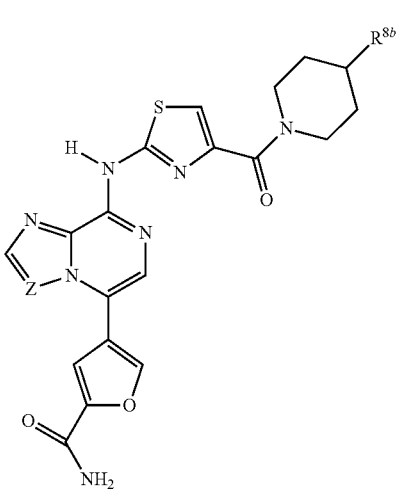
VIj
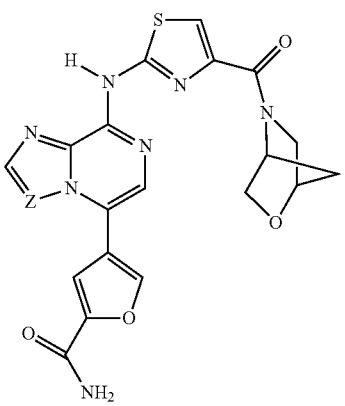

VIk 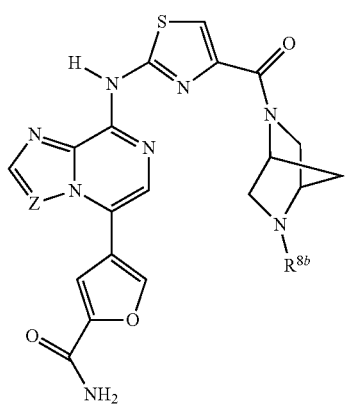

VIl 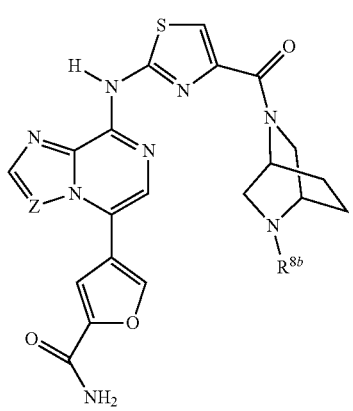

and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula VIm, VIn, VIo, VIp, VIq, VIr, VIs, VIt, VIu, VIv, VIw or VIx:

VIm 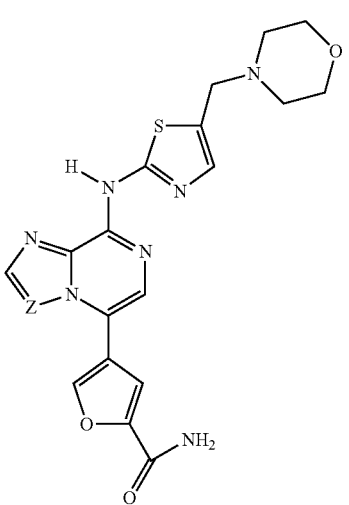

VIn, VIo 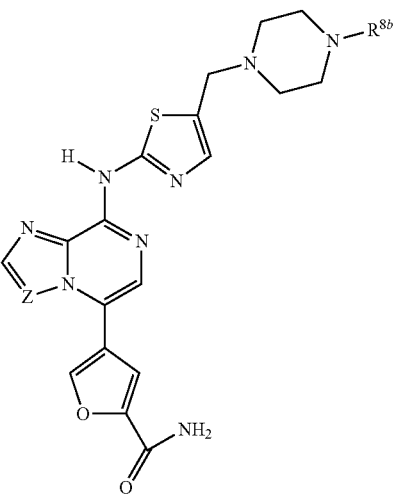

VIp 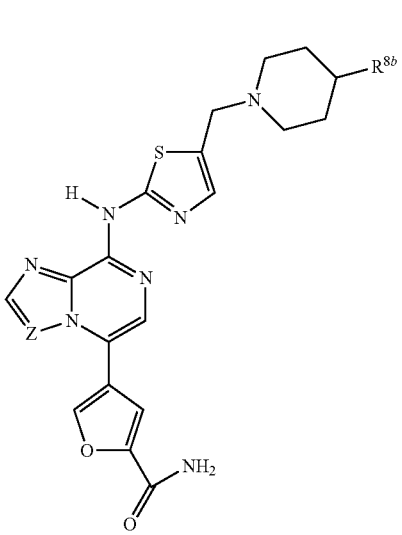

VIq
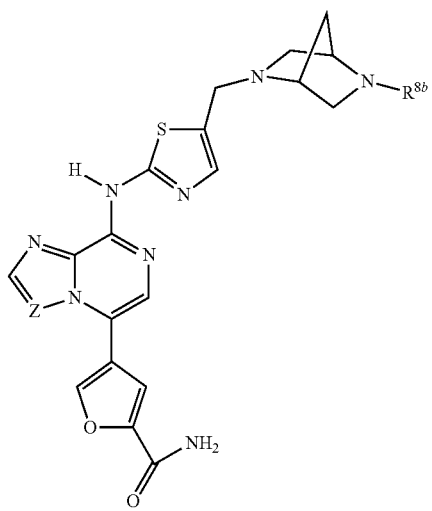
VIr
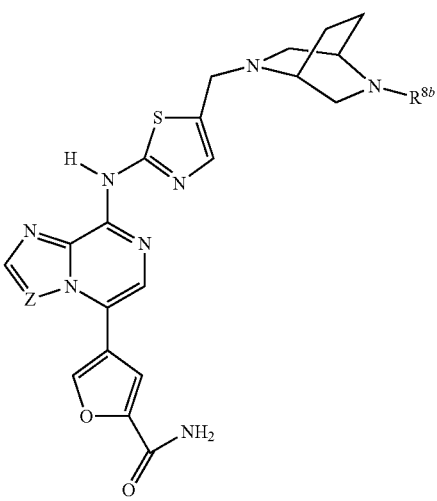
VIs
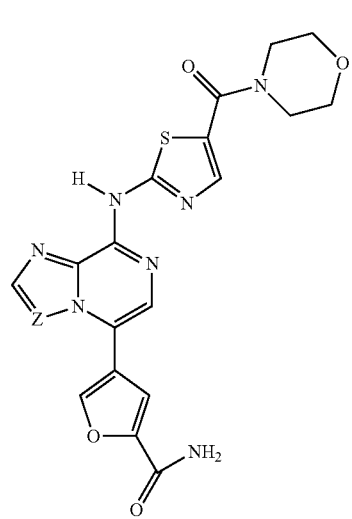
VIt
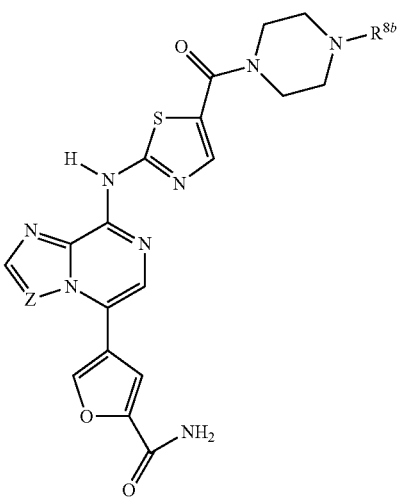
VIu
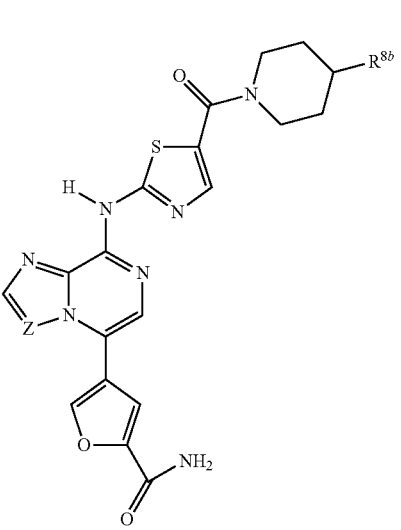
VIv
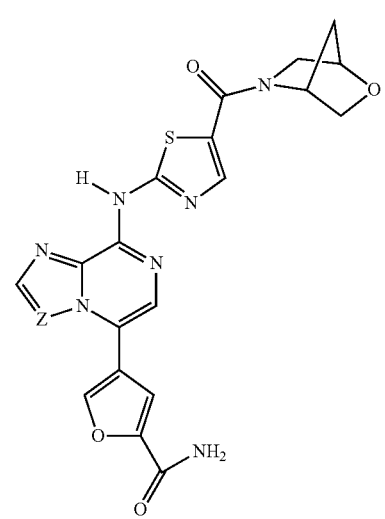

VIw

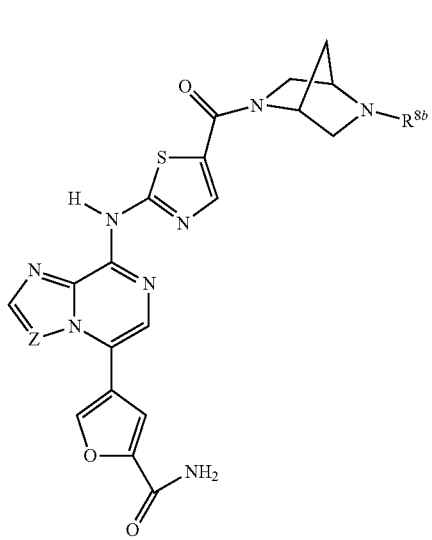

VIx

VIIa

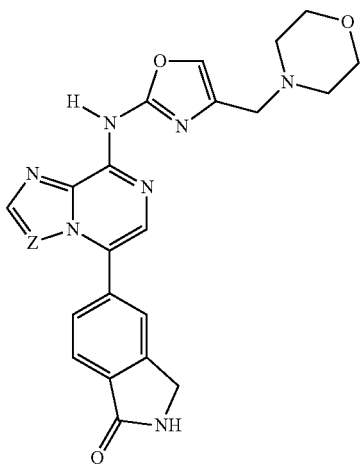

VIIb

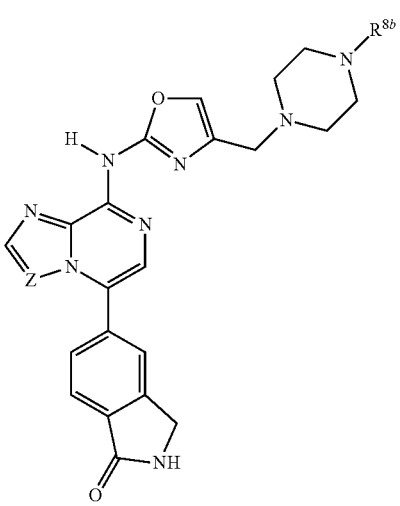

VIIc

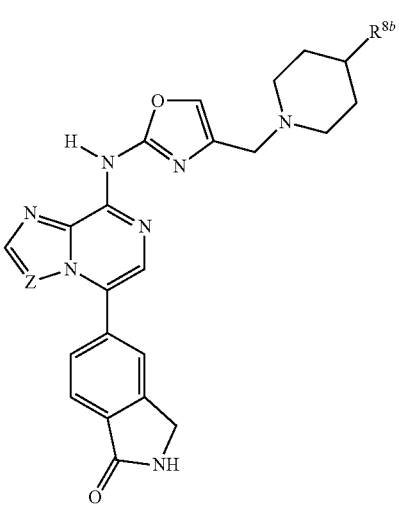

and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula VIIa, VIIb, VIIc, VIId, VIIe, VIIf, VIIg, VIIh, VIIi, VIIj, VIIk or VIII:

VIId
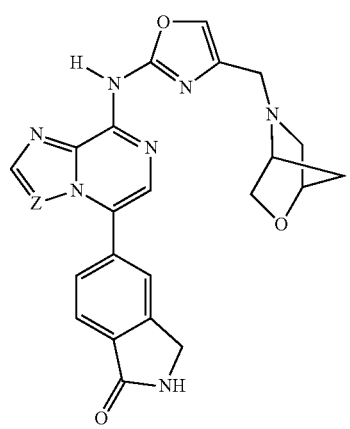
VIIe
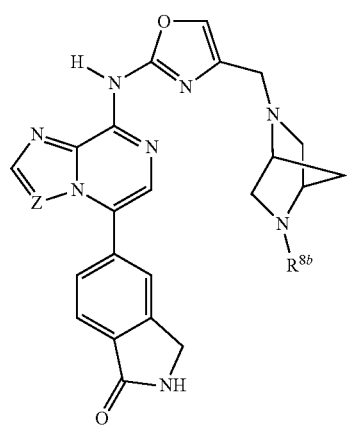
VIIf
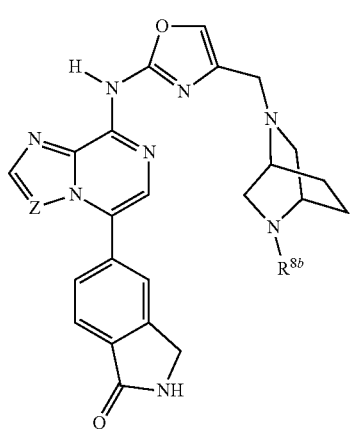
VIIg
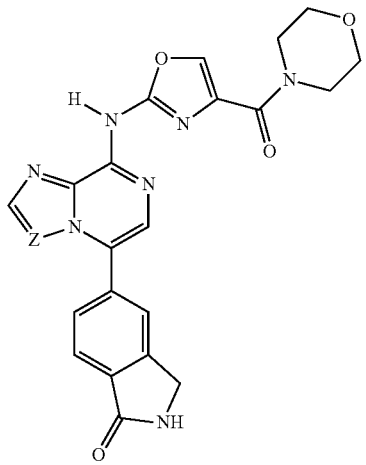
VIIh
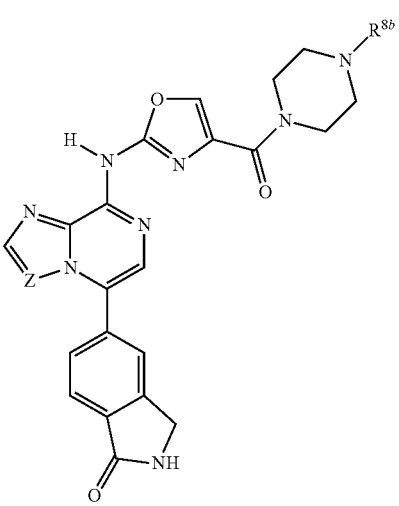
VIIi
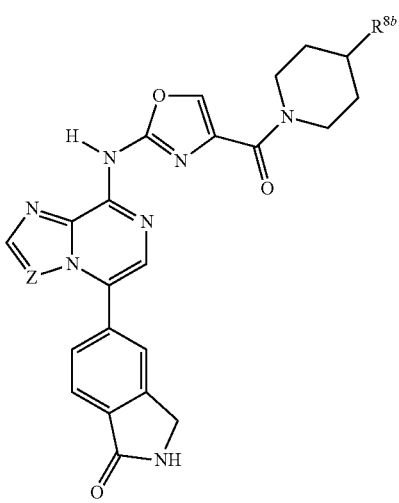

VIIj
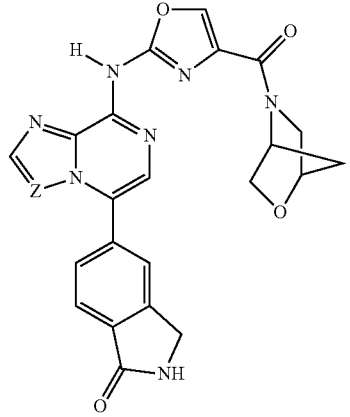

VIIk
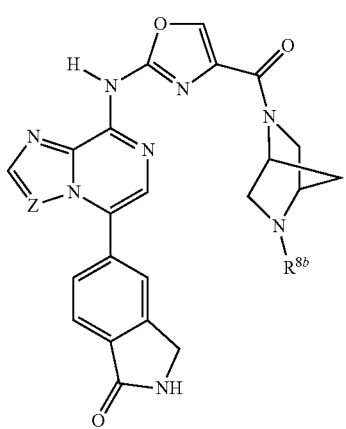

VIII
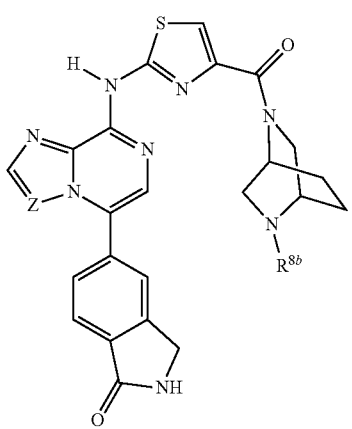

and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula VIIm, VIIn, VIIo, VIIp, VIIq, VIIr, VIIs, VIIt, VIIu, VIIv, VIIw or VIIx:

VIIm
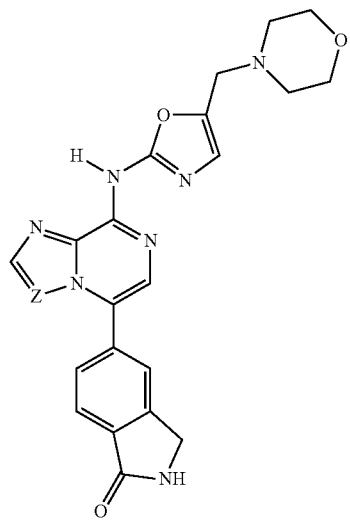

VIIn
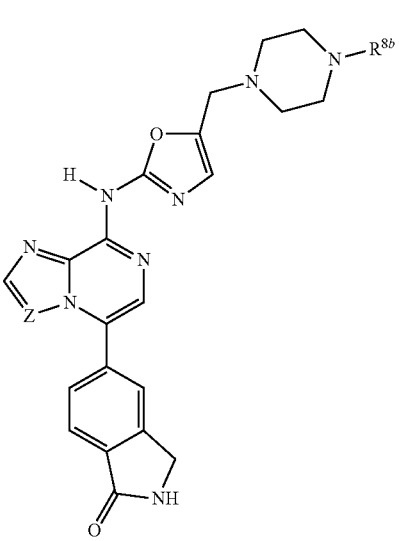

VIIo
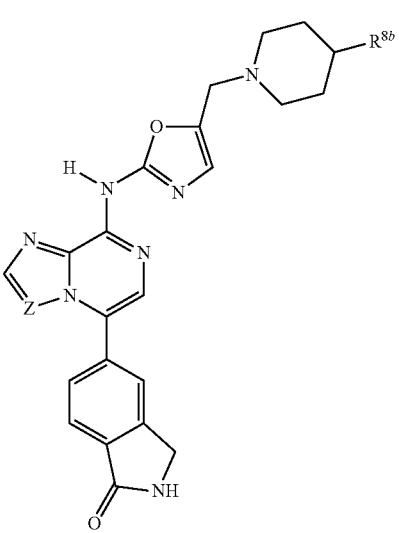

-continued
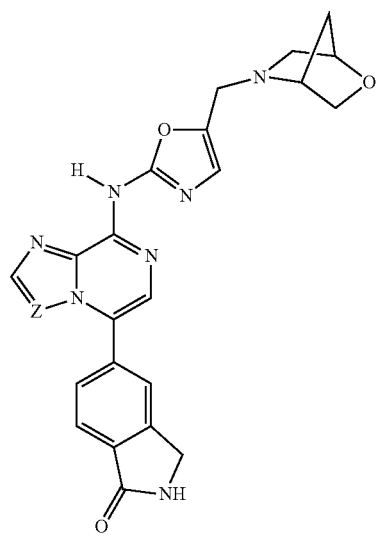
VIIp
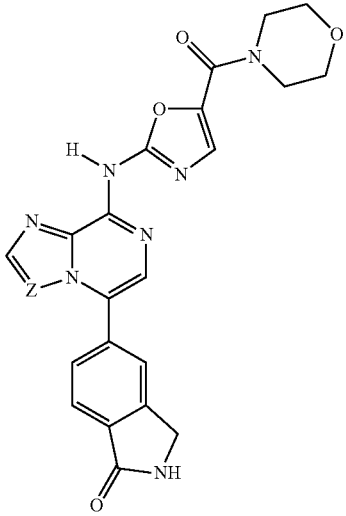
VIIs
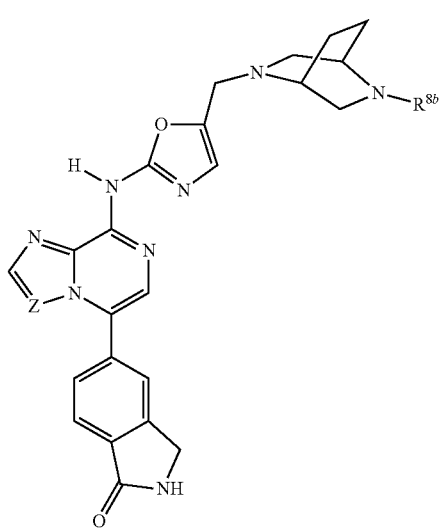
VIIq
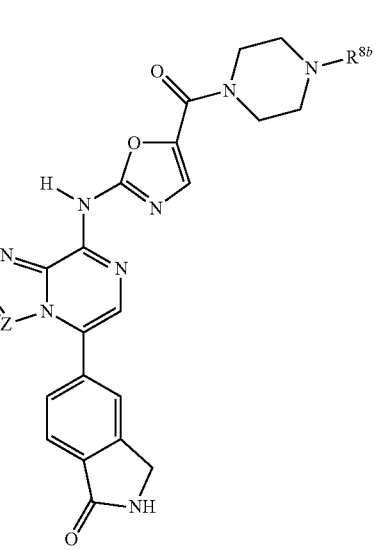
VIIt
VIIr
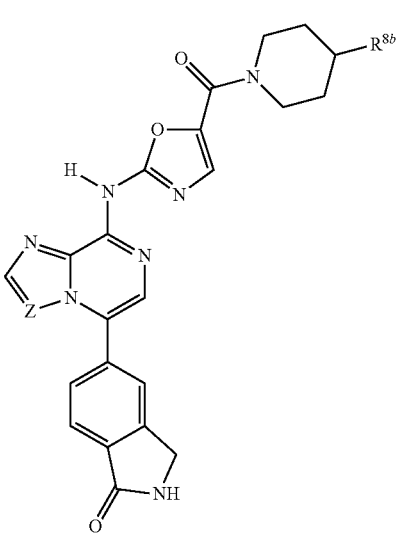
VIIu -continued VIIv
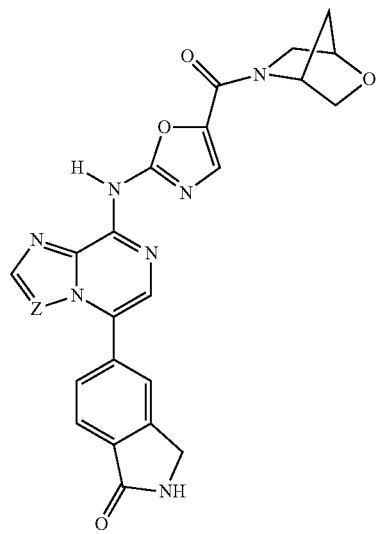

VIIw
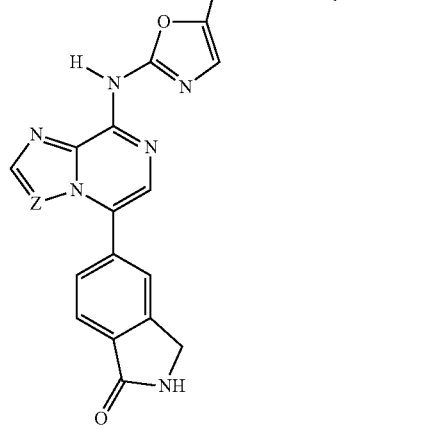

VIIx
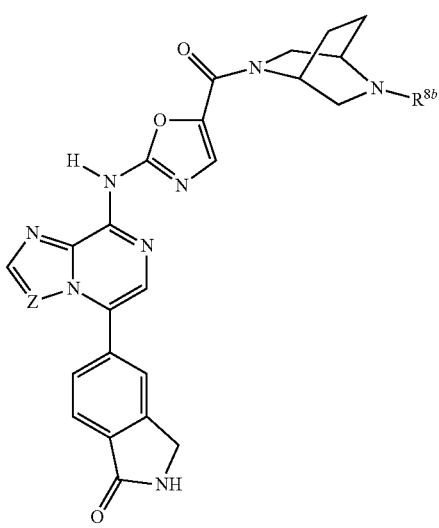

and wherein $R^{8b}$ is hydrogen; substituted or unsubstituted $C_1$-$C_6$ alkyl or substituted or unsubstituted $C_1$-$C_6$ cycloalkyl;

or a pharmaceutically acceptable salt, solvate or prodrug thereof; and stereoisomers, isotopic variants and tautomers thereof.

In one embodiment, with respect to compounds of formula I, the compound is according to formula VIIIa, VIIIb, VIIIc, VIIId, VIIIe, VIII, VIIIg, VIIIh, VIIIi, VIIIj, VIIIk or VIIIl:

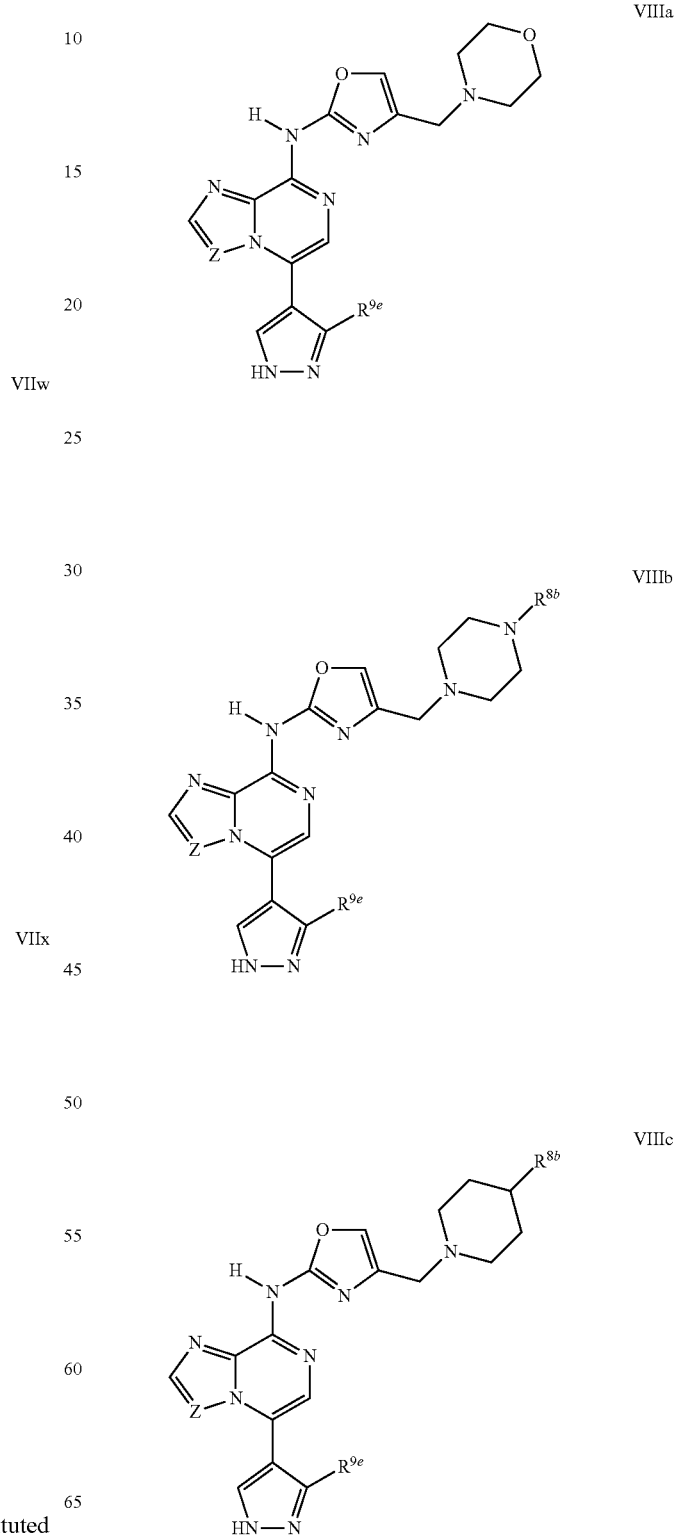

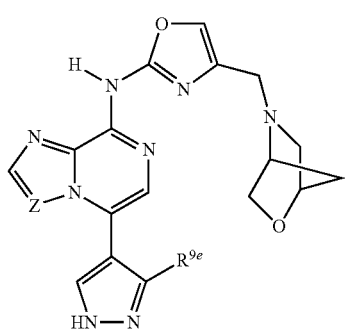
VIIId
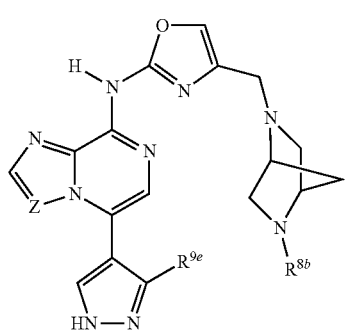
VIIIe
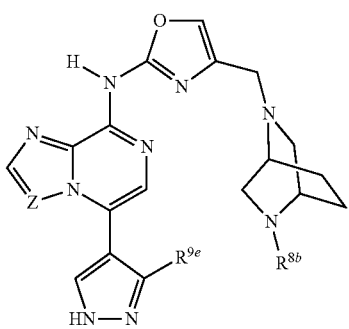
VIIIf
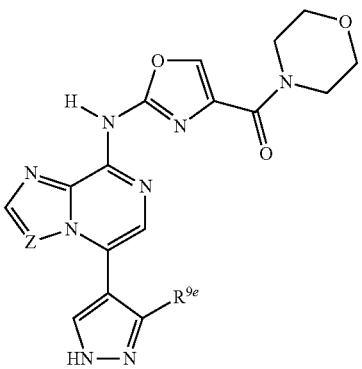
VIIIg
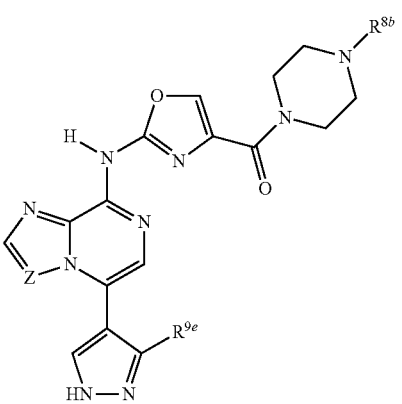
VIIIh
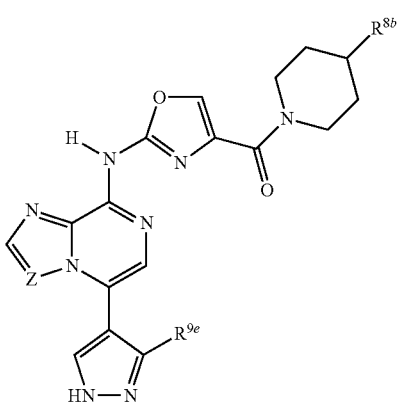
VIIIi
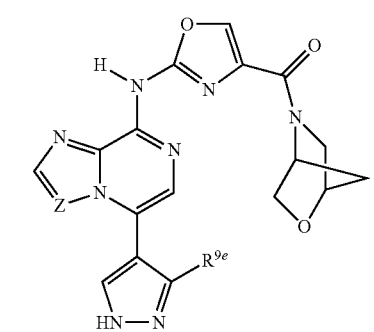
VIIIj
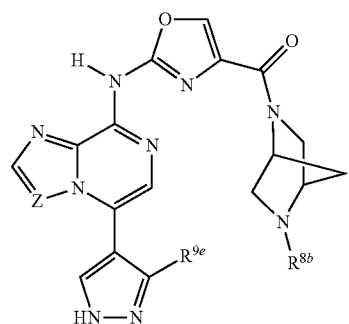
VIIIk VIIIl

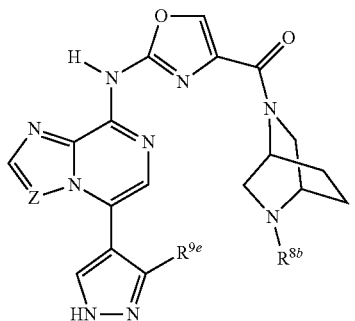

and wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formula I, the compound is according to formula VIIIm, VIIIn, VIIIo, VIIIp, VIIIq, VIIIr, VIIIs, VIIIt, VIIIu, VIIIv, VIIIw or VIIIx:

VIIIm

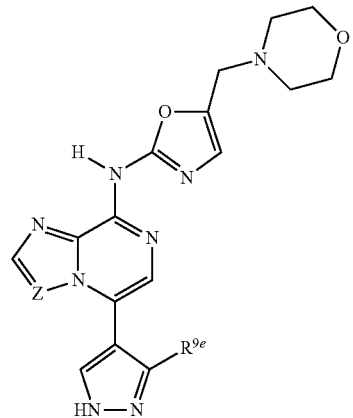

VIIIn

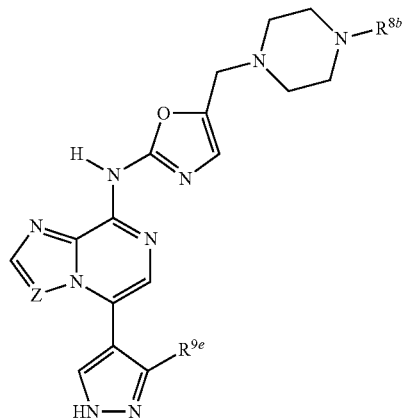

VIIIo

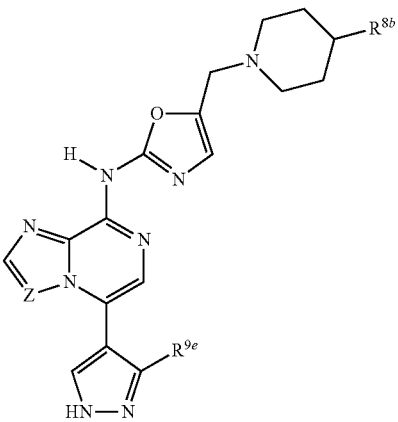

VIIIp

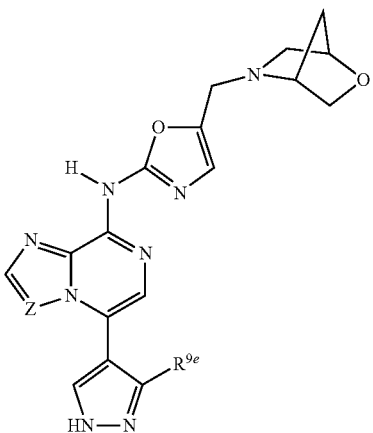

VIIIq

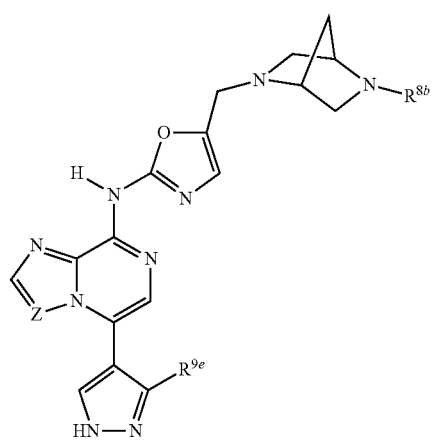

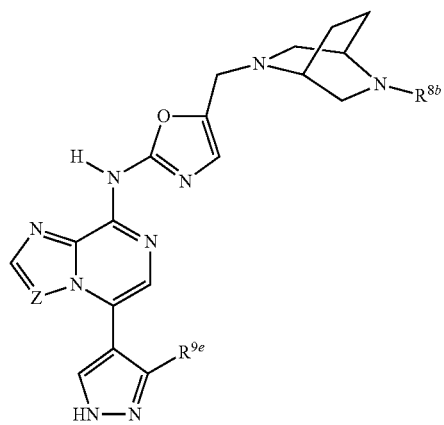
VIIIr
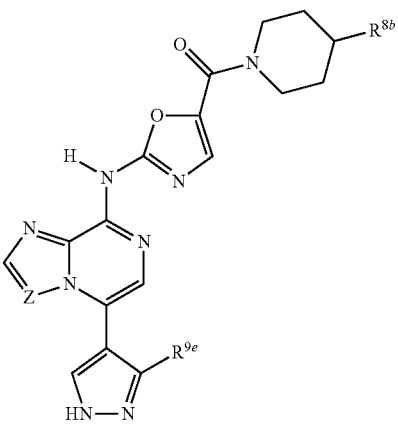
VIIIu
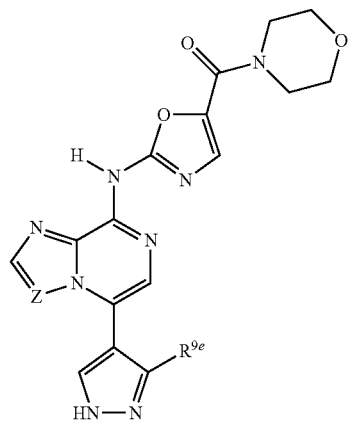
VIIIs
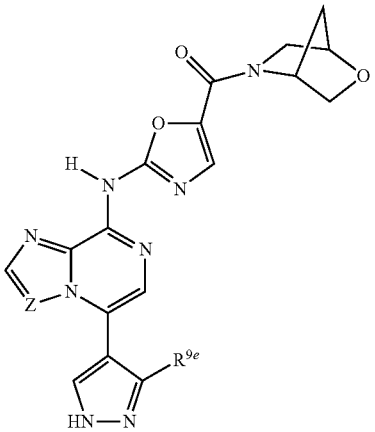
VIIIv
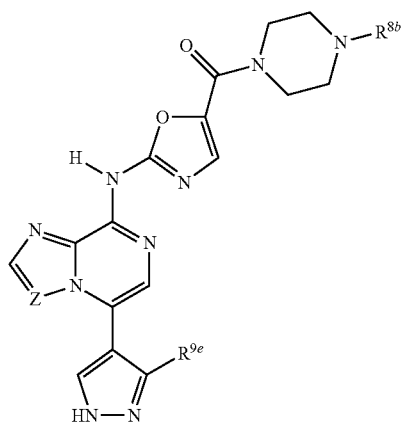
VIIIt
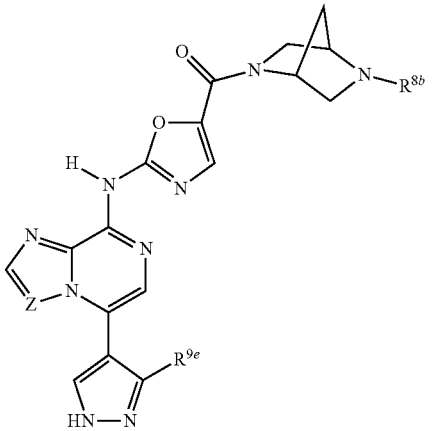
VIIIw VIIIx

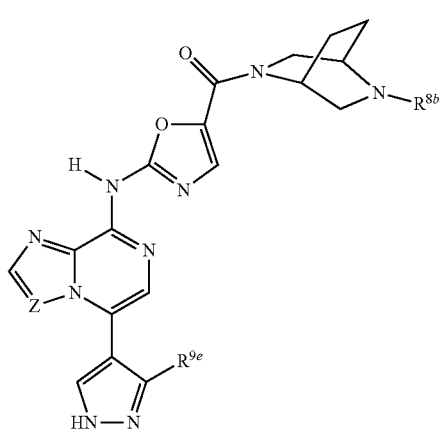

IXc

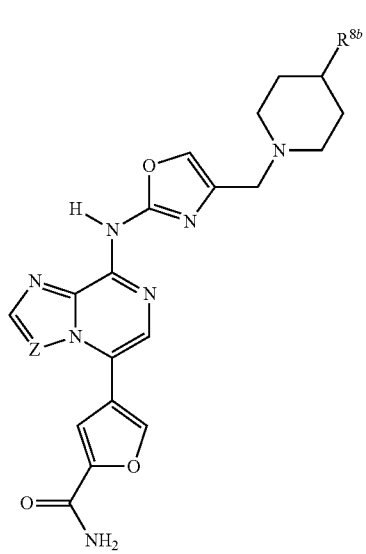

and wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formula I, the compound is according to formula IXa, IXb, IXc, IXd, IXe, IXf, IXg, IXh, IXi, IXj, IXk or IXl:

IXa

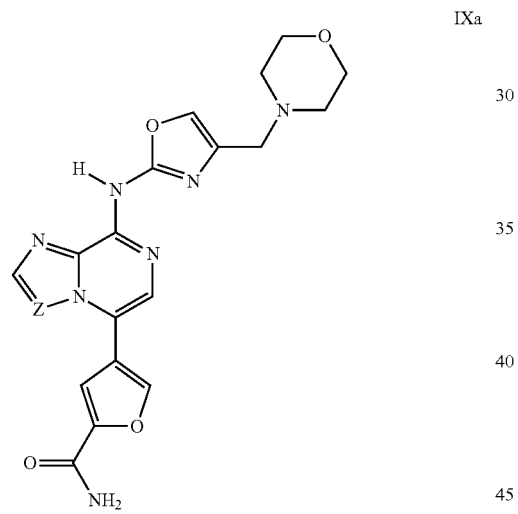

IXd

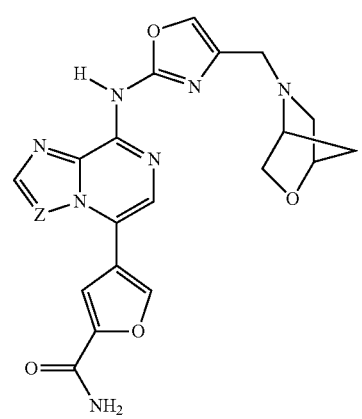

IXb

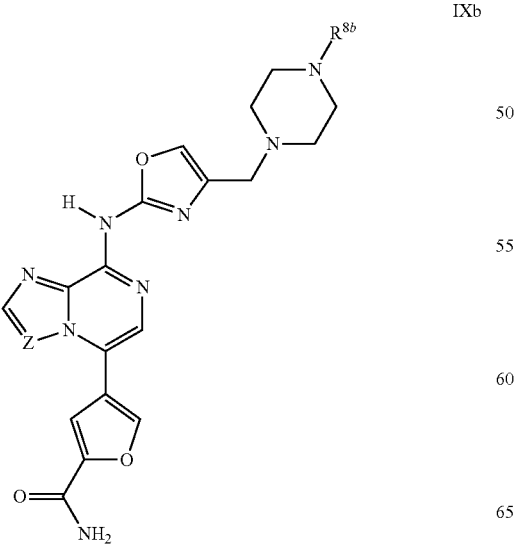

IXe

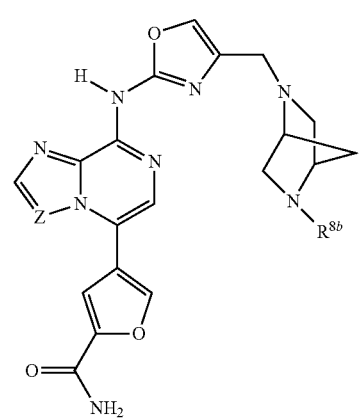

77
-continued
IXf
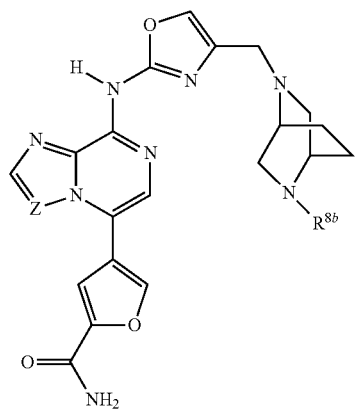
IXg
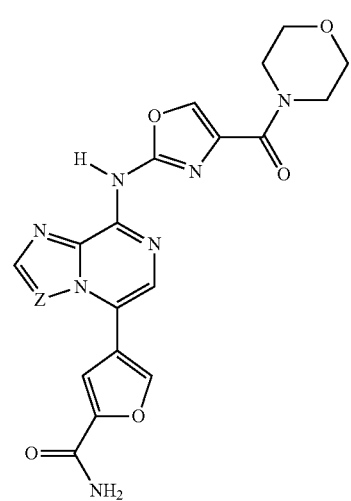
IXh
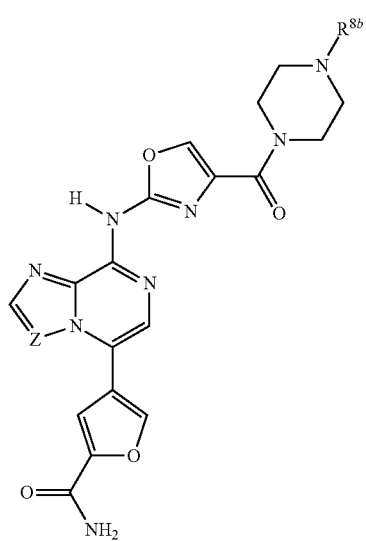
78
-continued
IXi
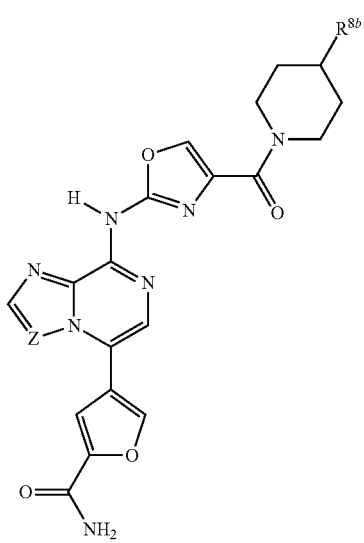
IXj
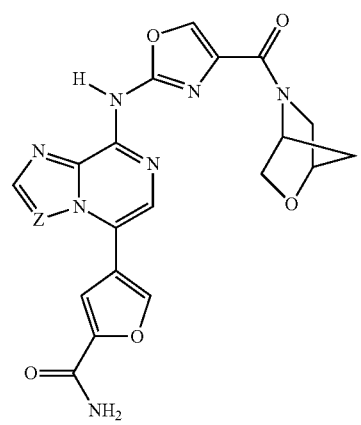
IXk
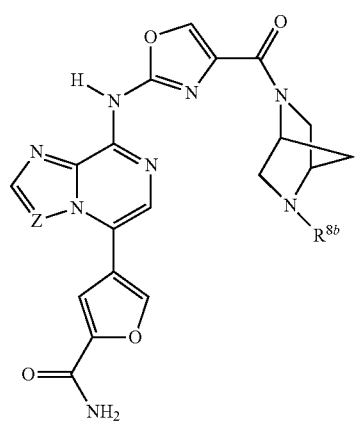

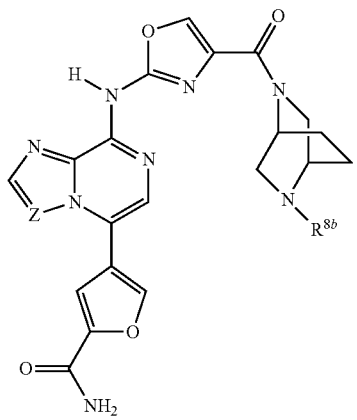

IXl

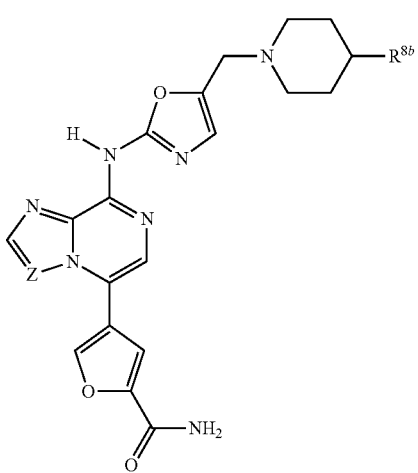

IXo and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formula I, the compound is according to formula IXm, IXn, IXo, IXp, IXq, IXr, IXs, IXt, IXu, IXv, IXw or IXx:

IXm

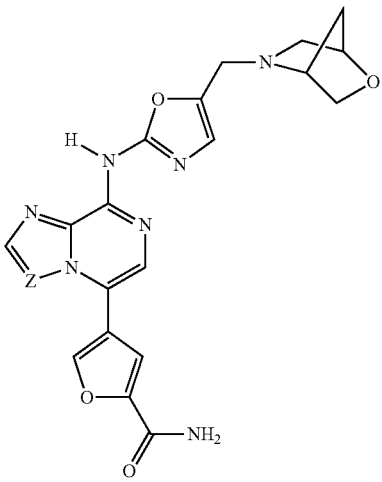

IXp

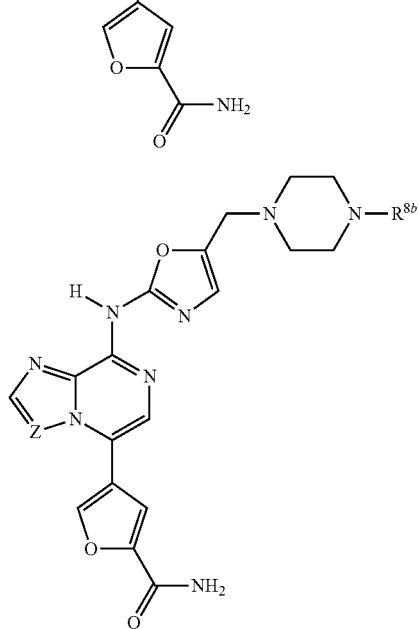

IXn

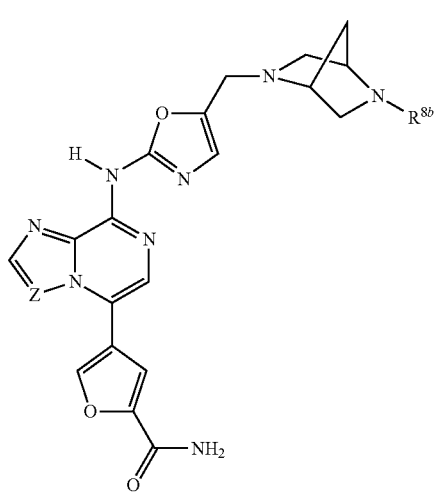

IXq

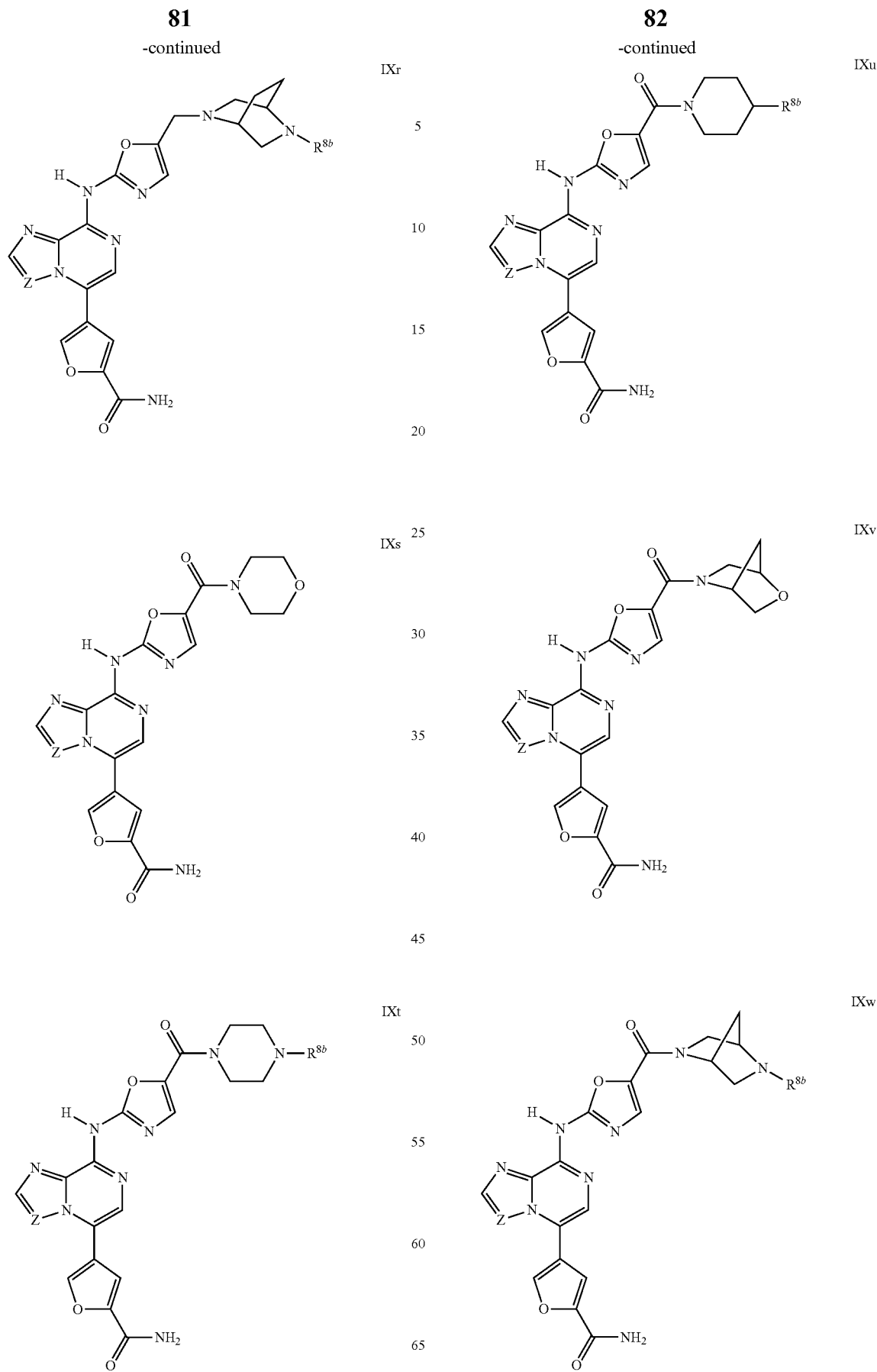

-continued

IXx

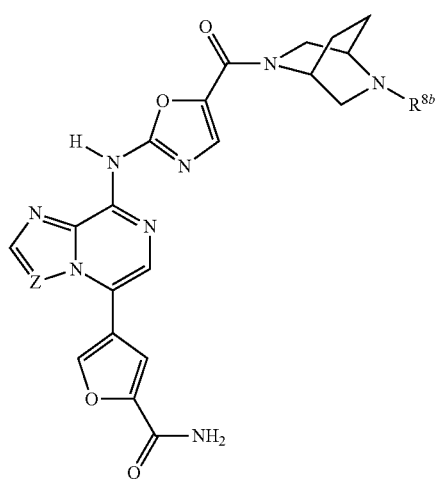

Xb

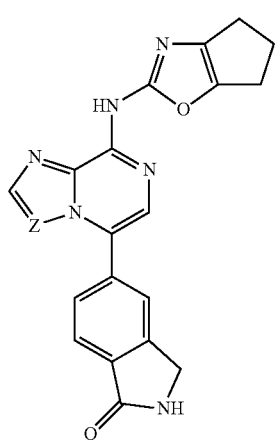

and wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers, isotopic variants and tautomers thereof.

In one embodiment, with respect to compounds of formulae IVa-IXl, $R^{8b}$ is H.

In one embodiment, with respect to compounds of formulae IVa-IXl, $R^{8b}$ is cycloalkyl.

In one embodiment, with respect to compounds of formulae IVa-IXl, $R^{8b}$ is cyclopropyl.

In one embodiment, with respect to compounds of formulae IVa-IXl, $R^{8b}$ is substituted or unsubstituted $C_1$-$C_6$ alkyl.

In one embodiment, with respect to compounds of formulae IVa-IXl, $R^{8b}$ is Me, Et, Pr, i-Pr, t-Bu, i-Bu, $CF_3$, $CH_2CF_3$, or cyclopropylmethyl.

In one embodiment, with respect to compounds of formulae Va-l and VIIIa-l, $R^{9e}$ is H. In another embodiment, $R^{9e}$ is Me. In yet another embodiment, $R^{9e}$ is CN or $CONH_2$.

In one embodiment, with respect to formula I, the compound is according to formula Xa, Xb or Xc:

Xa

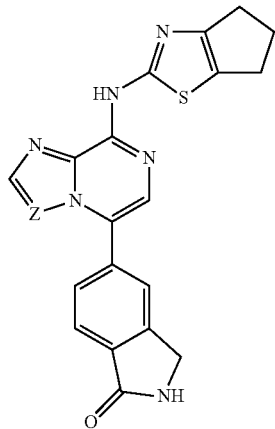

Xc and wherein $R^{8c}$ is hydrogen, or substituted or unsubstituted $C_1$-$C_6$ alkyl.

In one embodiment, with respect to compounds of formula I, the compound is according to formula Xd, Xe or Xf:

Xd

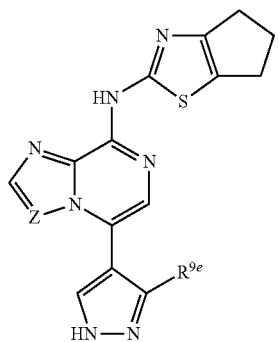

85
-continued

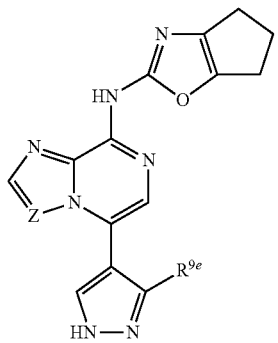
Xe

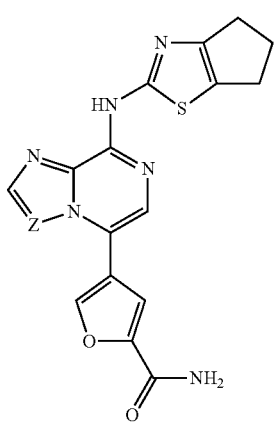
Xf and wherein $R^{8c}$ is hydrogen, or substituted or unsubstituted $C_1$-$C_6$ alkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formula I, the compound is according to formula Xg, Xh or Xi:

86
-continued

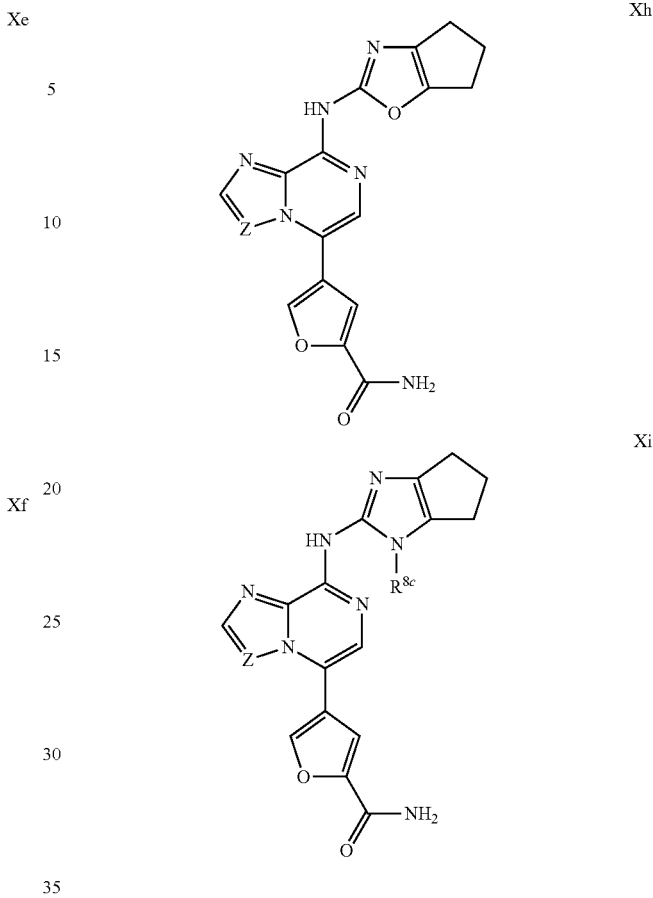

wherein $R^{8c}$ is hydrogen, or substituted or unsubstituted $C_1$-$C_6$ alkyl; and $R^{9e}$ is hydrogen, $C_1$-$C_6$ alkyl, amino, amido, or CN; or a pharmaceutically acceptable salt, solvate or prodrug thereof; and stereoisomers, isotopic variants and tautomers thereof.

In one embodiment, with respect to compounds of formulae I-Xi, Z is CH.

In one embodiment, with respect to compounds of formulae I-Xi, Z is N.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. A prodrug may be inactive when administered to a subject but is converted in vivo to an active compound of the invention. "Pharmaceutically acceptable prodrugs" as used herein refers to those prodrugs of the compounds useful in the present invention, which are, within the scope of sound medical judgment, suitable for use in contact with the tissues of patients with undue toxicity, irritation, allergic response commensurate with a reasonable benefit/risk ratio, and effective for their intended use of the compounds of the invention. The term "prodrug" means a compound that is transformed in vivo to yield an effective compound useful in the present invention or a pharmaceutically acceptable salt, hydrate or solvate thereof. The transformation may occur by various mechanisms, such as through hydrolysis in blood. The compounds bearing metabolically cleavable groups have the advantage that they may exhibit improved bioavailability as a result of enhanced solubility and/or rate of absorption conferred upon the parent compound by virtue of the presence of the metabolically cleavable group, thus, such compounds act as pro-drugs. A thorough discussion is provided in Design of Prodrugs, H. Bundgard, ed., Elsevier (1985); Methods in Enzymology; K. Widder et al, Ed., Academic Press, 42, 309-396 (1985); A Textbook of Drug Design and Development, Krogsgaard-Larsen and H. Bundgard, ed., Chapter 5; "Design and Applications of Prodrugs" 113-191 (1991); Advanced Drug Delivery Reviews, H. Bundgard, 8, 1-38, (1992); J. Pharm. Sci., 77, 285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

PHARMACEUTICAL COMPOSITIONS

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intra-articular, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the fuzed pyrazine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following examples illustrate representative pharmaceutical compositions that may be prepared in accordance with this invention. The present invention, however, is not limited to the following pharmaceutical compositions.

Formulation 1

Tablets

A compound of the invention may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention may be admixed as dry powder with a starch diluents in an approximately 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention is dissolved or suspended in a buffered sterile saline injectable aqueous medium to a concentration of approximately 5 mg/mL.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

METHODS OF TREATMENT

The present compounds are used as therapeutic agents for the treatment of conditions in mammals that are causally related or attributable to aberrant activity of MMP1 and/or MAPKAPK5. Accordingly, the compounds and pharmaceutical compositions of this invention find use as therapeutics for preventing and/or treating inflammatory diseases in mammals including humans.

In a method of treatment aspect, this invention provides a method of treating a mammal susceptible to or afflicted with a condition associated with extra-cellular matrix (ECM) degradation, in particular arthritis, and more particularly, rheumatoid arthritis which method comprises administering an effective amount of one or more of the compounds of the invention or a pharmaceutical composition as just described.

In another method of treatment aspect, the invention provides a method of treating a mammal susceptible to or afflicted with a condition associated with an abnormal cellular expression of MMP1, which comprises administering a therapeutically effective amount of a compound of the invention, or a pharmaceutical composition thereof.

In another method of treatment aspect, the present invention provides a method of treatment or prophylaxis of a condition characterized by abnormal matrix metallo proteinase activity, which comprises administering a therapeutically effective matrix metallo proteinase inhibiting amount of one or more of the compounds of the invention, or pharmaceutical composition thereof.

In yet another method of treatment aspect, this invention provides methods of treating a mammal susceptible to or afflicted with diseases and disorders which are mediated by or result in inflammation such as, for example rheumatoid arthritis and osteoarthritis, myocardial infarction, various autoimmune diseases and disorders, uveitis and atherosclerosis; itch/pruritus such as, for example psoriasis; and renal disorders wherein said method comprises administering an effective condition-treating or condition-preventing amount of one or more of the compounds of the invention or pharmaceutical compositions just described.

This invention also relates to the use of the present compounds in the manufacture of a medicament for treatment or prophylaxis of a condition prevented, ameliorated or eliminated by administration of an inhibitor of Mitogen-Activated Protein Kinase-Activated Protein Kinase 5, or a condition characterised by abnormal collagenase activity, or a condition associated with ECM degradation or a condition selected from diseases involving inflammation, most preferably in for the treatment of rheumatoid arthritis.

The invention also provides a compound of the invention for use in the treatment of a condition associated with extra-cellular matrix (ECM) degradation, in particular arthritis, e.g. rheumatoid arthritis.

The invention also provides a compound of the invention for use in the treatment of a condition associated with inflammation, such as, for example rheumatoid arthritis and osteoarthritis, myocardial infarction, various autoimmune diseases and disorders, uveitis and atherosclerosis; itch/pruritus such as, for example psoriasis; and renal disorders.

The invention also provides a compound of the invention for use in the treatment of a condition prevented, ameliorated or eliminated by administration of an inhibitor of Mitogen-Activated Protein Kinase-Activated Protein Kinase 5, or a condition characterised by abnormal collagenase activity.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

A preferred regimen of the present method comprises the administration to a subject in suffering from a disease condition characterized by inflammatory, with an effective matrix metallo-protease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

In one embodiment, the treatment regimen involves intra-articular administration of a compound of the invention or a pharmaceutical composition as described herein.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as inflammatory and autoimmune conditions, the regimen for treatment usually extends over many months or years, and accordingly oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses.

When used to prevent the onset of an inflammatory condition, the compounds of this invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity, and that are determined to safe and efficacious for such combined administration.

GENERAL SYNTHETIC PROCEDURES

The triazolopyrazine and imidazopyrazine compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative bicycloheteroaryls that have been listed hereinabove. The compounds of the invention may be prepared from known or commercially available starting materials and reagents by one skilled in the art of organic synthesis.

All reagents were of commercial grade and were used as received without further purification, unless otherwise stated. Commercially available anhydrous solvents were used for reactions conducted under inert atmosphere. Reagent grade solvents were used in all other cases, unless otherwise specified. Column chromatography was performed on silica gel 60 (35-70 µm). Thin layer chromatography was carried out using pre-coated silica gel F-254 plates (thickness 0.25 mm). $^1$H NMR spectra were recorded on a Bruker DPX 400 NMR spectrometer (400 MHz). Chemical shifts (δ) for $^1$H NMR spectra are reported in parts per million (ppm) relative to tetramethylsilane (δ 0.00) or the appropriate residual solvent peak, i.e. CHCl$_3$ (δ 7.27), as internal reference. Multiplicities are given as singlet (s), doublet (d), triplet (t), quartet (q), multiplet (m) and broad (br). Coupling constants (J) are given in Hz. Electrospray MS spectra were obtained on a Micromass platform LC/MS spectrometer. Column Used for all LCMS analysis: Waters Acquity HPLC BEH C18 1.7 µm, 2.1 mm ID×50 mm L (Part No. 186002350)). Preparative HPLC: Waters XBridge Prep C18 5 µm ODB 19 mm ID×100 mm L (Part No. 186002978). All the methods are using MeCN/H$_2$O gradients. H$_2$O contains either 0.1% TFA or 0.1% NH$_3$.

List of Abbreviations Used in the Experimental Section:

| DCM: | Dichloromethane | EtOAc | ethyl acetate |
|---|---|---|---|
| DiPEA: | N,N-diisopropylethylamine | APCI | atmospheric pressure chemical ionization |
| MeCN | Acetonitrile | | |
| BOC | tert-Butyloxy-carbonyl | Rt | retention time |
| DMF | N,N-dimethylformamide | s | Singlet |
| TFA | Trifluoroacetic acid | br s | broad singlet |
| THF | Tetrahydrofuran | m | Multiplet |
| NMR | Nuclear Magnetic Resonnance | d | Doublet |
| | | PdCl$_2$dppf | [1,1'-Bis-(diphenylphosphino)-ferrocene]dichloropalladium(II) |
| DMSO | Dimethylsulfoxide | | |
| DPPA | Diphenylphosphorylazide | | |
| LC-MS | Liquid Chromatography-Mass Spectrometry | | |
| Ppm | part-per-million | TEA | Triethylamine |

Synthetic Preparation of Compounds of the Invention

Synthesis of Intermediates

Intermediate 1a: Preparation of 3,6-Dibromo-pyrazin-2-ylamine

General Reaction Scheme:

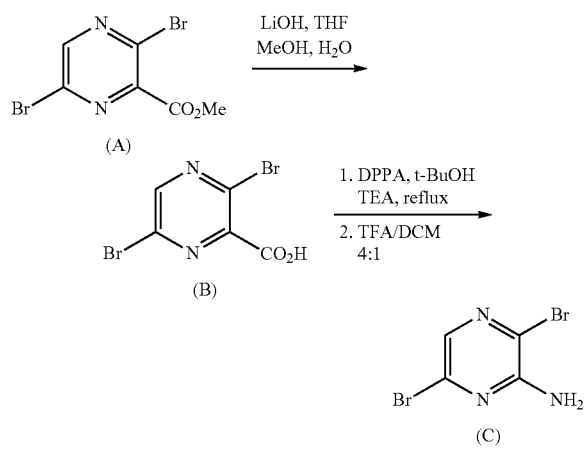

Step 1: Synthesis of compound (B) as described in the general reaction scheme;
3,6-Dibromo-Pyrazine-2-Carboxylic Acid LiOH (655 mg, 27 mmol) is added to a solution of 3,6-dibromo-pyrazine-2-carboxylic acid methyl ester (A) (*J. Med. Chem.* 1969, 12, 285-87) (2.7 g, 9 mmol) in THF:water:MeOH (18:4.5:4.5 mL). The reaction is stirred at 5° C. for 30 min, concentrated in vacuo, taken up in DCM and washed with 1N HCl. The organic phase is dried over MgSO$_4$ and concentrated in vacuo to afford compound (B). $^1$H NMR (250 MHz, CDCl$_3$) δ (ppm) 8.70 (s, 1H).

Step 2: Synthesis of compound (C) as described in the general reaction scheme;
3,6-Dibromo-pyrazin-2-ylamine Diphenylphosphorylazide (2.59 mL, 12 mmol) and triethylamine (1.67 mL, 12 mmol) are added to a solution of 2,5-dibromo-3-pyrazoic acid (3.52 g, 12 mmol) in t-butanol (90 mL). The reaction is heated at reflux for 18 hours. The reaction is quenched with water, then concentrated in vacuo and taken up in DCM. The organic solution is washed with water and 1N NaOH, dried over MgSO$_4$ and concentrated in vacuo. The resultant solid is filtered through a pad of silica using EtOAc, then concentrated and TFA:DCM (4:1, 12 mL) is added to the solid and stirred for 30 min. The solution is concentrated in vacuo then neutralised with 1N NaOH and extracted with DCM. The organic layer is dried over MgSO$_4$ and concentrated in vacuo to give the product. $^1$H NMR (250 MHz, d$_6$-DMSO) δ (ppm) 7.25 (br s, 2H), 7.68 (s, 1H); m/z (APCI) 254 (M+H)$^+$; m.p 135-139° C.

Intermediate 1a: Preparation of 3,6-Dibromo-pyrazin-2-ylamine

Alternatively 3-Chloro-6-bromo-pyrazin-2-ylamine can be used and is prepared according to the following scheme:

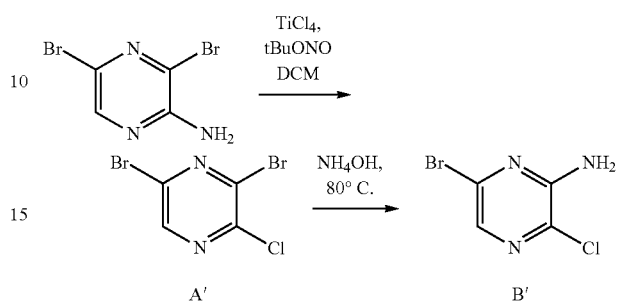

Step 1. Synthesis of compound (A) as described in the general reaction scheme;
3,6-dibromo-2-chloropyrazine To a well stirred solution of 2-chloro-3,6-dibromopyrazine (3.21 g, 12.692 mmol) in DCM (20 mL) cooled to 0° C. is added TiCl$_4$ (2.41 g, 12.692 mmol, 1.00 equiv.) in one portion, thus giving a dark red slurry. tButylnitrite (2.62 g, 25.385 mmol, 2.00 equiv.) is then added dropwise, causing the solution to turn bright yellow. The ice bath is then removed and the reaction is then allowed to proceed at room temperature. More TiCl$_4$ (1.50 g, 1.2 equiv.) is added and the mixture is stirred further for one hour. At that point an orange solution has formed and LC-MS shows full conversion of the starting material to the desired product which ionises very poorly. Water (100 mL) is added to the reaction, forming an emulsion. DCM (50 mL) is added, and the DCM layer is separated, and the aqueous layer is further extracted with DCM (3×50 mL) until the DCM layer is colorless. The DCM layers are gathered, washed with brine and dried over Na$_2$SO$_4$, to yield after solvent removal, compound A' (2.81 g, 82%) as an orange oil, which is used as such in the following step.

Step 2: Synthesis of compound (B') as described in the general reaction scheme;
2-Amino-3-chloro-6-bromopyrazine Compound A' described in the previous step (9.5 g, 37.55 mmol) is suspended in concentrated NH$_4$OH (60 mL) and the resulting mixture is heated in a pressure autoclave to 80° C., typically overnight. The vessel is then allowed to cool down to room temperature slowly, and is then further cooled in an ice bath, causing the precipitation of the desired material. The solid is separated by filtration, washed with cyclohexane, to afford after drying, the title compound B' (5 g) as a 83/17 mixture of regioisomers. The mixture is then purified by column chromatography. M+H+, m/z=209

Intermediate 2: 5,8-Dibromo-imidazo[1,2-a]pyrazine

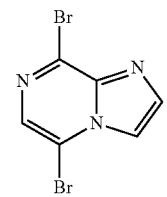 [SMILES: Brc1ncc(Br)n2ccnc12]

Bromoacetaldehyde diethyl acetal (49 mL, 326 mmol) and 48% hydrobromic acid is heated to reflux for 1.5 h, then poured into propan-2-ol (600 mL) and quenched with NaHCO$_3$. After filtering, 2,5-dibromo-3-aminopyrazine (41.34 g, 163 mmol) is added to the solution and heated at reflux overnight. The reaction is cooled and solvents removed in vacuo, followed by addition of aq. NaHCO$_3$ and extraction with EtOAc. The organic phase is dried over MgSO$_4$, filtered, and concentrated in vacuo to afford a brown solid. $^1$H NMR (250 MHz, CDCl$_3$) δ (ppm) 7.86 (s, 1H), 7.93-7.94 (d, 1H), 7.98-7.99 (d, 1H); m/z (APCI) 278 (M+H)$^+$; m.p 132-135° C.

Intermediate 3:
5,8-Dibromo-[1,2,4]-triazolo[1,5-a]pyrazine

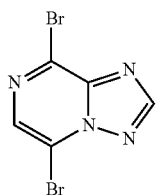 [SMILES: Brc1ncc(Br)n2ncnc12]

General Scheme:

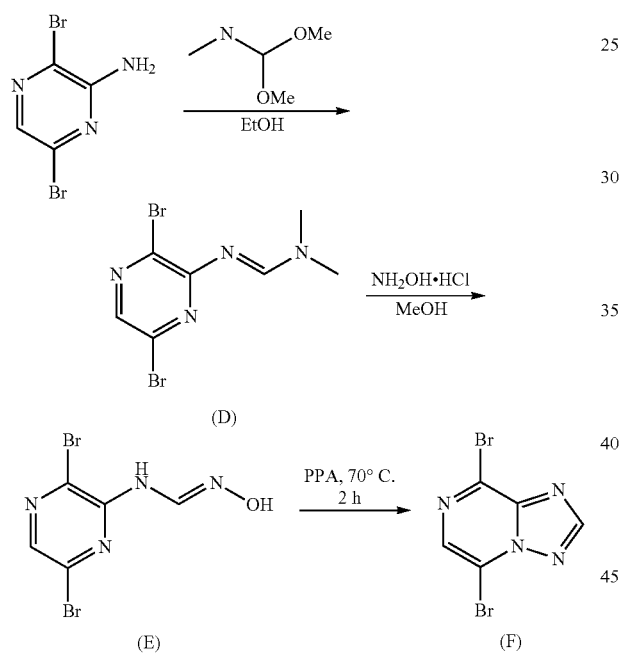

Step 1: N'-(3,6-Dibromo-pyrazin-2-yl)-N,N-dimethylformamidine (D)

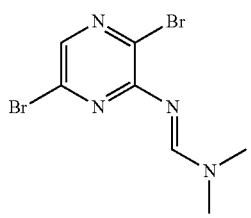

A mixture of 3,6-dibromo-pyrazin-2-ylamine (15.37 g, 60.80 mmol) and N,N-dimethylformamide dimethyl acetal (10.1 mL, 76.00 mmol), suspended in ethanol (150 mL), is refluxed for 2 hours. The reaction mixture is evaporated in vacuo affording the title compound. $^1$H-NMR (400 MHz, CDCl$_3$) δ (ppm) 3.20 (s, 3H), 3.21 (s, 3H), 7.93 (s, 1H), 8.48 (s, 1H). LCMS: Rt 3.81 min (99.1%), m/z (APCI) 307 (M+H)$^+$.

Step 2: N-(3,6-Dibromo-pyrazin-2-yl)-N'-hydroxyformamidine (E)

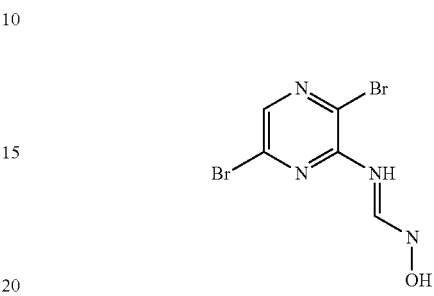

To a solution of N'-(3,6-dibromo-pyrazin-2-yl)-N,N-dimethylformamidine (18.6 g, 60.80 mmol) in methanol (200 mL) is added hydroxylamine hydrochloride (5.91 g, 85.12 mmol) in one portion. The reaction is stirred at room temperature for 16 hours. The solvent is evaporated and the solid residue is treated with cold (ice cooling) water and collected by filtration. The precipitate is washed twice with water and petroleum ether and dried in vacuo yielding the title compound. $^1$H-NMR (400 MHz, d$_6$-DMSO) δ (ppm) 7.82 (br s, 1H), 8.21 (s, 1H), 8.34 (m, 1H), 11.17 (br s, 1H). LCMS: Rt 3.17 min (98.7%), m/z (APCI) 295 (M+H)$^+$.

Step 3: 5,8-Dibromo-[1,2,4]triazolo[1,5-a]pyrazine (F)

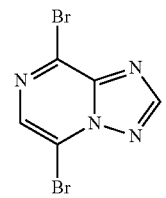

N-(3,6-dibromo-pyrazin-2-yl)-N'-hydroxyformamidine (17.4 mg, 58.80 mmol) is treated with polyphosphoric acid (150 g) for one hour at 50° C. and then for 1.75 hours at 70° C. After cooling to room temperature, water is added to the reaction mixture. The resultant suspension is brought to pH 8 by careful addition of solid NaHCO$_3$ in small portions. The precipitate formed is collected by filtration, washed once with 1N NaOH, three times with water and dried in vacuo. The residue is partitioned between ethyl acetate and 1N NaOH and the organic phase is washed one more time with 1N NaOH and once with brine. The organic phase is dried over MgSO$_4$, filtered and evaporated to give the title compound (10.15 g) as a white solid. $^1$H-NMR (400 MHz, d$_6$-DMSO) δ (ppm) 8.43 (s, 1H), 8.92 (s, 1H). LCMS: Rt 2.73 min (94.2%), m/z (APCI) 277 (M+H)$^+$.

Intermediate 4: 5-(4,4,5,5-Tetramethyl-[1,3,2]dioxaborolan-2-yl)-2,3-dihydro-isoindol-1-one

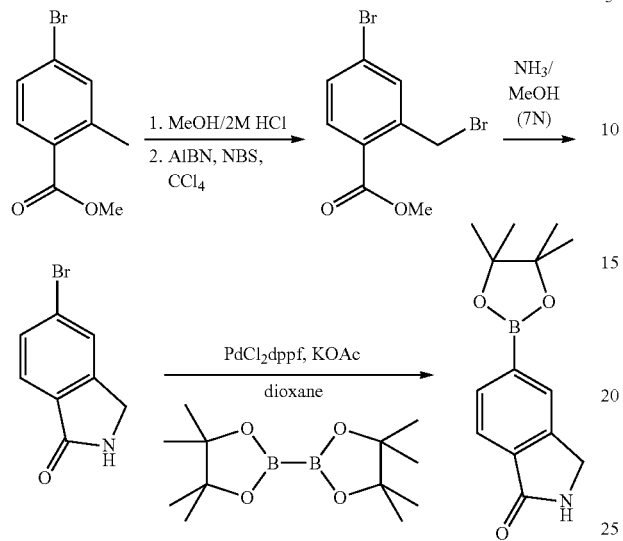

Step 1: 4-Bromo-2-bromomethyl-benzoic acid methyl ester

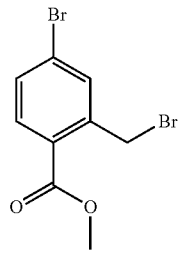

4-Bromo-2-methyl-benzoic acid (4.6 g, 21.39 mmol) is dissolved in 2M HCl in MeOH and refluxed for 3 hours. The solvent is evaporated to give the 4-bromo-2-methyl-benzoic acid methyl ester (4.24 g, 86%). This intermediate (18.51 mmol) is dissolved in carbon tetrachloride (100 mL) and N-bromosuccinimide (5.57 g, 24.06 mmol) is added. AIBN (122 mg, 740 µmol) is then added and the mixture purged with nitrogen for 5 minutes. The reaction mixture is then refluxed for four hours. After cooling to room temperature the reaction mixture is filtered and the filtrate is evaporated. The residue is purified by flash chromatography (silica gel, 2:1 petroleum ether/ethyl acetate) to give the title compound (3.42 g, 60%).

Step 2: 5-Bromo-2,3-dihydro-isoindol-1-one

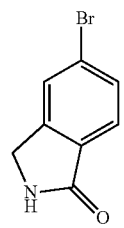 [SMILES: O=C1NCc2cc(Br)ccc21]

4-Bromo-2-bromomethyl-benzoic acid methyl ester (0.5 g, 16.2 mmol) is treated with methanolic ammonia (10 mL, 7 N $NH_3$ in MeOH) for 5 minutes at 90° C. After cooling to room temperature the precipitate formed is filtered off and washed with a small amount of methanol affording the title compound (224 mg, 65%) as a colourless solid.

$^1$H-NMR (400 MHz, $d_6$-DMSO) δ =4.41 (s, 2H, $CH_2$), 7.64 (d, 1H, $H_{ar}$), 7.70 (d, 1H, $H_{ar}$), 7.87 (s, 1H, $H_{ar}$), 8.67 (bs, 1H, NH). LCMS 99.6%, $R_t$=2.49 min, m/z 212 (M+H, $AP^+$ formic acid).

Step 3: 5-(4,4,5,5-Tetramethyl-[1,3,2]dioxaborolan-2-yl)-2,3-dihydro-isoindol-1-one

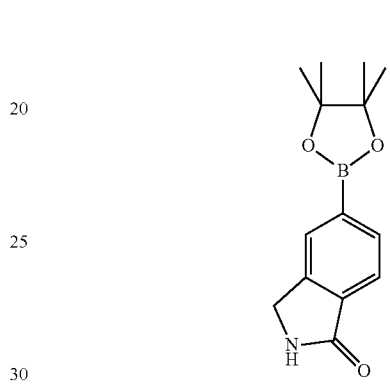

5-Bromo-2,3-dihydro-isoindol-1-one (230 mg, 1.08 mmol), bis(pinacolato)diboron (300 mg, 1.18 mmol), $Pda_2dppf$ (25 mg, 31 µmol) and KOAc (320 mg, 3.26 mmol) are suspended in dioxane (4 ml), purged with nitrogen for 5 minutes and then heated at 85° C. overnight. The solvent is removed in vacuo and the residue partitioned between ethyl acetate and water. The aqueous layer is extracted three times with ethyl acetate and the combined, organic phases are washed once with brine, filtered through $MgSO_4$ and evaporated. The solid residue is triturated with hexane and dried in vacuo to furnish the title compound (185 mg, 66%) as a grey solid.

$^1$H-NMR (400 MHz, $CDCl_3$) δ =1.37 (s, 12H, 4×$CH_3$), 4.45 (s, 2H, $CH_2$), 6.38 (bs, 1H, NH), 7.87 (d, 1H, $H_{ar}$), 7.93 (m, 2H, $H_{ar}$).

Intermediate 5: 4-(4,4,5,5-Tetramethyl-[1,3,2]dioxaborolan-2-yl)-furan-2-carboxylic acid amide

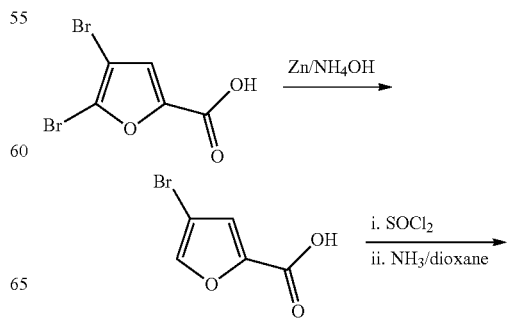

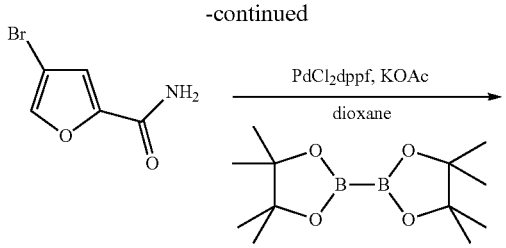

Step 1: 4-Bromo-furan-2-carboxylic acid amide

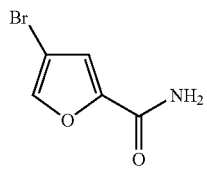

To a cooled (using a cold water bath) solution of 4,5-dibromo-furan-2-carboxylic acid (12.5 g, 46.32 mmol) in NH$_4$OH (100 mL) is added zinc dust (activated, powdered (washed with 2M HCl, water, MeOH, CH$_2$Cl$_2$) 4.54 g, 65.39 mmol) in small portions. The reaction mixture is stirred at room temperature for 10 minutes then filtered over celite and washed with water. The filtrate is cooled to −10° C. (ice/salt bath) and acidified slowly to pH 1 using conc. HCl. The aq layer is immediately extracted with ethyl acetate (4×). The organic phase is washed with brine, dried over MgSO$_4$, filtrated and concentrated in vacuo to give an oil (4.96 g) which solidifies on standing to give a white solid, which is used without further purification.

The solid (4.93 g, 25.81 mmol) is dissolved in thionyl chloride (44.2 mL) and refluxed for 1 hour. After removing the solvent in vacuo the residue is dissolved in dichloromethane (75 mL) and a solution of 0.5 M NH$_3$ in dioxane (52 mL) is added. The reaction mixture is stirred at room temperature for 1 hour, then 33% aq. NH$_3$ (5 mL) is added and the reaction stirred for additional 2 hours. The solvent is removed in vacuo and the residue taken-up with a solution of sat. NaHCO$_3$. The basic solution is extracted using ethyl acetate (3×), the combined organic layers are dried over MgSO$_4$ and concentrated in vacuo. Purification by silica gel column chromatography eluting with a mixture of (50:49:1) ethyl acetate:petroleum ether:acetic acid, affords the title compound (1.2 g, 22%).

Step 2: 4-(4,4,5,5-Tetramethyl-[1,3,2]dioxaborolan-2-yl)-furan-2-carboxylic acid amide

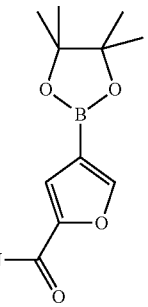

4-Bromo-furan-2-carboxylic acid amide (1.2 g, 6.32 mmol), bis(pinacolato)diboron (1.76 g, 6.94 mmol), PdCl$_2$dppf (0.154 g, 0.189 mmol) and KOAc (1.85 g, 18.94 mmol) are suspended in dioxane (20 mL), purged with nitrogen for 5 minutes and then heated at 85° C. overnight. The solvent is removed in vacuo and the residue partitioned between ethyl acetate and brine. The aqueous layer is extracted four times with ethyl acetate, filtered through MgSO$_4$ and evaporated. The solid residue is triturated with hexane and dried in vacuo to afford the title compound as a solid (0.984 g, 66%). N.B. compound is usually 50-60% pure by $^1$H-NMR.

Intermediate 6: 4-(1-morpholinomethyl)thiazol-2-ylamine

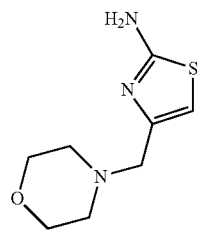 [SMILES: Nc1nc(CN2CCOCC2)cs1]

Morpholine (350 μL, 4.00 mmol) is added to a solution of 4-chloromethyl-thiazol-2-ylamine hydrochloride (368 mg, 2.00 mmol) in DMF (7 mL). The reaction is stirred at 90° C. for 16 h. The reaction is diluted with ethyl acetate and washed with water. The aqueous layer is concentrated in vacuo and extracted with ethyl acetate. The combined organic layers are dried over MgSO$_4$ and evaporated to give brown crystals which are used without further purification. $^1$H-NMR (400 MHz, d$_6$-DMSO) δ=2.41-2.42 (m, 4H, CH$_2$CH$_2$), 3.30 (s, 2H, CH$_2$), 3.55-3.60 (m, 4H, CH$_2$CH$_2$), 6.33 (s, 1H, H$_{ar}$), 6.85 (bs, 2H, NH$_2$).

Intermediate 7: 5-(tert-butyl-dimethylsilyloxymethyl)-thiazol-2-ylamine

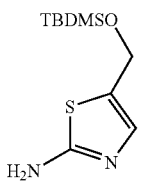

A solution of 5-(hydroxymethyl)-thiazol-2-ylamine (0.787 g, 6.05 mmol), TBDMSCl (1.003 g, 6.65 mmol) and imidazole (0.49 g, 7.26 mmol) in DMF (15 mL) is stirred at room temperature for 24 h. The reaction mixture is diluted with ether and water. The organic layer is washed with water (3×). The aqueous washings are backwashed with ether (2×). The organic layers are combined, dried over MgSO$_4$ and condensed. The crude material is purified using a plug of silica and eluting with 1:1 petrol:ethyl acetate to give the product (0.656 g, 44%). $^1$H-NMR (400 MHz, d$_6$-DMSO) δ =0.01 (s, 6H, 2×CH$_3$), 0.82 (s, 9H, tBu), 4.61 (s, 2H, CH$_2$), 4.74 (brs, 2H, NH$_2$), 6.8 (s, 1H, CH). LCMS: Rt 2.62 min (92.7%). MS (MH$^+$, m/z) 245.

Intermediate 8:
(2-aminothiazol-5-yl)(morpholino)methanone

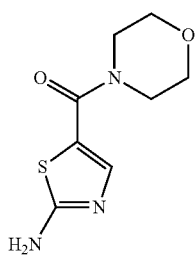

To a mixture of 5-(2-amino thiazole)-carboxylic acid (0.40 g, 2.77 mmol), morpholine (0.241 mL, 2.77 mmol), HOBt (0.41 g, 3.05 mmol) and triethylamine (0.77 mL, 5.54 mmol) in dichloromethane at 0° C. is added EDCI (0.58 g, 3.05 mmol) and the reaction stirred at room temperature. After 3 h DMF (10 mL) is added to improve solubility and the reaction is heated at 30° C. overnight. The reaction is condensed then water added to afford a precipitate. The mixture is cooled then filtered and the resulting solid product dried under vacuum (0.32 g, 54%). $^1$H-NMR (400 MHz, d$_6$-DMSO)S=3.6 (s, 8H, (CH$_2$CH$_2$)$_2$), 7.38 (s, 1H, H$_{ar}$), 7.48 (s, 2H, NH$_2$). MS (MH$^+$, m/z) 214.

Intermediate 9: 2-Amino-5-(4-morpholino methyl)thiazole

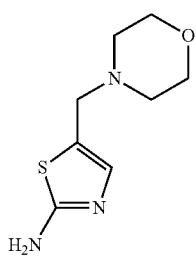

To a solution of morpholine (68 mg, 0.78 mmol) in methanol (3 mL) and acetic acid (0.045 mL, 0.78 mmol) is added sodium acetate (64 mg, 0.78 mmol) followed by 2-amino-5-formyl thiazole (100 mg, 0.78 mmol). The reaction is then heated to 40° C. for 1 h. Sodium cyanoborohydride (98 mg, 1.56 mmol) is added and the reaction stirred at 40° C. overnight. The reaction is cooled, condensed and purified by column chromatography, eluting with 3% methanolic ammonia (7 N) in dichloromethane to give the title compound (91 mg, 58%). $^1$H-NMR (400 MHz, CDCl$_3$) δ=2.451-2.47 (m, 4H; CH$_2$CH$_2$), 3.68-3.71 (m, 4H, CH$_2$CH$_2$), 4.98 (s, 2H, CH$_2$), 6.87 (s, 1H, H$_{ar}$). MS (MH$^+$, m/z) 200.

Intermediate 10:
1-(2-morpholinoethyl)-1H-imidazol-2-amine

Step 1: 4-(2-(2-nitro-1H-imidazol-1-yl)ethyl)morpholine

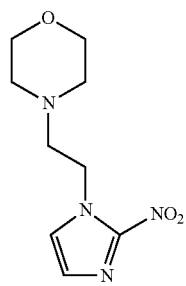 [SMILES: O=[N+]([O-])c1nccn1CCN1CCOCC1]

2-Nitroimidazole (0.55 g, 4.86 mmol), 4-(2-chloroethyl) morpholine hydrochloride (0.90 g, 4.86 mmol), sodium iodide (0.18 g, 1.21 mmol) and sodium methoxide (0.59 g, 10.0 mmol) are dissolved in DMF (25 mL). The mixture is heated at 100° C. under a nitrogen atmosphere for 14 h. The reaction mixture is cooled and solvent removed in vacuo. The residue is partitioned between ethyl acetate (30 mL) and sat. NaHCO$_3$ (aq.) (30 mL). The aqueous layer is extracted with ethyl acetate (4×30 mL). The organic layers are combined, dried (MgSO4) and solvent removed in vacuo. The solid residue is purified by column chromatography, eluting with 3% methanol in dichloromethane to give a yellow oil (638 mg, 58%). $^1$H-NMR (400 MHz, d$_6$-DMSO) δ =2.39-2.45 (m, 4H), 2.66 (t, 2H, J=6 Hz), 3.52 (t, 4H, J=4.8 Hz), 4.52-4.54 (t, 2H, J=6 Hz), 7.19 (s, 1H, H$_{ar}$), 7.68 (s, 1H, H$_{ar}$).

Step 2: 1-(2-morpholinoethyl)-1H-imidazol-2-amine

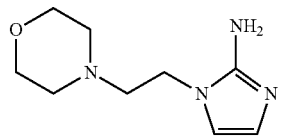 [SMILES: Nc1nccn1CCN1CCOCC1]

The product from Step 1 (0.64 g, 2.81 mmol) is suspended in methanol (20 mL) and water (2 mL). Palladium on carbon (0.065 g, 0.281 mmol) is added and the mixture is degassed with nitrogen for 10 min before sodium borohydride (0.15 g, 3.93 mmol) is added portion-wise. The reaction is cooled with an ice bath and after 30 mins warmed to room temperature and stirred for 16 h at room temperature. The palladium is filtered through celite and washed with methanol (3×30 mL). The filtrate is concentrated in vacuo and the residue partitioned between dichloromethane (100 mL) and water (10 mL). The aqueous layer is extracted with dichloromethane (5×50 mL+1 mL MeOH). The organic layers are combined, dried (MgSO$_4$) and solvent removed in vacuo to give an orange oil (0.42 g, 77%). NMR (400 MHz, CDCl3) δ =2.47-

2.60 (m, 4H), 2.64-2.66 (m, 2H), 3.62-3.72 (m, 4H), 3.77-3.83 (m, 2H), 4.76 (brs, 2H), 6.49 (s, H), 6.61 (s, 1H).

Example 1

5-(8-(4-(morpholinomethyl)thiazol-2-ylamino)imidazo[1,2-a]pyrazin-5-yl)isoindolin-1-one Step 1: tert-butyl 4-(5-bromo-[1,2,4]triazolo[1,5-a]pyrazin-8-ylamino)piperidine-1-carboxylate

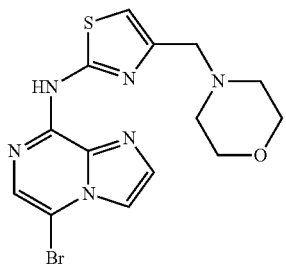 [SMILES: Brc1cnc(Nc2nc(CN3CCOCC3)cs2)c2nccn12]

Intermediate 2 (5,8-Dibromoimidazo[1,2-a]pyrazine, 177 mg, 0.63 mmol), Intermediate 6 (4-(1-morpholinomethyl)thiazol-2-ylamine, 140 mg, 0.70 mmol), sodium tert-butoxide (86 mg, 0.89 mmol), palladium dibenzylidene acetone (23 mg, 0.026 mmol) and Xantphos (30 mg, 0.051 mmol) were suspended in toluene (4 mL). The mixture is degassed with nitrogen for 5 min and then stirred at 90° C. for 16 h. The solvent is evaporated in vacuo then water is added and the resulting brown precipitate collected. The solid is washed with water then ether and dried in air. The solid residue is purified by column chromatography, eluting with 2% methanolic ammonia (7 N) in dichloromethane to give a yellow powder (82 mg, 34%). $^1$H-NMR (400 MHz, d$_6$-DMSO) δ =2.47 (s, 4H, CH$_2$CH$_2$), 3.53 (s, 2H, CH$_2$), 3.62 (s, 4H, CH$_2$CH$_2$), 6.99 (s, 1H, H$_{ar}$), 7.85 (s, 1H, H$_{ar}$), 8.16 (s, 1H, H$_{ar}$), 11.79 (s, 1H, NH). MS (MH$^+$, m/z) 395.

Step 2: 5-(8-(4-(morpholinomethyl)thiazol-2-ylamino)imidazo[1,2-a]pyrazin-5-yl)isoindolin-1-one

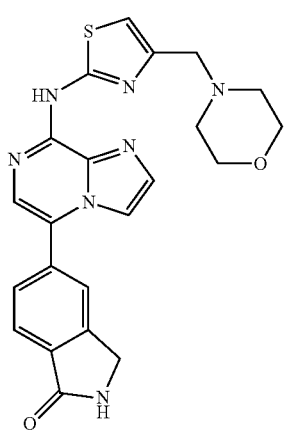

The product of Step 1 (35 mg, 0.09 mmol), Intermediate 4 (5-(4,4,5,5-Tetramethyl-[1,3,2]dioxaborolan-2-yl)-2,3-dihydro-isoindol-1-one, 29 mg, 0.11 mmol), tetrakis palladium triphenylphosphine (26 mg, 0.02 mmol), sodium carbonate solution (1.5 M, 0.472 mL, 0.71 mmol) and dioxane (2.8 mL) are combined in a flask. The mixture is degassed with nitrogen for 10 min then sealed and heated at 90° C. for 16 h. Brine is added and the mixture is washed with dichloromethane followed by ethyl acetate. The combined organic layers are dried over MgSO$_4$ and evaporated in vacuo to afford a brown oil. The crude material is purified by column chromatography, eluting with 3% methanolic ammonia (7 N) in dichloromethane to give the title compound as a yellow powder (16 mg, 40%). $^1$H-NMR (400 MHz, d$_6$-DMSO) δ =2.49 (s, 4H, CH$_2$CH$_2$), 3.55 (s, 2H, CH$_2$), 3.63 (s, 4H, CH$_2$CH$_2$), 7.00 (s, 1H, H$_{ar}$), 7.72 (s, 1H, H$_{ar}$), 7.81 (s, 1H, H$_{ar}$), 7.88 (s, 2H, H$_{ar}$), 8.00 (s, 1H, H$_{ar}$), 8.10 (s, 1H, H$_{ar}$), 8.74 (s, 1H, NH), 11.65 (s br, 1H, NH). LCMS: Rt 8.04 min (92.2%). MS (MH$^+$, m/z) 448.

Example 2

5-(8-(5-(hydroxymethyl)thiazol-2-ylamino)imidazo[1,2-a]pyrazin-5-yl)isoindolin-1-one Step 1: N-(5-bromoimidazo[1,2-a]pyrazin-8-yl)-5-((tert-butyldimethylsilyloxy)methyl)thiazol-2-amine

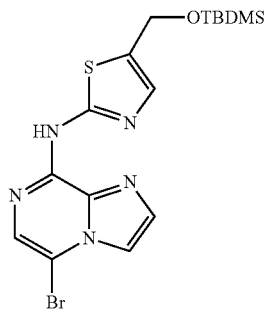 [SMILES: CC(C)(C)[Si](C)(C)OCc1cnc(Nc2ncc(Br)n3ccnc23)s1]

Prepared from Intermediate 2 and Intermediate 7 using the procedure described in Example 1, Step 1. MS (MH$^+$, m/z) 440.

Step 2: (2-(5-bromoimidazo[7,2-a]pyrazin-8-ylamino)thiazol-5-yl)methanol

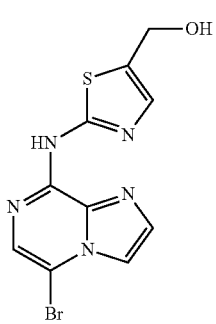 [SMILES: OCc1cnc(Nc2ncc(Br)n3ccnc23)s1]

The product of Step 1 (0.125 g, 0.28 mmol) is dissolved in THF (2 mL). To this solution is added TBAF solution (1M in THF, 0.31 mL, 0.31 mmol) and the reaction is stirred at room temperature overnight. The reaction is condensed and the residue purified by gradient column chromatography eluting with dichloromethane—5% methanolic ammonia (7 N) in dichloromethane to give the alcohol (64 mg, 69%). LCMS: Rt 2.54 min (97.7%). MS (MH+, m/z) 326.

Step 3: 5-(8-(5-(hydroxymethyl)thiazol-2-ylamino)imidazo[1,2-a]pyrazin-5-yl)isoindolin-1-one

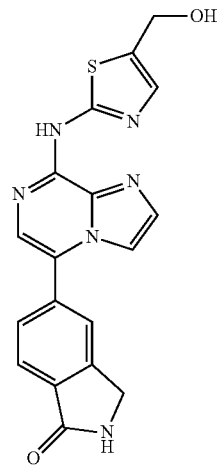 [SMILES: O=C1NCc2cc(-c3cnc(Nc4ncc(CO)s4)c4nccn34)ccc21]

Prepared from the product of Step 2 and Intermediate 4 (5-(4,4,5,5-Tetramethyl-[1,3,2]dioxaborolan-2-yl)-2,3-dihydro-isoindol-1-one) according to the procedure described in Example 1, Step 2. $^1$H-NMR (400 MHz, d$_6$-DMSO) δ=4.52 (s, 2H, CH$_2$), 4.67 (d, 2H, CH$_2$), 5.40 (t, 1H, OH), 7.36 (s, 1H, H$_{ar}$), 7.71 (s, 1H, H$_{ar}$), 7.81 (s, 1H, H$_{ar}$), 7.89 (m, 2H, H$_{ar}$), 7.99 (s, 1H, H$_{ar}$), 8.09 (s, 1H, H$_{ar}$), 8.79 (s, 1H, H), 11.61 (s br, 1H, NH). LCMS: Rt 2.04 min (90.0%). MS (MH+, m/z) 379.

Example 3

N-(5-(1H-pyrazol-4-yl)[1,2,4]triazolo[1,5-a]pyrazin-8-yl)-4-(morpholinomethyl)thiazol-2-amine Step 1: N-(5-bromo-[1,2,4]triazolo[1,5-a]pyrazin-8-yl)-4-(morpholinomethyl)thiazol-2-amine

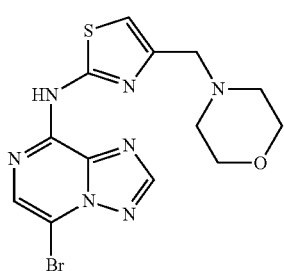 [SMILES: Brc1cnc(Nc2nc(CN3CCOCC3)cs2)c2ncnn12]

Intermediate 3 (5,8-Dibromo-[1,2,4]triazolo[1,5-a]pyrazine, 140 mg, 0.50 mmol), Intermediate 6 (4-(1-morpholinomethyl)thiazol-2-ylamine, 120 mg, 0.60 mmol), sodium tert-butoxide (68 mg, 0.71 mmol), palladium dibenzylidene acetone (19 mg, 0.02 mmol) and Xantphos (23 mg, 0.04 mmol) were suspended in toluene (4 mL). The mixture is degassed with nitrogen for 5 min and then stirred at 90° C. for 16 h. The solvent is evaporated in vacuo to leave a brown residue. The residue is purified by column chromatography, eluting with 2% methanolic ammonia (7 N) in dichloromethane to give the title compound as a yellow powder (53 mg, 27%). $^1$H NMR (400 MHz; d$_6$-DMSO) δ 2.53 (s, 4H, CH$_2$CH$_2$), 3.51 (s, 2H, CH$_2$), 3.61 (m, 4H, CH$_2$CH$_2$), 6.99 (s, 1H), 8.13 (s, 1H), 8.61 (s, 1H), 8.75 (s, 1H).

Step 2: N-(5-(1H-pyrazol-4-yl)-[1,2,4]triazolo[1,5-a]pyrazin-8-yl)-4-(morpholinomethyl)thiazol-2-amine

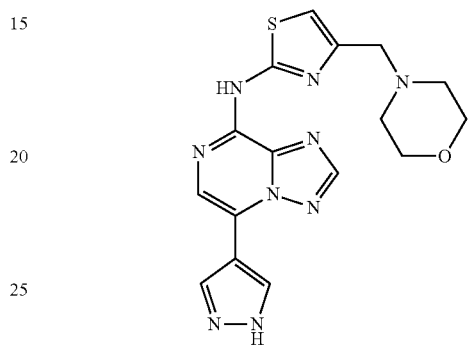

The product of Step 1 (43 mg, 0.11 mmol), 4-pyrazole boronic acid pinacol ester (32 mg, 0.16 mmol), tetrakis palladium triphenylphosphine (13 mg, 0.11 mmol) and sodium tert-butoxide are suspended in a mixture of DMF (2 mL) and water (0.66 mL). The reaction is degassed with nitrogen for 10 min before being sealed and stirred at 90° C. for 16 h. The reaction is condensed in vacuo and the residue purified by column chromatography, eluting with 3% methanolic ammonia (7 N) in dichloromethane to give the title compound as a pale yellow powder (12 mg, 29%). $^1$H NMR (400 MHz, d$_6$-DMSO) δ 2.48 (s, 4H, CH$_2$CH$_2$), 3.35 (s, 2H, CH$_2$), 3.63 (t, 4H, J=6 Hz, CH$_2$CH$_2$), 6.97 (s, 1H, H), 8.43 (s, 1H, H), 8.61 (brs, 2H), 8.81 (s, 1H, H), 12.9-12.4 (brs, 2H, NH×2). MS (MH+, m/z) 384.

Example 4

4-(8-(4-(piperidin-1-ylmethyl)thiazol-2-ylamino)-[1,2,4]triazolo[1,5-a]pyrazin-5-yl)furan-2-carboxamide Step 1: N-(5-bromo-[1,2,4]triazolo[1,5-a]pyrazin-8-yl)-4-(piperidin-1-ylmethyl)thiazol-2-amine

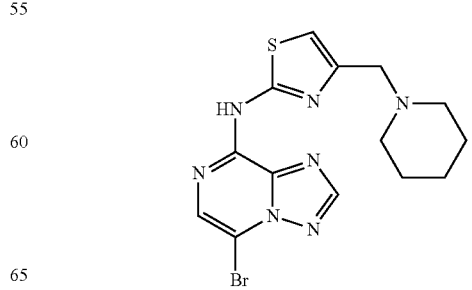

Prepared in a manner analogous to the procedure of Example 1, Step 1. NMR (400 MHz, d$_6$-DMSO) δ 1.42 (s, 2H), 1.53-1.55 (m, 4H), 2.37 (brs, 4H), 3.77 (s, 2H), 6.93 (s, 1H), 8.11 (s, 1H), 8.72 (s, 1H). MS (MH$^+$, m/z) 394.

Step 2: 4-(8-(4-(piperidin-1-ylmethyl)thiazol-2-ylamino)-1,2,41-triazolo[1,5-a]pyrazin-5-yl)furan-2-carboxamide

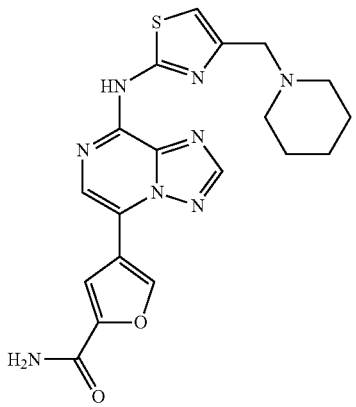 [SMILES: NC(=O)c1cc(-c2cnc(Nc3nc(CN4CCCCC4)cs3)c3ncnn23)co1]

The product of Step 1 (950 mg, 2.4 mmol), Intermediate 5 (4-(2-amido) furanyl boronic acid pinacol ester, 1.14 g, 4.8 mmol), tetrakis palladium triphenylphosphine (832 mg, 0.72 mmol), sodium carbonate solution (1.5 M, 12.8 mL, 19.2 mmol) and dioxane (15 mL) are combined in a flask. The mixture is degassed with nitrogen for 10 min then sealed and heated at 90° C. for 16 h. The solvent is evaporated to give a crude material which is purified by gradient column chromatography, eluting with 1-5% methanolic ammonia (7 N) in dichloromethane. The resulting yellow solid is triturated with 1:1 petrol:ether then 2:1 dichloromethane:ether to give the title compound (346 mg, 29%). NMR (400 MHz, d$_6$-DMSO) δ 1.43 (m, 2H, CH$_2$), 1.55 (m, 4H, CH$_2$CH$_2$), 2.45 (brs, 4H, CH$_2$CH$_2$), 3.50 (s, 2H, CH$_2$), 6.93 (s, 1H, H), 7.62 (s, 1H, H), 7.99 (s, 2H, H), 8.44 (s, 1H, H), 8.82 (d, 2H, J=5.2 Hz, H). LCMS: Rt 2.00 min (95.7%). MS (MH$^+$, m/z) 425.

Example 5

4-(8-(1-(2-morpholinoethyl)-1H-imidazol-2-ylamino)-[1,2,4]-triazolo[1,5-a]pyrazin-5-yl)furan-2-carboxamide Step 1: 5-bromo-N-(1-(2-morpholinoethyl)-1H-imidazol-2-yl)-[1,2,4]triazolo[1,5-a]pyrazin-8-amine

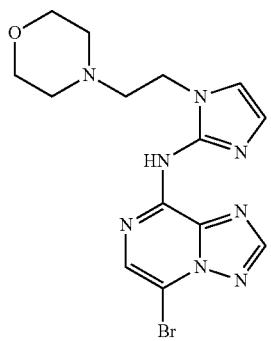 [SMILES: Brc1cnc(Nc2nccn2CCN2CCOCC2)c2ncnn12]

Prepared using Intermediate 3 and Intermediate 10 in a manner analogous to the procedure of Example 1, Step 1. NMR (400 MHz, CDCl3) δ 2.55 (brs, 4H), 2.71-2.80 (m, 2H), 3.68-3.83 (m, 4H), 4.15-4.26 (m, 2H), 6.92 (s, H), 7.05 (s, H), 7.71 (s, H), 8.31 (s, H), 8.58 (s, 1H).

Step 2: 4-(8-(1-(2-morpholinoethyl)-1H-imidazol-2-ylamino)-[1,2,4]triazolo[1,5-a]pyrazin-5-yl)furan-2-carboxamide

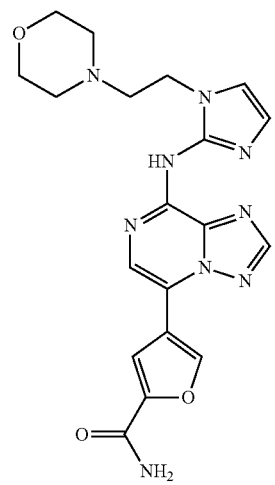 [SMILES: NC(=O)c1cc(-c2cnc(Nc3nccn3CCN3CCOCC3)c3ncnn23)co1]

Prepared in a manner analogous to the procedure of Example 3, Step 2.1H NMR (400 MHz, CDCl3) δ 2.54 (brs, 4H), 2.67-2.74 (m, 2H), 3.51-3.60 (m, 4H), 4.17 (brs, 2H), 6.95 (s, H), 7.13 (s, 1H), 7.58 (s, 1H), 7.80 (s, H), 7.94 (s, H), 8.01 (s, H), 8.17 (s, H), 8.55 (s, H), 8.68 (s, H). LCMS: Rt 2.37 min (93.0%). MS (MH$^+$, m/z) 424.

Examples 1-22 in Table 1 are made from the commercially available amino thiazoles and amino thiadiazoles and the Intermediates described above, or by procedures analogous to those described above.

TABLE 1

| Ex# | Structure | Name | MW | M + H+, m/z |
|---|---|---|---|---|
| 1 | 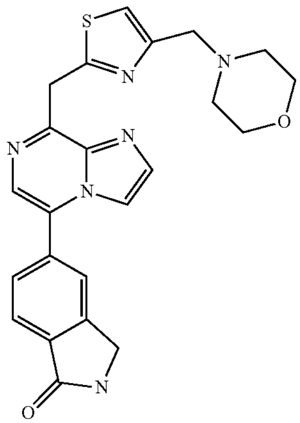 [SMILES: O=C1NCc2cc(-c3cnc(Cc4nc(CN5CCOCC5)cs4)c4nccn34)ccc21] | 5-(8-(4-(morpholinomethyl)thiazol-2-ylamino)imidazo[1,2-a]pyrazin-5-yl)isoindolin-1-one | 447.15 | 448 |
| 2 | 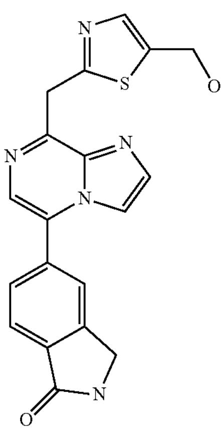 [SMILES: O=C1NCc2cc(-c3cnc(Cc4ncc(CO)s4)c4nccn34)ccc21] | 5-(8-(5-(hydroxymethyl)thiazol-2-ylamino)imidazo[1,2-a]pyrazin-5-yl)isoindolin-1-one | 482.22 | 379 |
| 3 | 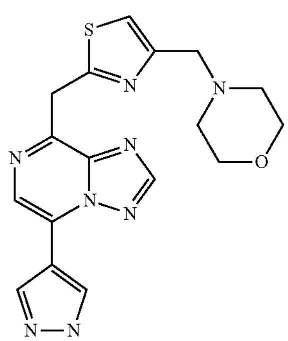 [SMILES: c1nc2c(Cc3nc(CN4CCOCC4)cs3)ncc(-c3cn[nH]c3)n2n1] | N-(5-(1H-pyrazol-4-yl)-[1,2,4]triazolo[1,5-a]pyrazin-8-yl)-4-(morpholinomethyl)thiazol-2-amine | 383.13 | 384 |
| 4 | 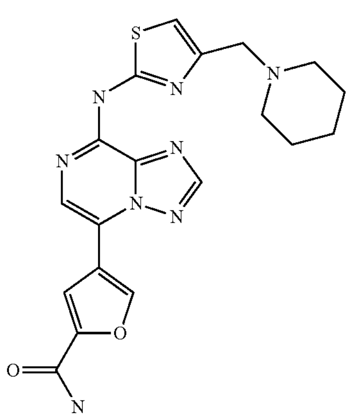 [SMILES: NC(=O)c1cc(-c2cnc(Nc3nc(CN4CCCCC4)cs3)c3ncnn23)co1] | 4-(8-(4-(piperidin-1-ylmethyl)thiazol-2-ylamino)-[1,2,4]triazolo[1,5-a]pyrazin-5-yl)furan-2-carboxamide | 424.14 | 425 |

TABLE 1-continued

| Ex# | Structure | Name | MW | M + H+, m/z |
|---|---|---|---|---|
| 5 | 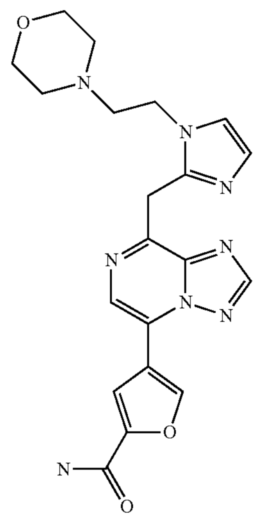 [SMILES: NC(=O)c1cc(-c2cnc(Cc3nccn3CCN3CCOCC3)c3ncnn23)co1] | 4-(8-(1-(2-morpholinoethyl)-1H-imidazol-2-ylamino)-[1,2,4]triazolo[1,5-a]pyrazin-5-yl)furan-2-carboxamide | 423.18 | 424 |
| 6 | 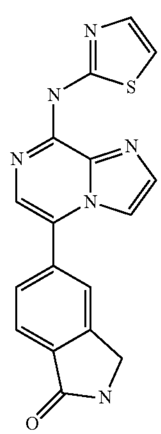 [SMILES: O=C1NCc2cc(-c3cnc(Nc4nccs4)c4nccn34)ccc21] | 5-(8-(thiazol-2-ylamino)imidazo[1,2-a]pyrazin-5-yl)isoindolin-1-one | 348.08 | 349 |
| 7 | 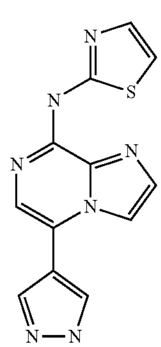 [SMILES: c1csc(Nc2ncc(-c3cn[nH]c3)n3ccnc23)n1] | N-(5-(1H-pyrazol-4-yl)imidazo[1,2-a]pyrazin-8-yl)thiazol-2-amine | 283.06 | 284 |

TABLE 1-continued

| Ex# | Structure | Name | MW | M + H+, m/z |
|---|---|---|---|---|
| 8 | 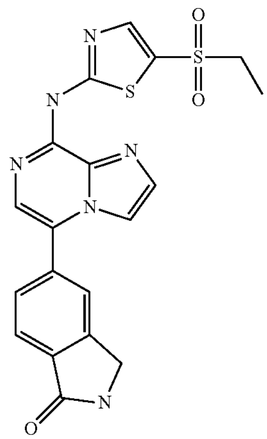 [SMILES: CCS(=O)(=O)c1cnc(Nc2ncc(-c3ccc4c(c3)CNC4=O)n3ccnc23)s1] | 5-(8-(5-(ethylsulfonyl)thiazol-2-ylamino)imidazo[1,2-a]pyrazin-5-yl)isoindolin-1-one | 440.07 | 441 |
| 9 | 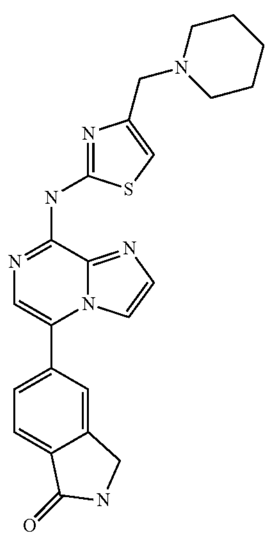 [SMILES: O=C1NCc2cc(-c3cnc(Nc4nc(CN5CCCCC5)cs4)c4nccn34)ccc21] | 5-(8-(4-(piperidin-1-ylmethyl)thiazol-2-ylamino)imidazo[1,2-a]pyrazin-5-yl)isoindolin-1-one | 445.17 | 446 |
| 10 | 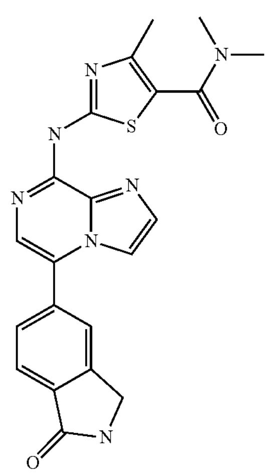 [SMILES: Cc1nc(Nc2ncc(-c3ccc4c(c3)CNC4=O)n3ccnc23)sc1C(=O)N(C)C] | N,N,4-trimethyl-2-(5-(1-oxoisoindolin-5-yl)imidazo[1,2-a]pyrazin-8-ylamino)thiazole-5-carboxamide | 433.13 | 434 |

TABLE 1-continued

| Ex# | Structure | Name | MW | M + H+, m/z |
|---|---|---|---|---|
| 11 | 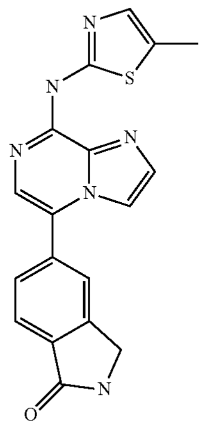 [SMILES: Cc1cnc(Nc2ncc(-c3ccc4c(c3)CNC4=O)n3ccnc23)s1] | 5-(8-(5-methylthiazol-2-ylamino)imidazo[1,2-a]pyrazin-5-yl)isoindolin-1-one | 362.09 | 363 |
| 12 | 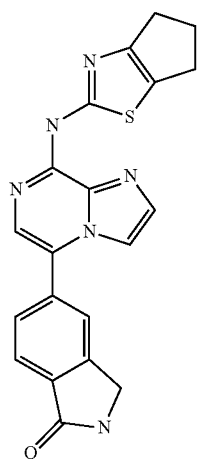 [SMILES: O=C1NCc2cc(-c3cnc(Nc4nc5c(s4)CCC5)c4nccn34)ccc21] | 5-(8-(5,6-dihydro-4H-cyclopenta[d]thiazol-2-ylamino)imidazo[1,2-a]pyrazin-5-yl)isoindolin-1-one | 388.11 | 389 |
| 13 | 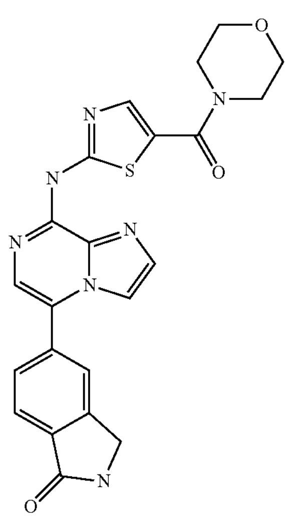 [SMILES: O=C1NCc2cc(-c3cnc(Nc4ncc(C(=O)N5CCOCC5)s4)c4nccn34)ccc21] | 5-(8-(5-(morpholine-4-carbonyl)thiazol-2-ylamino)imidazo[1,2-a]pyrazin-5-yl)isoindolin-1-one | 461.13 | 462 |

TABLE 1-continued

| Ex# | Structure | Name | MW | M + H+, m/z |
|---|---|---|---|---|
| 14 | 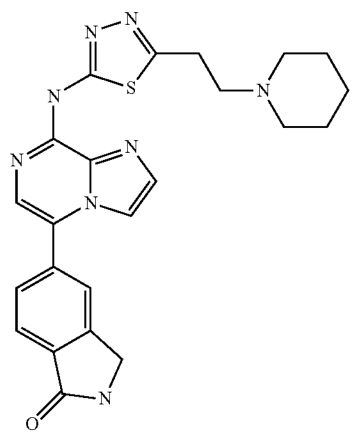 [SMILES: O=C1NCc2cc(-c3cnc(Nc4nnc(CCN5CCCCC5)s4)c4nccn34)ccc21] | 5-(8-(5-(2-(piperidin-1-yl)ethyl)-1,3,4-thiadiazol-2-ylamino)imidazo[1,2-a]pyrazin-5-yl)isoindolin-1-one | 460.18 | 461 |
| 15 | 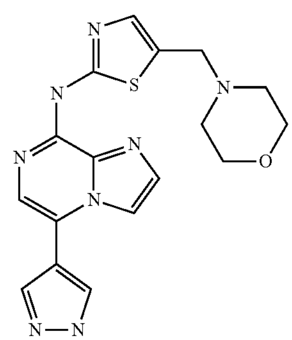 [SMILES: c1cn2c(-c3cn[nH]c3)cnc(Nc3ncc(CN4CCOCC4)s3)c2n1] | N-(5-(1H-pyrazol-4-yl)imidazo[1,2-a]pyrazin-8-yl)-5-(morpholinomethyl)thiazol-2-amine | 382.13 | 383 |
| 16 | 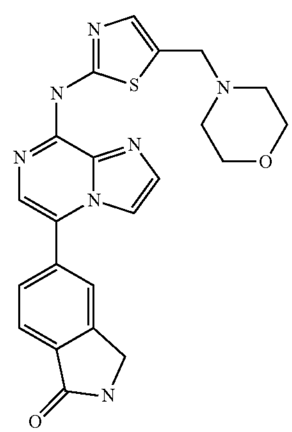 [SMILES: O=C1NCc2cc(-c3cnc(Nc4ncc(CN5CCOCC5)s4)c4nccn34)ccc21] | 5-(8-(5-(morpholinomethyl)thiazol-2-ylamino)imidazo[1,2-a]pyrazin-5-yl)isoindolin-1-one | 447.15 | 448 |
| 17 | 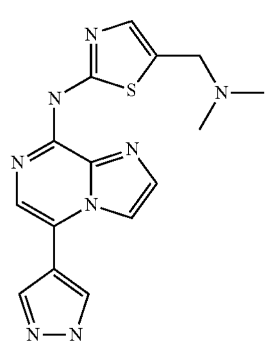 [SMILES: CN(C)Cc1cnc(Nc2ncc(-c3cn[nH]c3)n3ccnc23)s1] | N-(5-(1H-pyrazol-4-yl)imidazo[1,2-a]pyrazin-8-yl)-5-((dimethylamino)methyl)thiazol-2-amine | 340.12 | 341 |

TABLE 1-continued

| Ex# | Structure | Name | MW | M + H+, m/z |
|---|---|---|---|---|
| 18 | 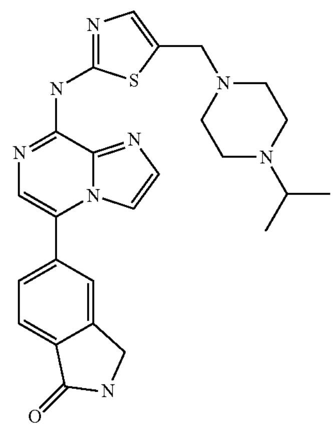 [SMILES: CC(C)N1CCN(Cc2cnc(Nc3ncc(-c4ccc5c(c4)CNC5=O)n4ccnc34)s2)CC1] | 5-(8-(5-((4-isopropylpiperazin-1-yl)methyl)thiazol-2-ylamino)imidazo[1,2-a]pyrazin-5-yl)isoindolin-1-one | 488.21 | 489 |
| 19 | 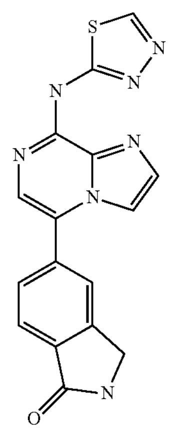 [SMILES: O=C1NCc2cc(-c3cnc(Nc4nncs4)c4nccn34)ccc21] | 5-(8-(1,3,4-thiadiazol-2-ylamino)imidazo[1,2-a]pyrazin-5-yl)isoindolin-1-one | 349.07 | 350 |
| 20 | 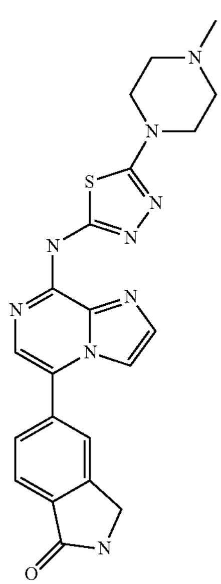 [SMILES: CN1CCN(c2nnc(Nc3ncc(-c4ccc5c(c4)CNC5=O)n4ccnc34)s2)CC1] | 5-(8-(5-(4-methylpiperazin-1-yl)-1,3,4-thiadiazol-2-ylamino)imidazo[1,2-a]pyrazin-5-yl)isoindolin-1-one | 447.16 | 448 |

TABLE 1-continued

| Ex# | Structure | Name | MW | M + H+, m/z |
|---|---|---|---|---|
| 21 | 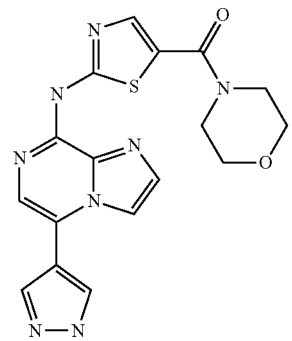 [SMILES: O=C(c1cnc(Nc2ncc(-c3cn[nH]c3)n3ccnc23)s1)N1CCOCC1] | (2-(5-(1H-pyrazol-4-yl)imidazo[1,2-a]pyrazin-8-ylamino)thiazol-5-yl)(morpholino)methanone | 396.11 | 397 |
| 22 | 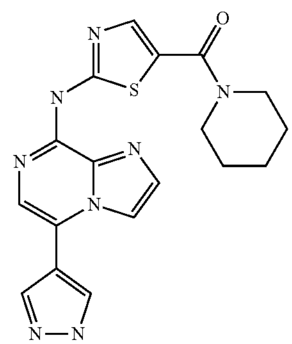 [SMILES: O=C(c1cnc(Nc2ncc(-c3cn[nH]c3)n3ccnc23)s1)N1CCCCC1] | (2-(5-(1H-pyrazol-4-yl)imidazo[1,2-a]pyrazin-8-ylamino)thiazol-5-yl)(piperidin-1-yl)methanone | 394.13 | 395 |
| 23 | 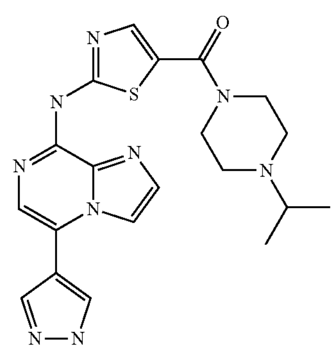 [SMILES: CC(C)N1CCN(C(=O)c2cnc(Nc3ncc(-c4cn[nH]c4)n4ccnc34)s2)CC1] | (2-(5-(1H-pyrazol-4-yl)imidazo[1,2-a]pyrazin-5-ylamino)thiazol-5-yl)(4-isopropylpiperazin-1-yl)methanone | 437.17 | 438 |
| 24 | 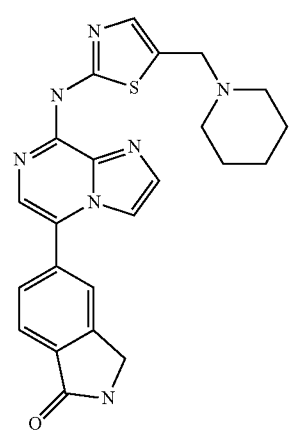 | 5-(8-(5-(piperidin-1-ylmethyl)thiazol-2-ylamino)imidazo[1,2-a]pyrazin-5-yl)isoindolin-1-one | 445.17 | 446 |

TABLE 1-continued

| Ex# | Structure | Name | MW | M + H+, m/z |
|---|---|---|---|---|
| 25 | 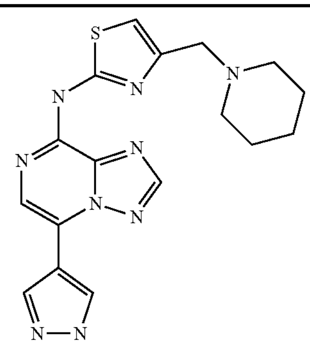 | N-(5-(1H-pyrazol-4-yl)-[1,2,4]triazolo[1,5-a]pyrazin-8-yl)-4-(piperidin-1-ylmethyl)thiazol-2-amine | 381.15 | 425 |

Purification Conditions and Characterization

Routinely, post-synthesis all compounds may be purified using reverse phase HPLC using a Gilson preparative HPLC system (322 pump, 155 UV/VIS detector, 215 liquid handler). The Gilson 215 acts as both auto-sampler and fraction collector. Compounds can also be purified by flash chromatography on silica gel.

Compounds are characterised by mass spectrometry using single quadrupole instrumentation with an electrospray source.

Biological Assays Demonstrating the Usefulness of the Compounds

Example 1

MAPKAP-K5 Assay

MAPKAP-K5 reactions are performed in FlashPlate format using 0.1 or 0.2 µCi 33P-ATP; 0.6 µM ATP; 1 mU MAPKAP-K5; 3 µM MAPKAP-K5 peptide substrate, incubated at room temperature for 30 minutes.

Flashplate Assay:

The MAPKAP-K5 kinase reaction is performed in a 384 well polypropylene plate (Matrix Technologies) and then transferred to a streptavidin-coated 384 well flashplate (Perkin-Elmer). To wells containing 2 µL test compound or standard inhibitor, 13 µL Enzyme mix or diluent are added using a Hydra (Robbins Scientific). Reactions are started by addition of 10 µL of [2.5×] substrate cocktail using a Multidrop (Thermo-Labsystems), to give final concentrations in the assay of:

1 mU MAPKAP-K5
3 µM MAPKAP-K5 peptide substrate
~0.6 µM ATP
0.004 µCi [33P]-γ-ATP/µL
1× reaction buffer Plates are incubated at room temperature for 30 minutes. Reactions are terminated by the addition of 254, EDTA (50 mM) to each well using a Micro-fill (Biotek). Reactions are transferred to a streptavidin-coated flashplate using a Zymark robotic system. Plates are incubated for 60 minutes at room temperature. All wells are washed 3 times with 100 µL phosphate buffered saline using a Tecan plate washer. Radioactivity is determined by scintillation counting of the flashplate (empty wells) on a Packard TopCount.

Enzyme Mix:
  Enzyme
  50 mM Tris Hcl (pH 7.5)
  0.1 mM EGTA
  2 mM DTT
  1 mg/ml BSA
Reaction Buffer:
  50 mM Tris Hcl (pH 7.5)
  0.1 mM EGTA
  10 mM Magnesium acetate
  2 mM DTT Example 2

Development of an Assay for the Identification of Regulators of the Expression of MMP1 by Activated Primary Synovial Fibroblasts To identify compounds that decrease the ECM-degrading activity of cells, the ECM-degrading activity of cells may be induced to allow proper detection of this activity, and to achieve a clearer read-out. In the context of RA, the cells of choice are mammalian synovial fibroblasts and the triggers that may be used to induce the ECM-degrading activity are cytokines relevant in the field of arthritis: for instance TNF-α, IL1β, IL6, OSM, IL17, and MIF1-α. This list is not comprehensive due to the plethora of cytokines potentially involved in the RA pathogenesis (Smolen and Steiner, 2003). To set up an in vitro assay that is as close as possible to the complexity of the pathology, the trigger applied should be a mixture of factors generated by contacting cytokine-producing cells relevant in the field of arthritis, such as monocytes, macrophages, T-cells, and B-cells, with a trigger. The cytokine-producing cells will respond to the contact by producing a complex and unbiased mixture of factors. If the cytokine-producing cell used is also found in a pannus, and the cytokine applied to produce this trigger is found in the synovial fluid of rheumatoid arthritis patients, the mixture of factors ultimately produced will contain part of the factors that are present in the joints of arthritis patients.

Principle of the 'MMP Assay'

Matrix Metallo Proteases (MMPs) possess various physiological roles, as e.g. the maturation of other proteases, growth factors, and the degradation of extra-cellular matrix components. MMP1 is one of the members of the MMP family that is able to degrade native collagen, the main component of bone and cartilage. An increased expression of MMP1 by synovial fibroblasts (SFs) is diagnostic for the progression of the arthritic disease and is predictive for erosive processes in the joint (Cunnane et al., 2001). The expression of MMP1 by SFs can be increased by the activation of SFs with triggers relevant for rheumatoid arthritis, as cytokines like TNF-α or IL1β (Andreakos et al., 2003). Taken together, measurement of the levels of MMP1 produced by activated SFs is a readout that is highly relevant in the context of RA as this event reflects the level of activation of SFs towards an erosive phenotype as it is seen in the pannus. If a reduced expression of a candidate drug target in activated SFs leads to the reduction of MMP1 expression by these cells, the drug target is then proven to be involved in the regulation of MMP1 expression and thus considered relevant for the development of therapeutic strategies for the treatment of RA.

In the following examples, the development of an assay, further referred to as 'MMP assay', monitors the MMP1 production by synovial fibroblasts (SFs) in response to diverse activating triggers (Example 2.1). The use of this assay is then described for the validation of gene products that are considered drug targets for the development of RA therapies (Example 2.2). The validation of drug targets is performed using recombinant adenoviruses, further referred to as knock-down viruses or Ad-siRNAs, that mediate the expression in cells of shRNA's which reduce the expression levels of targeted genes by a RNAi (RNA interference)-based mechanism (see WO 03/020931). The identification of compounds modulating the activity of the validated drug targets is then described in Table B. The use of the 'MMP assay' for the testing of compounds that modulate the activity of the drug targets identified is described further below.

Control Viruses Used:

The control viruses used in these studies are listed below. dE1/dE2A adenoviruses are generated from these adapter plasmids by co-transfection of the helper plasmid pWEAd5AflII-rITR.dE2A in PER.E2A packaging cells, as described in WO99/64582.

Negative Control Viruses:

Ad5-eGFP_KD: Target sequence: GCTGACCCTGAAGT-TCATC (SEQ ID NO: 1). Cloned using Sap1-sites into vector and virus generated as described in WO03/020931.

Ad5-Luc_v13_KD: Target sequence GGTTACCTAAGGGT-GTGGC (SEQ ID NO: 2). Cloned using Sap1-sites into vector and virus generated as described in WO03/020931.

Ad5-M6PR_v1_KD: Target sequence CTCTGAGTGCAGT-GAAATC (SEQ ID NO: 3). Cloned using Sap1-sites into vector and virus generated as described in WO03/020931.

Positive Control Viruses:

Ad5-MMP1_v10_KD: Target sequence ACAAGAGCAA-GATGTGGAC (SEQ ID NO: 4). Cloned using Sap1-sites into vector and virus generated as described in WO03/020931.

Viruses Used for Target Validation:

Ad5-MAPKAPK5_v13_KD: Target sequence CGGCACTT-TACAGAGAAGC (SEQ ID NO: 5). Cloned using Sap1-sites into vector and virus generated as described in WO03/020931.

Ad5-MAPKAPK5_v12_KD: Target sequence ATGATGT-GTGCCACACACC (SEQ ID NO: 6). Cloned using Sap1-sites into vector and virus generated as described in WO03/020931.

Example 2.1

Development of the MMP Assay

A 384-well format ELISA for measurement of MMP1 is developed. Various primary antibodies are tested, as well as various ELISA protocols. The following protocol is developed and validated to measure MMP1 levels in SF supernatant in 384 well plates: white Lumitrac 600 384 well plates (Greiner) are coated with 2 μg/mL anti-MMP1 antibody MAB1346 (Chemicon). The antibody is diluted in buffer 40 (1.21 g Tris base (Sigma), 0.58 g NaCl (Calbiochem) and 5 ml 10% $NaN_3$ (Sigma) in 1 L milliQ water and adjusted to pH 8.5). After overnight incubation at 4° C., plates are washed with PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 μL/well Casein buffer (2% Casein (VWR International) in PBS). Next day, casein buffer is removed from ELISA plates and replaced by 50 μL/well EC buffer (4 g casein, 2.13 g $Na_2HPO_4$ (Sigma), 2 g bovine albumin (Sigma), 0.69 g $NaH_2PO_4.H_2O$ (Sigma), 0.5 g CHAPS (Roche), 23.3 g NaCl, 4 mL 0.5 M EDTA pH 8 (Invitrogen), 5 mL 10% $NaN_3$ in 1 L milliQ and adjusted to pH 7.0). 0.25 mM DTT (Sigma) is added to the thawed samples plates. After removal of the EC buffer, 20 μL of sample is transferred to the ELISA plates. After overnight incubation at 4° C. plates are washed twice with PBS and once with PBST (PBS with 0.05% Tween-20 (Sigma)) and incubated with 35 μL/well biotinylated anti-MMP1 antibody solution (R&D). This secondary antibody is diluted in buffer C (0.82 g $NaH_2PO_4.H_2O$, 4.82 g $Na_2HPO_4$, 46.6 g NaCl, 20 g bovine albumin and 4 mL 0.5M EDTA pH 8 in 2 L milliQ and adjusted to pH 7.0) at a concentration of 5 μg/mL. After 2 h of incubation at RT, plates are washed as described above and incubated with 50 μL/well streptavidin-HRP conjugate (Biosource). Streptavidin-HRP conjugate is diluted in buffer C at a concentration of 0.25 μg/mL. After 45 min, plates are washed as described above and incubated for 5 min with 50 μL/well BM Chem ELISA Substrate (Roche). Readout is performed on the Luminoscan Ascent Luminometer (Labsystems) with an integration time of 200 msec or with an Envision reader (Perkin Elmer).

Figure 2:
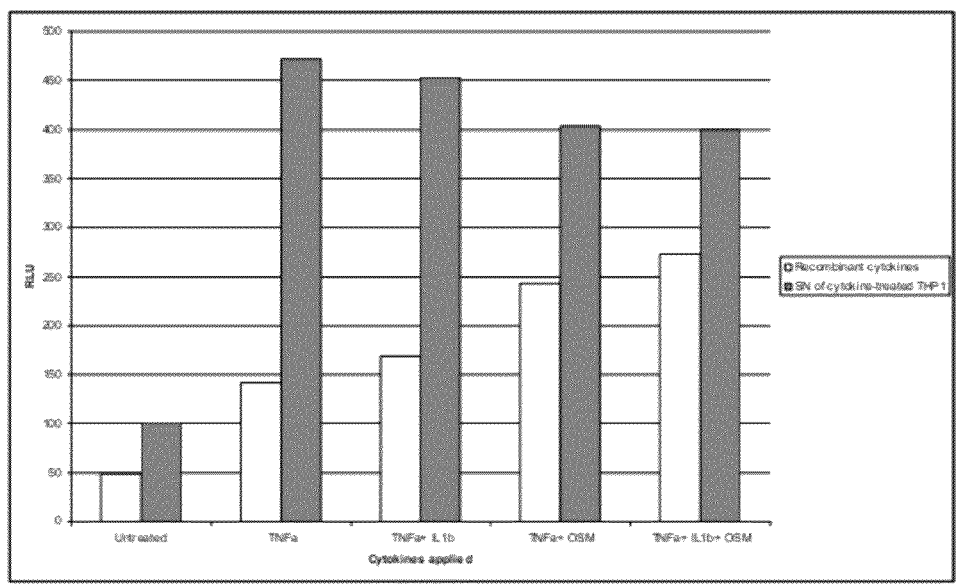
FIG. 2. This chart shows the increased expression of MMP1 in synovial fibroblasts triggered with cytokines involved in rheumatoid arthritis pathology.

The increase of MMP1 expression by SFs upon treatment with cytokines relevant in the field of RA (TNF-α, IL1β and OSM) or a combination thereof is shown in FIG. 2 as white bars. For this experiment, SFs are seeded in 96 well plates, 3,000 cells/well. 24 h later, the medium is changed to M199 medium supplemented with 1% FBS. One day after the medium change, cytokines or combinations thereof are added to the cultures, each cytokine being added to a final concentration of 25 ng/mL. 72 h after cytokine addition, the supernatant is collected and processed in the MMP1 ELISA as described in the protocol given above. In parallel with this experiment, SFs are triggered, using the same protocol, with the supernatant of THP1 cells (2-fold diluted in M199+1% FBS) treated with the same cytokines or combinations of cytokines for 48 h in M199 medium+1% FBS. MMP1 levels for these samples are shown in FIG. 2 as grey bars. The induction of the MMP1 expression by SFs triggered with the supernatants of TNF-α-treated THP1 cells is stronger (>4.5 fold induction) as compared to the SFs triggered with recombinant TNF-α alone (3-fold induction) and almost equals the 5-fold induction obtained by a mixture of 3 purified cytokines (TNF-α, IL1βb, OSM). This result indicates that the supernatant of TNF-α-induced THP1 cells contains, besides TNF-α, additional pro-inflammatory factors that activate SFs towards MMP1 expression. As the role of TNF-α in the RA pathogenesis is validated (TNF-α-blockers such as Infliximab and Etanercept show some efficacy in the treatment of RA patients) and the THP-1 cells are representative for monocytes/macrophages present in the joint of RA patients, the TNF-α-based trigger mixture prepared by contacting THP-1 cells with TNF-α will contain factors present in the joints of RA patients and subsequently is relevant to RA. This TNF- α-based complex trigger, further referred to as the 'complex trigger', will further be used as basis for the 'MMP assay'.

Figure 3:
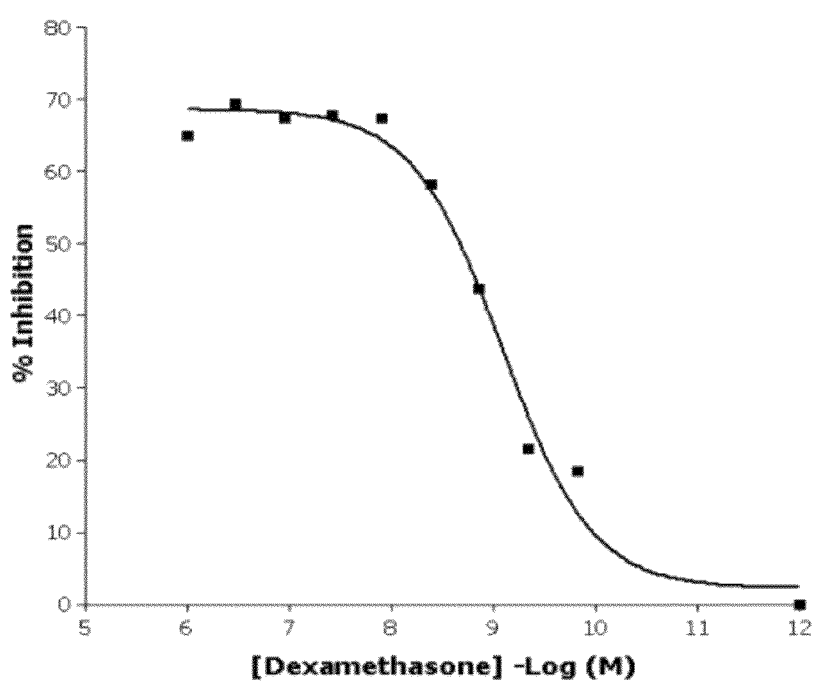
FIG. 3. This graph shows the dose-dependent inhibition of the "TNF-α-based trigger"-induced expression of MMP1 by SFs by a known anti-inflammatory compound.

Inhibition of the activation of SF by the 'complex trigger' is shown using dexamethasone, a potent anti-inflammatory agent that also strongly reduces collagen-induced arthritis in rodents (Yang et al., 2004) (FIG. 3). Dexamethasone is shown to dose-dependently reduce amounts of MMP1 produced by complex trigger activated SFs. SFs are seeded at a density of 3000 cells/well in 96 well plates. 24 hrs after seeding, increasing concentrations of dexamethasone are added to the cells. After overnight incubation, medium of every well is refreshed to supernatant of THP-1 cells treated with TNF-α (50% diluted in M199+0.5% FBS), and the same concentration of dexamethasone as added the day before. 48 hrs after treatment, the supernatant is collected and subjected to the MMP1 ELISA described above. The addition of dexamethasone clearly reduced the MMP1 expression by SFs, with an $IC_{50}$ value of about 1 nM (see FIG. 3). These data show that the MMP1 expression by activated SFs can be reduced by the addition of a physiologically relevant inhibitor and represent a proof of principle for the 'MMP assay'.

Example 2.2

MAPKAPK5 Modulates SF 'Complex Trigger'-Induced MMP1 Expression (A) Ad-siRNA Virus Functions to Knock Down MAPKAPK5 Expression.

Recombinant adenoviruses mediating the expression of siRNA's targeting MAPKAPK5 and eGFP are generated according to the procedure described in WO03/020931. The target sequence used in the recombinant adenovirus is: CGGCACTTTACAGAGAAGC (SEQ ID NO: 5) as well as ATGATGTGTGCCACACACC (SEQ ID NO: 6). The target sequence within the eGFP mRNA used in the recombinant adenovirus is: GCTGACCCTGAAGTTCATC (SEQ ID NO: 1). These sequences are cloned into the adapter plasmid using Sap1 sites. dE1/dE2A adenoviruses are generated from these adapter plasmids by co-transfection of the helper plasmid pWEAd5AflII-rITR.dE2A in PER.E2A packaging cells, as described in WO99/64582.

Figure 4:
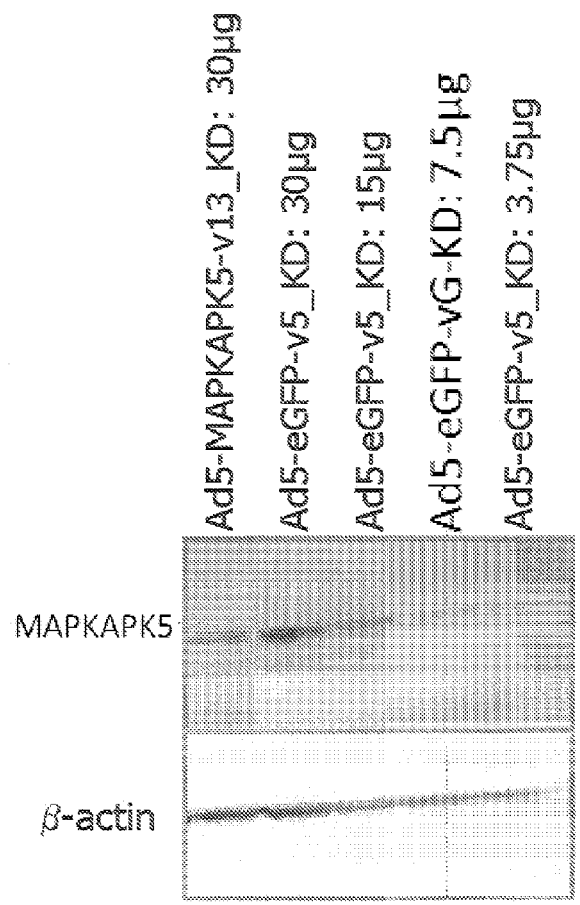
FIG. 4. This gel shows the reduction, at the protein level, of the expression of MAPKAPK5 in SFs by infection of the cells with Ad-siRNA virus targeting MAPKAPK5.

The functionality of an adenovirus targeting MAPKAPK5 is tested as follows. These adenoviruses are used to infect primary human SFs cultured in petri dishes as follows. On day 1, 500.000 SFs are seeded per petri dish. One day later, the cells are infected with Ad5-MAPKAPK5-v13_KD (1.6E9 VP/mL) or Ad5-eGFP-v5_KD (1.3E10 VP/mL) at an MOI of 4000 (based on the titers (number of virus particles per mL) defined for the viruses by Q-rt-PCR). On day 7, cells are detached from the petri dish according to standard procedure using a trypsin EDTA solution. The trypsin is then neutralized by addition of DMEM growth medium supplemented with 10% FBS. The cells are then collected by a centrifugation step (1000 rpm, 5 min). The pellet is lysed in 100 µL of fresh RIPA buffer (50 mM Tris pH7.5, 150 mM NaCl, 1% deoxycholate, 1% Triton X100, 0.1% SDS). The samples are then sonicated for 10 sec. The protein concentration of the samples is then determined using the BCA kit (Pierce, Cat N° 23227) as described by the provider, using BSA as a standard. To 30 µg of cell lysate diluted to 19.5 µl in RIPA buffer, 3.5 µL of reducing agent (NuPage reducing agent N°10, Invitrogen NP0004) and 7.5 µL of sample buffer (NuPage LDS sample buffer, Invitrogen NP0007) are added. The 30 µL sample is then boiled for 5 min and loaded on a 10% polyacrylamide gel (Invitrogen NP0301). To allow the estimation of the level of protein knock-down, 15 µg, 7.5 µg and 3.75 µg of the lysate of the Ad5-eGFP-v5_KD infected cells are also loaded onto the gel. The gel is then run for 2 hours at 100V in 1×MOPS/SDS NuPage running buffer (Invitrogen NP001). 10 µl of Seablue Plus Prestained standard (Invitrogen LC5925) is used to estimate protein size on the gel. The proteins on the gel are then transferred onto a PVDF membrane (Invitrogen LC2002) by a wet blotting procedure using a transfer buffer prepared by mixing 100 ml Nupage Transfer buffer 20* (NP0006-1), 400 mL methanol and 1500 mL Milli Q water. Before the transfer, the membrane is first soaked in methanol and in transfer buffer. The transfer is performed at 100V for 90 minutes. The membrane is then blocked by 30 min soaking in blocking buffer (2% blocking blocking powder (Amersham, RPN 2109) prepared in PBST (PBS supplemented with 0.1% Tween 20 (Sigma, P1379)). After blocking, the immunodetection is performed using a mouse monoclonal antibody against MAPKAPK5 (BD Biosciences, Cat N°612080) diluted 250 fold in blocking buffer. After overnight incubation with this primary antibody, the membrane is washed 3 times with PBST and incubated 1 hr with the secondary antibody ((Polyclonal goat anti-mouse Ig, I-IRP conjugated (DAKO P0447) diluted 50000 fold in blocking buffer. The blot is then washed 3 times in PBST and the detection is performed with ECL advance (RPN2109, Amersham) on a Kodakimager according to the manufacturers instructions. The Western Blotting revealed a lower expression level of MAPKAPK5 in the Ad5-MAPKAPK5-v13_KD infected cells compared to the cells infected with the Ad5-eGFP-v5_KD negative control virus. Comparison with the diluted Ad5-eGFP-v5_KD infected samples allowed to estimate the reduction in expression to be 2-fold. Equal loading of the 30 µg samples is demonstrated by immunodetection of β-actin after removal of the MAPKAPK5 antibody by a 'stripping procedure' (5 minutes boiling of the membrane in PBST). Immunodetection of β-actin is performed according to the method described for MAPKAPK5 detection, but using a goat polyclonal antibody against β-actin (Santa Cruz, Cat N° SC-1615) at a 1000 fold dilution as primary antibody and a rabbit anti goat antibody at a 50000 fold dilution as a secondary antibody. Results of this experiment are given in FIG. 4. Taken together, this experiment demonstrated the functionality of the Ad-siRNA virus produced to reduce the MAPKAPK5 expression levels in primary human SFs.

(B) MAPKAPK5 Knock-Down Ad-siRNA Reduces SF-Induced MMP1 Expression

Figure 5:
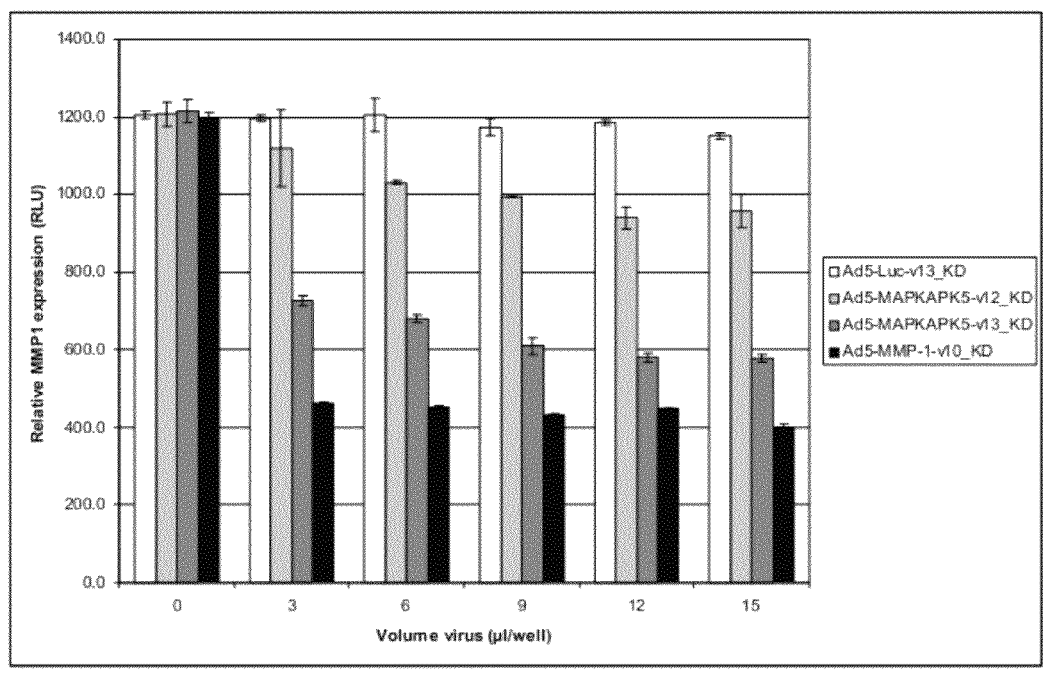
FIG. 5. This chart shows the reduction of 'complex trigger' induced levels of MMP1 expression by SFs by an Ad-siRNA virus targeting MAPKAPK5.

The efficacy of Ad5-MAPKAPK5-v13_KD virus in the 'MMP assay' is tested as follows. Day 1, SFs (passage 9 to 10) are seeded in 96 well plates at a density of 3000 cells per well in complete synovial growth medium (Cell Applications). One day later, the cells are infected with increasing amounts (3, 6; 9, 12 or 15 µl) of following viruses: Ad5-eGFP-v5_KD, Ad5-MAPKAPK5-v12_KD, Ad5-MAPKAPK5-v13_KD, Ad5-MMP1-v10_KD. The virus load is corrected by addition of the neutral virus Ad5-Luc-v13_KD to bring the final virus volume on the cells to 15 µL in every well. This correction guarantees that the effects observed do not result from the virus load applied to the cells. The cells are then incubated for 5 days before the activation step. This step involves the replacement, in every well, of the growth medium by 75 of M199 medium supplemented with 25 µL of 'complex trigger'. 48 hrs after the activation step, the supernatant is collected and subjected to the MMP1 ELISA as described in Example 1. The results of the experiment are shown in FIG. 5. The quality of the experiment is demonstrated by the efficacy of the Ad-siRNA virus targeting MMP1 itself. This positive control virus strongly reduces the MMP1 expression by SFs, whereas the negative control virus, designed to target the expression of luciferase, does not influence the levels of MMP1 expression. Two viruses used to validate the MAP-KAPK5 target (Ad5-MAPKAPK5-v12_KD and Ad5-MAPKAPK5-v13) do also lead to a clear reduction of the complex trigger induced MMP1 expression by primary human SFs. It can be concluded, from this experiment, that MAPKAPK5 represents a valuable drug target that is shown to modulate MMP1 expression in SFs. Similarly, the inhibition of MAPKAPK5 enzymatic activity by a small molecule compound is expected to reduce the 'complex cytokine' induced MMP1 expression in the 'MMP assay'. The inhibition of MAPKAPK5 enzymatic activity by a small molecule compound is also predicted to reduce the degradation of the joint associated with RA.

(C) In Vitro 'MMP Assay' Testing of Compounds Inhibiting MAPKAPK5

Compounds inhibiting the MAPKAPK5 activity in a biochemical assay (i.e. cell free, using purified enzyme), are tested in the 'MMP assay' according to following protocol.

The compound master stocks (all at 10 mM concentration in 100% DMSO) are diluted 10-fold in water (Distilled water, GIBCO, DNAse and RNAse free) to obtain a 1 mM intermediate work stock in 10% DMSO. This intermediate work stock is further diluted either 3-fold (or 10-fold) in 10% DMSO to obtain an intermediate work stock of 333 µM (or 100 µM) concentration, respectively, in 10% DMSO. The 1 mM as well as 333 µM (or 100 µM) intermediate work stocks are then further diluted 10-fold in 1.1% DMSO to obtain the 10× workstocks at 100 µM and 33.3 µM (or 10 µM) concentration in 2% DMSO. This 10× work stock is then diluted 10-fold in M199 medium supplemented with 1% FBS to obtain the final '1× compound preparation' containing the compounds at 10 µM and 3.33 µM (or 1 µM) as well as 0.2% DMSO. These are the final conditions at which the compounds are tested on the cells. In parallel, the 10× work stock is diluted 10-fold in 'complex trigger' (i.e. the supernatant of TNF-α treated THP1 cells produced as described in Example 1) that is diluted 2-fold in M199 supplemented with 1% FBS to produce the '1× compound in 50% complex trigger preparation'.

At day 1, RASFs are seeded in 96 well plates (Flat bottom, tissue culture treated, Greiner) at a density of 3000 cells/well in complete synovial growth medium (Cell Applications). Day 5, the compounds are added to the cultured cells as follows. Medium is completely removed from the cells and replaced by 75 µL of the '1× compound preparations' containing the compounds at either 10 µM or 3.33 µM (or 1 µM) in M199 medium supplemented with 1% FBS and 0.2% DMSO. After an incubation period of 2 hours, which allows the compounds to equilibrate and enter the cells; 25 µL of the '1× compound in 50% complex trigger preparations' are added to the wells on top of the '1× compound preparation', in the wells containing the corresponding compounds at corresponding concentration. In this way, an 8-fold diluted complex trigger is ultimately applied to the cells. An incubation of 48 hrs is then performed and 200 of the cell supernatant is then processed in the MMP1 ELISA as described above, delivering raw data (RLU: relative luminescence units). Following controls are included in the experiments. A maximal signal control, in which the cells are activated by the complex trigger but only the 0.2% DMSO vehicle (and thus no compound) is added. This control indicates the maximal level of MMP1 that can be achieved in the test. A minimal signal control is also included in these experiments. Here, cells are not triggered. The medium of the cells is then changed to 100 µl M199 medium supplemented with 1% FBS at day 5. This control returns the basal MMP1 levels produced by the RASFs. The percent inhibition of the MMP1 expression achieved by the compounds is then calculated based on the RLU data returned by the ELISA with following formula: [[(maximal MMP1 levels−minimal MMP1 levels)−(MMP1 level compound X at concentration Y−minimal MMP1 levels)]/(maximal MMP1 levels−minimal MMP1 levels)]×100.

Toxicity of the compounds is assessed as follows. Day 1, SFs are seeded in white, tissue culture treated 96 well plates at a density of 3000 cells per well in 100 µL complete synovial growth medium. The compound handling, compound addition to the cells as well as activation of the cells is further performed as described above in this example for the determination of the MMP1 levels. After the 48 hrs incubation period, the medium is removed from the wells, replaced by 50 µL fresh M199 medium supplemented with 1% FBS. 50 µL of substrate (Promega Celltiter Glow cell viability kit) is then added to the wells. After an incubation period of 10 min, luminescence signal is measured. A reduction of the luminescence signal by more than 50% as compared to the maximal control wells is considered to reflect significant toxicity. No toxicity is observed for the compounds tested in the 'MMP assay'.

It should be understood that factors such as the differential cell penetration capacity of the various compounds can contribute to discrepancies between the activity of the compounds in the in vitro biochemical and cellular MMP assays.

Example 3

Assay to Assess Effect of Compounds on Cytokine Release by Human PBMCs

Human peripheral blood mononuclear cells (PBMCs) are isolated from "buffy coats" prepared from the blood of healthy volunteers, isolated essentially according to method of Bøyum (1984). In brief, buffy coat is diluted 1:1 with 1×PBS (Gibco) and 30 mL is carefully put on top of 20 mL Lymphoprep™ (Lucron Bioproducts) in 50 mL Falcon tubes. After centrifugation (35 min, 400 g, 18° C.) the mononuclear cells are collected from the white interphase and washed 3 times with 1×PBS by resuspending and centrifugation (10 min, 200 g). Isolated PBMCs are finally resuspended in RPMI 1640 (Cat. No. 21875, Gibco) that is supplemented with 10% heat-inactivated FBS (Hyclone).

For the assay PBMCs are seeded at 2.5E6 cells/mL in 160 µL in 96-well plates (Nunc). Serial dilution of the test compounds are made first in DMSO (Sigma) and then diluted 50-fold in M199 medium (Gibco) containing 1% heat-inactivated FBS. Compounds are further 1/10 diluted in the assay plates to obtain final DMSO concentration of 0.2%. Cells are preincubated with the compounds for 1 hr at 37° C., 5% $CO_2$. Then, cells are stimulated with LPS (*Escherichia coli* serotype 026:B6, Cat. No. L2654, Sigma) that is added in a volume of 20 µL to a final concentration of 1 µg/mL and cells are further cultured for 24 hr. The plates are centrifuged and the supernatant is collected and stored at −80° C. until analysis of appropriate dilutions in ELISAs.

The following 384-well chemiluminescent ELISA protocol was developed to measure TNFα levels in the supernatant: White Lumitrac 600 384-well plates (Greiner) are coated with (40 µL/well) anti-TNFα capture antibody (Cat. No. 551220, BD Pharmingen) that is diluted to 1 µg/mL in 1×PBS (Gibco). After overnight incubation at 4° C., plates are washed with 1×PBS (80 g NaCl, 2 g KCl (Sigma), 11.5 g $Na_2HPO_4.7H_2O$ and 2 g $KH_2PO_4$ in 10 L milliQ; pH 7.4) and blocked with 100 µL/well buffer B (1×PBS containing 1% BSA (Sigma), 5% sucrose (Sigma) and 0.05% $NaN_3$ (Sigma)). After 4 hr incubation at RT, blocking buffer is removed and plates are washed once with PBST (1×PBS with 0.05% Tween-20 (Sigma)). Then, 40 µL of sample is transferred to the ELISA plates and plates are incubated at 4° C. The next day, plates are washed 3 times (twice with PBST and once with PBS) and 35 µL/well biotinylated anti-TNFα antibody (Cat. No. 554511, BD Pharmingen) diluted first to a concentration of 250 ng/ml in buffer D (1×PBS with 1% BSA) is added. After 2 h of incubation at RT, plates are washed as described above and 35 µL/well of a 1/2000 dilution of streptavidin-HRP conjugate (Cat. No. SNN2004, Biosource) in buffer D is added. After 45 min, plates are washed as described above and incubated for 5 min with 50 µl/well BM Chemiluminescence ELISA Substrate POD (Roche). Readout is performed on the Luminoscan Ascent Luminometer (Labsystems) with an integration time of 100 msec delivering raw data (RLU: relative luminescence units). The following controls are included in the experiments, a maximal signal control, in which the cells are activated by LPS but only the 0.2% DMSO vehicle (and thus no compound) is added. This control indicates the maximal level of TNFα that can be achieved in the test. A minimal signal control is also included in these experiments. Here, cells are not triggered. This control returns the basal TNFα levels produced by the PBMCs. The percent inhibition (PIN) of the TNFα release, achieved by the compounds is then calculated based on the RLU data returned by the ELISA with following formula: 100−[((TNFα level compound X at concentration Y−minimal TNFα levels)/(maximal TNFα levels−minimal TNFα levels))×100]. Where compounds are tested at 8 concentrations (1/3 serial dilution), EC50-values can be calculated by curve fitting of the means of the PIN data achieved for a compound at each test concentration.

To assay the effect of compounds on the release of IL1 and IL6 by LPS stimulated PBMC cultures, appropriate dilutions of the supernatant can be measured using the same ELISA protocol as described above. Matched pair antibodies for IL1 and IL6 ELISA (all from R&D Systems) may be used as follows: anti-IL1 capture antibody (Cat. No. MAB601) used at 0.5 µg/mL, biotinylated anti-IL1 detection antibody (Cat. No. BAF201) used at 50 ng/mL; anti-IL6 capture antibody (Cat. No. MAB206) used at 1 µg/mL; biotinylated anti-IL6 detection antibody (Cat. No. BAF206) used at 50 ng/mL.

For the purpose of Table 2 below, the MAPKAPK5 $IC_{50}$ of each compound, which can be determined using the assay method described herein, is expressed as follows:
++++ compound exhibited MAPKAPK5 $IC_{50}$ 1-100 nM
+++ compound exhibited MAPKAPK5 $IC_{50}$ 101-500 nM
++ compound exhibited MAPKAPK5 $IC_{50}$ 501-1000 nM
+ compound exhibited MAPKAPK5 $IC_{50}$>1000 nM
N.A. No data available for compound

| EX# | NAME | MAPKAPK5 |
|---|---|---|
| 1 | 5-(8-(4-(MORPHOLINOMETHYL)THIAZOL-2-YLAMINO)IMIDAZO[1,2-A]PYRAZIN-5-YL)ISOINDOLIN-1-ONE | +++ |
| 2 | 5-(8-(5-(HYDROXYMETHYL)THIAZOL-2-YLAMINO)IMIDAZO[1,2-A]PYRAZIN-5-YL)ISOINDOLIN-1-ONE | N.A. |
| 3 | N-(5-(1H-PYRAZOL-4-YL)-[1,2,4]TRIAZOLO[1,5-A]PYRAZIN-8-YL)-4-(MORPHOLINOMETHYL)THIAZOL-2-AMINE | + |
| 4 | 4-(8-(4-(PIPERIDIN-1-YLMETHYL)THIAZOL-2-YLAMINO)-[1,2,4]TRIAZOLO[1,5-A]PYRAZIN-5-YL)FURAN-2-CARBOXAMIDE | ++++ |
| 5 | 4-(8-(1-(2-MORPHOLINOETHYL)-1H-IMIDAZOL-2-YLAMINO)-[1,2,4]TRIAZOLO[1,5-A]PYRAZIN-5-YL)FURAN-2-CARBOXAMIDE | N.A. |
| 6 | 5-(8-(THIAZOL-2-YLAMINO)IMIDAZO[1,2-A]PYRAZIN-5-YL)ISOINDOLIN-1-ONE | +++ |
| 7 | N-(5-(1H-PYRAZOL-4-YL)IMIDAZO[1,2-A]PYRAZIN-8-YL)THIAZOL-2-AMINE | + |
| 8 | 5-(8-(5-(ETHYLSULFONYL)THIAZOL-2-YLAMINO)IMIDAZO[1,2-A]PYRAZIN-5-YL)ISOINDOLIN-1-ONE | N.A. |
| 9 | 5-(8-(4-(PIPERIDIN-1-YLMETHYL)THIAZOL-2-YLAMINO)IMIDAZO[1,2-A]PYRAZIN-5-YL)ISOINDOLIN-1-ONE | ++++ |
| 10 | N,N,4-TRIMETHYL-2-(5-(1-OXOISOINDOLIN-5-YL)IMIDAZO[1,2-A]PYRAZIN-8-YLAMINO)THIAZOLE-5-CARBOXAMIDE | +++ |
| 11 | 5-(8-(5-METHYLTHIAZOL-2-YLAMINO)IMIDAZO[1,2-A]PYRAZIN-5-YL)ISOINDOLIN-1-ONE | ++ |
| 12 | 5-(8-(5,6-DIHYDRO-4H-CYCLOPENTA[D]THIAZOL-2-YLAMINO)IMIDAZO[1,2-A]PYRAZIN-5-YL)ISOINDOLIN-1-ONE | + |
| 13 | 5-(8-(5-(MORPHOLINE-4-CARBONYL)THIAZOL-2-YLAMINO)IMIDAZO[1,2-A]PYRAZIN-5-YL)ISOINDOLIN-1-ONE | ++ |
| 14 | 5-(8-(5-(2-(PIPERIDIN-1-YL)ETHYL)-1,3,4-THIADIAZOL-2-YLAMINO)IMIDAZO[1,2-A]PYRAZIN-5-YL)ISOINDOLIN-1-ONE | ++ |
| 15 | N-(5-(1H-PYRAZOL-4-YL)IMIDAZO[1,2-A]PYRAZIN-8-YL)-5-(MORPHOLINOMETHYL)THIAZOL-2-AMINE | + |
| 16 | 5-(8-(5-(MORPHOLINOMETHYL)THIAZOL-2-YLAMINO)IMIDAZO[1,2-A]PYRAZIN-5-YL)ISOINDOLIN-1-ONE | +++ |
| 17 | N-(5-(1H-PYRAZOL-4-YL)IMIDAZO[1,2-A]PYRAZIN-8-YL)-5-((DIMETHYLAMINO)METHYL)THIAZOL-2-AMINE | + |
| 18 | 5-(8-(5-((4-ISOPROPYLPIPERAZIN-1-YL)METHYL)THIAZOL-2-YLAMINO)IMIDAZO[1,2-A]PYRAZIN-5-YL)ISOINDOLIN-1-ONE | +++ |
| 19 | 5-(8-(1,3,4-THIADIAZOL-2-YLAMINO)IMIDAZO[1,2-A]PYRAZIN-5-YL)ISOINDOLIN-1-ONE | + |
| 20 | 5-(8-(5-(4-METHYLPIPERAZIN-1-YL)-1,3,4-THIADIAZOL-2-YLAMINO)IMIDAZO[1,2-A]PYRAZIN-5-YL)ISOINDOLIN-1-ONE | ++ |
| 21 | (2-(5-(1H-PYRAZOL-4-YL)IMIDAZO[1,2-A]PYRAZIN-8-YLAMINO)THIAZOL-5-YL)(MORPHOLINO)METHANONE | N.A. |
| 22 | (2-(5-(1H-PYRAZOL-4-YL)IMIDAZO[1,2-A]PYRAZIN-8-YLAMINO)THIAZOL-5-YL)(PIPERIDIN-1-YL)METHANONE | N.A. |
| 23 | (2-(5-(1H-PYRAZOL-4-YL)IMIDAZO[1,2-A]PYRAZIN-8-YLAMINO)THIAZOL-5-YL)(4-ISOPROPYLPIPERAZIN-1-YL)METHANONE | + |
| 24 | 5-(8-(5-(PIPERIDIN-1-YLMETHYL)THIAZOL-2-YLAMINO)IMIDAZO[1,2-A]PYRAZIN-5-YL)ISOINDOLIN-1-ONE | + |
| 25 | N-(5-(1H-PYRAZOL-4-YL)-[1,2,4]TRIAZOLO[1,5-A]PYRAZIN-8-YL)-4-(PIPERIDIN-1-YLMETHYL)THIAZOL-2-AMINE | + |

The present invention relates also to a method of treatment or prevention of inflammatory diseases, which comprises administering to a subject in need thereof, a therapeutically effective inhibitor of Mitogen-Activated Protein Kinase-Activated Protein Kinase 5 inhibiting amount of a compound according to Formula I.

Another aspect of the present method invention relates to a method of treatment or prophylaxis of a condition characterised by abnormal matrix metallo proteinase activity, which comprises administering a therapeutically effective amount of a matrix metallo proteinase inhibiting compound according to Formula I.

A further aspect of the present method invention is a method of treatment or prophylaxis of a condition selected from diseases involving degradation of extra-cellular matrix, which comprises administering a therapeutically effective matrix metallo proteinase inhibiting amount of a compound according to Formula I.

A yet further aspect of the present method invention is a method of treatment or prophylaxis of a condition selected from diseases involving abnormal cellular expression of MMP1, which comprises administering a therapeutically effective matrix metallo proteinase inhibiting amount of a compound according to Formula I.

A special embodiment of the present method invention is a method of treatment or prevention of rheumatoid arthritis, which comprises administering to a subject in need thereof, a therapeutically effective amount of a compound according to Formula I.

This invention also relates to the use of the present compounds in the manufacture of a medicament for treatment or prophylaxis of a condition prevented, ameliorated or eliminated by administration of an inhibitor of Mitogen-Activated Protein Kinase-Activated Protein Kinase 5, or a condition characterised by abnormal collagenase activity, or a condition selected from diseases involving inflammation, most preferably in for the treatment of rheumatoid arthritis.

Administering of the compound of the present invention to the subject patient includes both self-administration and administration by another person. The patient may be in need of treatment for an existing disease or medical condition, or may desire prophylactic treatment to prevent or reduce the risk for diseases and medical conditions affected by a disturbance in bone metabolism. The compound of the present invention may be delivered to the subject patient orally, transdermally, via inhalation, injection, nasally, rectally or via a sustained release formulation.

A preferred regimen of the present method comprises the administration to a subject in suffering from a disease condition characterized by inflammatory, with an effective matrix metallo-protease inhibiting amount of a compound of the present invention for a period of time sufficient to reduce the abnormal levels of extracellular matrix degradation in the patient, and preferably terminate, the self-perpetuating processes responsible for said degradation. A special embodiment of the method comprises administering of an effective matrix metallo-protease inhibiting amount of a compound of the present invention to a subject patient suffering from or susceptible to the development of rheumatoid arthritis, for a period of time sufficient to reduce or prevent, respectively, collagen and bone degradation in the joints of said patient, and preferably terminate, the self-perpetuating processes responsible for said degradation.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A preferred therapeutically effective amount of the compound of the present invention to administer to a subject patient is about 0.1 mg/kg to about 10 mg/kg administered from once to three times a day. For example, an effective regimen of the present method may administer about 5 mg to about 1000 mg of said compound of the present invention from once to three times a day. It will be understood, however, that the specific dose level for any particular subject patient will depend upon a variety of factors including the age, body weight, general health, sex, diet, time of administration, route of administration, rate of excretion, drug combination and the severity of the particular inflammatory condition. A consideration of these factors is well within the purview of the ordinarily skilled clinician for the purpose of determining the therapeutically effective or prophylactically effective dosage amount needed to prevent, counter, or arrest the progress of the condition.

Compounds of the invention can be incorporated into pharmaceutical compositions suitable for administration. Such compositions typically comprise at least one compound of the invention and at least one pharmaceutically acceptable carrier. As used herein the language "pharmaceutically acceptable carrier" is intended to include solid carriers such as lactose, magnesium stearate, terra alba, sucrose, talc, stearic acid, gelatin, agar, pectin, acacia or the like; and liquids such as vegetable oils, arachis oil and sterile water, or the like, any and all solvents, dispersion media, coatings, antibacterial and antifungal agents, isotonic and absorption delaying agents, and the like, compatible with pharmaceutical administration. This listing of pharmaceutically acceptable carriers is not to be construed as limiting. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum mono stearate and gelatin.

Sterile injectable solutions can be prepared by incorporating the active compound (e.g., a compound according to an embodiment of the invention) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

A compound according to an embodiment of the invention may be provided as a salt, preferably as a pharmaceutically acceptable salt of compounds of formula I. Examples of pharmaceutically acceptable salts of these compounds include those derived from organic acids such as acetic acid, malic acid, tartaric acid, citric acid, lactic acid, oxalic acid, succinic acid, fumaric acid, maleic acid, benzoic acid, salicylic acid, phenylacetic acid, mandelic acid, methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl)aminomethane; and the like.

Salts of compounds according to an embodiment of the invention may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of the invention contains an acidic function, a base salt of said compound may be prepared by reacting said compound with a suitable base. The acid or base salt may separate directly or can be obtained by concentrating the solution e.g. by evaporation. The compounds of this invention may also exist in solvated or hydrated forms.

It will be appreciated by those skilled in the art that the foregoing description is exemplary and explanatory in nature, and is intended to illustrate the invention and its preferred embodiments. Through routine experimentation, an artisan will recognise apparent modifications and variations that may be made without departing from the spirit of the invention. Thus, the invention is intended to be defined not by the above description, but by the following claims and their equivalents.

REFERENCES

Choy E H, Panayi G S. (2001). N Engl J. Med. 344: 907-16.

Firestein G S. (2003). Nature. 423:356-61.

Smolen J S, Steiner G. (2003). Nat Rev Drug Discov. 2: 473-88.

Lee D M, Weinblatt M E (2001). Lancet. 358: 903-11.

Kremer J. M., Westhovens R., Leon M., Di Giorgio E., Alten R., Steinfeld S., Russell A., Dougados M., Emery P., Nuamah I. F., Williams G. R., Becker J.-C., Hagerty D. T., Moreland L. W. (2003) N Engl J. Med. 349:1907-1915.

Edwards J. C. W., Szczepanski L., Szechinski J., Filipowicz-Sosnowska A., Emery P., Close D. R., Stevens R. M., Shaw T. (2004) N Engl J. Med. 350:2572-2581.

O'Dell J R, Leff R, Paulsen G, Haire C, Mallek J, Eckhoff P J, Fernandez A, Blakely K, Wees S, Stoner J, Hadley S, Felt J, Palmer W, Waytz P, Churchill M, Klassen L, Moore G. (2002) Arthritis Rheum. 46:1164-70.

St Clair E W, van der Heijde D M, Smolen J S, Maini R N, Bathon J M, Emery P, Keystone E, Schiff M, Kalden J R, Wang B, Dewoody K, Weiss R, Baker D; (2004) Combination of infliximab and methotrexate therapy for early rheumatoid arthritis: a randomized, controlled trial. Arthritis Rheum. 50:3432-43.

Gomez-Reino J J, et al. (2003). Arthritis Rheum. 48: 2122-7.

O'Dell J R. (2004) Therapeutic strategies for rheumatoid arthritis. N Engl J. Med. 350(25):2591-602.

New L, Jiang Y, Han J. (2003) Regulation of PRAK subcellular location by p38 MAP kinases. Mol Biol Cell. 14(6): 2603-16.

Shi Y, Kotlyarov A, Laabeta K, Gruber A D, Butt E, Marcus K, Meyer H E, Friedrich A, Volk H D, Gaestel M. (2003) Elimination of protein kinase MK5/PRAK activity by targeted homologous recombination. Mol Cell Biol. 23:7732-41.

Seternes O M, Mikalsen T, Johansen B, Michaelsen E, Armstrong C G, Morrice N A, Turgeon B, Meloche S, Moens U, Keyse S M. (2004) Activation of MK5/PRAK by the atypical MAP kinase ERK3 defines a novel signal transduction pathway.

EMBO J. 23:4780-91.

Andreakos E, et al. (2003). Arthritis Rheum. 48: 1901-12.

Cunnane G, et al. (2001). Arthritis Rheum 44: 2263-74.

Coussens L M, et al. (2002). Science 295: 2387-92.

Creemers E E, et al. (2001). Circ Res. 2001 89:201-10

Gapski R, et al. (2004). J Periodontol. 75:441-52.

Reif S, Somech R, Brazovski E, Reich R, Belson A, Konikoff F M, Kessler A. (2005) Digestion. 71:124-130.

Rosenberg G A. (2002). Glia. 39:279-91.

Schanstra J P, et al. (2002). J Clin Invest. 110:371-9.

Suzuki R, et al. (2004). Treat Respir Med. 3:17-27.

From the foregoing description, various modifications and changes in the compositions and methods of this invention will occur to those skilled in the art. All such modifications coming within the scope of the appended claims are intended to be included therein.

It should be understood that factors such as the differential cell penetration capacity of the various compounds can contribute to discrepancies between the activity of the compounds in the in vitro biochemical and cellular assays.

All publications, including but not limited to patents and patent applications, cited in this specification are herein incorporated by reference as if each individual publication were specifically and individually indicated to be incorporated by reference herein as though fully set forth.

At least some of the chemical names of compounds of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

Chemical structures shown herein were prepared using either ChemDraw® or ISIS®/DRAW. Any open valency appearing on a carbon, oxygen or nitrogen atom in the structures herein indicates the presence of a hydrogen atom. Where a chiral center exists in a structure but no specific stereochemistry is shown for the chiral center, both enantiomers associated with the chiral structure are encompassed by the structure.

What is claimed is:

1. A compound according to formula I:

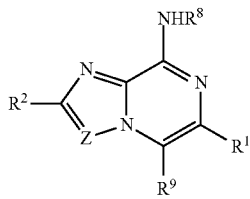

wherein

Z is N; $R^1$ is H, or substituted or unsubstituted $C_1$-$C_6$ alkyl; $R^2$ is H, $C_1$-$C_6$ alkyl, $C_3$-$C_7$ cycloalkyl or $C_3$-$C_7$ cycloalkyl-$C_1$-$C_6$ alkyl, optionally substituted with one or more of F and Cl; $R^8$ is substituted or unsubstituted heteroaryl; $R^9$ is selected from substituted or unsubstituted aryl and substituted or unsubstituted heteroaryl; or a pharmaceutically acceptable salt, solvate or prodrug thereof; and stereoisomers and tautomers thereof.

2. The compound according to claim 1 wherein $R^8$ is substituted or unsubstituted 5-membered heteroaryl.

3. The compound according to claim 2 wherein $R^8$ is selected from substituted or unsubstituted pyrrolyl, furanyl, thienyl, pyrazolyl, oxazolyl, imidazolyl, thiazolyl, 1,3,4-thiadiazolyl, and 1,2,4-thiadiazolyl.

4. The compound according to claim 3 wherein $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is selected from $C_1$-$C_6$ alkyl, substituted $C_1$-$C_6$ alkyl, carbamoyl, $C_1$-$C_6$ hydroxyalkyl, $C_1$-$C_6$ haloalkyl, $C_1$-$C_6$ alkoxy, cyano, amino, sulfo, aryl, $C_3$-$C_7$ cycloalkyl, aralkyl, 3-7-membered heterocycloalkyl and heteroaryl.

5. The compound according to claim 4 wherein $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is selected from is Me, i-Pr, cyclopropyl, $CH_2OH$, $CONH_2$, $CONMe_2$, $NMe_2$, $NEt_2$, $SO_2Me$, or $SO_2Et$.

6. The compound according to claim 1 wherein $R^8$ is selected from substituted pyrrolyl, furanyl, thienyl, pyrazolyl, oxazolyl, imidazolyl, thiazolyl, 1,3,4-thiadiazolyl, and 1,2,4-thiadiazolyl and the substitution is -L-$R^{8d}$;

wherein

L is selected from bond, alkylene, heteroalkylene, —O—, —N($R^{8e}$)—, —CO—, —CO$_2$—, —SO—, —SO$_2$—, —CON($R^{8e}$)—, —SO$_2$N($R^{8e}$)—, —N($R^{8e}$)CO—, —N($R^{8e}$)SO$_2$—, —N($R^{8e}$)CON($R^{8e}$)—, —N($R^{8e}$)SO$_2$N($R^{8e}$)—; and $R^{8d}$ is selected from substituted or unsubstituted $C_1$-$C_6$ alkyl, substituted or unsubstituted $C_3$-$C_7$ cycloalkyl, substituted or unsubstituted aryl, substituted or unsubstituted 3-7-membered heterocycloalkyl, substituted or unsubstituted heteroaryl, substituted or unsubstituted amino, substituted or unsubstituted aralkyl, substituted or unsubstituted heteroarylalkyl and substituted or unsubstituted aminoalkyl; and $R^{8e}$ is selected from H, substituted or unsubstituted $C_1$-$C_6$ alkyl and substituted or unsubstituted $C_3$-$C_7$ cycloalkyl.

7. The compound according to claim 6, wherein $R^8$ is

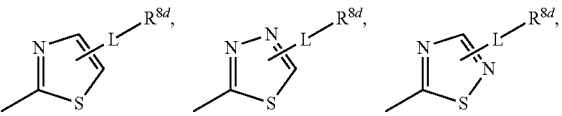

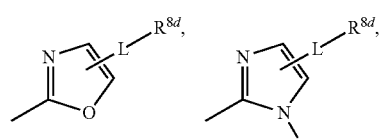

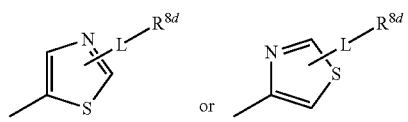

wherein L, and $R^{8d}$ are as in claim 6; and $R^{8c}$ is independently selected from hydrogen, and substituted or unsubstituted $C_1$-$C_6$ alkyl.

8. The compound according to claim 7, wherein L is —CON($R^{8e}$)— or SO$_2$N($R^{8e}$)—;

$R^{8d}$ is selected from substituted or unsubstituted $C_1$-$C_6$ alkyl, substituted or unsubstituted $C_3$-$C_7$ cycloalkyl, substituted or unsubstituted aryl, substituted or unsubstituted 3-7-membered heterocycloalkyl, substituted or unsubstituted heteroaryl, substituted or unsubstituted aralkyl, substituted or unsubstituted heteroarylalkyl and substituted or unsubstituted aminoalkyl; and $R^{8e}$ is selected from H, substituted or unsubstituted $C_1$-$C_6$ alkyl.

9. The compound according to claim 7, wherein L is —CONH— or SO$_2$NH—; and $R^{8d}$ is selected from H, $C_1$-$C_6$ alkylaminoethyl, di$C_1$-$C_6$ dialkylaminoethyl, $C_3$-$C_7$ cycloalkyl, heterocycloalkyl, arylalkyl, and heteroarylalkyl.

10. The compound according to claim 9, wherein L is —CONH— or SO$_2$NH—; and $R^{8d}$ is selected from H, methylaminoethyl, ethylaminoethyl, dimethylaminoethyl, diethylaminoethyl, substituted or unsubstituted pyrrolidinyl, benzyl and pyridylmethyl.

11. The compound according to claim 7, wherein L is bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; and $R^{8d}$ is

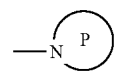

and wherein the ring P is substituted or unsubstituted heterocycloalkyl.

12. A compound according to formula IIa, IIb, IIc, IId, IIe, or IIf:

IIa
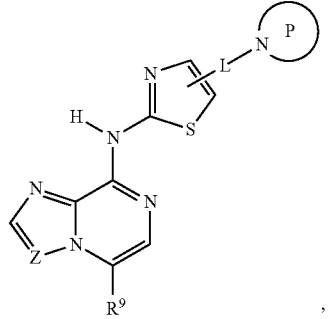

IIb
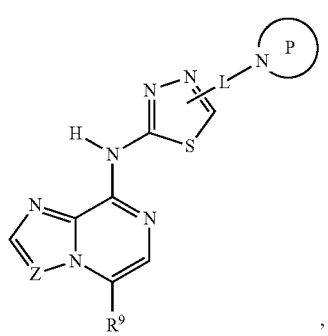

IIc
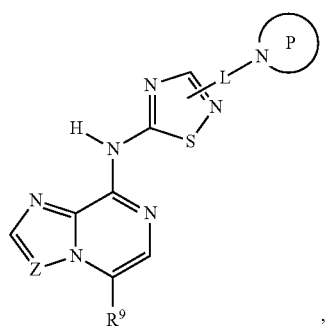

IId
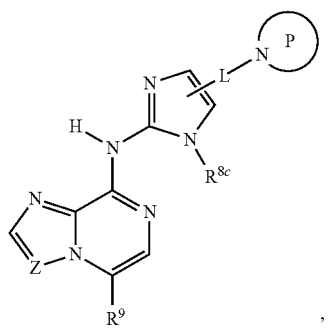

IIe
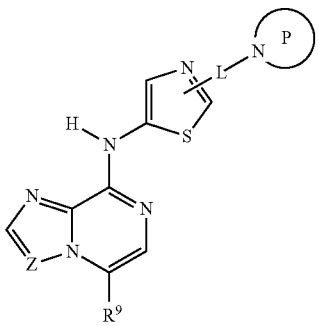

or

IIf
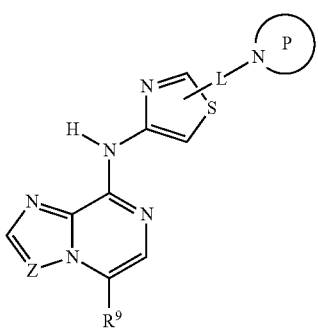

and wherein Z is N, L is bond, —CO—, $SO_2$, —$(CH_2)_{m1}$—, —$O(CH_2)_{m1}$—, —$NH(CH_2)_{m1}$—, —$CON(H)(CH_2)_{m1}$—, or —$SO_2NH(CH_2)_{m1}$—; the subscript m1 is selected from 1-4, $R^{8c}$ is independently selected from hydrogen, and substituted or unsubstituted $C_1$-$C_6$ alkyl, and the ring P is substituted or unsubstituted heterocycloalkyl; and $R^9$ is independently selected from substituted or unsubstituted aryl and heteroaryl; or a pharmaceutically acceptable salt, solvate or prodrug thereof; and stereoisomers and tautomers thereof.

13. The compound according to claim 12, wherein L is a bond.

14. The compound according to claim 12, wherein L is —CO—.

15. The compound according to claim 12, wherein L is —$SO_2$—.

16. The compound according to claim 12, wherein L is —CON(H)—$CH_2$—$CH_2$—, or —$SO_2$NH—$CH_2$—$CH_2$—.

17. The compound according to claim 12, wherein L is —$OCH_2$—$CH_2$— or —$NHCH_2$—$CH_2$—.

18. The compound according to claim 12, wherein the ring P is substituted or unsubstituted piperidine, morpholine or piperazine.

19. The compound according to claim 12, wherein the ring P is substituted or unsubstituted:

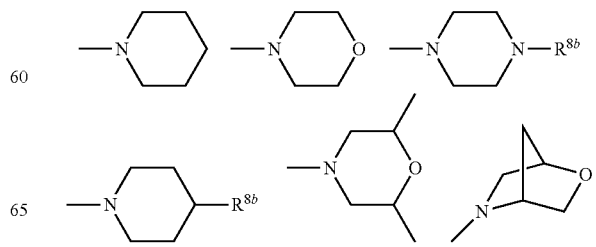

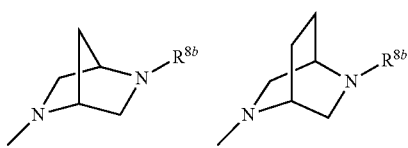

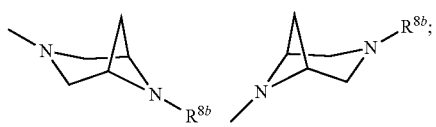

and $R^{8b}$ is hydrogen, substituted or unsubstituted $C_1$-$C_6$ alkyl or substituted or unsubstituted $C_3$-$C_7$ cycloalkyl.

20. The compound according to claim 19 wherein $R^{8b}$ is H, Me, Et, Pr, i-Pr, t-Bu, $CH_2CONH_2$, cyclopropyl or cyclopropylmethyl.

21. The compound according to claim 1 wherein the compound is according to formula IIIa, IIIb, IIIc, IIId, IIIe, IIIf, IIIg, IIIh, IIIi, IIIj, IIIk, IIIl, or IIIm:

IIIa

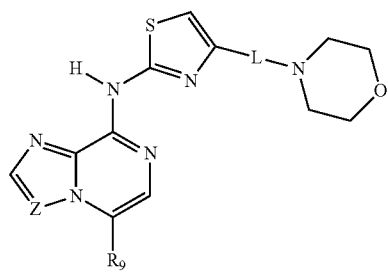

IIIb

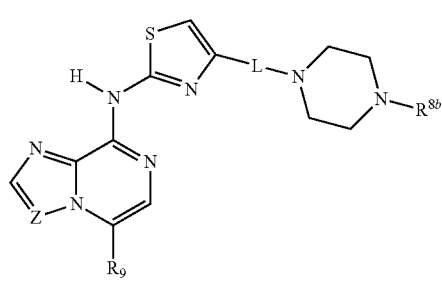

IIIc

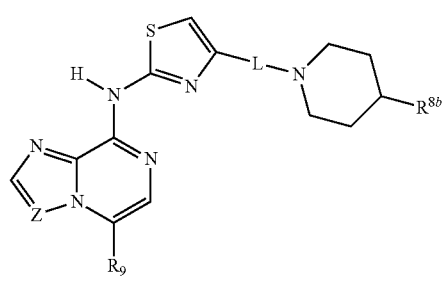

IIId

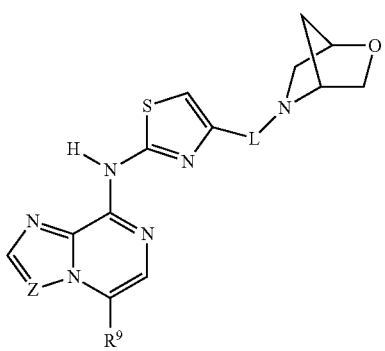

IIIe

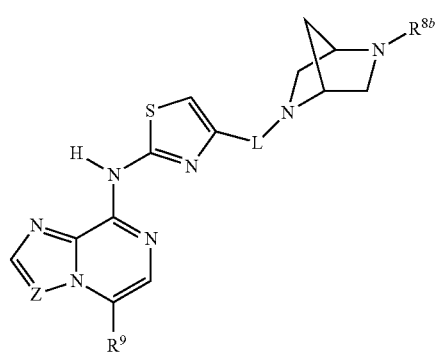

IIIf

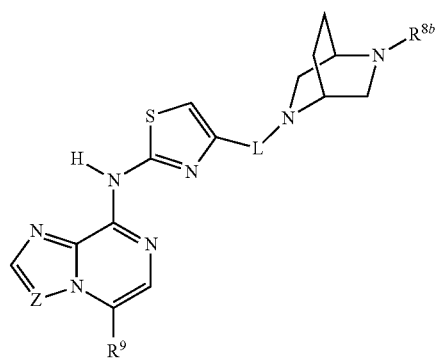

IIIg

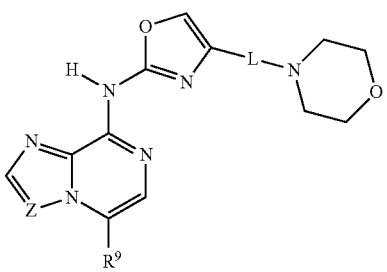

IIIh

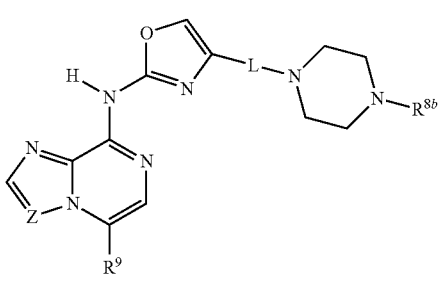

IIIi

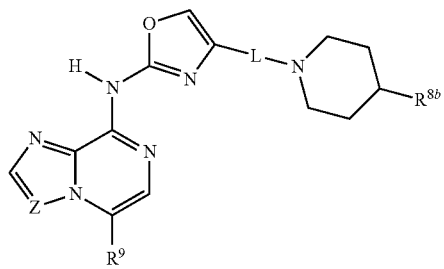

IIIk

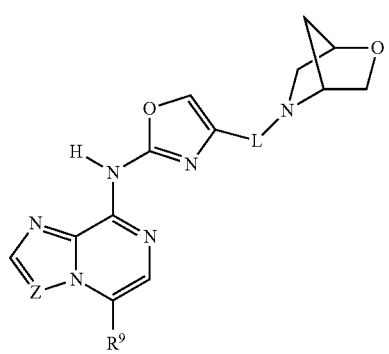

IIIl

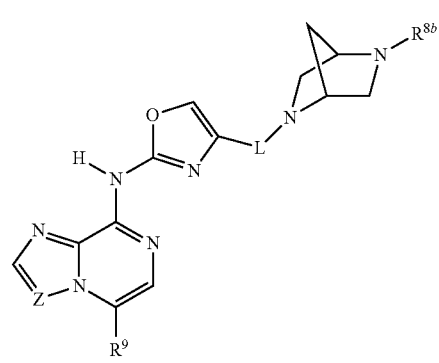

IIIm

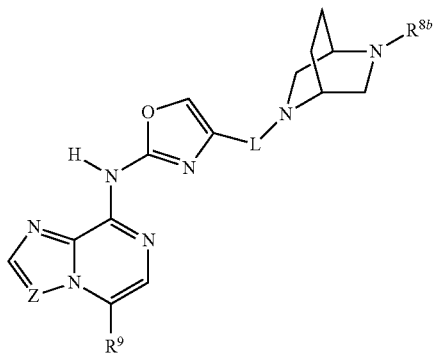

IIIn

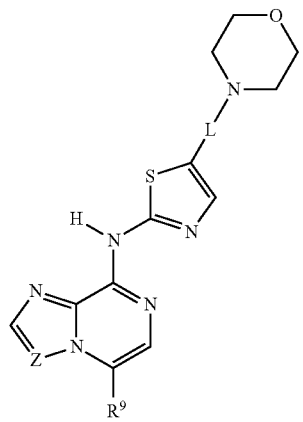

IIIo

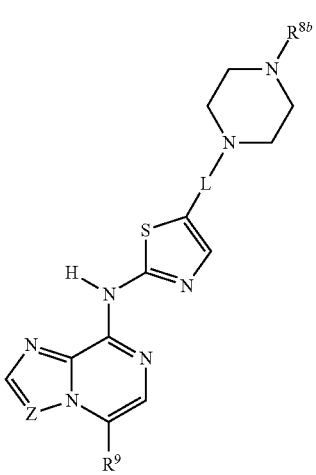

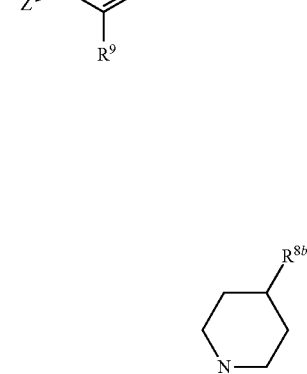

IIIp

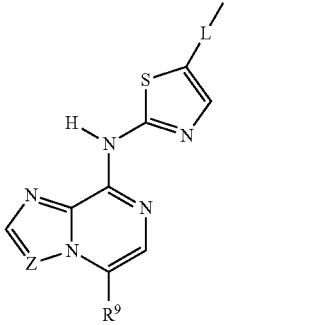

and wherein L is bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; R$^{8b}$ is hydrogen, substituted or unsubstituted C$_1$-C$_6$ alkyl or substituted or unsubstituted C$_3$-C$_7$ cycloalkyl; and R$^9$ is independently selected from substituted or unsubstituted aryl and heteroaryl; or a pharmaceutically acceptable salt, solvate or prodrug thereof; and stereoisomers and tautomers thereof.

22. The compound according to claim 1 wherein the compound is according to formula IIIn, IIIo, IIIp, IIIq, IIIs, IIIt, IIIu, IIIv, IIIw, IIIx, or IIIy:

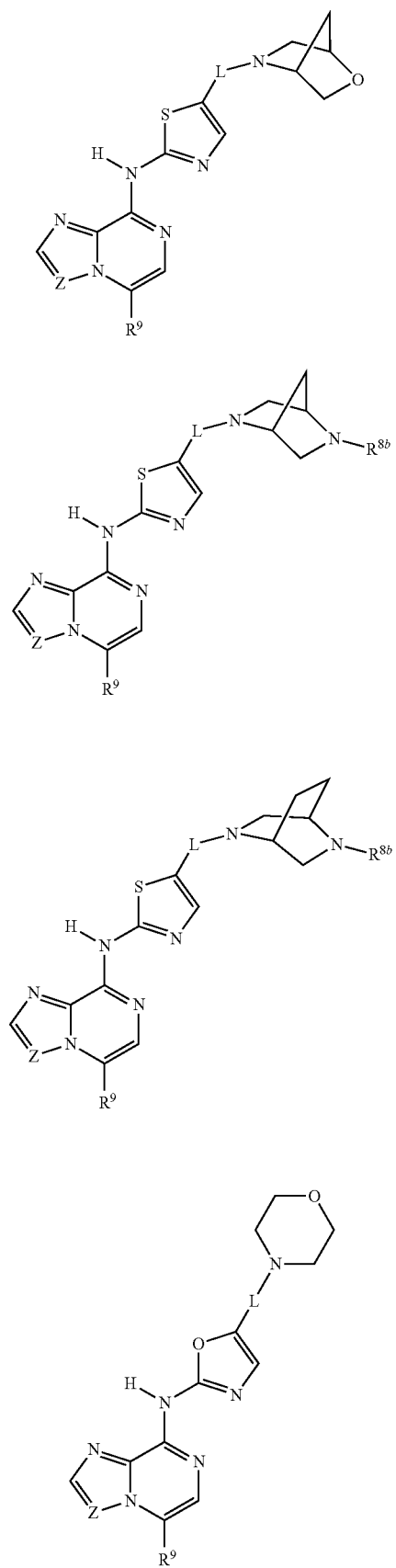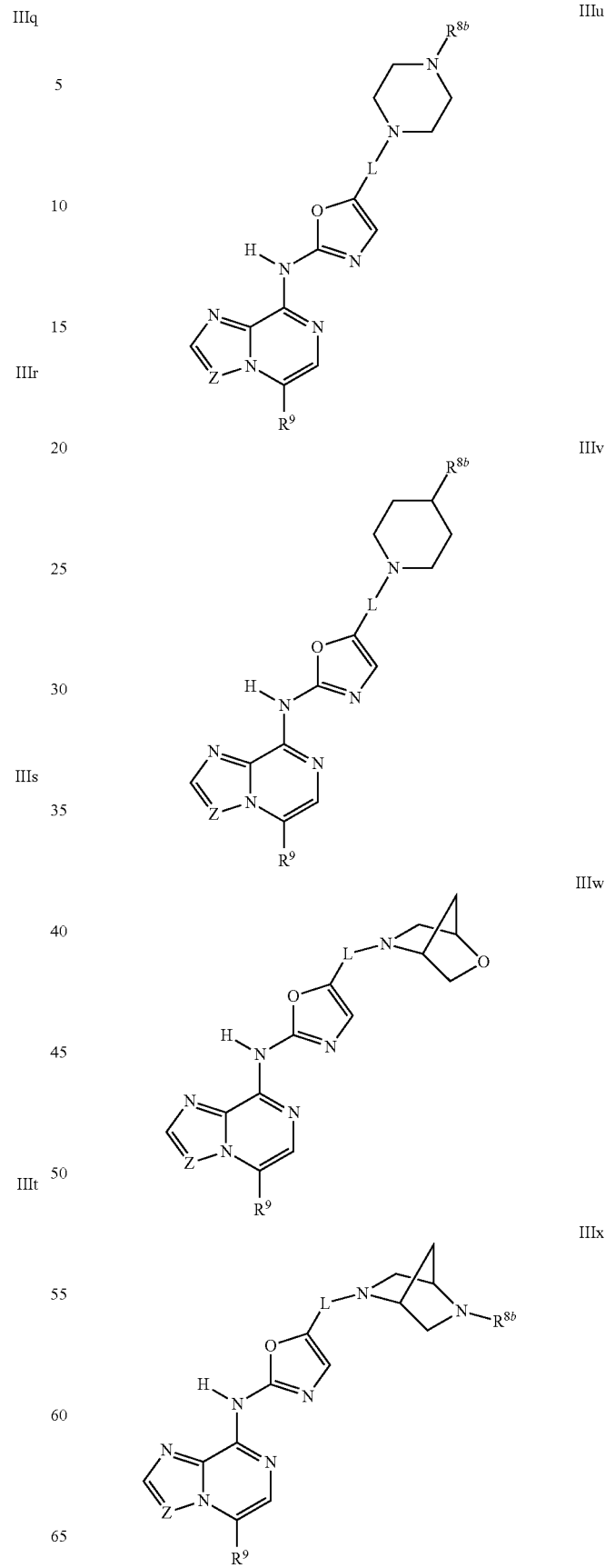

-continued

IIIy

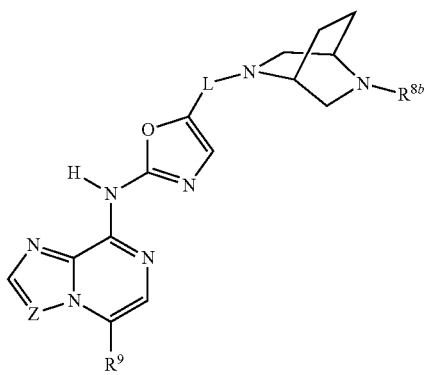

and wherein L is bond, —CO—, SO$_2$, —(CH$_2$)$_{m1}$—, —O(CH$_2$)$_{m1}$—, —NH(CH$_2$)$_{m1}$—, —CON(H)(CH$_2$)$_{m1}$—, or —SO$_2$NH(CH$_2$)$_{m1}$—; the subscript m1 is selected from 1-4; R$^{8b}$ is hydrogen, substituted or unsubstituted C$_1$-C$_6$ alkyl or substituted or unsubstituted C$_3$-C$_7$ cycloalkyl; and R$^9$ is independently selected from substituted or unsubstituted aryl and heteroaryl; or a pharmaceutically acceptable salt, solvate or prodrug thereof; and stereoisomers and tautomers thereof.

23. The compound according to claim 21, wherein L is a bond.

24. The compound according to claim 21, wherein L is —CH$_2$—.

25. The compound according to claim 21, wherein L is —CO—.

26. The compound according to claim 21, wherein L is —SO$_2$—.

27. The compound according to claim 21, wherein L is —CON(H)—CH$_2$—CH$_2$—, or —SO$_2$NH—CH$_2$—CH$_2$—.

28. The compound according to claim 21, wherein L is —OCH$_2$—CH$_2$— or —NHCH$_2$—CH$_2$—.

29. The compound according to claim 21, wherein R$^{8b}$ is H, Me, Et, Pr, i-Pr, t-Bu, i-Bu, cyclopropyl or cyclopropylmethyl.

30. The compound according to claim 1, wherein R$^9$ is selected from substituted or unsubstituted phenyl.

31. The compound according to claim 1, wherein R$^9$ is selected from substituted or unsubstituted pyridyl, indolyl, isoindolyl, pyrrolyl, furanyl, thienyl, pyrazolyl, oxazolyl, and thiazolyl.

32. The compound according to claim 1, wherein R$^9$ is

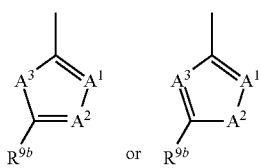

and each of A$^1$, A$^2$ and A$^3$ is independently selected from S, O, N, NR$^{9a}$, and CR$^{9a}$; each of R$^{9a}$ is independently H or substituted or unsubstituted C$_1$-C$_6$ alkyl; and R$^{9b}$ is CONH$_2$, CONHMe, or CN.

33. The compound according to claim 1, wherein R$^9$ is

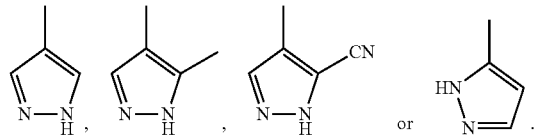

34. The compound according to claim 1, wherein R$^9$ is

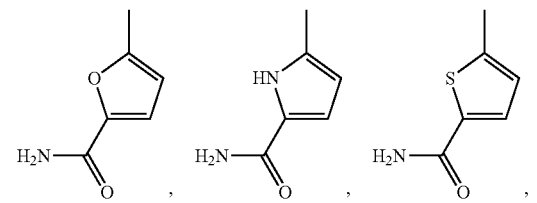

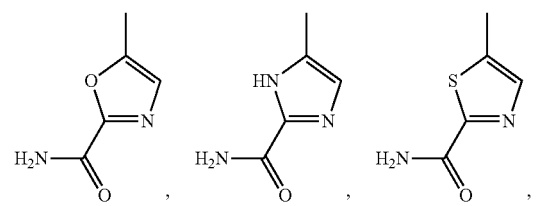

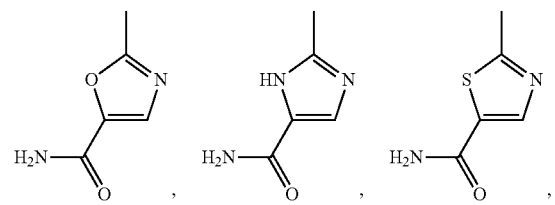

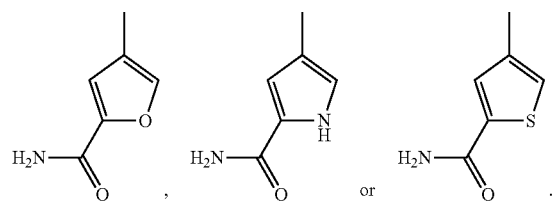

35. The compound according to claim 1, wherein R$^9$ is

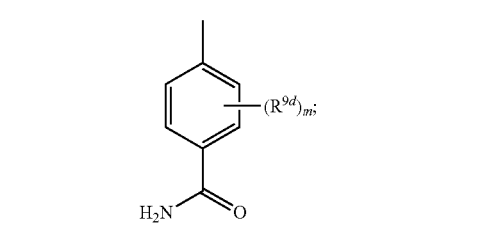

and wherein the subscript m is selected from 0-4 and each R$^{9d}$ is independently substituted or unsubstituted C$_1$-C$_6$ alkyl or halo.

36. The compound according to claim 1, wherein $R^9$ is

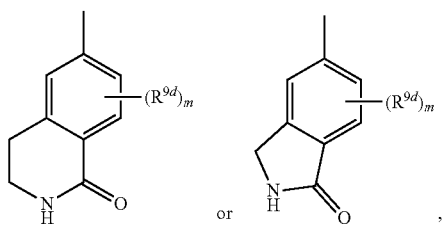

and wherein the subscript m is selected from 0-4 and each $R^{9d}$ is independently substituted or unsubstituted $C_1$-$C_6$ alkyl or halo.

37. The compound according to claim 1, wherein $R^9$ is

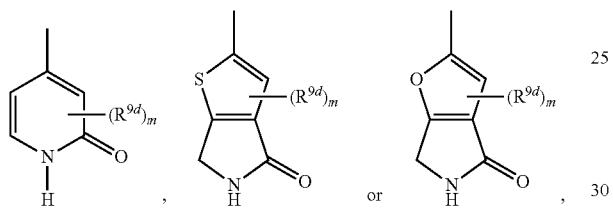

wherein the subscript m is selected from 0-3 and each $R^{9d}$ is independently substituted or unsubstituted $C_1$-$C_6$ alkyl or halo.

38. The compound according to claim 35, wherein m is 1 or 2 and each $R^{9d}$ is Me, Cl or F.

39. The compound according to claim 1 wherein the compound is according to formula IVa, IVb, IVc, IVd, IVe, IVf, IVg, IVh, IVi, IVj, IVk or IVl:

IVa

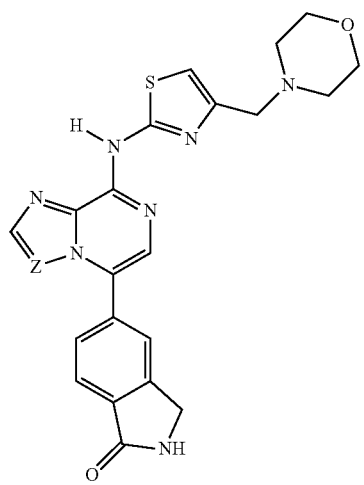

IVb

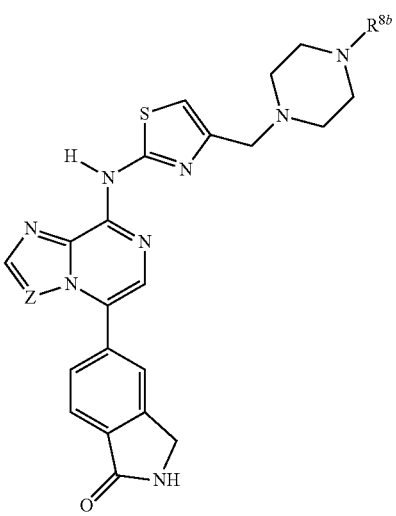

IVc

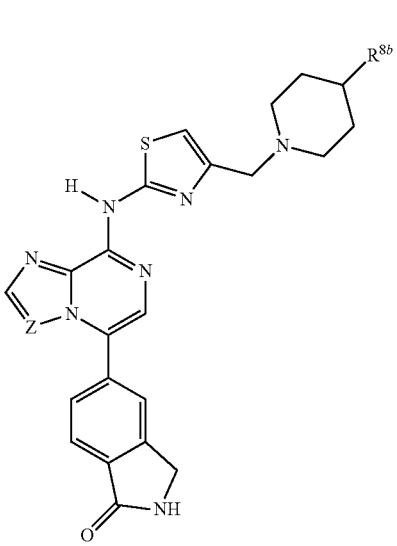

IVd

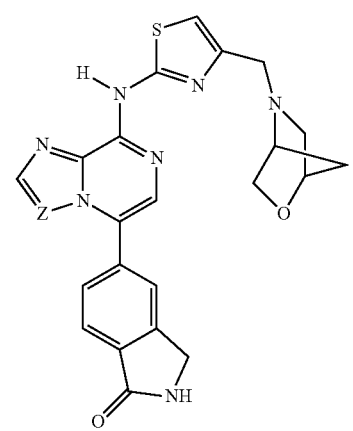

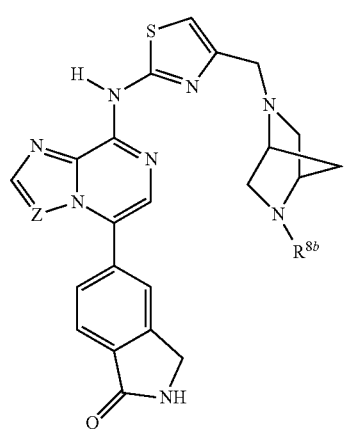
IVe
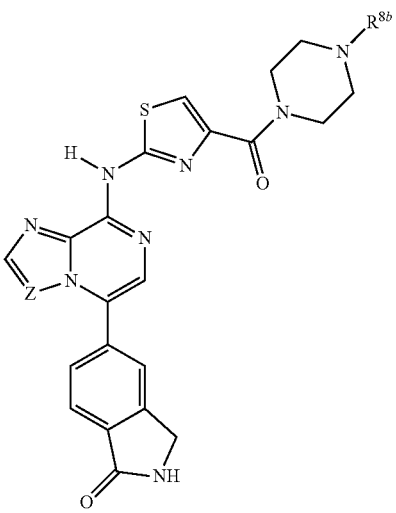
IVh
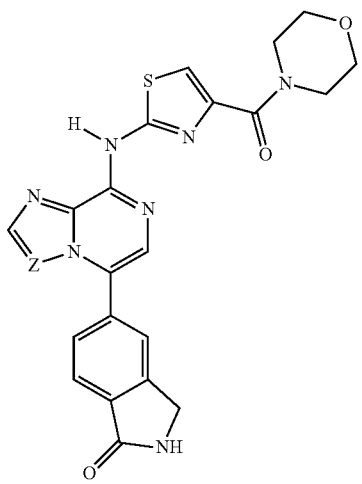
IVf
IVi
IVg
IVj

IVk

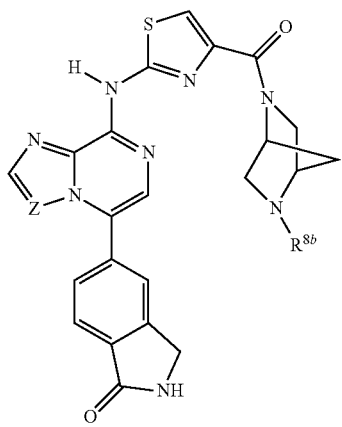

IVl

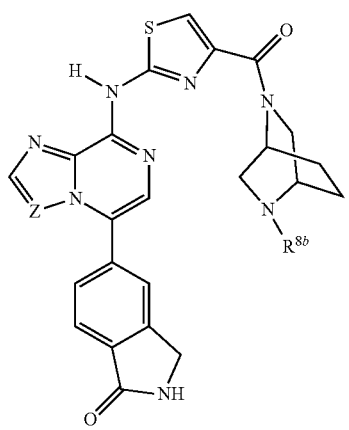

wherein R[8b] is hydrogen, substituted or unsubstituted C$_1$-C$_6$ alkyl or substituted or unsubstituted C$_3$-C$_7$ cycloalkyl; or a pharmaceutically acceptable salt, solvate or prodrug thereof; and stereoisomers and tautomers thereof.

40. The compound according to claim 1 wherein the compound is according to formula IVm, IVn, IVo, IVp, IVq, IVr, IVs, IVt, IVu, IVv, IVw or IVx:

IVm

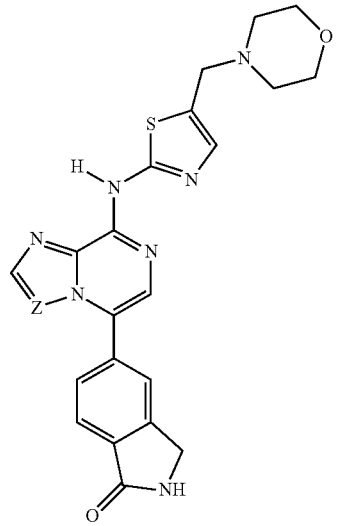

IVn

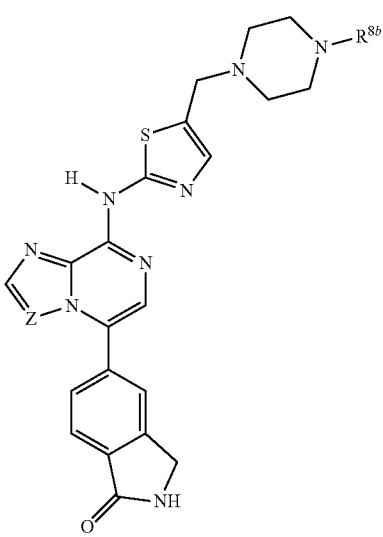

IVo

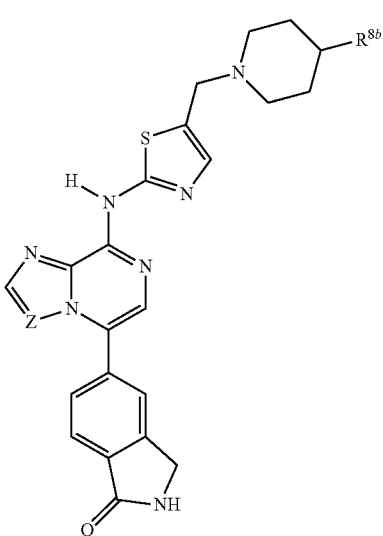

IVp

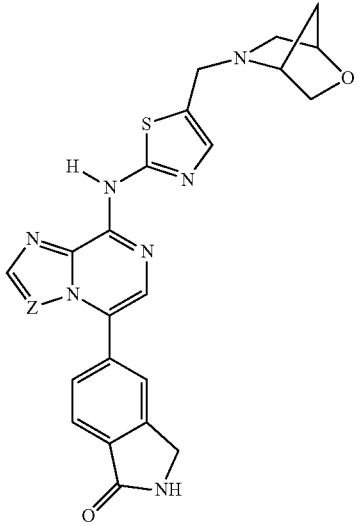

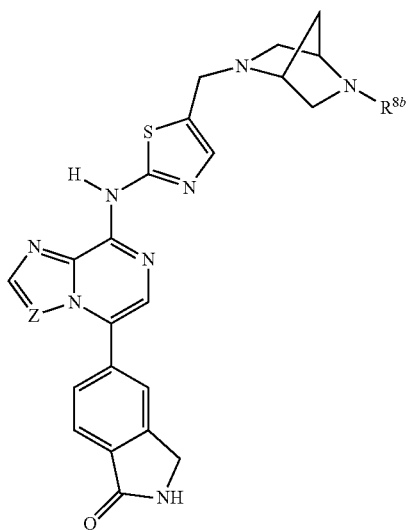
IVq
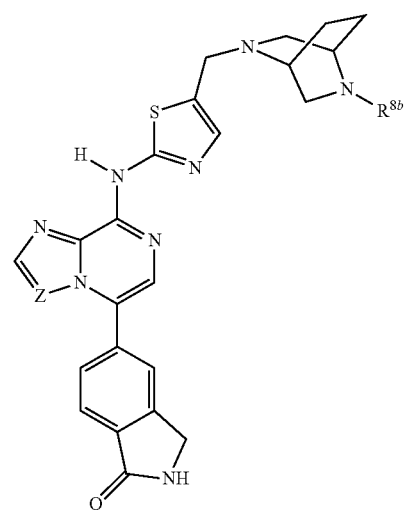
IVr
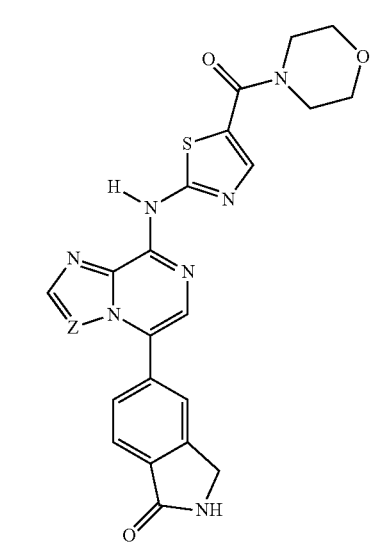
IVs
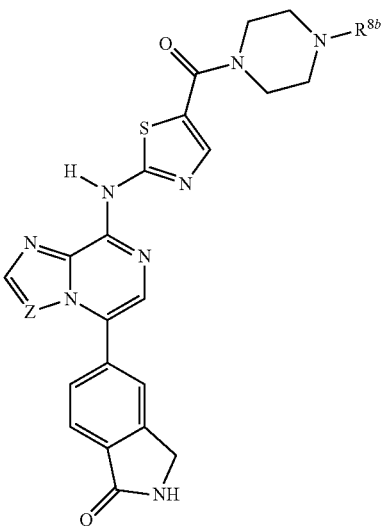
IVt
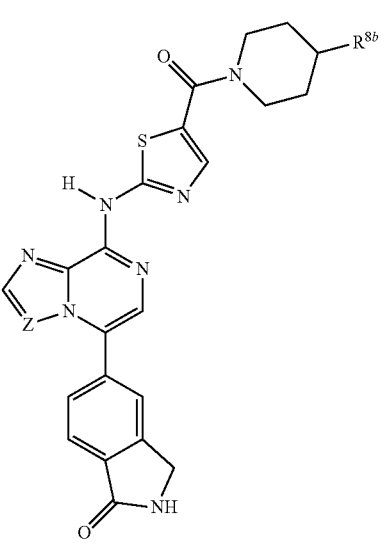
IVu
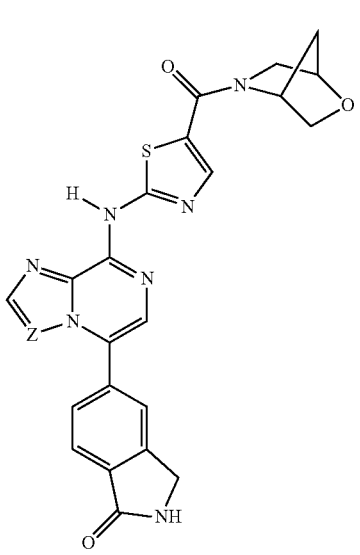
IVv IVw

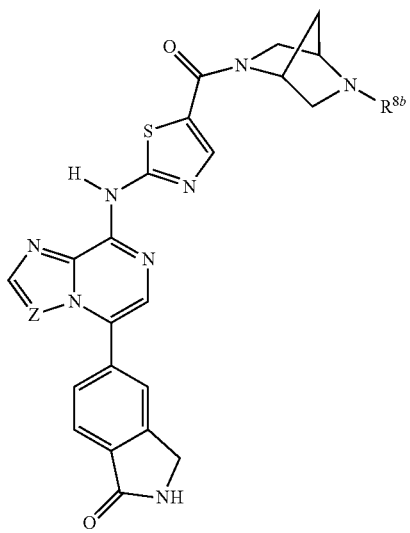

IVx

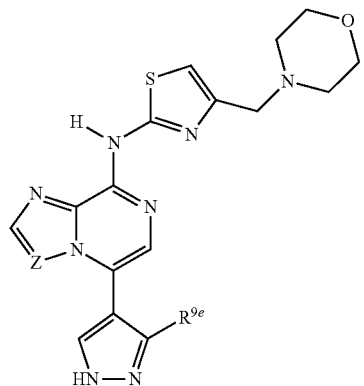

wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.

41. The compound according to claim 1 wherein the compound is according to formula Va, Vb, Vc, Vd, Ve, Vf, Vg, Vh, Vi, Vj, Vk or Vl:

Va

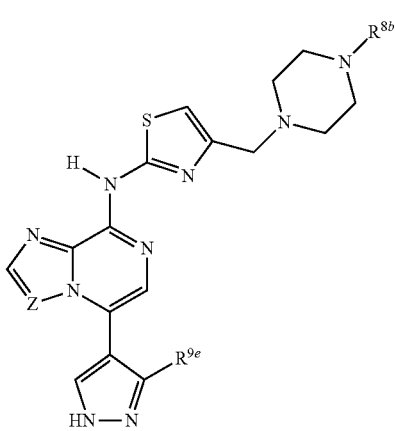

Vb

Vc

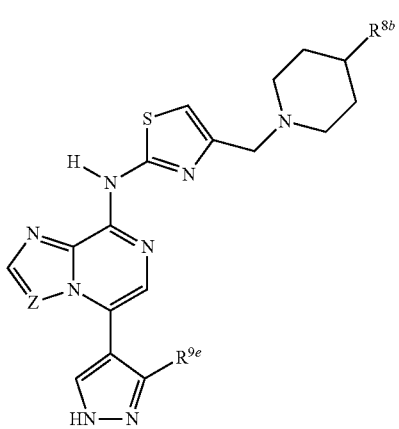

Vd

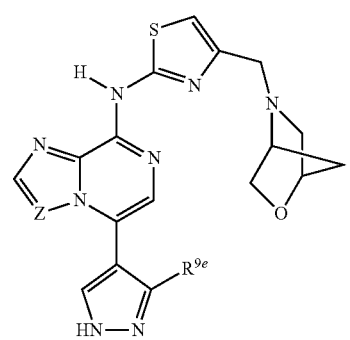

Ve

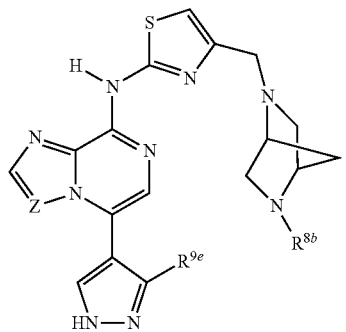

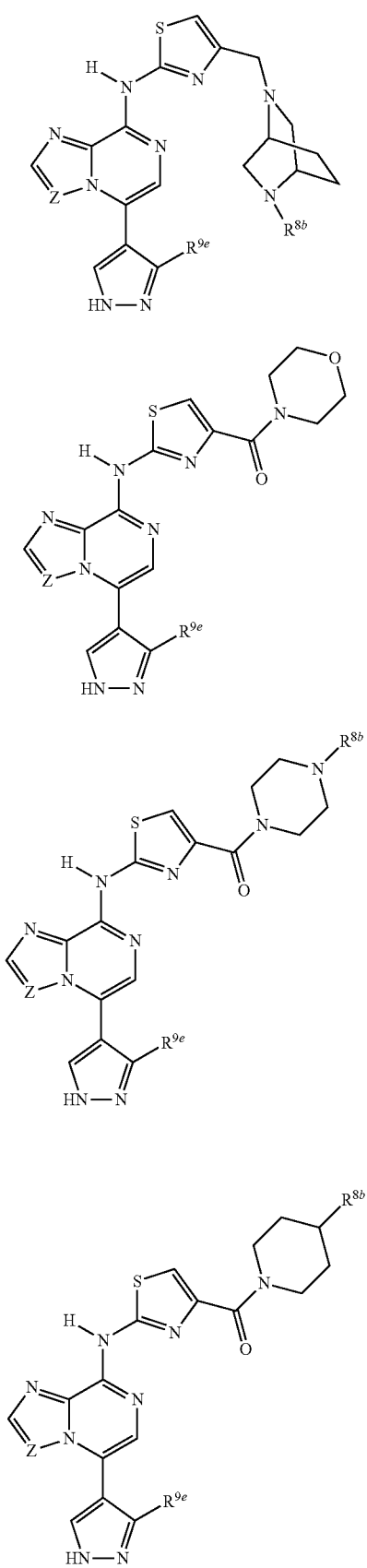
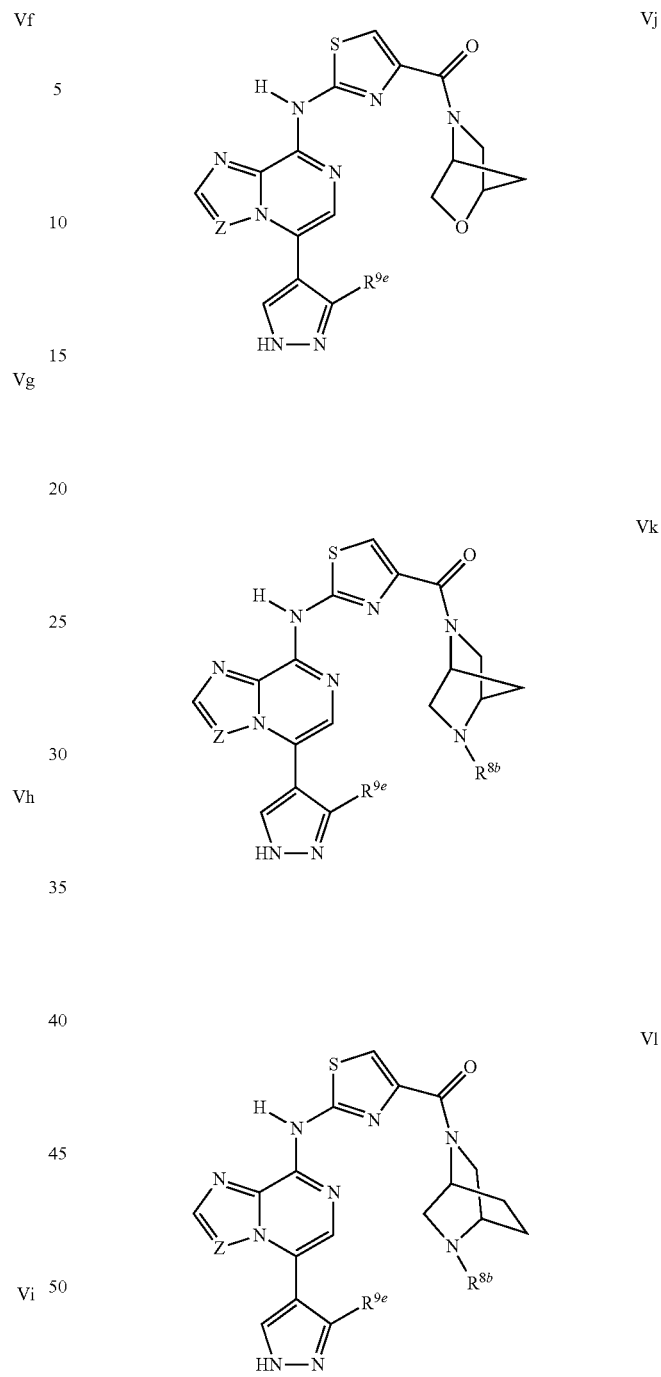

wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, Me, or CN; or a pharmaceutically acceptable salt, solvate or prodrug thereof; and stereoisomers and tautomers thereof.

42. The compound according to claim 1 wherein the compound is according to formula Vm, Vn, Vo, Vp, Vq, Vr, Vs, Vt, Vu, Vv, Vw or Vx:

Vm
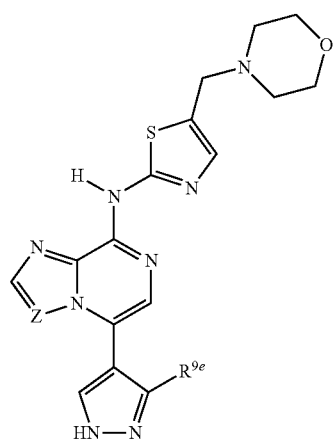
Vn
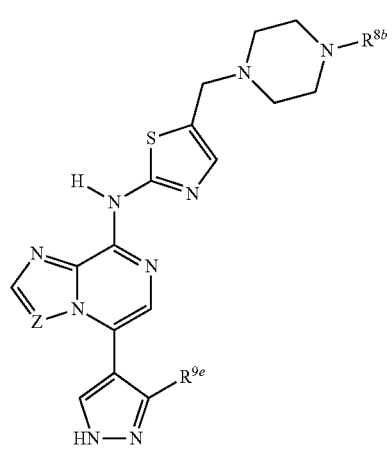
Vo
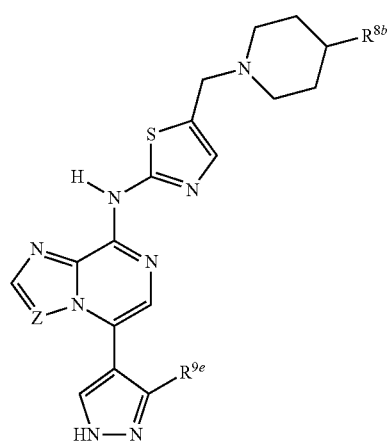
-continued
Vp
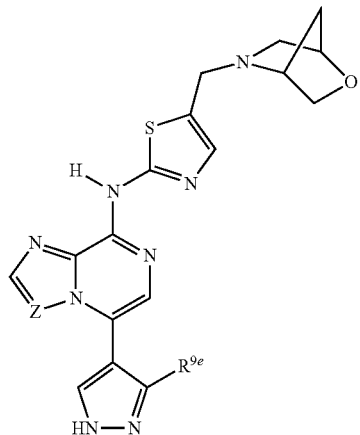
Vq
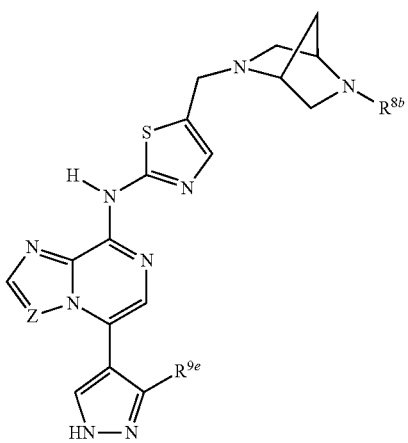
Vr
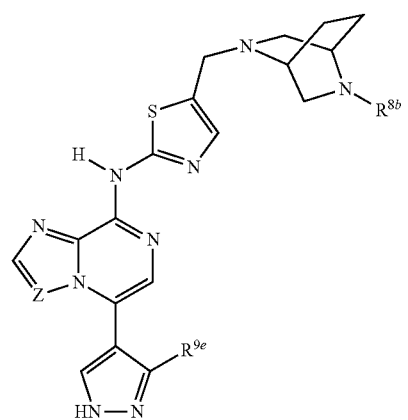

Vs

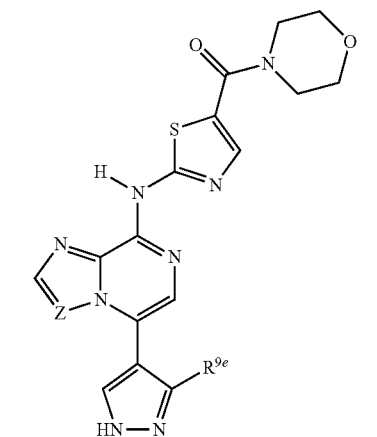

Vt

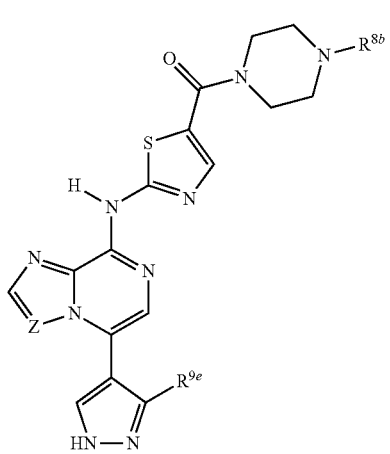

Vu

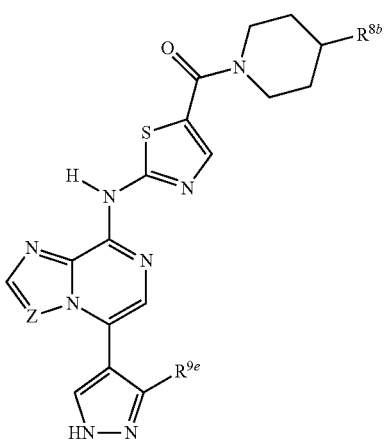

Vv

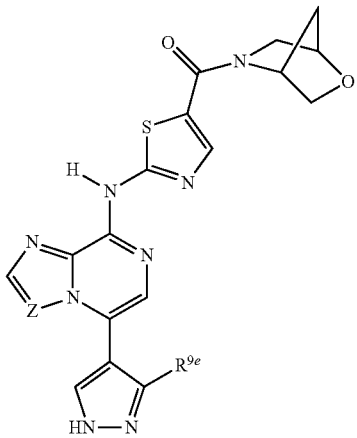

Vw

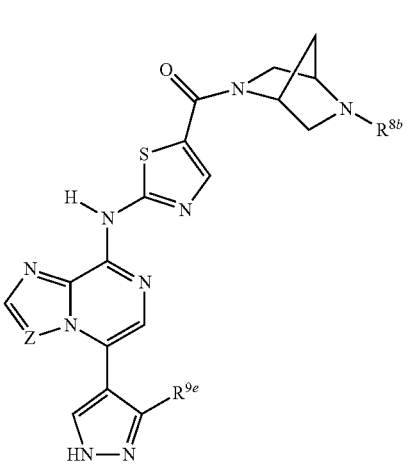

Vx

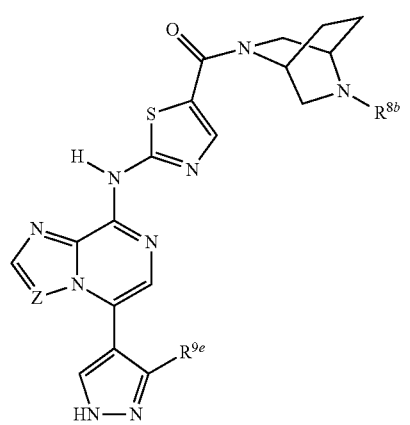

wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, Me, or CN; or a pharmaceutically acceptable salt, solvate or prodrug thereof; and stereoisomers and tautomers thereof.

43. The compound according to claim 1 wherein the compound is according to formula VIa, VIb, VIc, VId, VIe, VIf, VIg, VIh, VIi, VIj, VIk or VII:

VIa
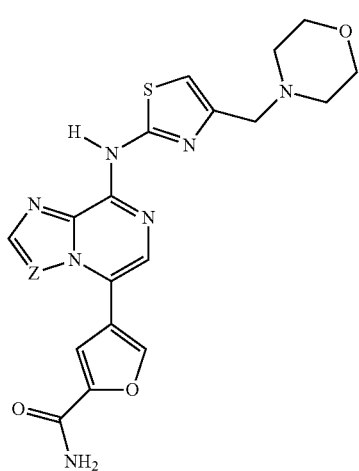
VId
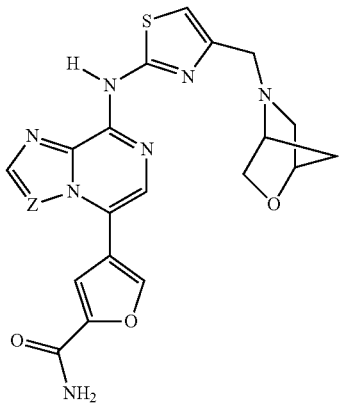
VIb
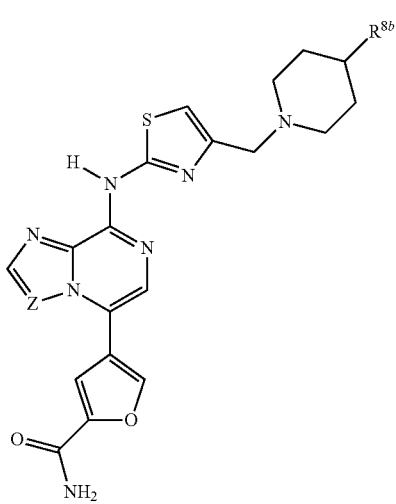
VIe
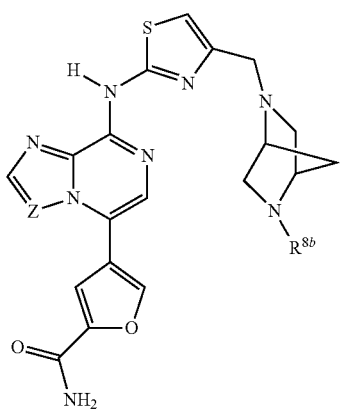
VIc
VIf
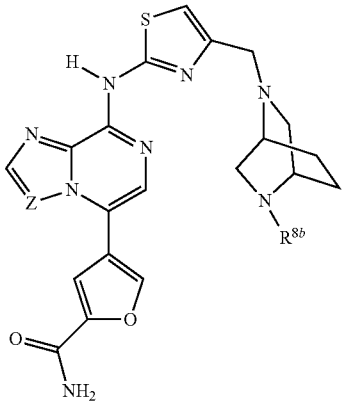

VIg

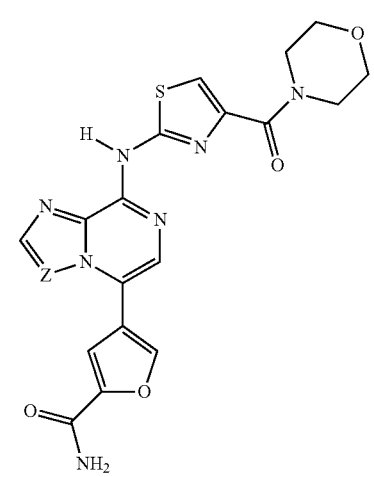

VIh

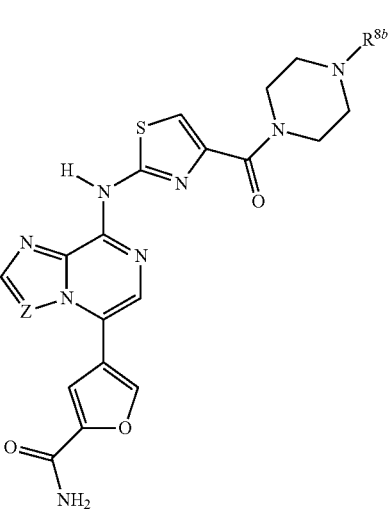

VIi

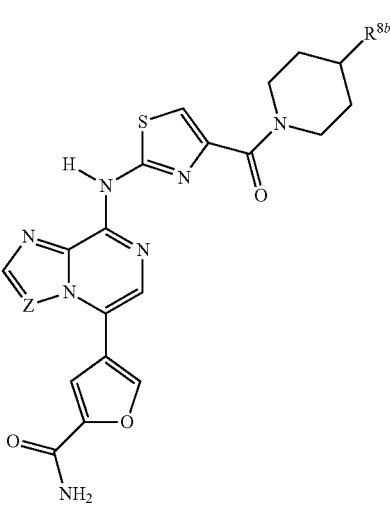

VIj

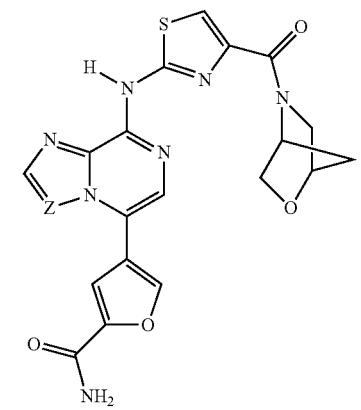

VIk

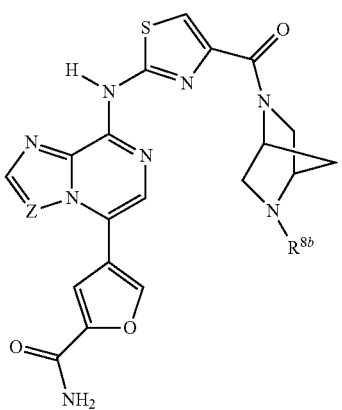

VIl

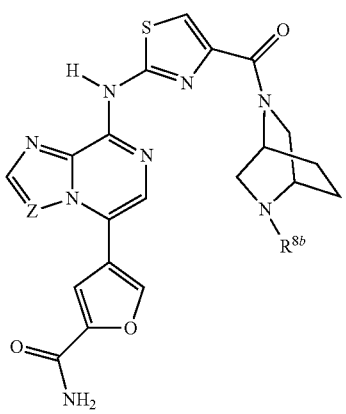

wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.

44. The compound according to claim 1 wherein the compound is according to formula VIm, VIn, VIo, VIp, VIq, VIr, VIs, VIt, VIu, VIv, VIw or VIx:

173
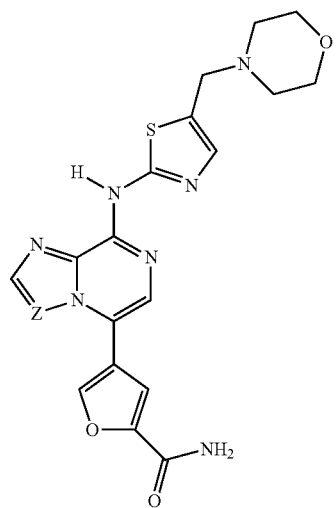
VIm
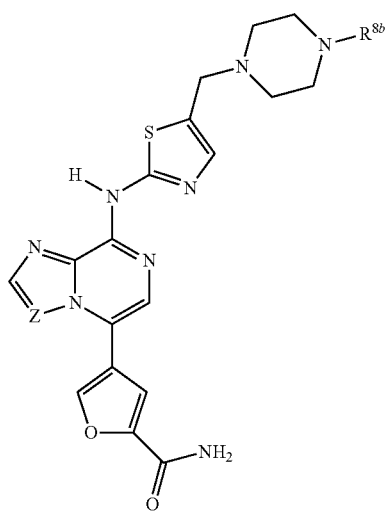
VIn
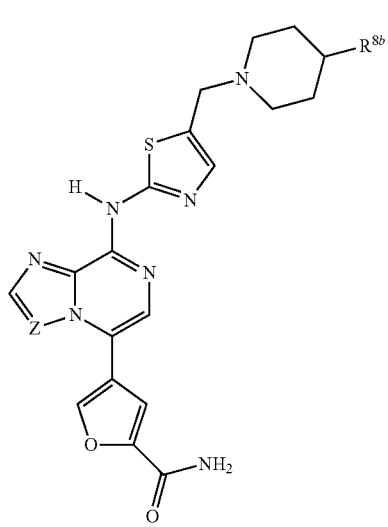
VIo
174
-continued
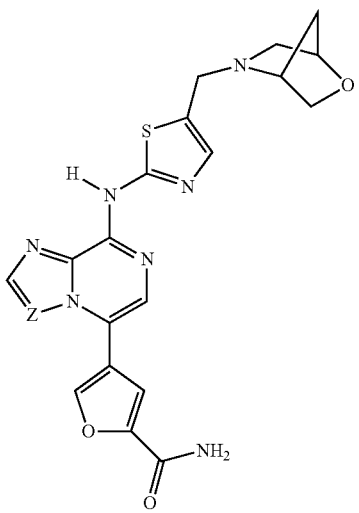
VIp
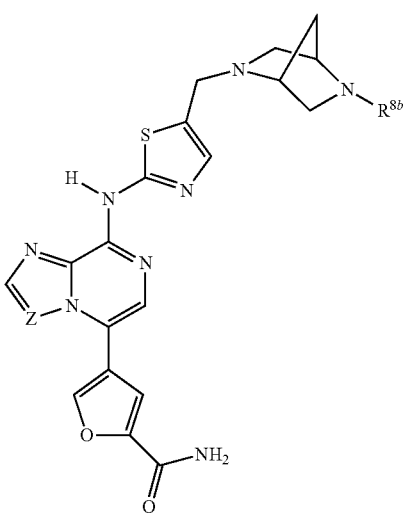
VIq
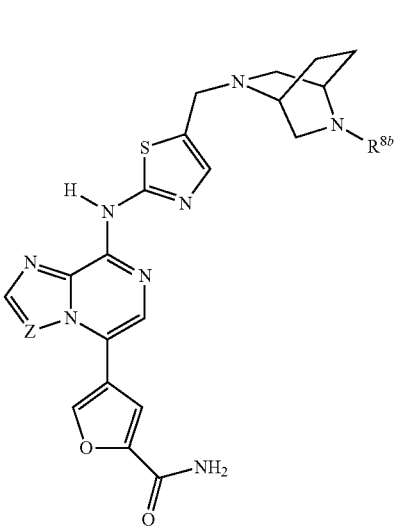
VIr -continued
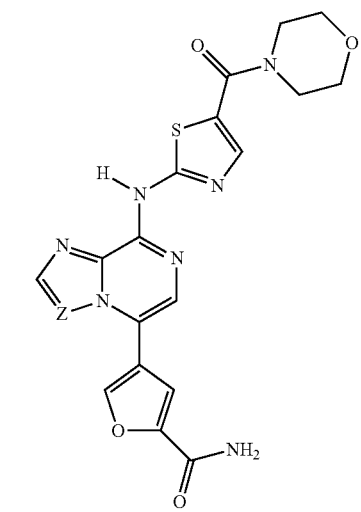
VIs
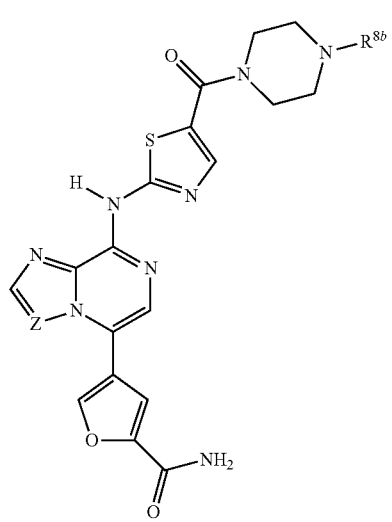
VIt
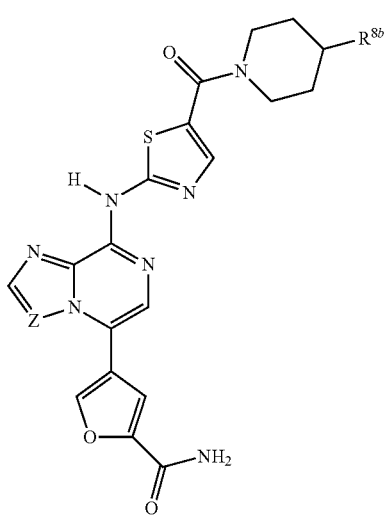
VIu
-continued
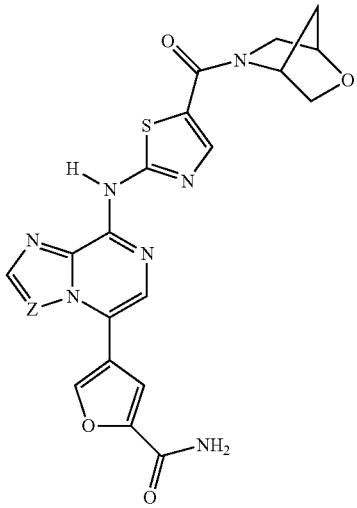
VIv
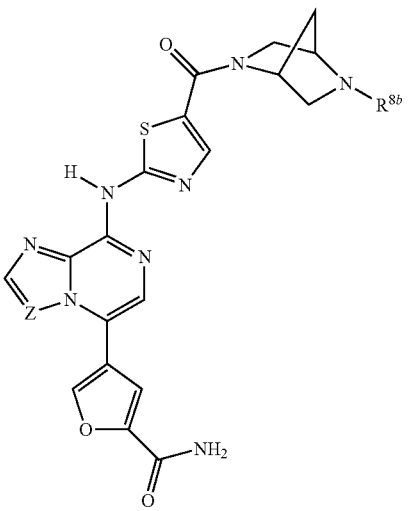
VIw
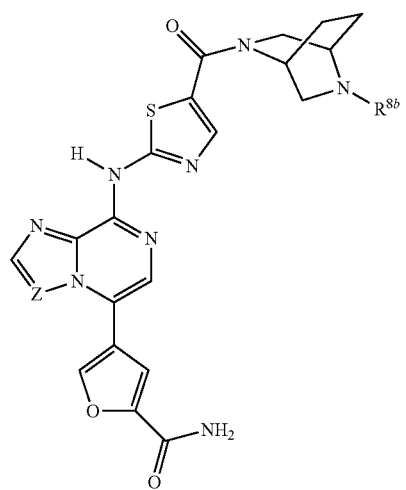
VIx
wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.

45. The compound according to claim 1 wherein the compound is according to formula VIIa, VIIb, VIIc, VIId, VIIe, VIIf, VIIg, VIIh, VIIi, VIIj, VIIk or VIII:
VIIa
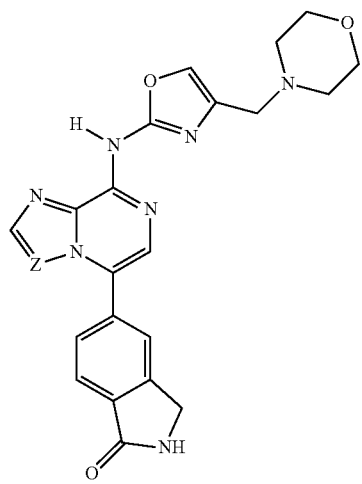
VIIb
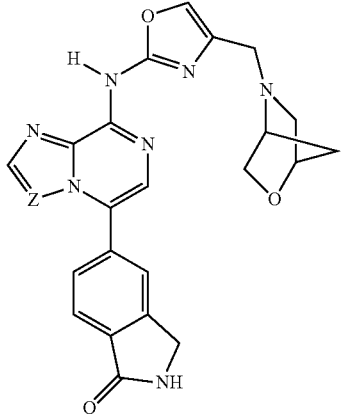
VIIc
VIId
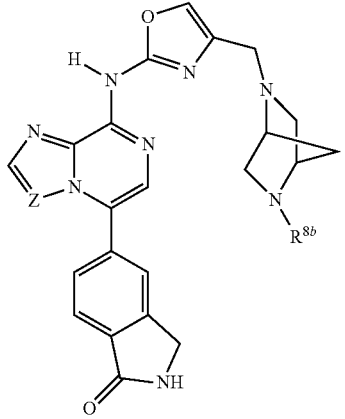
VIIe
VIIf
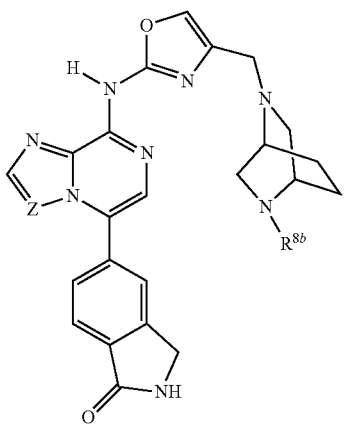

179
-continued

VIIg

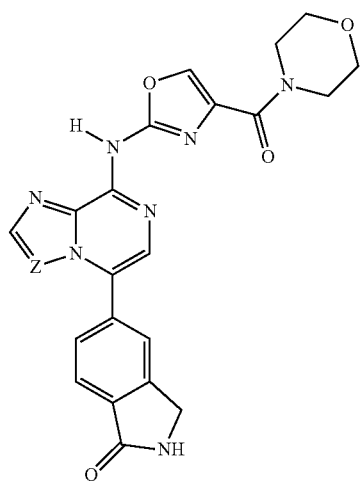

VIIh

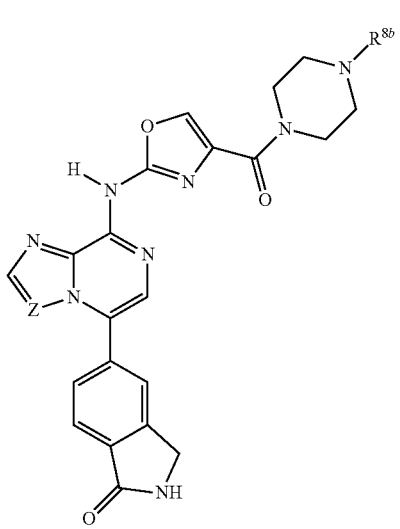

VIIi

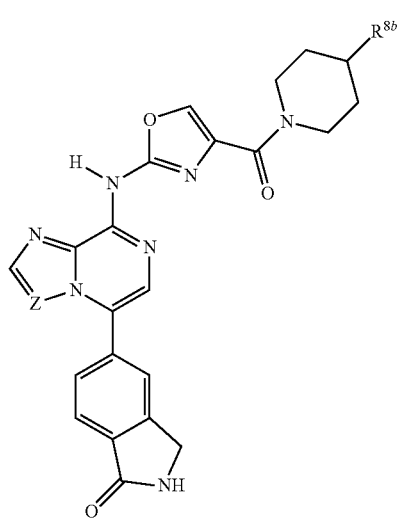

180
-continued

VIIj

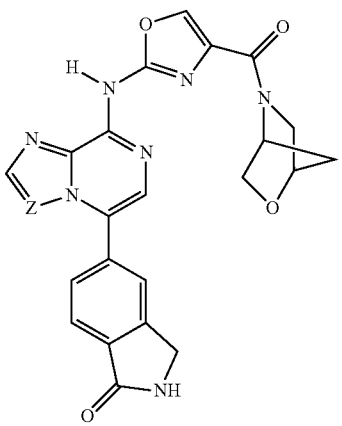

VIIk

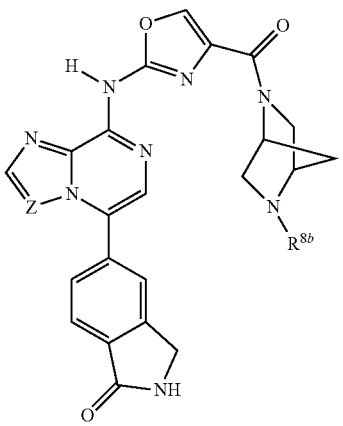

VIII

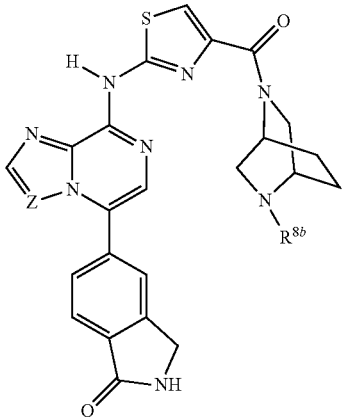

wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.

46. The compound according to claim 1 wherein the compound is according to formula VIIm, VIIn, VIIo, VIIp, VIIq, VIIr, VIIs, VIIt, VIIu, VIIv, VIIw or VIIx:

VIIm
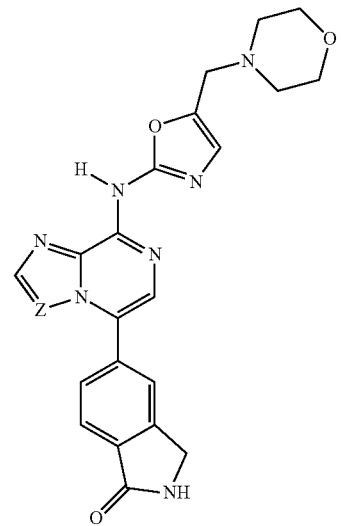
VIIp
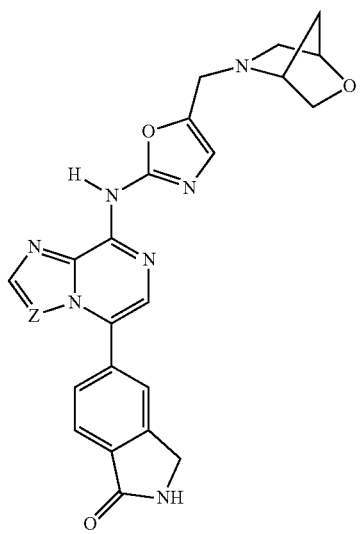
VIIn
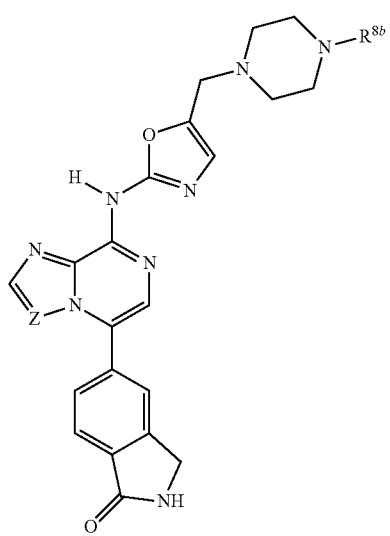
VIIq
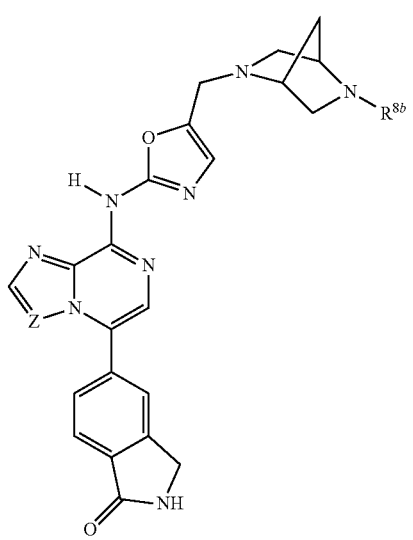
VIIo
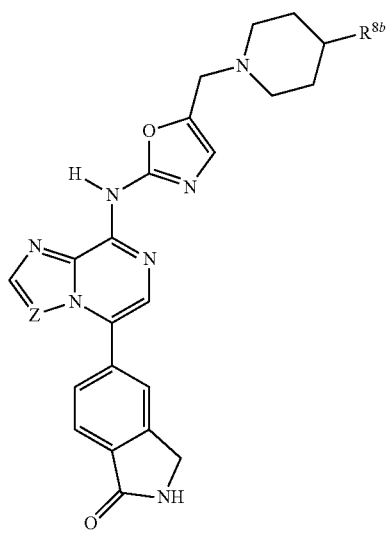
VIIr
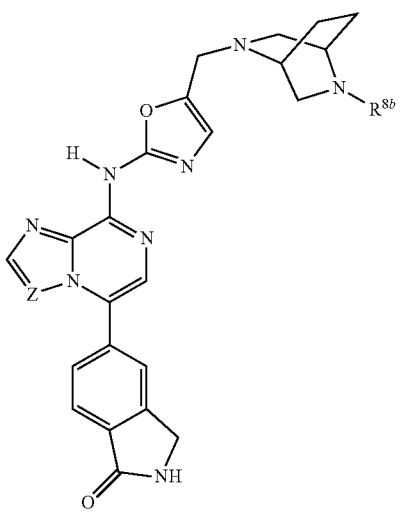

VIIs
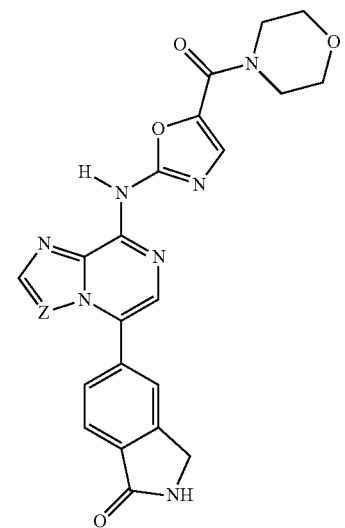
VIIt
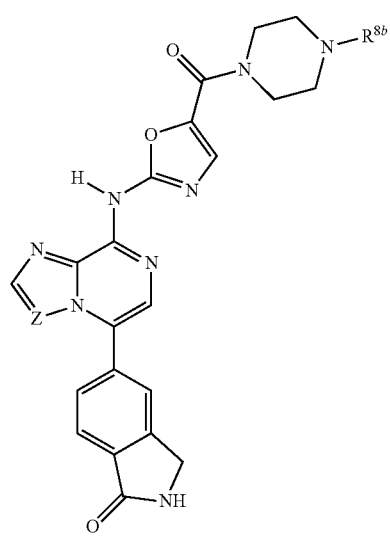
VIIu
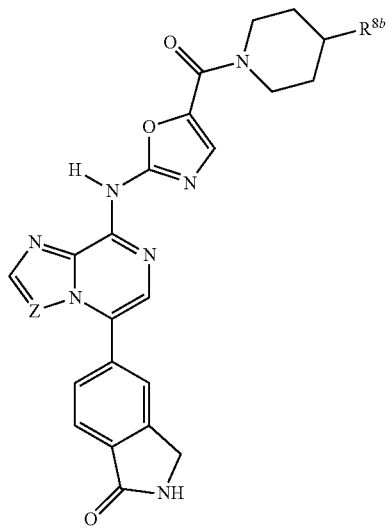
VIIv
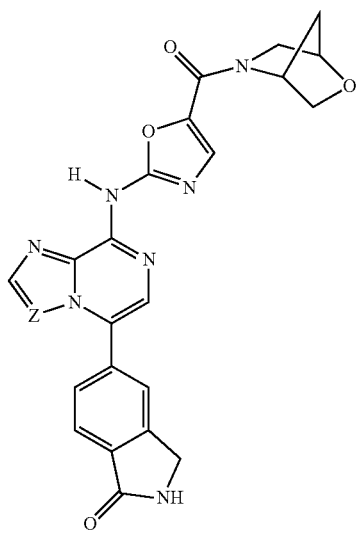
VIIw
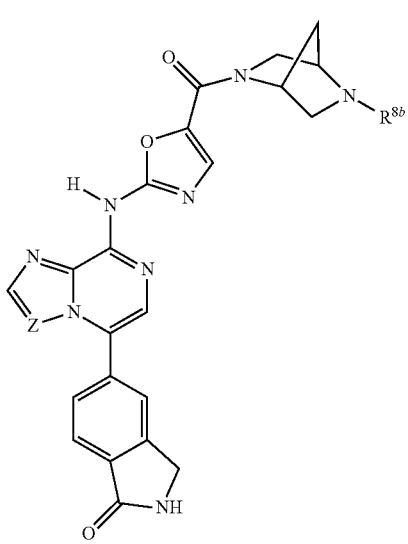
VIIx
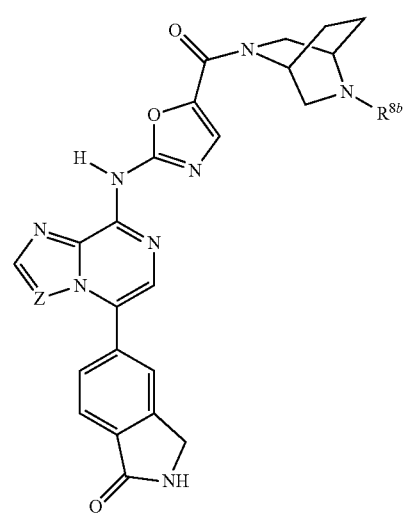
wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.
47. The compound according to claim 1 wherein the compound is according to formula VIIIa, VIIIb, VIIIc, VIIId, VIIIe, VIII, VIIIg, VIIIh, VIIIi, VIIIj, VIIIk or VIIIl:
VIIIa
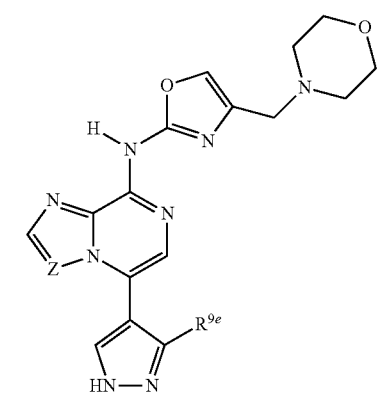
VIIIb
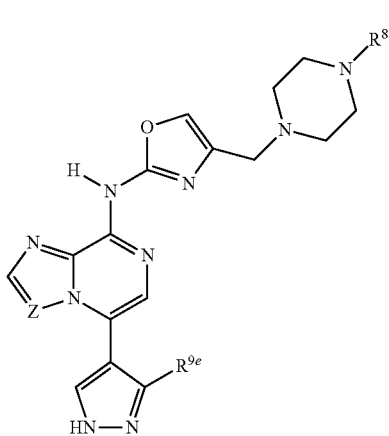
VIIIc
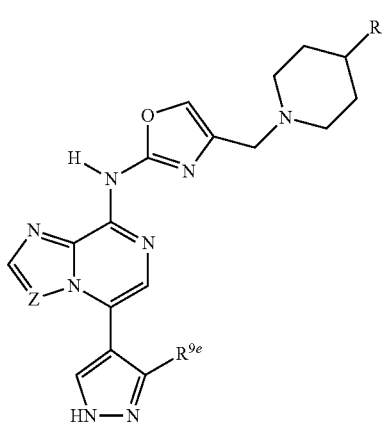
VIIId
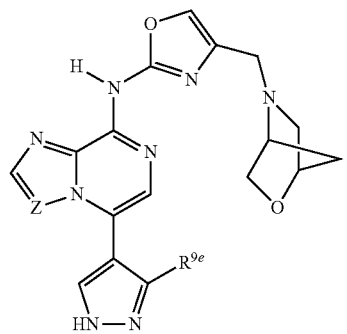
VIIIe
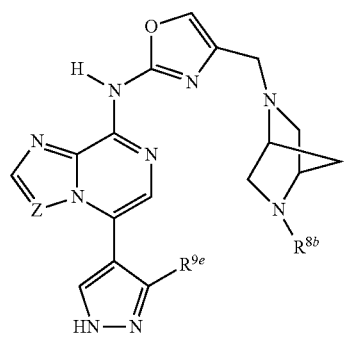
VIIIf
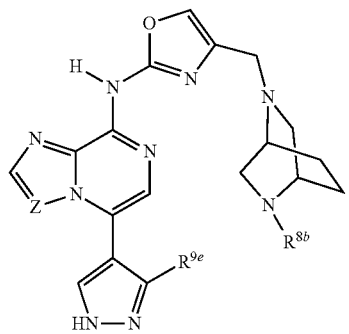
VIIIg
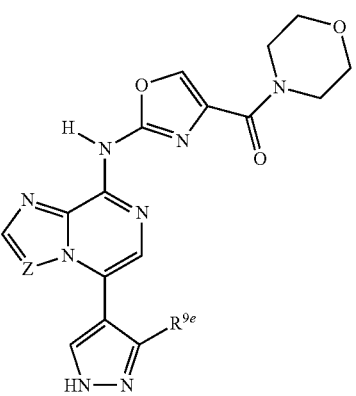

VIIIh 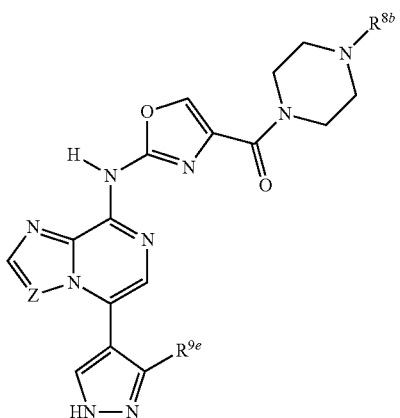

VIIIi 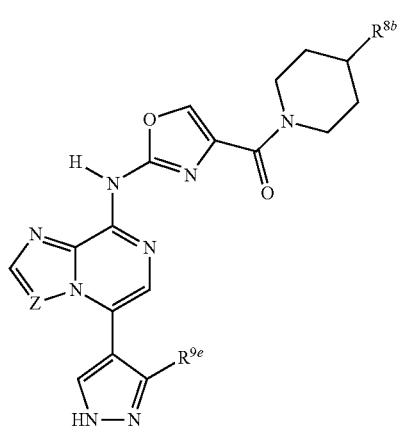

VIIIj 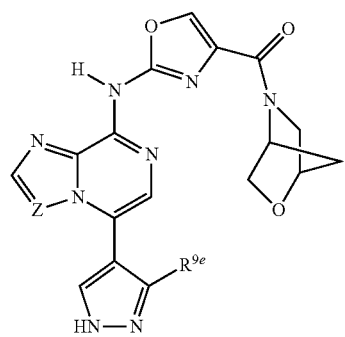

VIIIk 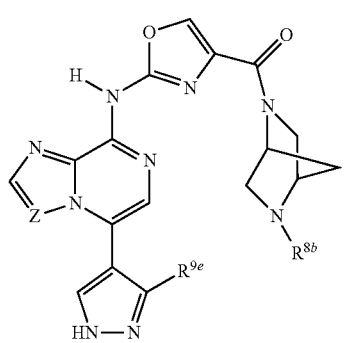

VIIIl 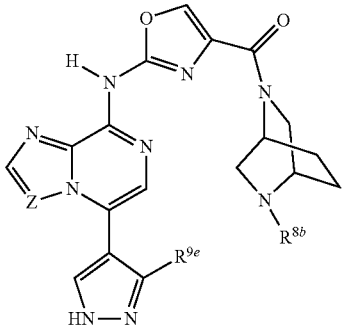

wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, Me, or CN; or a pharmaceutically acceptable salt, solvate or prodrug thereof; and stereoisomers and tautomers thereof.

48. The compound according to claim 1 wherein the compound is according to formula VIIIm, VIIIn, VIIIo, VIIIp, VIIIq, VIIIr, VIIIs, VIIIt, VIIIu, VIIIv, VIIIw or VIIIx:

VIIIm 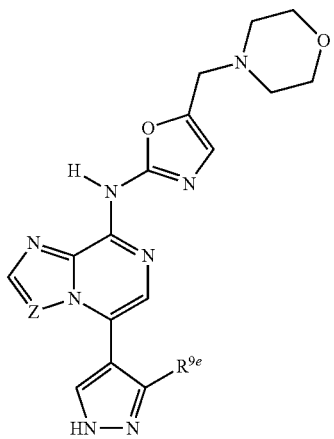

VIIIn 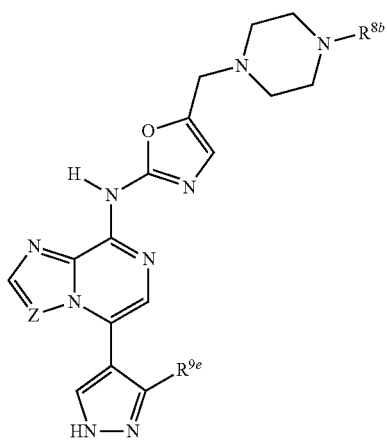

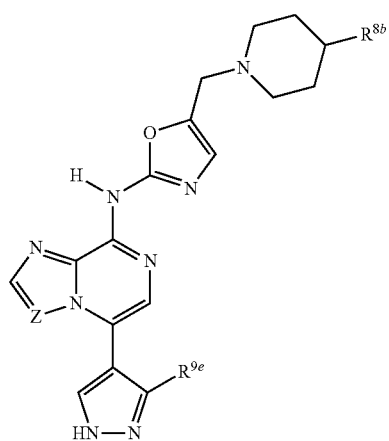
VIIIo
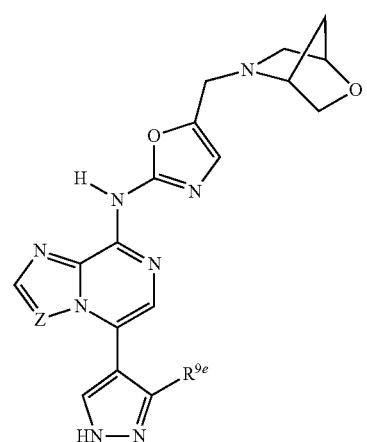
VIIIp
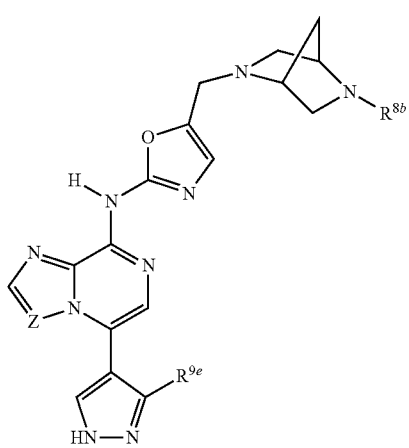
VIIIq
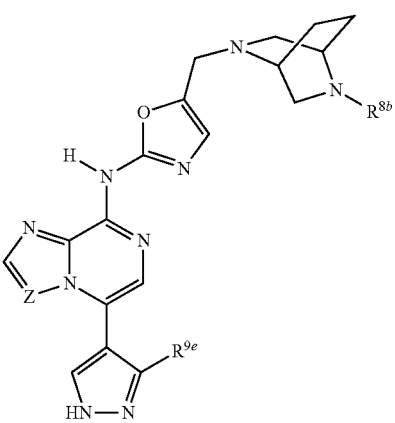
VIIIr
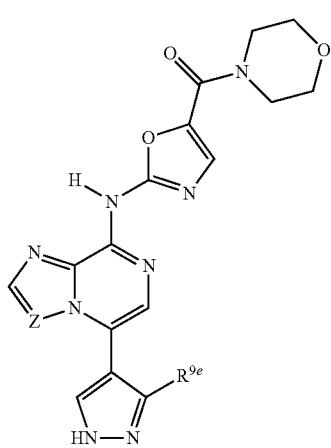
VIIIs
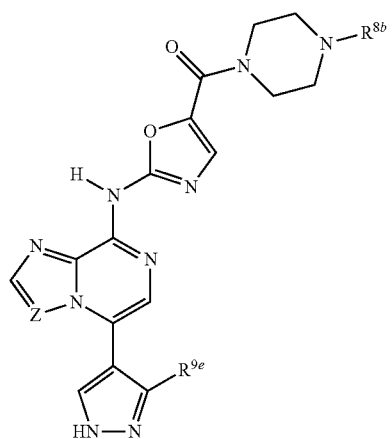
VIIIt -continued

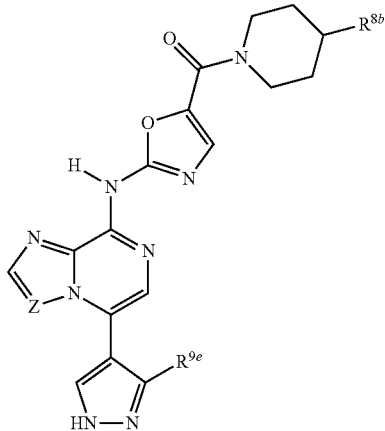
VIIIu

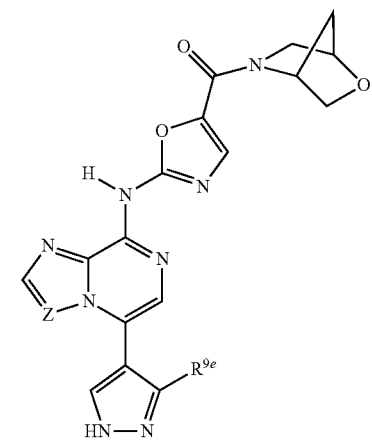
VIIIv

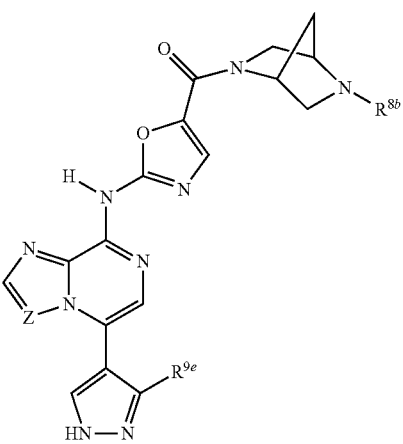
VIIIw

-continued

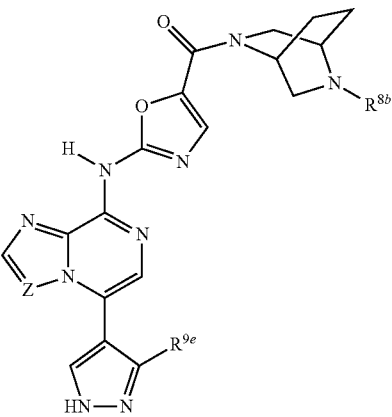
VIIIx wherein $R^{8b}$ is hydrogen, substituted or unsubstituted $C_1$-$C_6$ alkyl or substituted or unsubstituted $C_3$-$C_7$ cycloalkyl; and $R^{9e}$ is hydrogen, Me, or CN; or a pharmaceutically acceptable salt, solvate or prodrug thereof; and stereoisomers and tautomers thereof.

49. The compound according to claim 1 wherein the compound is according to formula IXa, IXb, IXc, IXd, IXe, IXf, IXg, IXh, IXi, IXj, IXk or IXl:

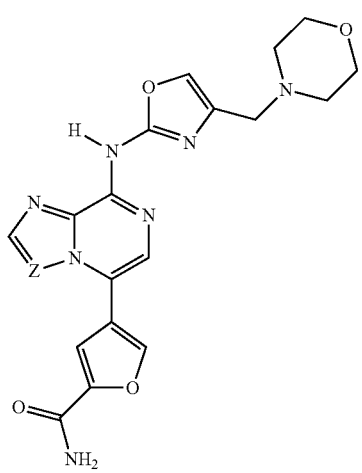
IXa

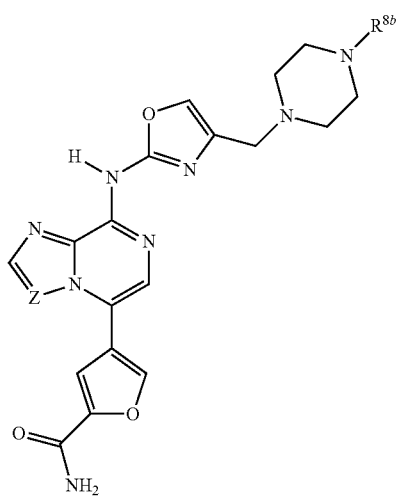
IXb

-continued
IXc
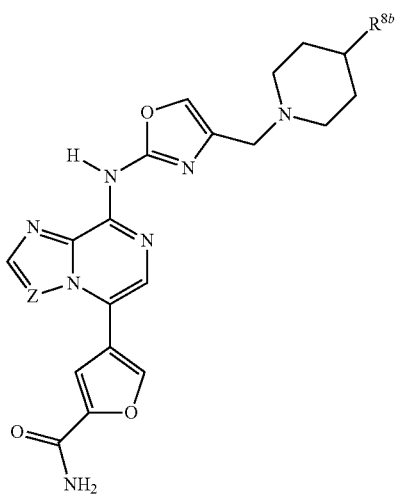
IXd
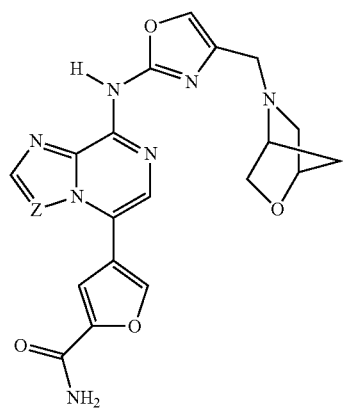
IXe
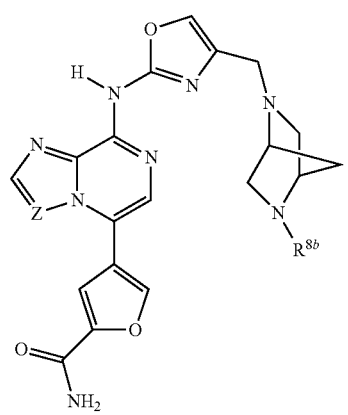
-continued
IXf
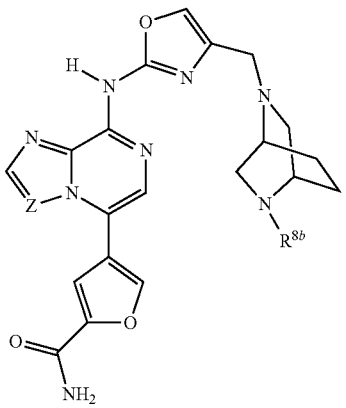
IXg
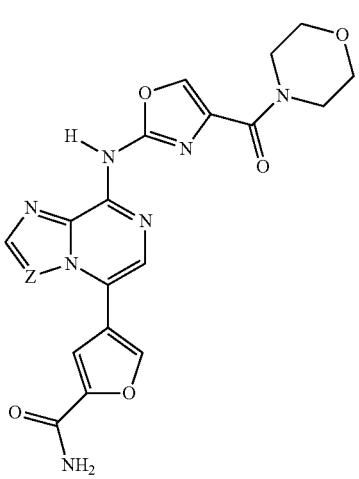
IXh
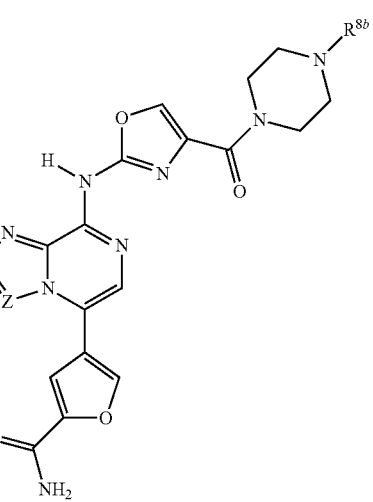

-continued

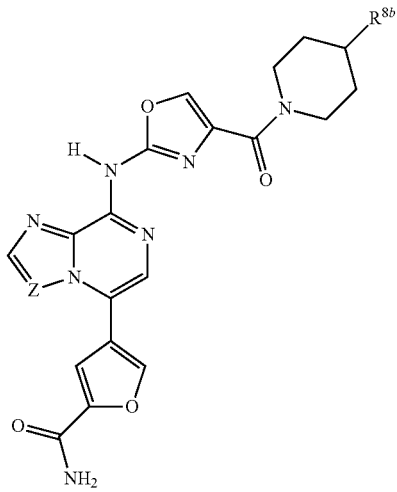

IXi

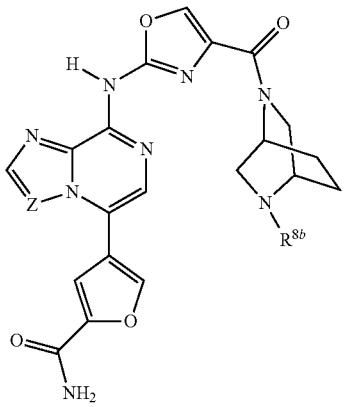

IXl wherein R^(8b) is hydrogen, substituted or unsubstituted C$_1$-C$_6$ alkyl or substituted or unsubstituted C$_3$-C$_7$ cycloalkyl; or a pharmaceutically acceptable salt, solvate or prodrug thereof; and stereoisomers and tautomers thereof.

50. The compound according to claim 1 wherein the compound is according to formula IXm, IXn, IXo, IXp, IXq, IXr, IXs, IXt, IXu, IXv, IXw or IXx:

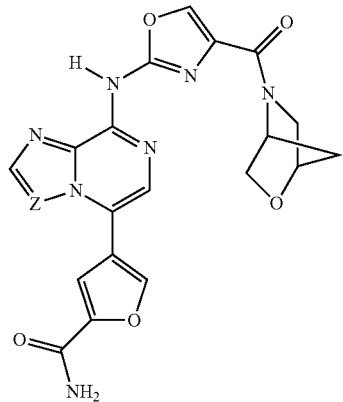

IXj

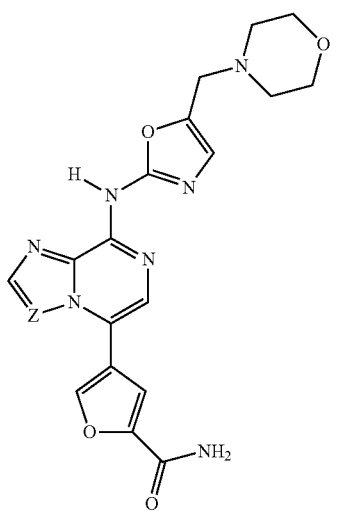

IXm

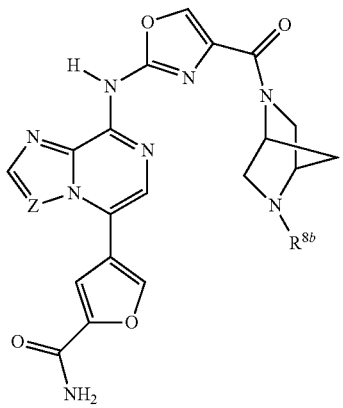

IXk

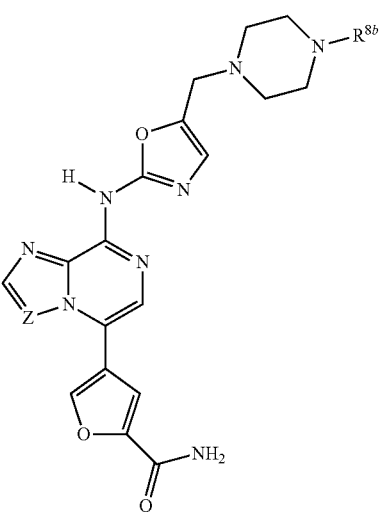

IXn

-continued
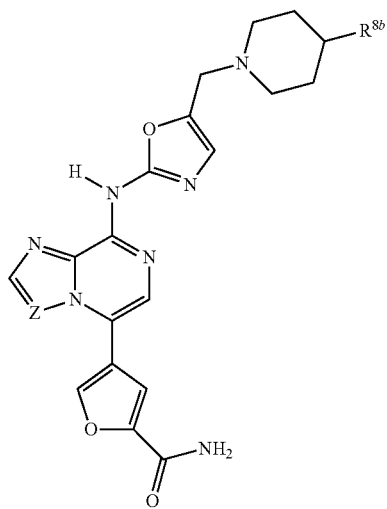
IXo
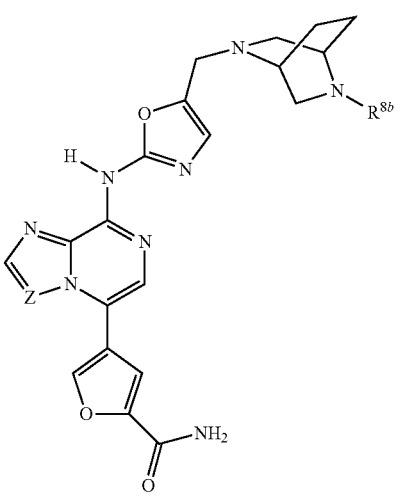
IXr
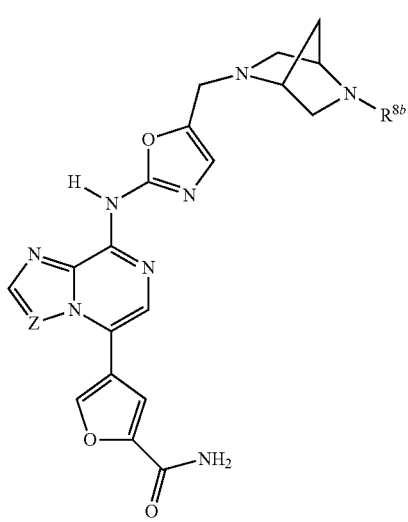
IXp
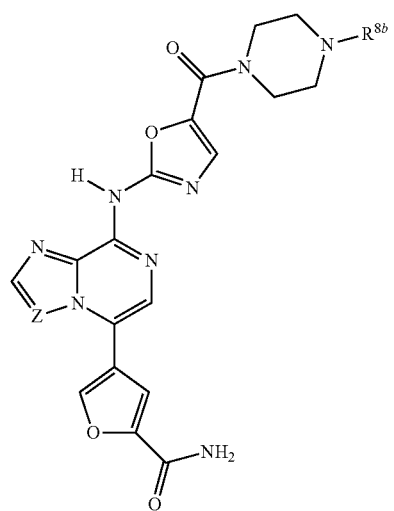
IXs
IXq
IXt IXu

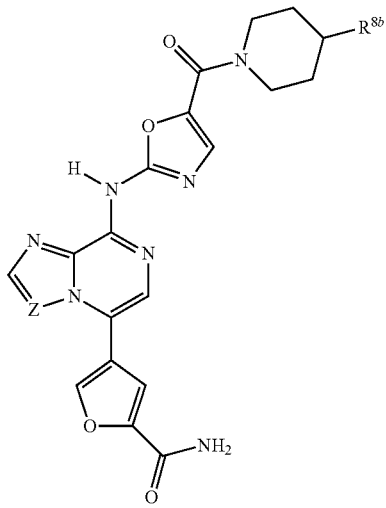

IXv

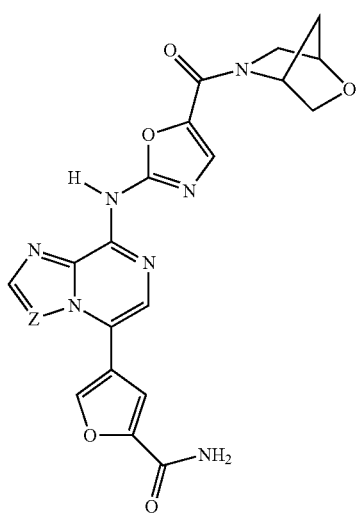

IXw

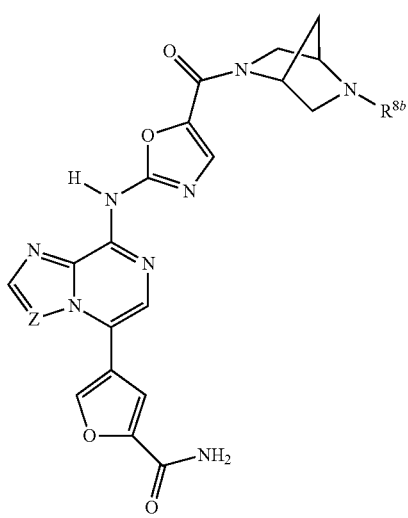

IXx

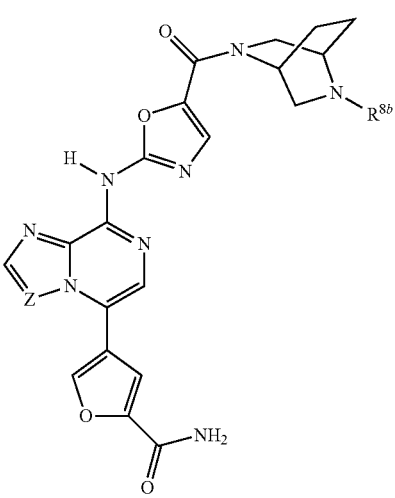

wherein $R^{8b}$ is hydrogen, substituted or unsubstituted $C_1$-$C_6$ alkyl or substituted or unsubstituted $C_3$-$C_7$ cycloalkyl; or a pharmaceutically acceptable salt, solvate or prodrug thereof; and stereoisomers and tautomers thereof.

51. The compound according to claim 39, wherein $R^{8b}$ is H.

52. The compound according to claim 39, wherein $R^{8b}$ is $C_3$-$C_7$ cycloalkyl.

53. The compound according to claim 52, wherein $R^{8b}$ is cyclopropyl.

54. The compound according to claim 39, wherein $R^{8b}$ is substituted or unsubstituted $C_1$-$C_6$ alkyl.

55. The compound according to claim 39, wherein $R^{8b}$ is Me, Et, Pr, i-Pr, t-Bu, i-Bu, $CF_3$, $CH_2CF_3$, or cyclopropylmethyl.

56. The compound according to claim 1 wherein the compound is according to formula Xa, Xb or Xc:

Xa

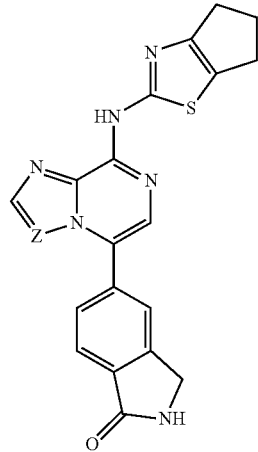

201

-continued

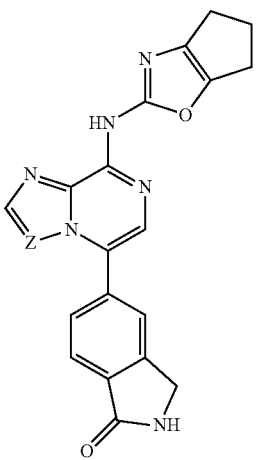

Xb

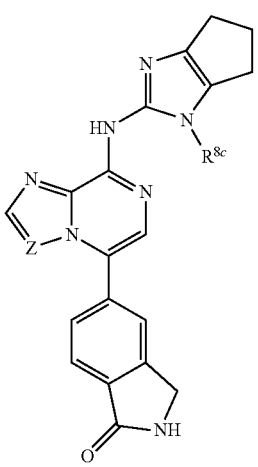

Xc wherein $R^{8c}$ is hydrogen, or substituted or unsubstituted $C_1$-$C_6$ alkyl.

57. The compound according to claim 1 wherein the compound is according to formula Xd, Xe or Xf:

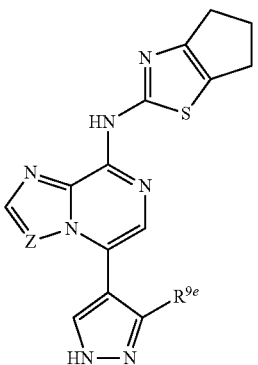

Xd

202

-continued

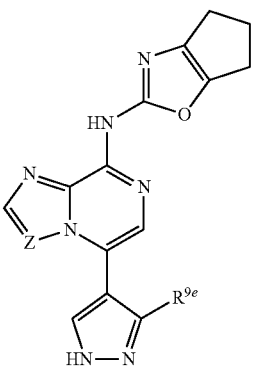

Xe

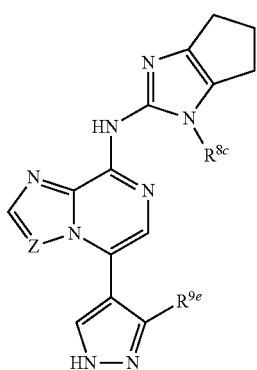

Xf wherein $R^{8c}$ is hydrogen, or substituted or unsubstituted $C_1$-$C_6$ alkyl; and $R^{9e}$ is hydrogen, Me, or CN; or a pharmaceutically acceptable salt, solvate or prodrug thereof; and stereoisomers and tautomers thereof.

58. The compound according to claim 1 wherein the compound is according to formula Xg, Xh or Xi:

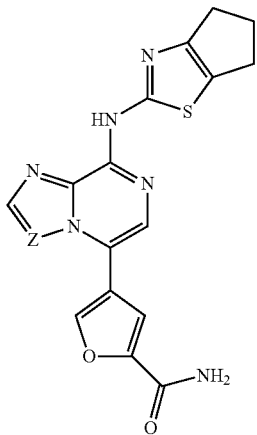

Xg

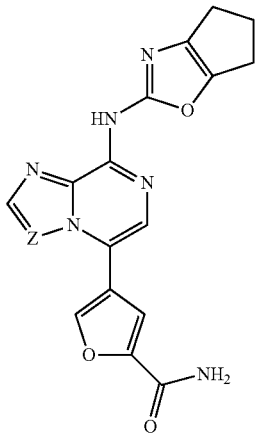

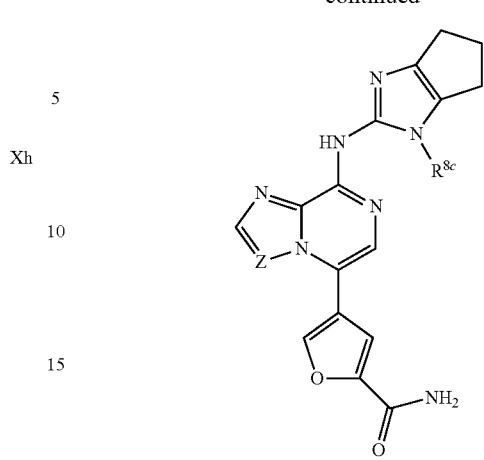

and wherein $R^{8c}$ is hydrogen, or substituted or unsubstituted $C_1$-$C_6$ alkyl; or a pharmaceutically acceptable salt, solvate or prodrug thereof; and stereoisomers and tautomers thereof.

59. A pharmaceutical composition comprising a pharmaceutically acceptable carrier and a pharmaceutically effective amount of a compound according to claim 1.

60. The pharmaceutical composition of claim 59, wherein the carrier is a parenteral carrier.

61. The pharmaceutical composition of claim 59, wherein the carrier is an oral carrier.

62. The pharmaceutical composition of claim 59, wherein the carrier is a topical carrier.

* * * * *